United States Patent
Lim et al.

(10) Patent No.: US 11,976,061 B2
(45) Date of Patent: May 7, 2024

(54) PREPARATION OF BENZIMIDAZOLONE DERIVATIVES AS NOVEL DIACYLGLYCERIDE O-ACYLTRANSFERASE 2 INHIBITORS

(71) Applicant: Merck Sharp & Dohme LLC, Rahway, NJ (US)

(72) Inventors: Yeon-Hee Lim, South San Francisco, CA (US); Eric R. Ashley, San Bruno, CA (US); Jianming Bao, Princeton, NJ (US); Chen Cheng, Millbrae, CA (US); James P. Roane, Brisbane, CA (US); Emma Helen Southgate, Mountain View, CA (US)

(73) Assignee: Merck Sharp & Dohme, LLC, Rahway, NJ (US)

( * ) Notice: Subject to any disclaimer, the term of this patent is extended or adjusted under 35 U.S.C. 154(b) by 0 days.

(21) Appl. No.: 17/494,906

(22) Filed: Oct. 6, 2021

(65) Prior Publication Data
US 2022/0112182 A1   Apr. 14, 2022

Related U.S. Application Data

(60) Provisional application No. 63/089,068, filed on Oct. 8, 2020.

(51) Int. Cl.
| | | |
|---|---|---|
| C07D 409/14 | (2006.01) |
| C07D 235/26 | (2006.01) |
| C07D 405/12 | (2006.01) |
| C07D 409/12 | (2006.01) |
| C07D 417/14 | (2006.01) |
| C07D 471/04 | (2006.01) |

(52) U.S. Cl.
CPC ......... C07D 409/14 (2013.01); C07D 235/26 (2013.01); C07D 405/12 (2013.01); C07D 409/12 (2013.01); C07D 417/14 (2013.01); C07D 471/04 (2013.01)

(58) Field of Classification Search
CPC .. C07D 409/14; C07D 409/12; C07D 235/26; C07D 405/12; C07D 417/14; C07D 471/04
See application file for complete search history.

(56) References Cited

FOREIGN PATENT DOCUMENTS

| | | |
|---|---|---|
| WO | 2018093696 A1 | 5/2018 |
| WO | 2018093698 A1 | 5/2018 |

OTHER PUBLICATIONS

Sato, Kenjiro et al., Discovery of a Novel Series of N-Phenylindoline-5-sulfonamide Derivatives as Potent, Selective, and Orally Bioavailable Acyl CoA:Monoacylglycerol Acyltransferas- 2 Inhibitors, Journal of Medicinal Chemistry, 2015, 3892-3909, 58(9).

*Primary Examiner* — Rebecca L Anderson
(74) *Attorney, Agent, or Firm* — Kristi K. Harman; Catherine D. Fitch

(57) ABSTRACT

Invented are compounds of Formula I

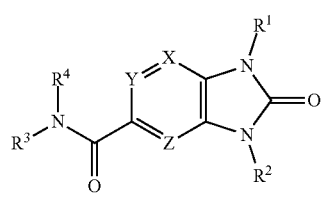

and the pharmaceutically acceptable salts, esters, and prodrugs thereof, which are DGAT2 inhibitors. Also provided are methods of making compounds of Formula I, pharmaceutical compositions comprising compounds of Formula I, and methods of using these compounds to treat hepatic steatosis, nonalcoholic steatohepatitis (NASH), fibrosis, type-2 diabetes mellitus, obesity, hyperlipidemia, hypercholesterolemia, atherosclerosis, cognitive decline, dementia, cardiorenal diseases such as chronic kidney diseases and heart failure and related diseases and conditions, comprising administering a compound of Formula I to a patient in need thereof.

39 Claims, No Drawings

PREPARATION OF BENZIMIDAZOLONE DERIVATIVES AS NOVEL DIACYLGLYCERIDE O-ACYLTRANSFERASE 2 INHIBITORS

FIELD OF THE INVENTION

The present invention is directed to novel pharmaceutical compounds which inhibit diacylglyceride O-acyltransferase 2 ("DGAT2"), and may be useful for preventing, treating or acting as a reversing agent for hepatic steatosis, nonalcoholic steatohepatitis (NASH), fibrosis, type-2 diabetes mellitus, obesity, hyperlipidemia, hypercholesterolemia, atherosclerosis, cognitive decline, dementia, cardiorenal diseases such as chronic kidney diseases and heart failure, and related diseases and conditions, as well as methods of making such compounds and pharmaceutical compositions comprising such a compound and a pharmaceutical carrier.

BACKGROUND OF THE INVENTION

Triacylglycerols ("TGs") serve several functions in living organisms. One such function of TGs is in the storage of energy. TGs also play a role in the synthesis of membrane lipids. TG synthesis in cells may protect them from the potentially toxic effects of excess fatty acid ("FA"). In enterocytes and hepatocytes, TGs are synthesized for the assembly and secretion of lipoproteins which transport FA between tissues. TGs play a role in the skin's surface water barrier, and TGs in adipose tissue provide insulation for organisms.

The glycerol phosphate and the monoacylglycerol pathways are the major pathways for the biosynthesis of TG. However, the last step in the synthesis of TG involves the reaction of a fatty acyl-CoA and diacylglycerol ("DAG") to form TG. The reaction is catalyzed by acyl-CoA:diacylglycerol acyltransferase ("DGAT") enzymes. There have been identified two DGAT enzymes, DGAT1 and DGAT2. Although DGAT1 and DGAT2 catalyze the same reaction, they differ significantly at the level of DNA and protein sequences. DGAT2 can utilize endogenous fatty acid to synthesize TG in in vitro assays, whereas DGAT1 appears to be more dependent on exogenous fatty acid (Yen et al., *J. Lipid Research*, 2008, 49, 2283). Inactivation of DGAT2 impaired cytosolic lipid droplet growth, whereas inactivation of DGAT1 exerts opposite effect. (Li et al., *Arterioscler. Thromb. Vasc. Biol.* 2015, 35, 1080).

DGAT2 is an integral membrane protein of the endoplasmic reticulum and is expressed strongly in adipose tissue and the liver. DGAT2 appears to be the dominant DGAT enzyme controlling TG homeostasis in vivo. DGAT2 deficient mice survive for only a few hours after birth. On the other hand, DGAT1 deficient mice are viable (Yen et al., *J. Lipid Research*, 2008, 49, 2283).

Despite this perinatal lethal phenotype, the metabolic role of DGAT2 has been mostly understood from effort exploiting anti-sense oligonucleotides (ASO) in rodents. In this setting, DGAT2 knockdown in ob/ob mice with a DGAT2 gene-specific ASO resulted in a dose dependent decrease in very low density lipoprotein ("VLDL") and a reduction in plasma TG, total cholesterol, and ApoB (Liu, et al., *Biochim. Biophys Acta* 2008, 1781, 97). In the same study, DGAT2 antisense oligonucleotide treatment of ob/ob mice showed a decrease in weight gain, adipose weight and hepatic TG content. Id. In another study, antisense treatment of ob/ob mice improved hepatic steatosis and hyperlipidemia (Yu, et al., *Hepatology*, 2005, 42, 362). Another study showed that diet-induced hepatic steatosis and insulin resistance was improved by knocking down DGAT2 in rats. These effects seem to be unique to inhibition of DGAT2, as ASO against DGAT1 did not lead to similar beneficial effects. Although the molecular mechanism behind these observations remains uncertain, the collective data suggest that suppression of DGAT2 is associated with reduced expression of lipogenic genes (SREBP1c, ACC1, SCD1, and mtGPAT) and increased expression of oxidative/thermogenic genes (CPT1, UCP2) (Choi et al., *J. Bio. Chem.*, 2007, 282, 22678).

In light of the above, inhibitors of DGAT2 are useful for treating disease related to the spectrum of metabolic syndrome such as hepatic steatosis, non-alcoholic steatohepatitis (NASH), fibrosis, type-2 diabetes mellitus, obesity, hyperlipidemia, hypercholesterolemia, atherosclerosis, cognitive decline, dementia, cardiorenal diseases such as chronic kidney diseases and heart failure and related diseases and conditions.

DGAT2 inhibitor compounds are described in WO2021064590, WO2016036633, WO2016036636, WO2016036638, WO2018093696, WO2018093698, WO2013150416, US20150259323, WO2015077299, WO2017011276, WO2018033832, US201801628, WO2003053363.

SUMMARY OF THE INVENTION

The present invention relates to compounds represented by Formula I.

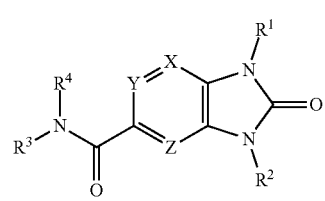

as well as pharmaceutically acceptable salts, esters, and prodrugs thereof, which are DGAT2 inhibitors. Also provided are methods of making compounds of Formula I, pharmaceutical compositions comprising compounds of Formula I, and methods of using these compounds to treat hepatic steatosis, nonalcoholic steatohepatitis (NASH), fibrosis, type-2 diabetes mellitus, obesity, hyperlipidemia, hypercholesterolemia, atherosclerosis, cognitive decline, dementia, cardiorenal diseases such as chronic kidney diseases and heart failure and related diseases and conditions, comprising administering a compound of Formula I to a patient in need thereof.

DETAILED DESCRIPTION OF THE INVENTION

Formula I

The present disclosure is directed to compounds having structural Formula I:

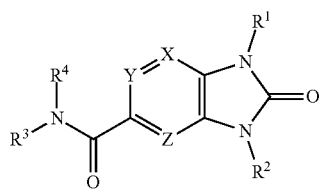

or pharmaceutically acceptable salts thereof wherein:
X, Y, and Z are independently selected from N or C($R^5$);
$R^1$ is
(1) phenyl unsubstituted or substituted with 1, 2, or 3 $R^6$, or
(2) 5- or 6-membered heteroaryl containing 1, 2, 3 or 4 heteroatoms independently selected from N, O, and S, wherein the heteroaryl is unsubstituted or substituted with 1, 2, or 3 $R^6$, or
(3) 8- to 10-membered fused heteroaryl containing 1, 2, 3 heteroatoms independently selected from N, O, and S, wherein the heteroaryl is unsubstituted or substituted with 1, 2, or 3 $R^6$;
$R^2$ is
(1) phenyl unsubstituted or substituted with 1, 2, or 3 $R^7$,
(2) 5- or 6-membered heteroaryl containing 1, 2 or 3 heteroatoms independently selected from N, O, and S, wherein the heteroaryl is unsubstituted or substituted with 1, 2, or 3 $R^7$,
(3) $C_{1-6}$alkyl unsubstituted or optionally mono-substituted or disubstituted with halogen, OH, $CF_3$, or —CN,
(4) ($C_{3-6}$)cycloalkyl unsubstituted or optionally mono-substituted or disubstituted with $C_{1-3}$alkyl, halogen, OH, $CF_3$, or CN,
(5) —($C_{3-6}$)alkylC(O)$NH_2$,
(6) 4- to 6-membered heterocyclyl containing 1 or 2 heteroatoms independently selected from N, O and S wherein the heterocyclyl is unsubstituted or substituted by 1, 2, or 3 $R^7$,
(7) —$CH_2$-aryl unsubstituted or substituted by 1, 2, or 3 $R^7$,
(8) —$SO_2$($C_{1-6}$)alkyl unsubstituted or substituted with 1, 2, or 3 $R^7$, or
(9) —$SO_2$-aryl unsubstituted or substituted with 1, 2, or 3 $R^7$;
$R^3$ is
(1) 4- to 7-membered heterocyclyl containing 1, 2, or 3 heteroatoms independently selected from N, O and S,
(2) 5- or 6-membered heteroaryl containing 1, 2 or 3 heteroatoms independently selected from N, O, and S,
(3) —($C_{1-6}$)alkyl-heteroaryl, wherein the heteroaryl is a 5- or 6-membered heteroaryl containing 1, 2, or 3 heteroatoms independently selected from N, O and S,
(4) —($C_{1-6}$)alkyl-aryl,
(5) —($C_{1-6}$)alkyl-heterocyclyl, wherein the heterocyclyl is a 3- to 6-membered ring containing 1 or 2 heteroatoms independently selected from N, O and S,
(6) —($C_{1-6}$)alkyl,
(7) —($C_{3-6}$)cycloalkyl,
(8) —($C_{1-6}$)hydroxyalkyl,
(9) —($C_{1-6}$)alkyl-S(O)$_2$—$NR^{8a}R^{8b}$, or
(10) —($C_{1-6}$)alkyl-S(O)$_2$—($C_{1-3}$)alkyl,
wherein each aryl, heteroaryl, cycloalkyl, or heterocyclyl is unsubstituted or substituted with 1, 2, or 3 $R^9$, and wherein each alkyl is unsubstituted or substituted with 1, 2, or 3 $R^{10}$;
$R^4$ is
(1) hydrogen, or
(2) ($C_{1-3}$)alkyl,
or $R^3$ and $R^4$ combine along with the nitrogen atom to which they are attached to form a mono- or bicyclic heterocyclyl ring containing 1 or 2 heteroatoms independently selected from N, O and S, wherein the heterocyclyl ring is unsubstituted or substituted by 1, 2, or 3 $R^{11}$,
when present, each $R^5$ is selected from
(1) hydrogen,
(2) ($C_{1-6}$)alkyl,
(3) ($C_{3-6}$)cycloalkyl,
(4) ($C_{1-6}$)haloalkyl,
(5) cyano, or
(6) halogen,
when present, each $R^6$ is independently selected from
(1) cyano,
(2) halogen,
(3) —$OC_{1-6}$alkyl,
(4) ($C_{3-6}$)cycloalkyl, optionally substituted with halogen, $C_{1-3}$alkyl, $C_{1-6}$haloalkyl, or OH,
(5) —C(=O)$NH_2$,
(6) —O($C_{3-6}$)cycloalkyl wherein the cycloalkyl is optionally substituted with halogen, $C_{1-3}$alkyl, or OH,
(7) hydroxy,
(8) N($R^{11}$)$_2$,
(9) ($C_{1-6}$)haloalkyl-,
(10) —O($C_{1-6}$)haloalkyl,
(11) —$SO_2$($C_{1-6}$)alkyl,
(12) —$SO_2$NH($C_{1-6}$)alkyl,
(13) —$SC_{1-6}$alkyl,
(14) N($R^{11}$)C(O)$R^{11}$,
(15) —$SC_{1-6}$haloalkyl, or
(16) ($C_{1-6}$)alkyl;
when present, each $R^7$ is independently selected from
(1) ($C_{1-3}$)alkyl,
(2) halogen,
(3) ($C_{1-6}$)alkoxy-,
(4) ($C_{1-6}$)haloalkyl-, or
(5) hydroxy;
when present, $R^{8a}$ and $R^{8b}$ are independently selected from
(1) hydrogen,
(2) ($C_{1-3}$)alkyl, or
(3) ($C_{3-7}$)cycloalkyl;
when present, each $R^9$ is independently selected from
(1) ($C_{1-3}$)alkyl,
(2) ($C_{1-3}$)haloalkyl-,
(3) oxo,
(4) ($C_{3-6}$)cycloalkyl,
(5) N($R^{11}$)$_2$, (6) hydroxy,
(7) ($C_{1-3}$)alkoxyl-,
(8) cyano, or
(9) halogen;

when present, $R^{10}$ is independently selected from
(1) ($C_{1-3}$)alkoxy-,
(2) hydroxy,
(3) halogen,
(4) ($C_{1-3}$)haloalkyl-, or
(5) $N(R^{11})_2$;

$R^{11}$, when present, is independently
(1) hydrogen, or
(2) ($C_{1-3}$)alkyl;

In Embodiment 1 of this disclosure are compounds of Formula I, or a pharmaceutically acceptable salt of any of the foregoing, wherein $R^1$ is
- a) phenyl optionally substituted with one to three substituents independently selected from halogen, hydroxy, CN, $C_{1-3}$alkyl, $C_{1-3}$haloalkyl, $C_{3-6}$cycloalkyl, $OC_{1-3}$alkyl, $OC_{1-3}$haloalkyl, $OC_{3-6}$cycloalkyl, $-SC_{1-3}$alkyl, $-SC_{1-3}$haloalkyl, $S(O)_2C_{1-3}$alkyl, and wherein the cycloalkyl is optionally substituted with, halogen or OH;
- b) a 6 membered heteroaryl containing one or two nitrogen atom optionally substituted with one to three substituents independently selected from halogen, hydroxy, $C_{1-6}$alkyl, $C_1$-6haloalkyl, $C_{3-6}$cycloalkyl, $OC_{1-3}$alkyl, $OC_{1-3}$haloalkyl, $O-C_{3-6}$cycloalkyl, or CN, and when the cycloalkyl is cyclopropyl, and the cyclopropyl is optionally substituted with halogen, or OH;
- c) a 5 membered heteroaryl containing one to four nitrogen atoms or hetero atoms independently selected from N, O, and S optionally substituted with one to two substituents independently selected from with halogen, ($C_{1-3}$)alkyl, ($C_{3-6}$)cycloalkyl, ($C_{1-3}$)haloalkyl-, OH or $OC_{1-3}$alkyl; or
- d) 8- to 10-membered fused heteroaryl containing 1, 2, 3 heteroatoms independently selected from N, O, and S, wherein the heteroaryl is unsubstituted or substituted with halogen, ($C_{1-3}$)alkyl, ($C_{3-6}$)cycloalkyl, ($C_{1-3}$)haloalkyl-, OH or $OC_{1-3}$alkyl.

In Embodiment 2 of this disclosure are compounds of Formula I, or of Embodiment 1, or a pharmaceutically acceptable salt of any of the foregoing, wherein $R^1$ is not alkyl.

In Embodiment 3a of this disclosure are compounds of Formula I, or any one of Embodiments 1-2, or a pharmaceutically acceptable salt of any of the foregoing, wherein $R^1$ is
- a) phenyl optionally substituted with halogen, $C_{1-3}$alkyl, $C_{1-3}$haloalkyl, $C_{3-6}$cycloalkyl, $O-C_{3-6}$cycloalkyl, CN, $NHC(O)C_{1-3}$alkyl, $NC_{1-3}$alkyl, $C(O)NH_2$, $SC_{1-3}$alkyl, $S(O)_2NHC_{1-3}$alkyl, $S(O)_2C_{1-3}$alkyl, $OC_{1-3}$alkyl, or $OC_{1-3}$haloalkyl, wherein the cycloalkyl is additionally optionally substituted with halogen;
- b) pyridyl optionally substituted with one to three substituents independently selected from halogen, $C_{1-3}$alkyl, $C_{3-6}$cycloalkyl, $OC_{1-3}$alkyl, or $OC_{1-3}$haloalkyl;
- c) 5 membered heteroaryl containing one to four nitrogen atoms or hetero atoms independently selected from N, O, and S optionally substituted with one to two substituents independently selected from with halogen, ($C_{1-3}$)alkyl, ($C_{3-6}$)cycloalkyl, ($C_{1-3}$)haloalkyl-, OH or $OC_{1-3}$alkyl, or
- d) 8- to 10-membered fused heteroaryl containing 1, 2, 3 heteroatoms independently selected from N, O, and S, wherein the heteroaryl is unsubstituted or substituted with halogen, ($C_1$. 3)alkyl, ($C_{3-6}$)cycloalkyl, ($C_{1-3}$)haloalkyl-, OH or $OC_{1-3}$alkyl.

In Embodiment 3b of this disclosure are compounds of Formula I, or any one of Embodiments 1-2, or a pharmaceutically acceptable salt of any of the foregoing, wherein $R^1$ is
- e) phenyl optionally substituted with halogen, $C_{1-3}$alkyl, $C_{3-6}$cycloalkyl, $O-C_{3-6}$cycloalkyl, $OC_{1-3}$alkyl, or $OC_{1-3}$haloalkyl, wherein the cycloalkyl is additionally optionally substituted with halogen;
- f) pyridyl optionally substituted with one to three substituents independently selected from halogen, $C_{1-3}$alkyl, $C_{3-6}$cycloalkyl, $OC_{1-3}$alkyl, or $OC_{1-3}$haloalkyl;
- g) 5 membered heteroaryl containing one to four nitrogen atoms or hetero atoms independently selected from N, O, and S optionally substituted with one to two substituents independently selected from with halogen, ($C_{1-3}$)alkyl, ($C_{3-6}$)cycloalkyl, ($C_{1-3}$)haloalkyl-, OH or $OC_{1-3}$alkyl, or
- h) 8- to 10-membered fused heteroaryl containing 1, 2, 3 heteroatoms independently selected from N, O, and S, wherein the heteroaryl is unsubstituted or substituted with halogen, ($C_1$. 3)alkyl, ($C_{3-6}$)cycloalkyl, ($C_{1-3}$)haloalkyl-, OH or $OC_{1-3}$alkyl.

In Embodiment 4a of this disclosure are compounds of Formula I, or any one of Embodiments 1-3, or a pharmaceutically acceptable salt of any of the foregoing, wherein $R^1$ is
- a) phenyl optionally substituted with one to three substituents independently selected from F, $CF_3$, CN, $N(CH_3)_2$, $C(O)NH_2$, $SCH_3$, $S(O)_2NHCH_3$, $S(O)_2CH_3$, $OCH_2CH_3$, $OCH(CH_3)_2$, $OCHF_2$, $OCH_2CHF_2$, $OCF_3$, $OCF_2CHF_2$, $NHC(O)CH_3$, cyclopropyl, O-cyclopropyl, wherein the cyclopropyl is additionally optionally substituted with 1-3 F;
- b) pyridyl optionally substituted with one to three substituents independently selected from $OC(F)_2(CH_3)$, $OCH_2CH_3$, $OCH(CH_3)_2$, $OCHF_2$, $OCH_2CHF_2$, $OCF_3$, $OCF_2CHF_2$, $OCF_2CHF_2$, or cyclopropyl;
- c) 5 membered heteroaryl containing one to four nitrogen atoms or hetero atoms independently selected from N, O, and S optionally substituted with one to two substituents independently selected from with halogen, ($C_{1-3}$)alkyl, ($C_{3-6}$)cycloalkyl, ($C_{1-3}$)haloalkyl-, OH or $OC_{1-3}$alkyl; or
- d) 8-10 membered fused heteroaryl containing one to three heteroatoms selected from N, O, or S atom optionally substituted with $CH_3$.

In Embodiment 4b of this disclosure are compounds of Formula I, or any one of Embodiments 1-3, or a pharmaceutically acceptable salt of any of the foregoing, wherein $R^1$ is
- a) phenyl optionally substituted with one to three substituents independently selected from F, $OCH_2CH_3$, $OCH(CH_3)_2$, $OCHF_2$, $OCH_2CHF_2$, $OCF_3$, $OCF_2CHF_2$, cyclopropyl, O-cyclopropyl, wherein the cyclopropyl is additionally optionally substituted with 1-3 F;
- b) pyridyl optionally substituted with one to three substituents independently selected from $OC(F)_2(CH_3)$, $OCH_2CH_3$, $OCHF_2$, $OCH_2CHF_2$, $OCF_3$, $OCF_2CHF_2$, or cyclopropyl;

c) 5 membered heteroaryl containing one to four nitrogen atoms or hetero atoms independently selected from N, O, and S optionally substituted with one to two substituents independently selected from with halogen, (C$_{1-3}$)alkyl, (C$_{3-6}$)cycloalkyl, (C$_{1-3}$)haloalkyl-, OH or OC$_{1-3}$alkyl; or
d) 8-10 membered fused heteroaryl containing one to three heteroatoms selected from N, O, or S atom.

In Embodiment 5a of this disclosure are compounds of Formula I, or any one of Embodiments 1-4, or a pharmaceutically acceptable salt of any of the foregoing, wherein R$^1$ is

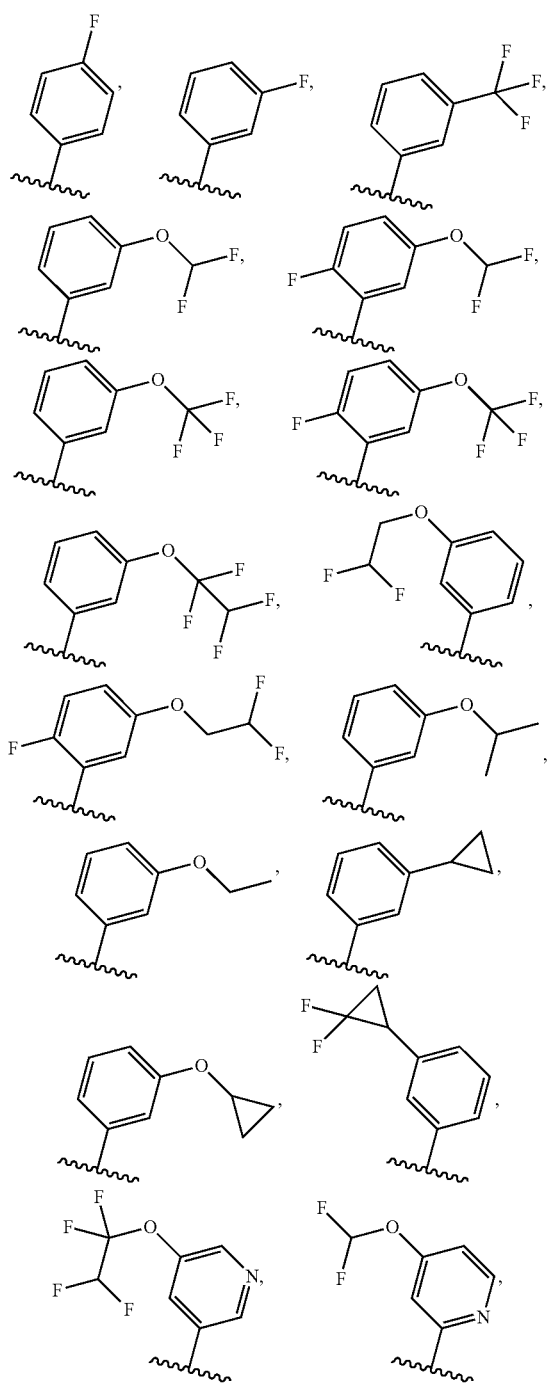

-continued

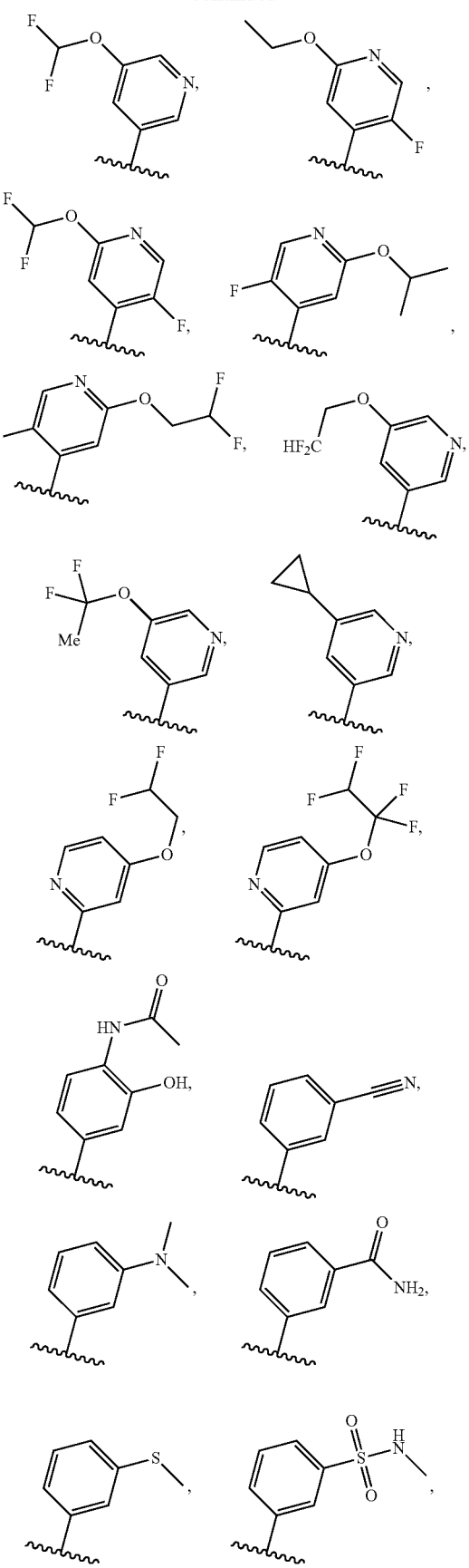

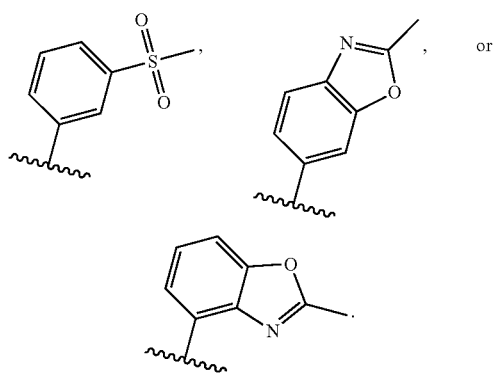

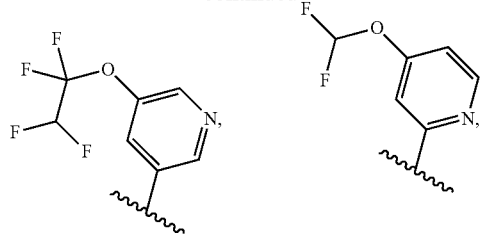

In Embodiment 5b of this disclosure are compounds of Formula I, or any one of Embodiments 1-4, or a pharmaceutically acceptable salt of any of the foregoing, wherein $R^1$ is

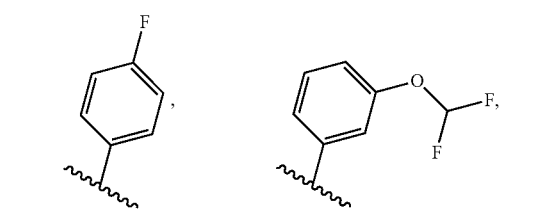

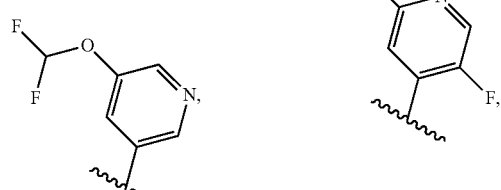

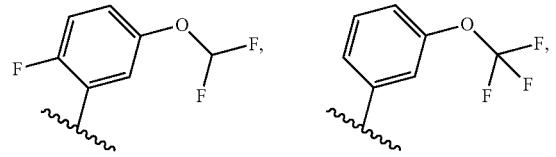

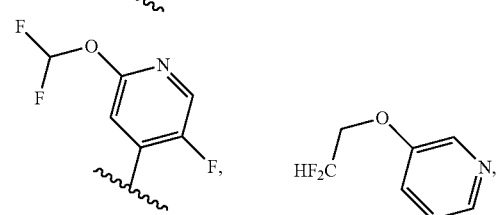

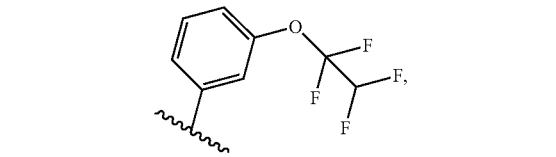

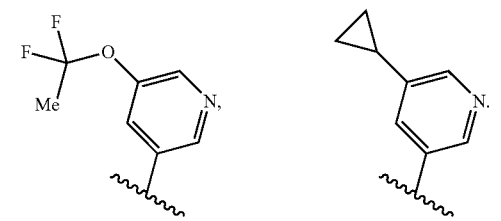

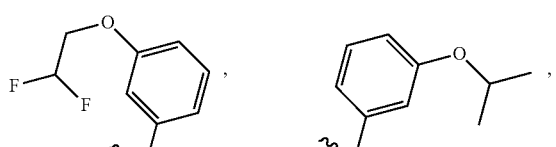

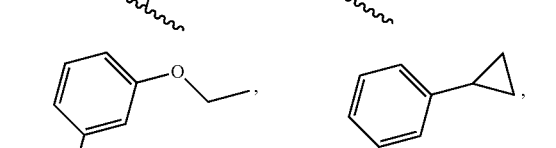

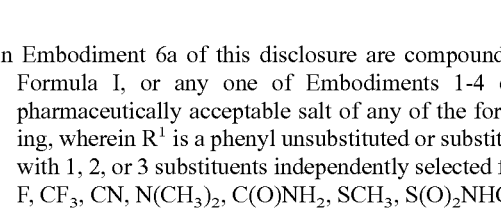

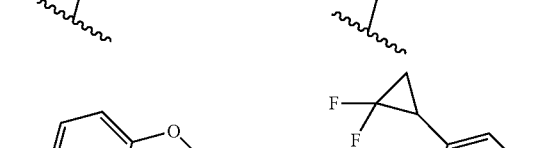

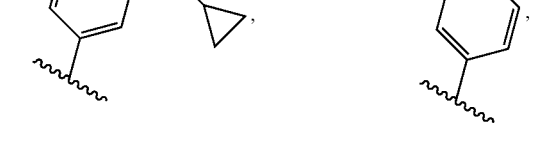

In Embodiment 6a of this disclosure are compounds of Formula I, or any one of Embodiments 1-4 or a pharmaceutically acceptable salt of any of the foregoing, wherein $R^1$ is a phenyl unsubstituted or substituted with 1, 2, or 3 substituents independently selected from F, $CF_3$, CN, $N(CH_3)_2$, $C(O)NH_2$, $SCH_3$, $S(O)_2NHCH_3$, $S(O)_2CH_3$, $OCHF_2$, $OCF_3$, $OCH(CH_3)(CH_3)$, $OCF_2CHF_2$, $OCH_2CHF_2$, $OCH_2CH_3$, $NHC(O)CH_3$, cyclopropyl, or O-cyclopropyl, wherein the cyclopropyl is additionally optionally substituted with one to three halogen atoms.

In Embodiment 6b of this disclosure are compounds of Formula I, or any one of Embodiments 1-4 or a pharmaceutically acceptable salt of any of the foregoing, wherein $R^1$ is a phenyl unsubstituted or substituted with 1, 2, or 3 substituents independently selected from F, $OCHF_2$, $OCF_3$, $OCH(CH_3)(CH_3)$, $OCF_2CHF_2$, $OCH_2CHF_2$, $OCH_2CH_3$, cyclopropyl, or O-cyclopropyl, wherein the cyclopropyl is additionally optionally substituted with one to three halogen atoms.

In Embodiment 7a of this disclosure are compounds of Formula I, or any one of Embodiments 1-4 or a pharmaceutically acceptable salt of any of the foregoing, wherein $R^1$ is a 5- or 6-membered heteroaryl containing 1 N and wherein the heteroaryl is unsubstituted or substituted with 1, 2, or 3 substituents independently selected from OCHF$_2$, OCH$_2$CH$_3$, OCF$_2$CHF$_2$, OCH(CH$_3$)$_2$, OCH$_2$CHF$_2$, OCF$_2$CH$_3$, F, or cyclopropyl.

In Embodiment 7b of this disclosure are compounds of Formula I, or any one of Embodiments 1-4 or a pharmaceutically acceptable salt of any of the foregoing, wherein R$^1$ is a 5- or 6-membered heteroaryl containing 1 N and wherein the heteroaryl is unsubstituted or substituted with 1, 2, or 3 substituents independently selected from OCHF$_2$, OCH$_2$CH$_3$, F, or cyclopropyl.

In Embodiment 8 of this disclosure are compounds of Formula I, or any one of Embodiments 1-4, or a pharmaceutically acceptable salt of any of the foregoing, wherein R$^1$ is

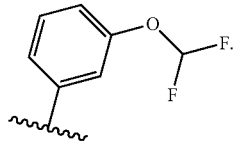 [SMILES: *c1cccc(OC(F)F)c1]

In Embodiment 9 of this disclosure are compounds of Formula I, or any one of Embodiments 1-4, or a pharmaceutically acceptable salt of any of the foregoing, wherein R$^1$ is

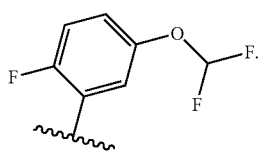

In Embodiment 10 of this disclosure are compounds of Formula I, or any one of Embodiments 1-4, or a pharmaceutically acceptable salt of any of the foregoing, wherein R$^1$ is

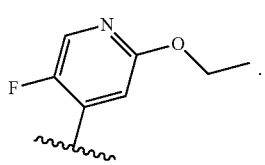 [SMILES: *c1cc(OCC)ncc1F]

In Embodiment 11 of this disclosure are compounds of Formula I, or any one of Embodiments 1-4, or a pharmaceutically acceptable salt of any of the foregoing, wherein R$^1$ is

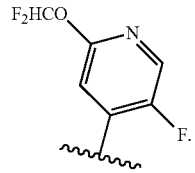

In Embodiment 12 of this disclosure are compounds of Formula I, or any one of Embodiments 1-4, or a pharmaceutically acceptable salt of any of the foregoing, wherein R$^1$ is

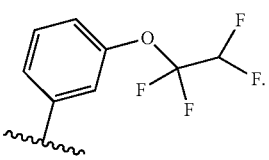 [SMILES: *c1cccc(OC(F)(F)C(F)F)c1]

In Embodiment 13 of this disclosure are compounds of Formula I, or any one of Embodiments 1-4, or a pharmaceutically acceptable salt of any of the foregoing, wherein R$^1$ is

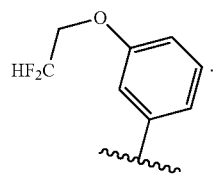

In Embodiment 14 of this disclosure are compounds of Formula I, or any one of Embodiments 1-4, or a pharmaceutically acceptable salt of any of the foregoing, wherein R$^1$ is

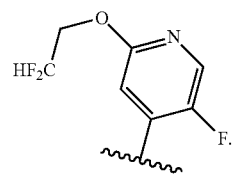

In Embodiment 15a of this disclosure are compounds of Formula I, or Embodiments 1-14, or a class thereof, or a pharmaceutically acceptable salt of any of the foregoing, wherein R$^2$ is
(1) 4 to 6 membered heteroaryl containing zero to one oxygen atoms and/or zero to two nitrogen atoms optionally mono-substituted or disubstituted with halogen, C$_1$-3haloalkyl, C$_{1-3}$alkyl, or OH,
(2) C$_{1-6}$alkyl unsubstituted or optionally mono-substituted, disubstituted or trisubstituted with halogen, OH, CF$_3$, or (C$_{3-6}$)cycloalkyl, phenyl, C(O)NH$_2$,
(3) C$_{3-6}$cycloalkyl optionally mono-substituted, disubstituted or trisubstituted with C$_{1-6}$ alkyl, halogen, OH, or CF$_3$,
(4) 4 to 6 membered heterocycle containing zero to one oxygen atoms and/or zero to two nitrogen atoms optionally mono-substituted or disubstituted with halogen, C$_1$-3haloalkyl, C$_{1-3}$alkyl, or OH,
(5) phenyl optionally substituted with C$_{1-6}$alkyl or halogen, or
(6) S(O)$_2$C$_{1-6}$alkyl, or S(O)$_2$-phenyl.

In Embodiment 15b of this disclosure are compounds of Formula I, or Embodiments 1-14, or a class thereof, or a pharmaceutically acceptable salt of any of the foregoing, wherein R$^2$ is
(1) 4 to 6 membered heteroaryl containing zero to one oxygen atoms and/or zero to two nitrogen atoms optionally mono-substituted or disubstituted with halogen, C$_1$-3haloalkyl, C$_{1-3}$alkyl, or OH,
(2) C$_{1-6}$alkyl unsubstituted or optionally mono-substituted, disubstituted or trisubstituted with halogen, OH, CF$_3$, or (C$_{3-6}$)cycloalkyl, (3) $C_{3-6}$cycloalkyl optionally mono-substituted, disubstituted or trisubstituted with $C_{1-6}$alkyl, halogen, OH, or $CF_3$,
(4) 4 to 6 membered heterocycle containing zero to one oxygen atoms and/or zero to two nitrogen atoms optionally mono-substituted or disubstituted with halogen, $C_1$-3haloalkyl, $C_{1-3}$alkyl, or OH,
(5) phenyl optionally substituted with $C_{1-6}$alkyl or halogen, or
(6) $S(O)_2C_{1-6}$alkyl.

In Embodiment 16a of this disclosure are compounds of Formula I, or Embodiments 1-15 or a class thereof, or a pharmaceutically acceptable salt of any of the foregoing, wherein $R^2$ is
(1) 5 or 6-membered heteroaryl containing 2 N atoms optionally substituted with $C_1$. 3alkyl or halogen,
(2) phenyl substituted with halogen,
(3) $C_{1-6}$alkyl, or $C_{3-6}$cycloalkyl wherein each alkyl or cycloalkyl is optionally mono-substituted, disubstituted or trisubstituted with $C_{1-6}$alkyl, halogen, C(O)NH$_2$, OH, CF$_3$, or CN,
(4) 5 membered saturated heterocycle containing one oxygen atom, optionally substituted with OH,
(5) 6 membered saturated heterocycle containing zero or one oxygen atom and zero or one nitrogen atoms optionally mono-substituted or disubstituted with halogen, $C_1$-3haloalkyl, or $C_{1-3}$alkyl, or
(6) $S(O)_2C_{1-6}$alkyl or $S(O)_2$-phenyl.

In Embodiment 16b of this disclosure are compounds of Formula I, or Embodiments 1-15 or a class thereof, or a pharmaceutically acceptable salt of any of the foregoing, wherein $R^2$ is
(1) 5 or 6-membered heteroaryl containing 2 N atoms optionally substituted with $C_1$-3alkyl or halogen,
(2) phenyl substituted with halogen,
(3) $C_{1-6}$alkyl, or $C_{3-6}$cycloalkyl wherein each alkyl or cycloalkyl is optionally mono-substituted, disubstituted or trisubstituted with $C_{1-6}$alkyl, halogen, OH, CF$_3$, or CN,
(4) 5 membered saturated heterocycle containing one oxygen atom, optionally substituted with OH,
(5) 6 membered saturated heterocycle containing zero or one oxygen atom and zero or one nitrogen atoms optionally mono-substituted or disubstituted with halogen, $C_1$-3haloalkyl, or $C_{1-3}$alkyl, or
(6) $S(O)_2C_{1-6}$alkyl.

In Embodiment 17 of this disclosure are compounds of Formula I, or Embodiments 1-16 or a class thereof, or a pharmaceutically acceptable salt of any of the foregoing, wherein $R^2$ is
(1) phenyl substituted with halogen,
(2) $C_{1-6}$alkyl, or $C_{3-6}$cycloalkyl wherein each alkyl or cycloalkyl is optionally mono-substituted, disubstituted or trisubstituted with $C_{1-6}$alkyl, halogen, OH, CF$_3$, or
(3) 6 membered saturated heterocycle containing zero or one oxygen atom and zero or one nitrogen atoms optionally mono-substituted or disubstituted with halogen, $C_1$-3haloalkyl, or $C_{1-3}$alkyl.

In Embodiment 18a of this disclosure are compounds of Formula I, or Embodiments 1-16, or a class thereof, or a pharmaceutically acceptable salt of any of the foregoing, wherein $R^2$ is $C_{1-6}$alkyl, $C_{3-6}$cycloalkyl, $C_{1-6}$alkylOH, $C_{1-6}$haloalkyl, phenyl, $C_{3-6}$heterocycle, $C_3$.6alkylC(O)NH$_2$, $S(O)_2$-phenyl, $C_{1-6}$alkyl-phenyl, wherein the alkyl is optionally substituted with 1-3 halogens or CF$_3$, and wherein the phenyl is optionally substituted with halogen.

In Embodiment 18b of this disclosure are compounds of Formula I, or Embodiments 1-16, or a class thereof, or a pharmaceutically acceptable salt of any of the foregoing, wherein $R^2$ is $C_{1-6}$alkyl, $C_{3-6}$cycloalkyl, $C_{1-6}$alkylOH, $C_{1-6}$haloalkyl, phenyl, $C_{3-6}$heterocycle, wherein the alkyl is optionally substituted with 1-3 halogens or CF$_3$, and wherein the phenyl is optionally substituted with halogen.

In Embodiment 19 of this disclosure are compounds of Formula I, or Embodiments 1-16, or a class thereof, or a pharmaceutically acceptable salt of any of the foregoing, wherein $R^2$ is phenyl substituted with halogen.

In Embodiment 20 of this disclosure are compounds of Formula I, or Embodiments 1-16, or a class thereof, or a pharmaceutically acceptable salt of any of the foregoing, wherein $R^2$ is $C_1$. 6alkyl.

In Embodiment 21 of this disclosure are compounds of Formula I, or Embodiments 1-16, or a class thereof, or a pharmaceutically acceptable salt of any of the foregoing, wherein $R^2$ is $C_1$. 6alkyl optionally substituted with 1-3 halogen or OH.

In Embodiment 22 of this disclosure are compounds of Formula I, or Embodiments 1-16, or a class thereof, or a pharmaceutically acceptable salt of any of the foregoing, wherein $R^2$ is $C_1$. 6haloalkyl.

In Embodiment 23 of this disclosure are compounds of Formula I, or Embodiments 1-16, or a class thereof, or a pharmaceutically acceptable salt of any of the foregoing, wherein $R^2$ is $C_1$. 6alkyl-OH.

In Embodiment 24 of this disclosure are compounds of Formula I, or Embodiments 1-16, or a class thereof, or a pharmaceutically acceptable salt of any of the foregoing, wherein $R^2$ is $C_3$. 6cycloalkyl.

In Embodiment 25 of this disclosure are compounds of Formula I, or Embodiments 1-16, or a class thereof, or a pharmaceutically acceptable salt of any of the foregoing, wherein $R^2$ is

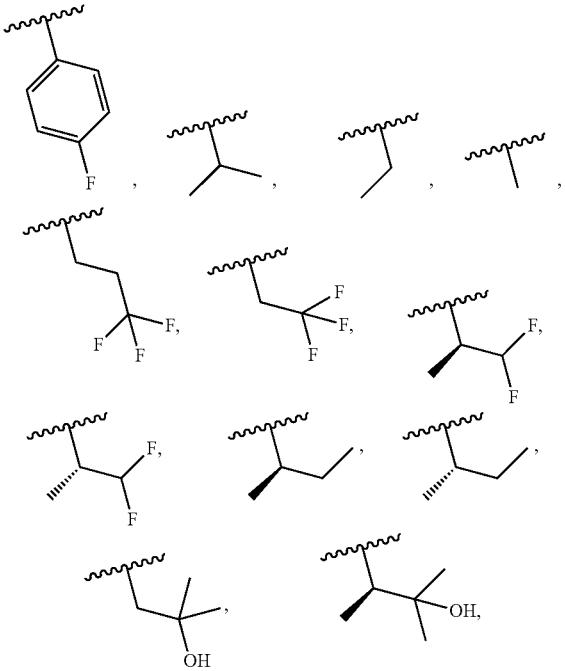

15

-continued

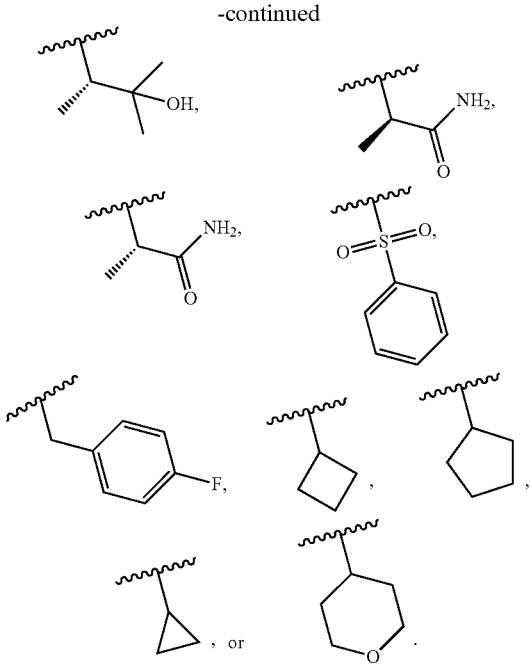

In Embodiment 26 of this disclosure are compounds of Formula I, or Embodiments 1-16, or a class thereof, or a pharmaceutically acceptable salt of any of the foregoing, wherein $R^2$ is

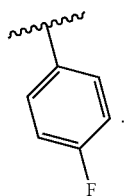 [SMILES: *c1ccc(F)cc1]

In Embodiment 27 of this disclosure are compounds of Formula I, or Embodiments 1-16, or a class thereof, or a pharmaceutically acceptable salt of any of the foregoing, wherein $R^2$ is

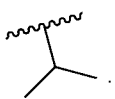

In Embodiment 28 of this disclosure are compounds of Formula I, or any one of Embodiments 1-16, or a pharmaceutically acceptable salt of any of the foregoing, wherein $R^2$ is

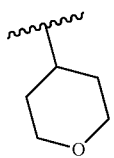

16

In Embodiment 29 of this disclosure are compounds of Formula I, or any one of Embodiments 1-25, or a pharmaceutically acceptable salt of any of the foregoing, wherein $R^3$ is
(1) 4- to 7-membered heterocyclyl containing 1, 2 or 3 heteroatoms independently selected from N, O and S,
(2) 5- or 6-membered heteroaryl containing 1, 2 or 3 heteroatoms independently selected from N, O, and S,
(3) —$(C_{1-6})$alkyl-heteroaryl, wherein the heteroaryl is a 5- or 6-membered heteroaryl containing 1, 2 or 3 heteroatoms independently selected from N, O and S, (4) —$(C_{1-6})$alkyl-aryl,
(5) —$(C_{1-6})$alkyl-heterocyclyl, wherein the heterocyclyl is a 3- to 6-membered ring containing 1 or 2 heteroatoms independently selected from N, O and S,
(6) —$(C_{1-6})$alkyl,
(7) —$(C_{3-6})$cycloalkyl, or
(8) $(C_{1-6})$hydroxyalkyl,
wherein each aryl, heteroaryl, cycloalkyl, or heterocyclyl is unsubstituted or substituted with 1, 2, or 3 $R^9$, and wherein each alkyl is unsubstituted or substituted with 1, 2, or 3 $R^{10}$.

In Embodiment 30 of this disclosure are compounds of Formula I, or any one of Embodiments 1-26, or a pharmaceutically acceptable salt of any of the foregoing, wherein $R^3$ is
(1) 4- to 6-membered heterocyclyl containing 1, 2 or 3 heteroatoms independently selected from N, O and S,
(2) —$(C_{3-6})$cycloalkyl,
(3) $(C_{1-6})$hydroxyalkyl, or
wherein each aryl, heteroaryl, cycloalkyl, or heterocyclyl is unsubstituted or substituted with 1, 2, or 3 $R^9$, and wherein each alkyl is unsubstituted or substituted with 1, 2, or 3 $R^{10}$.

In Embodiment 31 of this disclosure are compounds of Formula I, or any one of Embodiments 1-27, or a pharmaceutically acceptable salt of any of the foregoing, wherein $R^3$ is
(1) 4 to 6 membered cycloalkyl optionally monosubstituted, disubstituted, or trisubstituted with halogen, OH, $C_{1-6}$alkyl, or $C_{0-6}$alkyl(OH),
(2) 4 to 6 membered heterocyclyl containing 1 sulfur atom or 1 oxygen atom optionally mono-substituted, disubstituted, or trisubstituted with halogen, $C_{1-3}$alkyl, $C_1$-3alkyl(OH), or oxo, or
(3) $C_{1-6}$alkyl wherein the alkyl is optionally monosubstituted, disubstituted, or trisubstituted with halogen or OH.

In Embodiment 32 of this disclosure are compounds of Formula I, or any one of Embodiments 1-28 or a pharmaceutically acceptable salt of any of the foregoing, wherein $R^3$ is
(1) 4 to 6 membered cycloalkyl optionally monosubstituted, disubstituted, or trisubstituted with F, or OH,
(2) 4 to 6 membered heterocyclyl containing 1 sulfur atom optionally mono-substituted, disubstituted, or trisubstituted with oxo, $CHF_2$, or $CH_3$,
(3) 5 or 6 membered heterocyclyl containing 1 oxygen atom optionally mono-substituted, disubstituted, or trisubstituted with $CH_3$, or OH, (4) C$_{1-6}$alkyl-heterocyclyl, wherein the heterocyclyl is a 5 membered-heterocyclyl containing 1 oxygen atom optionally mono-substituted, disubstituted, or trisubstituted with OH,
(5) C$_{1-6}$alkyl-heteroaryl, wherein the heteroaryl contains 2 nitrogen atoms optionally mono-substituted, disubstituted, or trisubstituted with CH$_2$CH$_3$,
(6) 5 membered heteroaryl containing 2 nitrogen atoms and 1 sulfur atoms optionally mono-substituted, disubstituted, or trisubstituted with CH$_3$, or
(7) C$_{1-6}$alkyl, wherein the alkyl is optionally mono-substituted, disubstituted, or trisubstituted with halogen, or OH.

In Embodiment 33 of this disclosure are compounds of Formula I, or any one of Embodiments 1-28 or a pharmaceutically acceptable salt of any of the foregoing, wherein R$^3$ is
(1) 4 to 6 membered cycloalkyl optionally substituted with F, or OH,
(2) 4 to 6 membered heterocyclyl containing 1 sulfur atom optionally mono-substituted, disubstituted, or trisubstituted with oxo, or CH$_3$,
(3) 5 or 6 membered heterocyclyl containing 1 oxygen atom optionally mono-substituted, disubstituted, or trisubstituted with CH$_3$, or OH, or
(4) C$_{1-6}$alkyl, wherein the alkyl is optionally mono-substituted, disubstituted, or trisubstituted with halogen, or OH.

In Embodiment 34a of this disclosure are compounds of Formula I, or any one of Embodiments 1-29 or a pharmaceutically acceptable salt of any of the foregoing, wherein R$^3$ is
(1) 4 to 6 membered cycloalkyl optionally mono-substituted, disubstituted, or trisubstituted with F, or OH,
(2) 4 to 6 membered heterocyclyl containing 1 sulfur atom optionally mono-substituted, disubstituted, or trisubstituted with oxo, CHF$_2$, or CH$_3$,
(3) 5 or 6 membered heterocyclyl containing 1 oxygen atom optionally mono-substituted, disubstituted, or trisubstituted with CH$_3$, or OH,
(4) C$_{1-6}$alkyl-heterocyclyl containing 1 oxygen atom optionally mono-substituted, disubstituted, or trisubstituted with OH,
(5) C$_{0-6}$alkyl-heteroaryl, wherein the heteroaryl contains 2 nitrogen atoms, and 0-1 sulfur atoms optionally mono-substituted, disubstituted, or trisubstituted with CH$_3$, CH$_2$CH$_3$, or
(6) C$_{1-6}$alkyl, wherein the alkyl is optionally mono-substituted, disubstituted, or trisubstituted with halogen, or OH.

In Embodiment 34b of this disclosure are compounds of Formula I, or any one of Embodiments 1-29 or a pharmaceutically acceptable salt of any of the foregoing, wherein R$^3$ is
(1) 4 to 6 membered cycloalkyl optionally mono-substituted, disubstituted, or trisubstituted with F, or OH,
(2) 4 to 6 membered heterocyclyl containing 1 sulfur atom optionally mono-substituted, disubstituted, or trisubstituted with oxo, or CH$_3$,
(3) 5 or 6 membered heterocyclyl containing 1 oxygen atom optionally mono-substituted, disubstituted, or trisubstituted with CH$_3$, or OH, or
(4) C$_{1-6}$alkyl, wherein the alkyl is optionally mono-substituted, disubstituted, or trisubstituted with halogen, or OH.

In Embodiment 35a of this disclosure are compounds of Formula I, or any one of Embodiments 1-29, or a pharmaceutically acceptable salt of any of the foregoing, wherein R$^3$ is

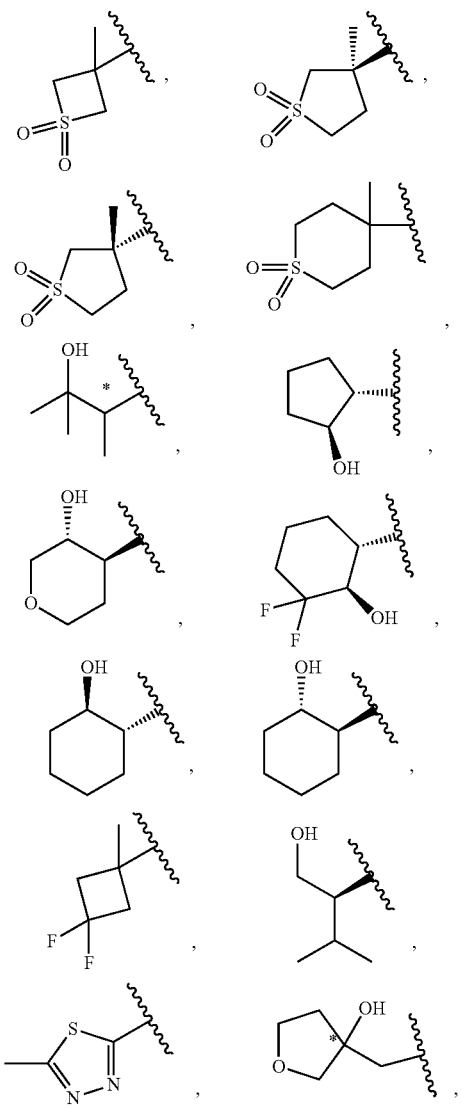

In Embodiment 35b of this disclosure are compounds of Formula I, or any one of Embodiments 1-29, or a pharmaceutically acceptable salt of any of the foregoing, wherein R$^3$ is

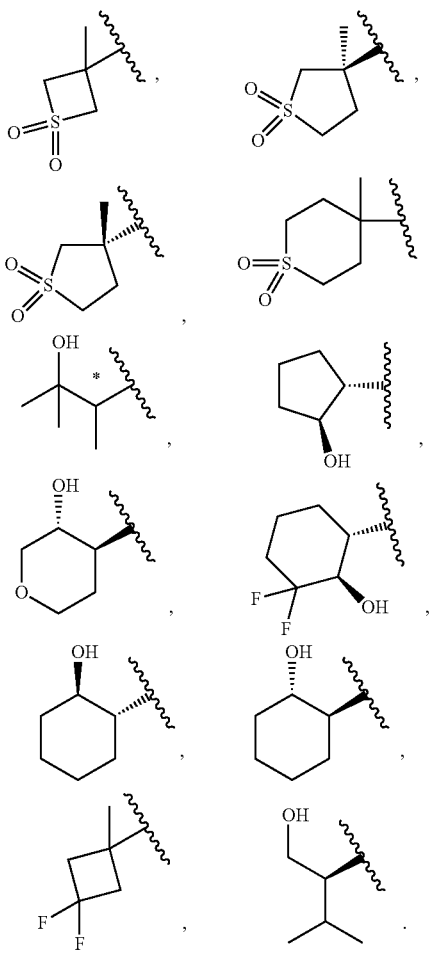

In Embodiment 36 of this disclosure are compounds of Formula I, or any one of Embodiments 1-29, or a pharmaceutically acceptable salt of any of the foregoing, wherein R³ is

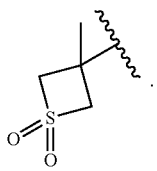

In Embodiment 37 of this disclosure are compounds of Formula I, or any one of Embodiments 1-29, or a pharmaceutically acceptable salt of any of the foregoing, wherein R³ is

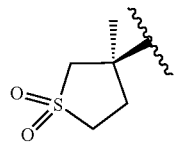

In Embodiment 38 of this disclosure are compounds of Formula I, or any one of Embodiments 1-29, or a pharmaceutically acceptable salt of any of the foregoing, wherein R³ is

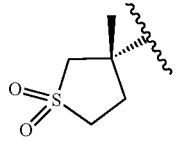

In Embodiment 39 of this disclosure are compounds of Formula I, or any one of Embodiments 1-29, or a pharmaceutically acceptable salt of any of the foregoing, wherein R³ is

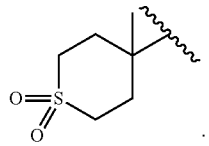 [SMILES: *C1(C)CCS(=O)(=O)CC1]

In Embodiment 40 of this disclosure are compounds of Formula I, or Embodiments 1-37, or a class thereof, or a pharmaceutically acceptable salt of any of the foregoing, wherein $R^4$ is H.

In Embodiment 41 of this disclosure are compounds of Formula I, or Embodiments 1-38, or a class thereof, or a pharmaceutically acceptable salt of any of the foregoing, wherein $R^5$ is H, halogen, or CN.

In Embodiment 42 of this disclosure are compounds of Formula I, or Embodiments 1-38, or a class thereof, or a pharmaceutically acceptable salt of any of the foregoing, wherein $R^5$ is H, F, Cl, or CN.

In Embodiment 43 of this disclosure are compounds of Formula I, or Embodiments 16-42, or a class thereof, or a pharmaceutically acceptable salt of any of the foregoing, wherein $R^6$ is
(1) cyano,
(2) halogen,
(3) —$OC_{1-6}$alkyl,
(4) ($C_{3-6}$)cycloalkyl, optionally substituted with halogen, $C_{1-3}$alkyl, $C_{1-6}$haloalkyl, or OH,
(5) —C(=O)NH₂,
(6) —O($C_{3-6}$)cycloalkyl wherein the cycloalkyl is optionally substituted with halogen, $C_{1-3}$alkyl, or OH,
(7) hydroxy,
(8) N($R^{11}$)₂,
(9) ($C_{1-6}$)haloalkyl-,
(10) —O($C_{1-6}$)haloalkyl-,
(11) —$SO_2(C_{1-6})$alkyl,
(12) —$SO_2NH(C_{1-6})$alkyl,
(13) —$SC_{1-6}$alkyl,
(14) —$SC_{1-6}$haloalkyl, or
(15) ($C_{1-6}$alkyl).

In Embodiment 44a of this disclosure are compounds of Formula I, or Embodiments 15-42, or a class thereof, or a pharmaceutically acceptable salt of any of the foregoing, wherein $R^6$ is halogen, hydroxy, CN, $C_{1-3}$alkyl, $C_{1-3}$haloalkyl, $C_{3-6}$cycloalkyl, $OC_{1-3}$alkyl, $OC_{1-3}$haloalkyl, $OC_3$-6cycloalkyl, $S(O)_2C_{1-3}$alkyl, NHC(O)

In Embodiment 44b of this disclosure are compounds of Formula I, or Embodiments 15-42, or a class thereof, or a pharmaceutically acceptable salt of any of the foregoing, wherein $R^6$ is halogen, hydroxy, CN, $C_{1-3}$alkyl, $C_{1-3}$haloalkyl, $C_{3-6}$cycloalkyl, $OC_{1-3}$alkyl, $OC_{1-3}$haloalkyl, $OC_{3-6}$cycloalkyl, $S(O)_2C_{1-3}$alkyl, and wherein the cycloalkyl is optionally substituted with halogen.

In Embodiment 45 of this disclosure are compounds of Formula I, or Embodiments 15-42, or a class thereof, or a pharmaceutically acceptable salt of any of the foregoing, wherein $R^6$ is $C_{1-3}$alkyl, $C_{3-6}$cycloalkyl, O—$C_{3-6}$cycloalkyl, $OC_{1-3}$alkyl, $OC_{1-3}$haloalkyl, or $S(O)_2C_{1-3}$alkyl, and wherein the cycloalkyl is additionally optionally substituted with 1-3 F.

In Embodiment 46a of this disclosure are compounds of Formula I, or Embodiments 15-42, or a class thereof, or a pharmaceutically acceptable salt of any of the foregoing, wherein $R^6$ is F, CF3, $OCHF_2$, $OCF_3$, $OCH_2CH_3$, $OCH(CH_3)_2$, $OCF_2CHF_2$, $OCH_2CHF_2$, cyclopropyl, or O-cyclopropyl, CN, $N(CH_3)_2$, $C(O)NH_2$, $SCH_3$, $S(O)_2NHCH_3$, $NHC(O)CH_3$, OH, $OCF_2CHF_2$, $S(O)_2CH_3$, and wherein the cyclopropyl is additionally optionally substituted with one to three halogen atoms.

In Embodiment 46b of this disclosure are compounds of Formula I, or Embodiments 15-42, or a class thereof, or a pharmaceutically acceptable salt of any of the foregoing, wherein $R^6$ is F, $OCHF_2$, $OCF_3$, $OCH_2CH_3$, $OCH(CH_3)_2$, $OCF_2CHF_2$, $OCH_2CHF_2$, cyclopropyl, or O-cyclopropyl, and wherein the cyclopropyl is additionally optionally substituted with one to three halogen atoms.

In Embodiment 47 of this disclosure are compounds of Formula I, or Embodiments 1-15 and 29-46, or a class thereof, or a pharmaceutically acceptable salt of any of the foregoing, wherein $R^7$ is halogen, $C_{1-6}$haloalkyl, or OH.

In Embodiment 48 of this disclosure are compounds of Formula I, or Embodiments 1-15 and 29-46, or a class thereof, or a pharmaceutically acceptable salt of any of the foregoing, wherein $R^7$ is F, $CF_3$, or OH.

In Embodiment 49 of this disclosure are compounds of Formula I, or Embodiments 1-45, or a class thereof, or a pharmaceutically acceptable salt of any of the foregoing, wherein $R^{8a}$ is H.

In Embodiment 50 of this disclosure are compounds of Formula I, or Embodiments 1-46, or a class thereof, or a pharmaceutically acceptable salt of any of the foregoing, wherein $R^{8b}$ is H.

In Embodiment 51 of this disclosure are compounds of Formula I, or Embodiments 1-30, 40-50, or a class thereof, or a pharmaceutically acceptable salt of any of the foregoing, wherein $R^9$ is =O, OH, $C_{1-6}$alkyl, $C_{1-6}$haloalky, halogen, or $C_{1-6}$alkylOH.

In Embodiment 52 of this disclosure are compounds of Formula I, or Embodiments 1-30, 40-50, or a class thereof, or a pharmaceutically acceptable salt of any of the foregoing, wherein $R^9$ is $O_2$, =O, OH, $C_{1-6}$alkyl, $C_{1-6}$haloalky, or $C_{1-6}$alkylOH.

In Embodiment 53a of this disclosure are compounds of Formula I, or Embodiments 1-30, 40-50, or a class thereof, or a pharmaceutically acceptable salt of any of the foregoing, wherein $R^9$ is $O_2$, =O, OH, $CH_3$, $CH_2CH_3$, F, $CF_3$, $CHF_2$, or $CH_2OH$.

In Embodiment 53b of this disclosure are compounds of Formula I, or Embodiments 1-30, 40-50, or a class thereof, or a pharmaceutically acceptable salt of any of the foregoing, wherein $R^9$ is =O, OH, $CH_3$, $CH_2CH_3$, F, $CF_3$, or $CH_2OH$.

In Embodiment 54 of this disclosure are compounds of Formula I, or Embodiments 1-30, 40-53, or a class thereof, or a pharmaceutically acceptable salt of any of the foregoing, wherein $R^{10}$ is =O, OH, $C_{1-6}$alkyl, $C_{1-6}$haloalky, or $C_{1-6}$alkylOH.

In Embodiment 55 of this disclosure are compounds of Formula I, or Embodiments 1-30, 40-53, or a class thereof, or a pharmaceutically acceptable salt of any of the foregoing, wherein $R^{10}$ is =O, OH, $CH_3$, $CH_2CH_3$, F, $CF_3$, or $CH_2OH$.

In Embodiment 56 of this disclosure are compounds of Formula I, or any one of Embodiments 1-51, or a pharmaceutically acceptable salt of any of the foregoing, wherein X is N, Y is $C(R^5)$, and Z is $C(R^5)$.

In Embodiment 57 of this disclosure are compounds of Formula I, or any one of Embodiments 1-51, or a pharmaceutically acceptable salt of any of the foregoing, wherein X is $C(R^5)$, Y is N, and Z is $C(R^5)$.

In Embodiment 58 of this disclosure are compounds of Formula I, or any one of Embodiments 1-51, or a pharmaceutically acceptable salt of any of the foregoing, wherein X is $C(R^5)$, Y is $C(R^5)$ and Z is N.

In Embodiment 59 of this disclosure are compounds of Formula I, or any one of Embodiments 1-51, or a pharmaceutically acceptable salt of any of the foregoing, wherein X, Y, and Z are $C(R^5)$.

In Embodiment 60 of this disclosure are compounds of Formula I, or any one of Embodiments 1-51, or a pharmaceutically acceptable salt of any of the foregoing, wherein X is N, Y is N and Z is $C(R^5)$.

In Embodiment 61 of this disclosure are compounds of Formula I, or any one of Embodiments 1-51, or a pharmaceutically acceptable salt of any of the foregoing, wherein X is N, Y is $C(R^5)$ and Z is N.

In Embodiment 62 of this disclosure are compounds of Formula I, or any one of Embodiments 1-51, or a pharmaceutically acceptable salt of any of the foregoing, wherein X is $C(R^5)$, Y is N and Z is N.

In Embodiment 63, the present invention provides a compound as described in any one of Examples 1-129 as set forth below, or a pharmaceutically acceptable salt thereof.

In Embodiment 64, the present invention is a compound, or a pharmaceutically acceptable salt thereof, which is

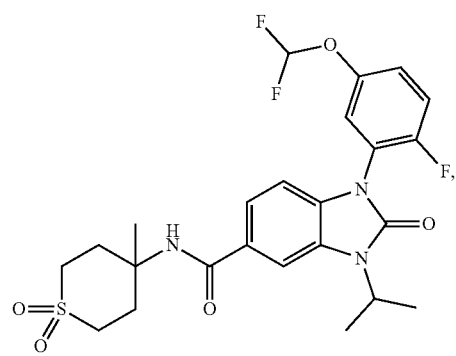 [SMILES: CC(C)n1c(=O)n(-c2cc(OC(F)F)ccc2F)c2ccc(C(=O)NC3(C)CCS(=O)(=O)CC3)cc21]

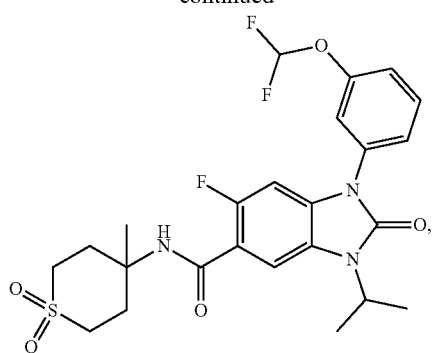
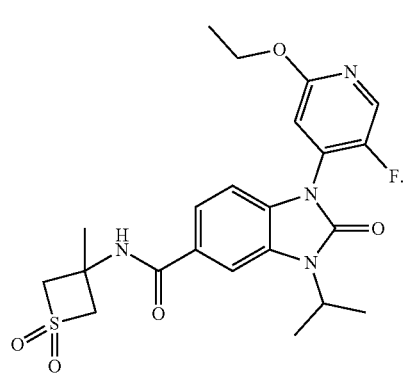
, or
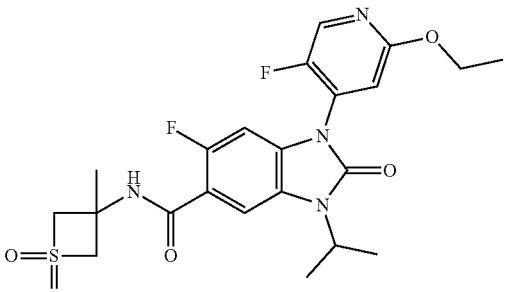
In Embodiment 65, the present invention is a compound, or a pharmaceutically acceptable salt thereof, which is
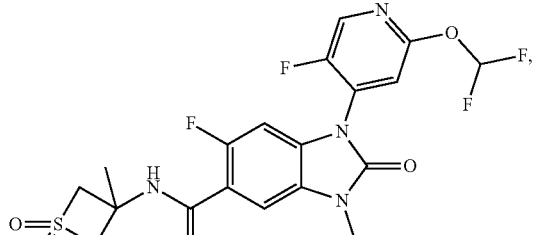
, or
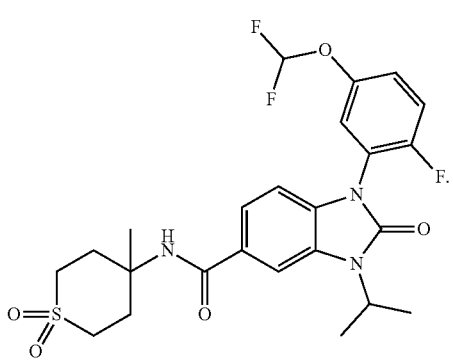
In Embodiment 66, the present invention is a compound, or a pharmaceutically acceptable salt thereof, which is In Embodiment 67, the present invention is a compound, or a pharmaceutically acceptable salt thereof, which is

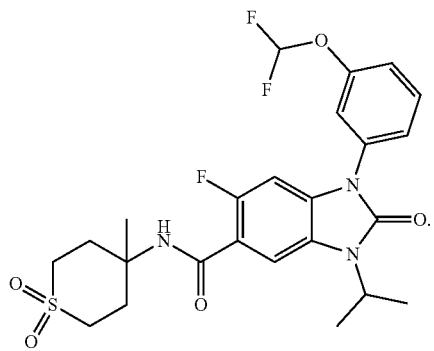 [SMILES: CC(C)n1c(=O)n(-c2cccc(OC(F)F)c2)c2cc(F)c(C(=O)NC3(C)CCS(=O)(=O)CC3)cc21]

In Embodiment 68, the present invention is a compound, or a pharmaceutically acceptable salt thereof, which is

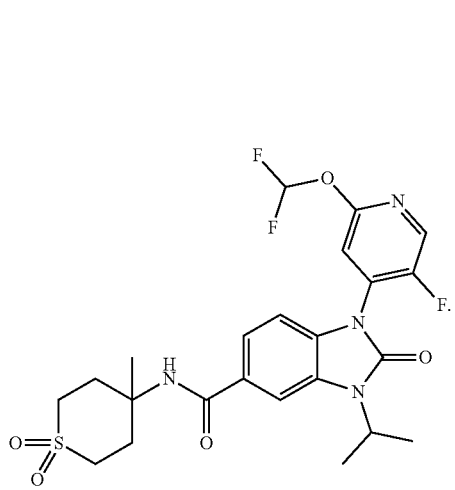 [SMILES: CC(C)n1c(=O)n(-c2cc(OC(F)F)ncc2F)c2ccc(C(=O)NC3(C)CCS(=O)(=O)CC3)cc21]

In Embodiment 69, the present invention is a compound, or a pharmaceutically acceptable salt thereof, which is

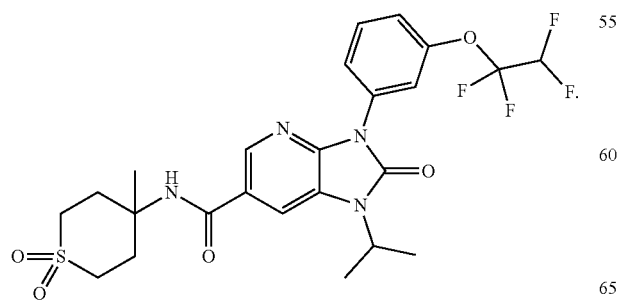

In Embodiment 70, the present invention is a compound, or a pharmaceutically acceptable salt thereof, which is 8

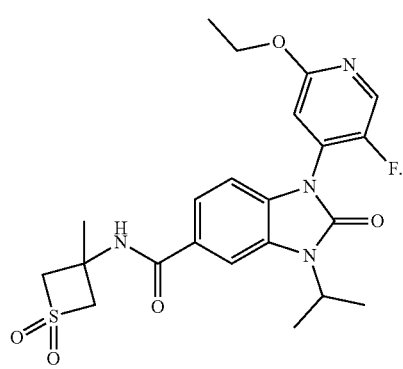 [SMILES: CCOc1cc(-n2c(=O)n(C(C)C)c3cc(C(=O)NC4(C)CS(=O)(=O)C4)ccc32)c(F)cn1]

In Embodiment 71, the present invention is a compound, or a pharmaceutically acceptable salt thereof, which is

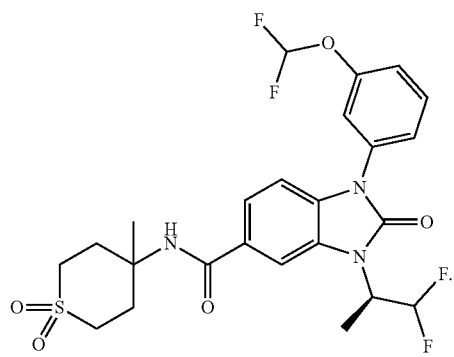 [SMILES: C[C@H](C(F)F)n1c(=O)n(-c2cccc(OC(F)F)c2)c2ccc(C(=O)NC3(C)CCS(=O)(=O)CC3)cc21]

In Embodiment 72, the present invention is a compound, or a pharmaceutically acceptable salt thereof, which is

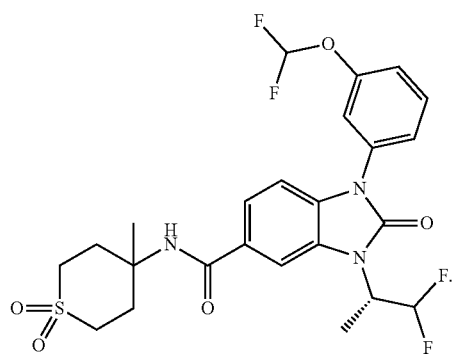 [SMILES: C[C@@H](C(F)F)n1c(=O)n(-c2cccc(OC(F)F)c2)c2ccc(C(=O)NC3(C)CCS(=O)(=O)CC3)cc21]

In Embodiment 73, the present invention is a compound, or a pharmaceutically acceptable salt thereof, which is

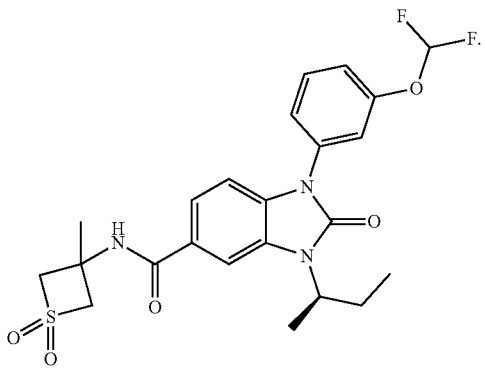 [SMILES: CC[C@@H](C)n1c(=O)n(-c2cccc(OC(F)F)c2)c2ccc(C(=O)NC3(C)CS(=O)(=O)C3)cc21]

In Embodiment 74, the present invention is a compound, or a pharmaceutically acceptable salt thereof, which is

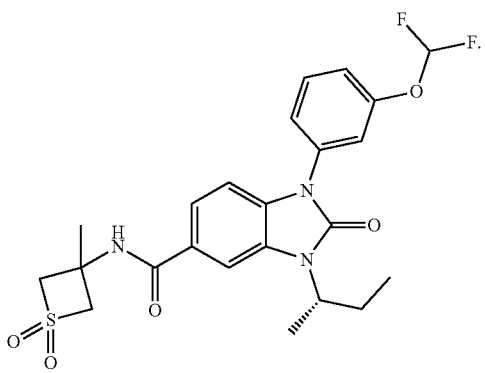 [SMILES: CC[C@H](C)n1c(=O)n(-c2cccc(OC(F)F)c2)c2ccc(C(=O)NC3(C)CS(=O)(=O)C3)cc21]

In Embodiment 75, the present invention is a compound, or a pharmaceutically acceptable salt thereof, which is

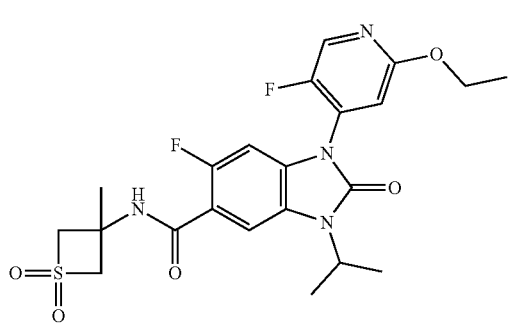

In Embodiment 76, the present invention is a compound, or a pharmaceutically acceptable salt thereof, which is

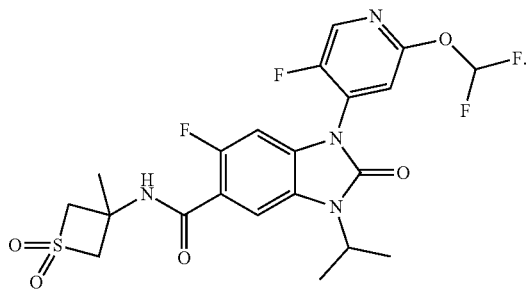 [SMILES: CC(C)n1c(=O)n(-c2cc(OC(F)F)ncc2F)c2cc(F)c(C(=O)NC3(C)CS(=O)(=O)C3)cc21]

In Embodiment 77, the present invention is a compound, or a pharmaceutically acceptable salt thereof, which is

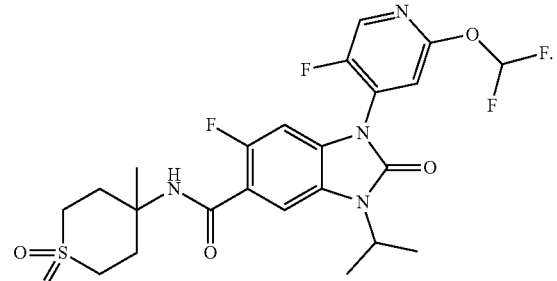

In Embodiment 78, the present invention is a compound, or a pharmaceutically acceptable salt thereof, which is

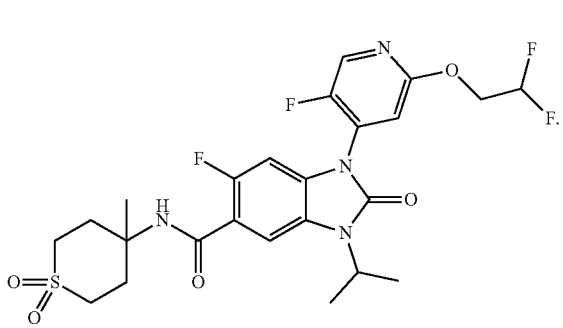 [SMILES: CC(C)n1c(=O)n(-c2cc(OCC(F)F)ncc2F)c2cc(F)c(C(=O)NC3(C)CCS(=O)(=O)CC3)cc21]

In Embodiment 79 of the invention, the compound of formula I, or a pharmaceutically acceptable salt thereof, is:
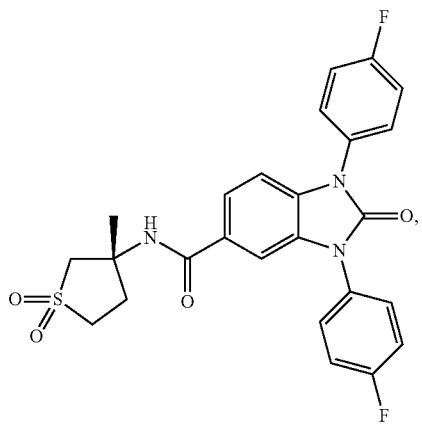
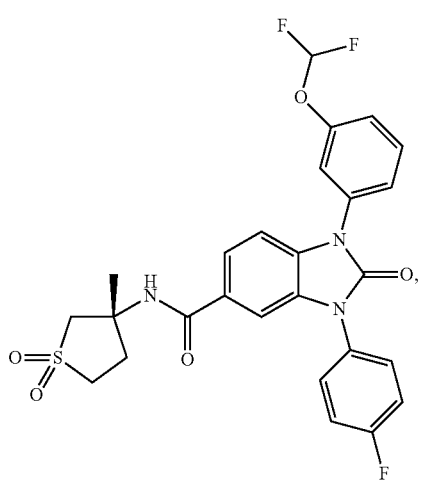
-continued
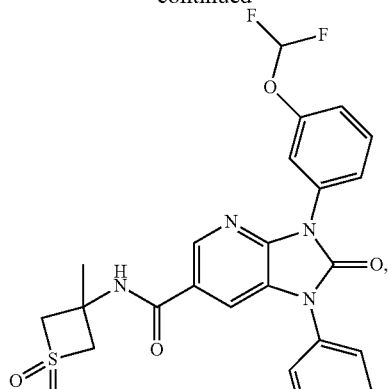
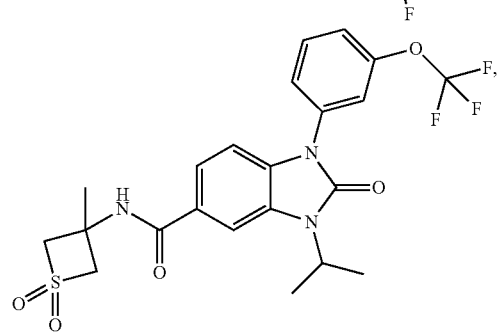
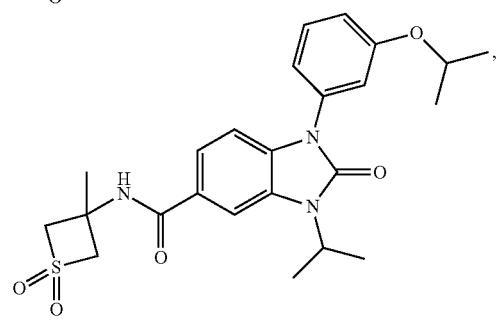
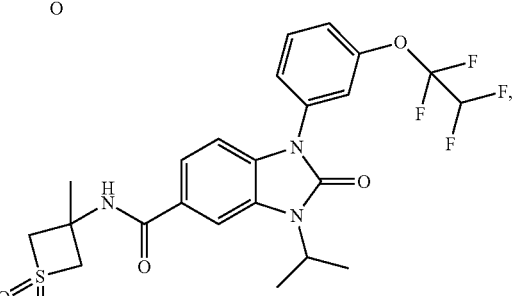
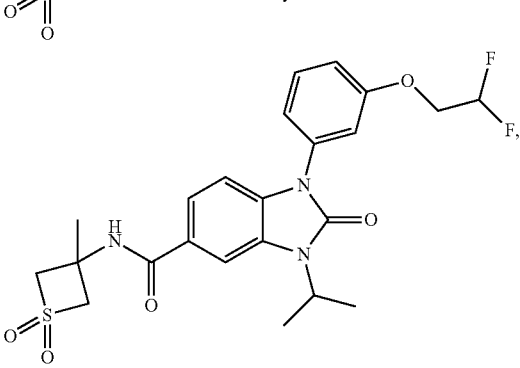

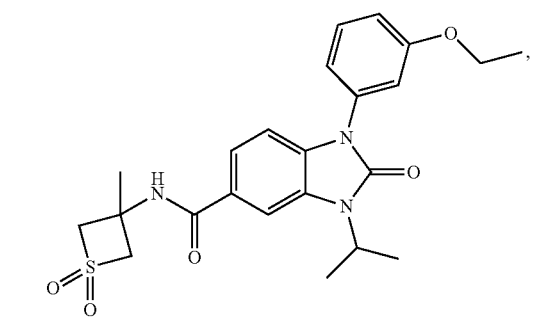
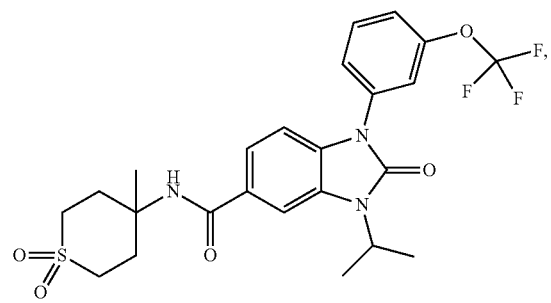
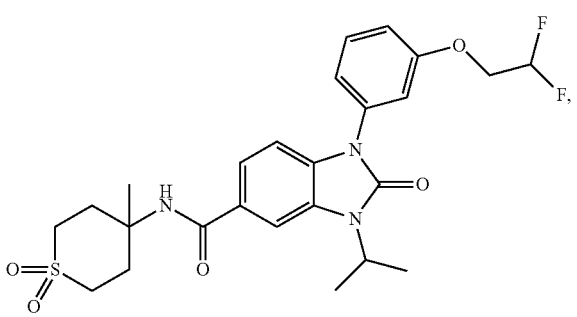
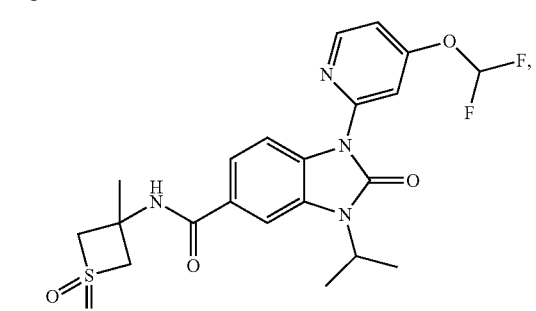
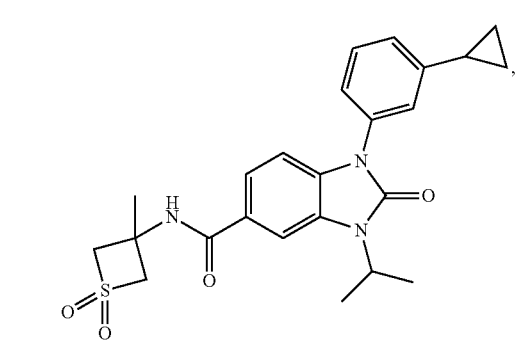
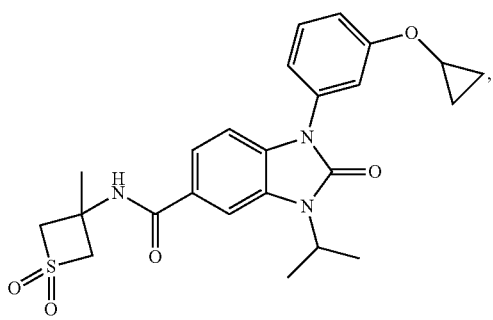
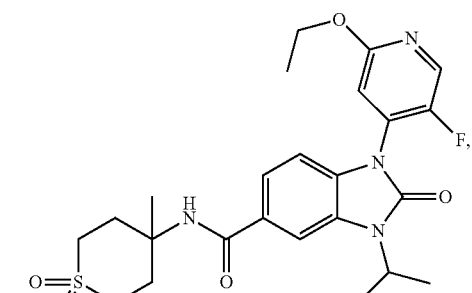
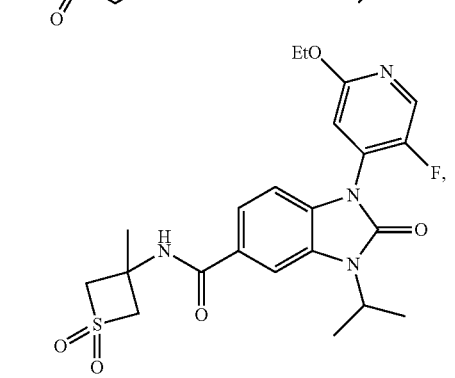
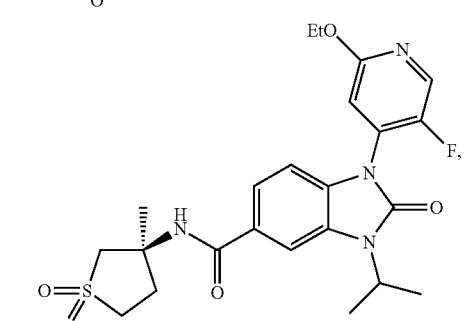
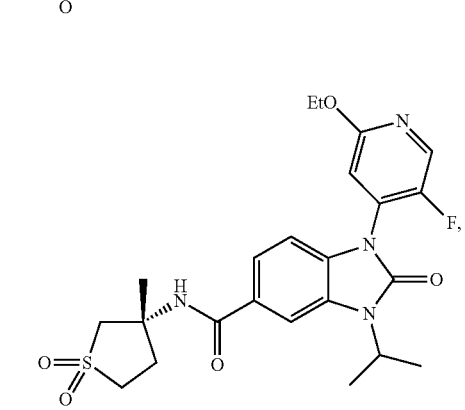

33
-continued
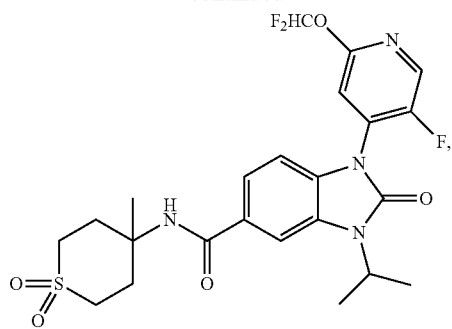
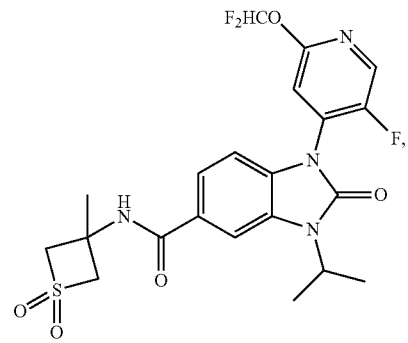
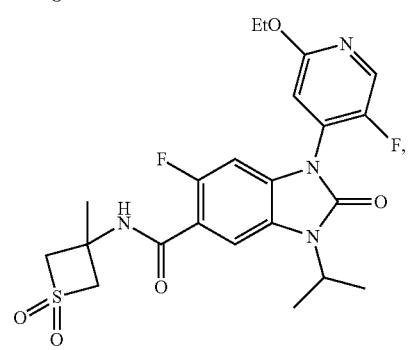
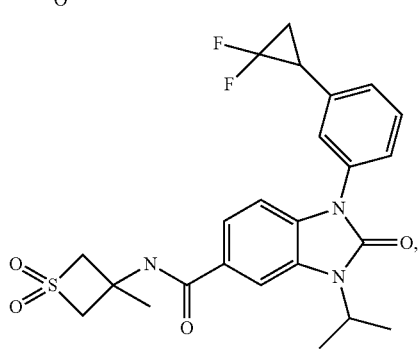
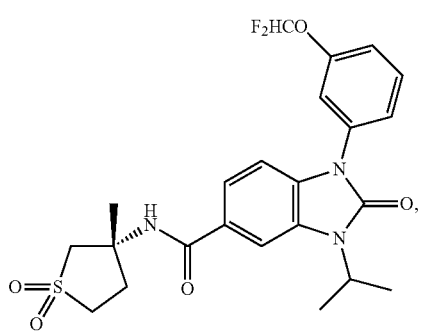
34
-continued
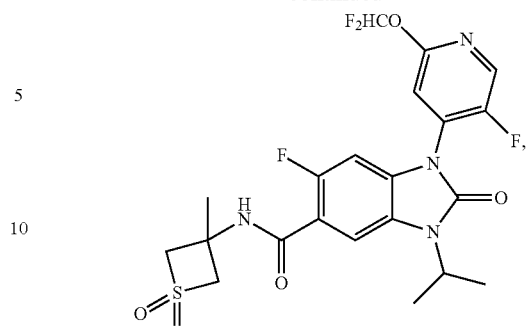
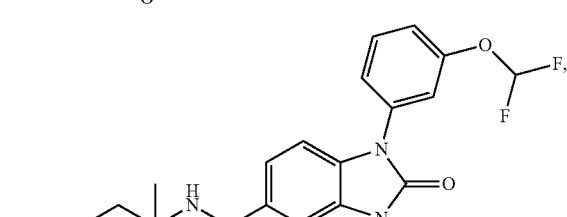

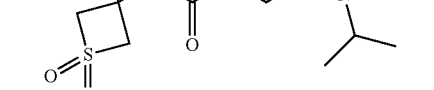

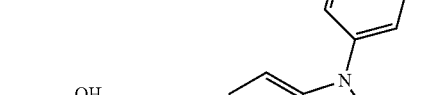
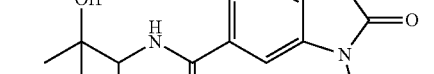

35
-continued
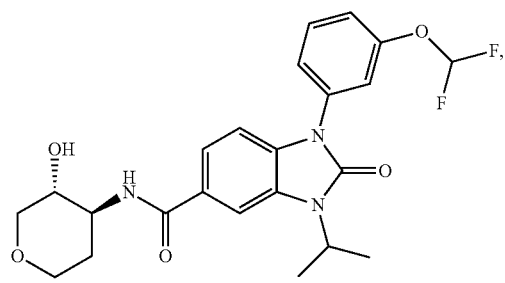
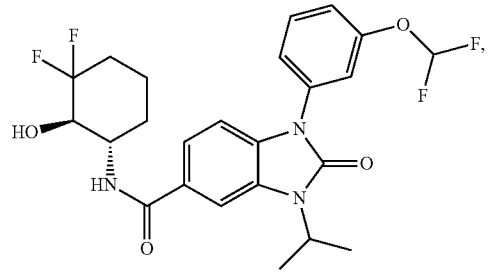
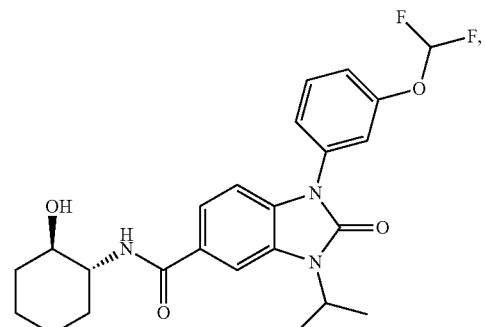
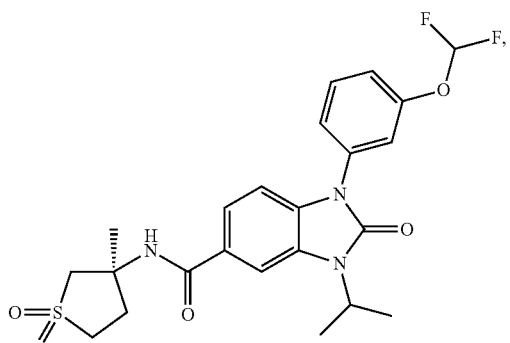
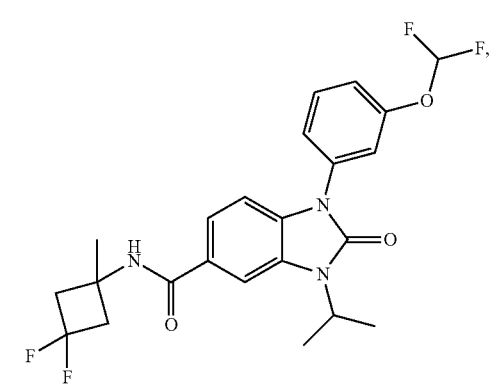
36
-continued
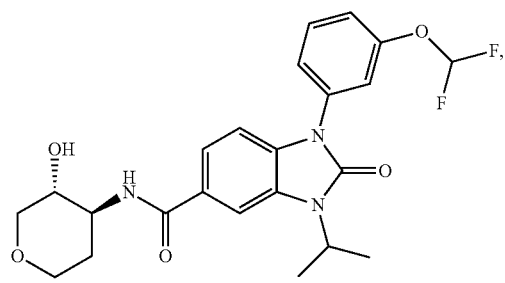
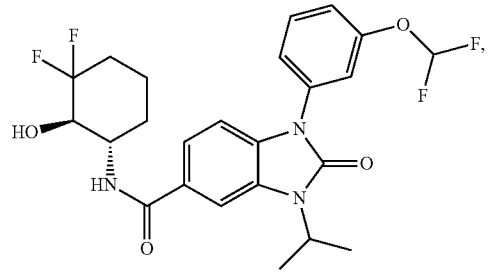
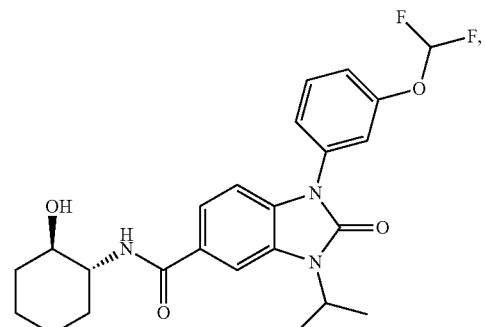
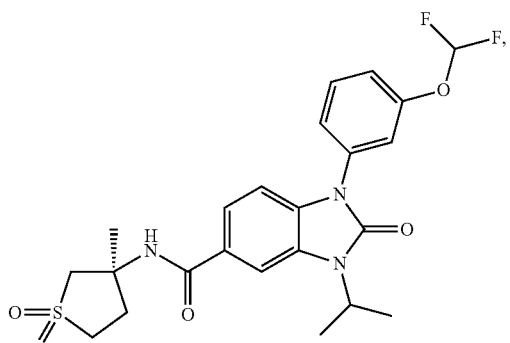
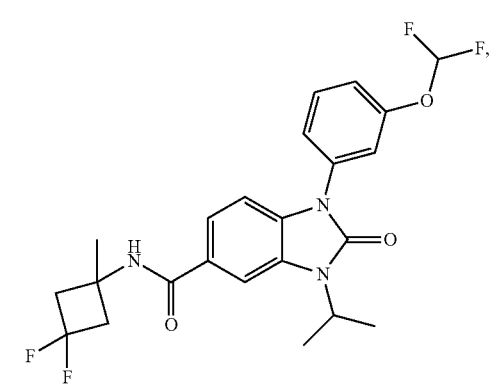

37
-continued
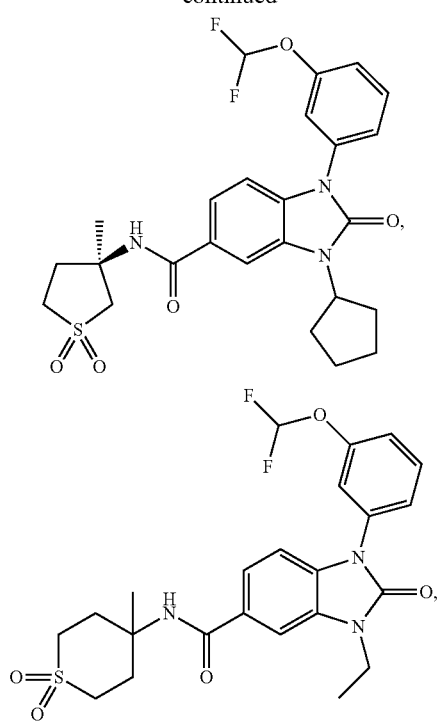
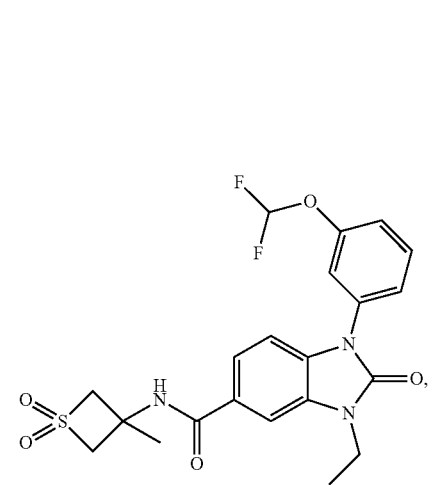
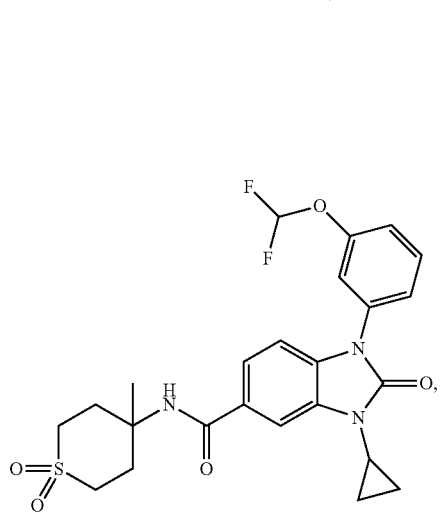
38
-continued
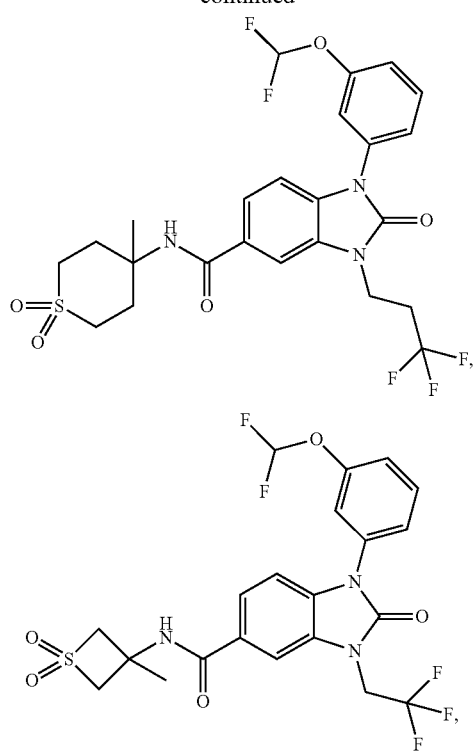
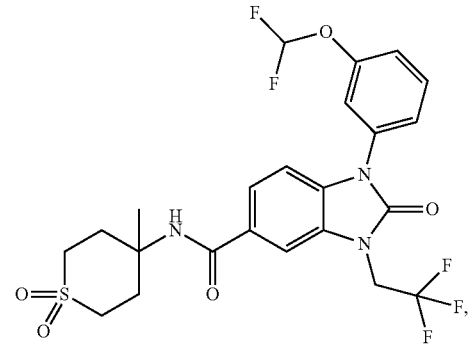
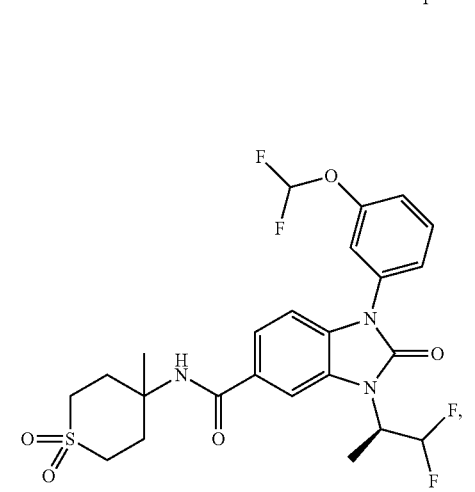

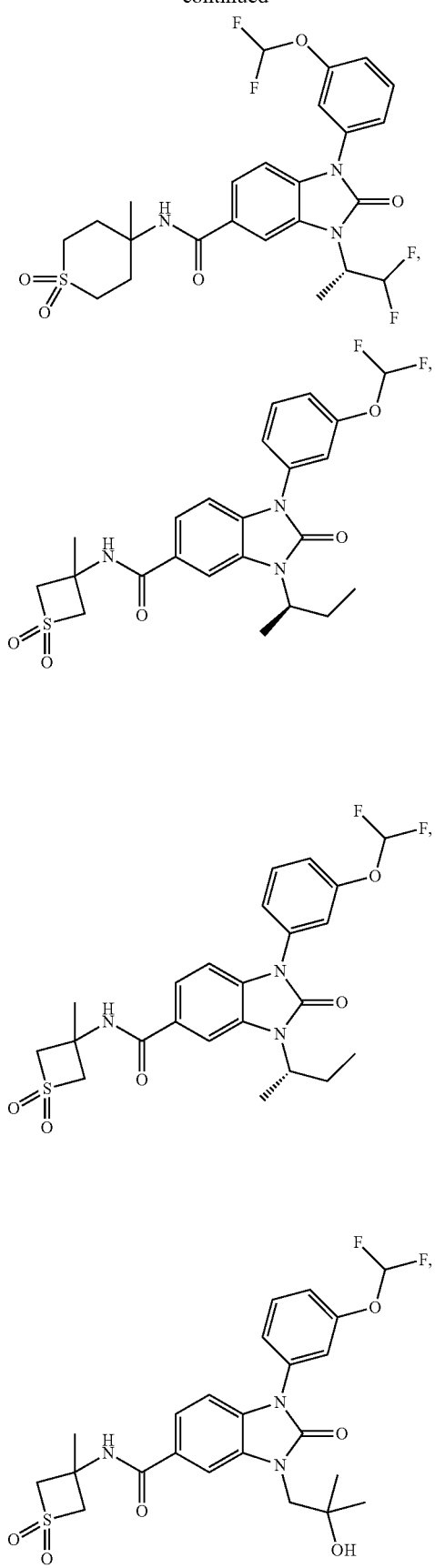
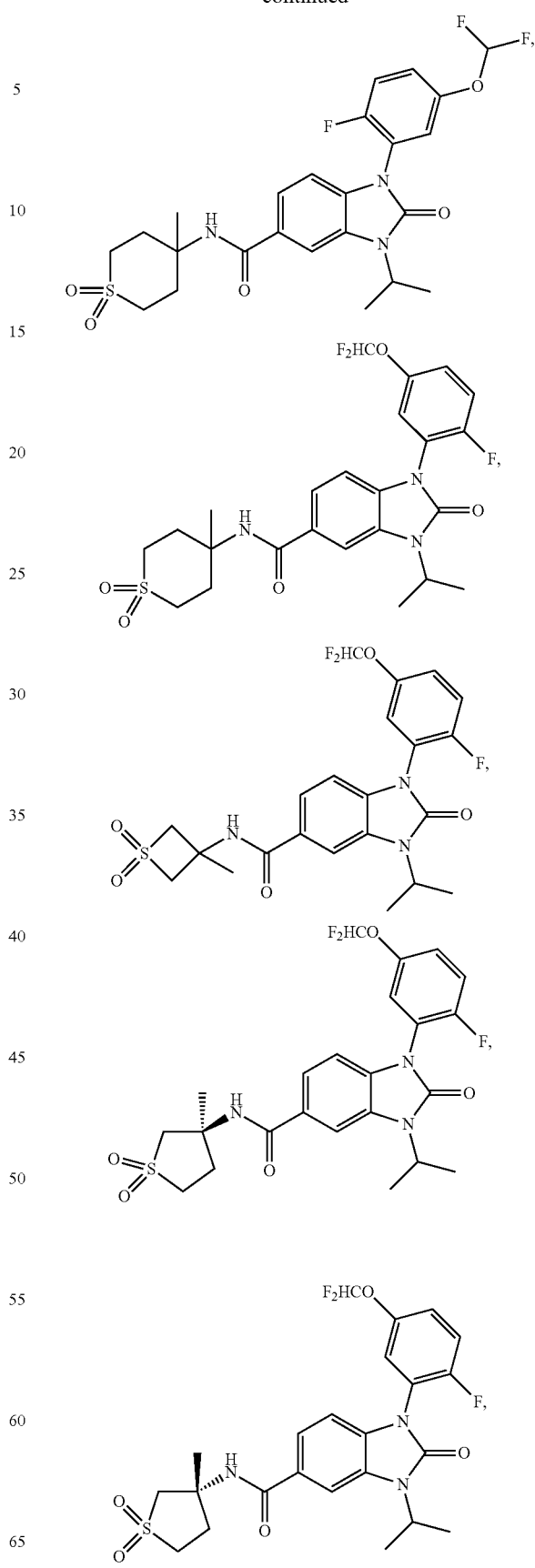

41
-continued
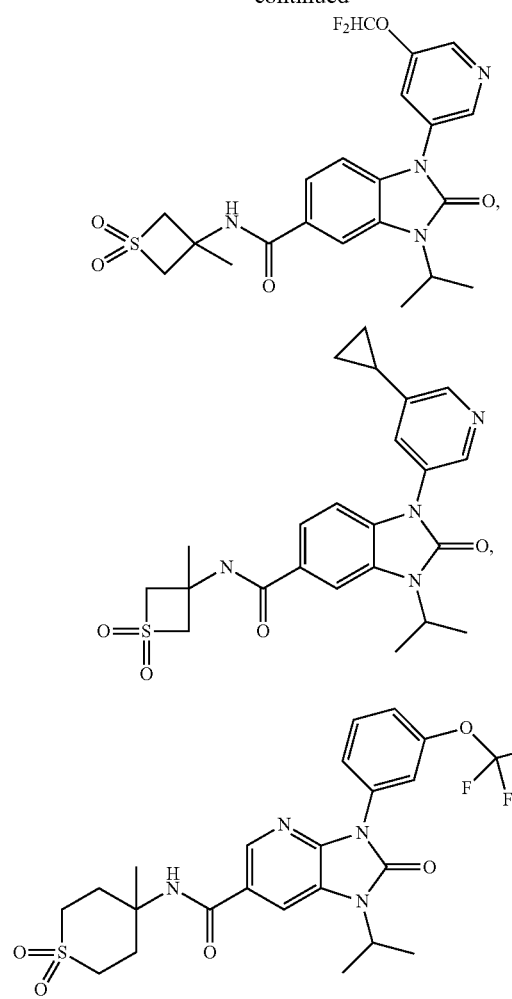
42
-continued
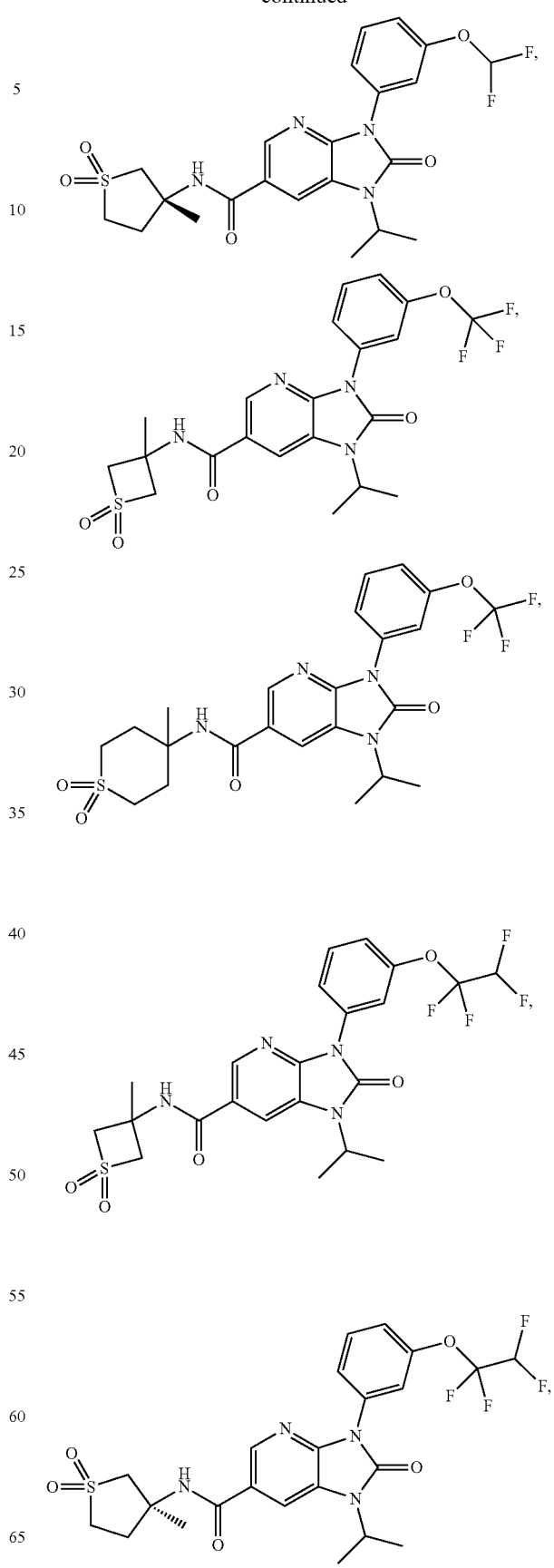

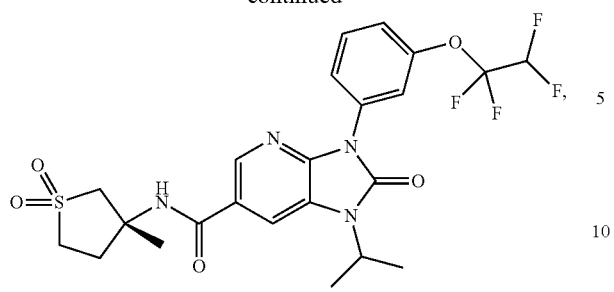
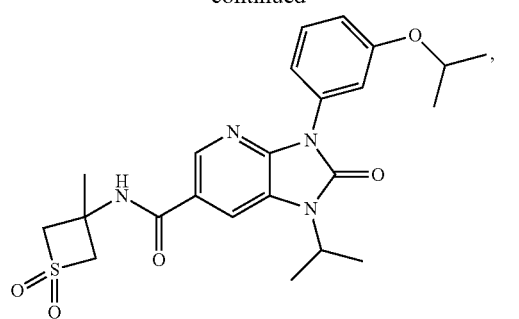

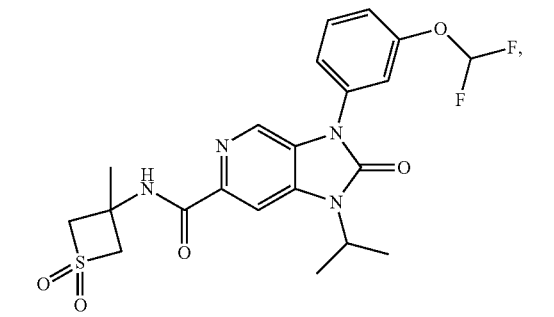
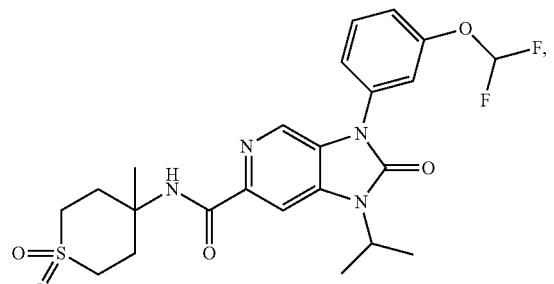
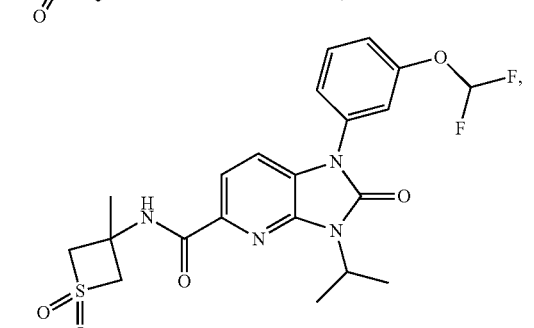
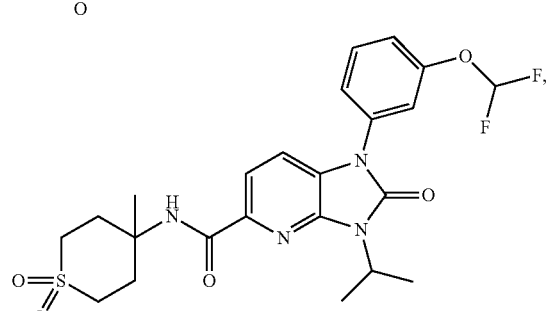
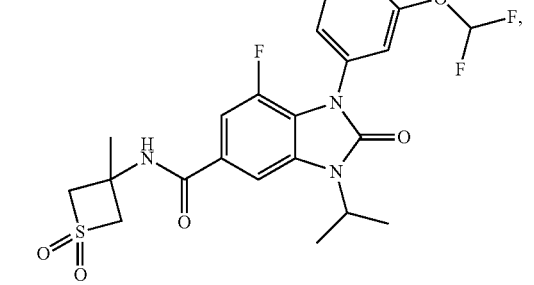
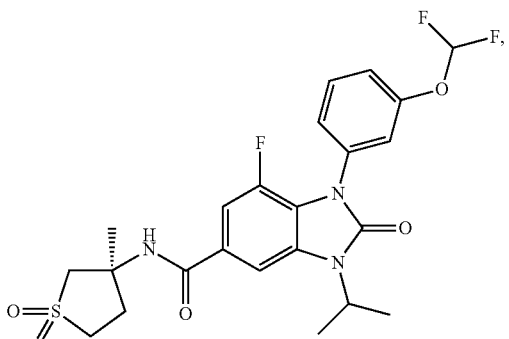
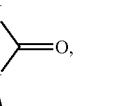
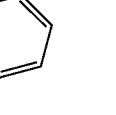

-continued
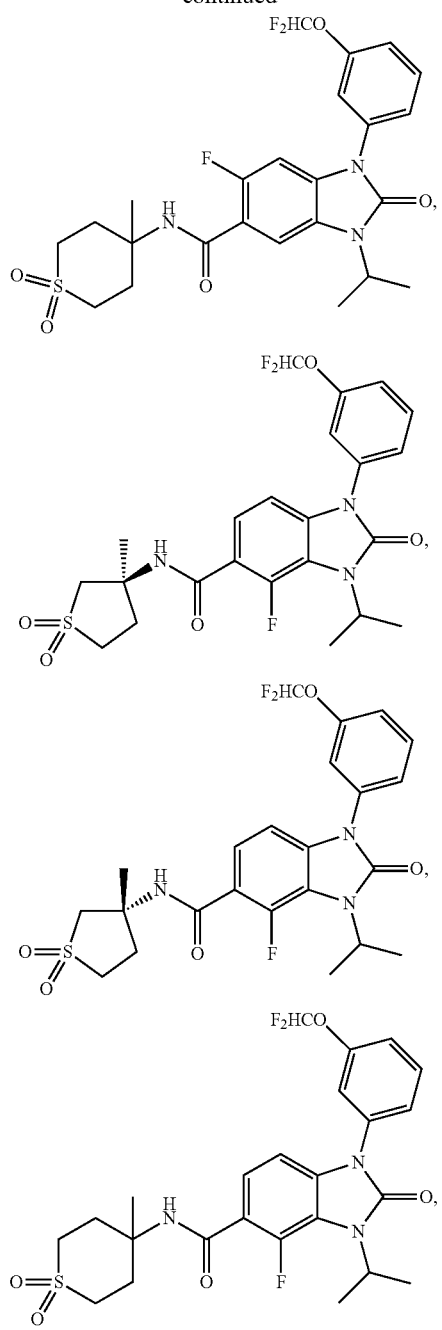
-continued
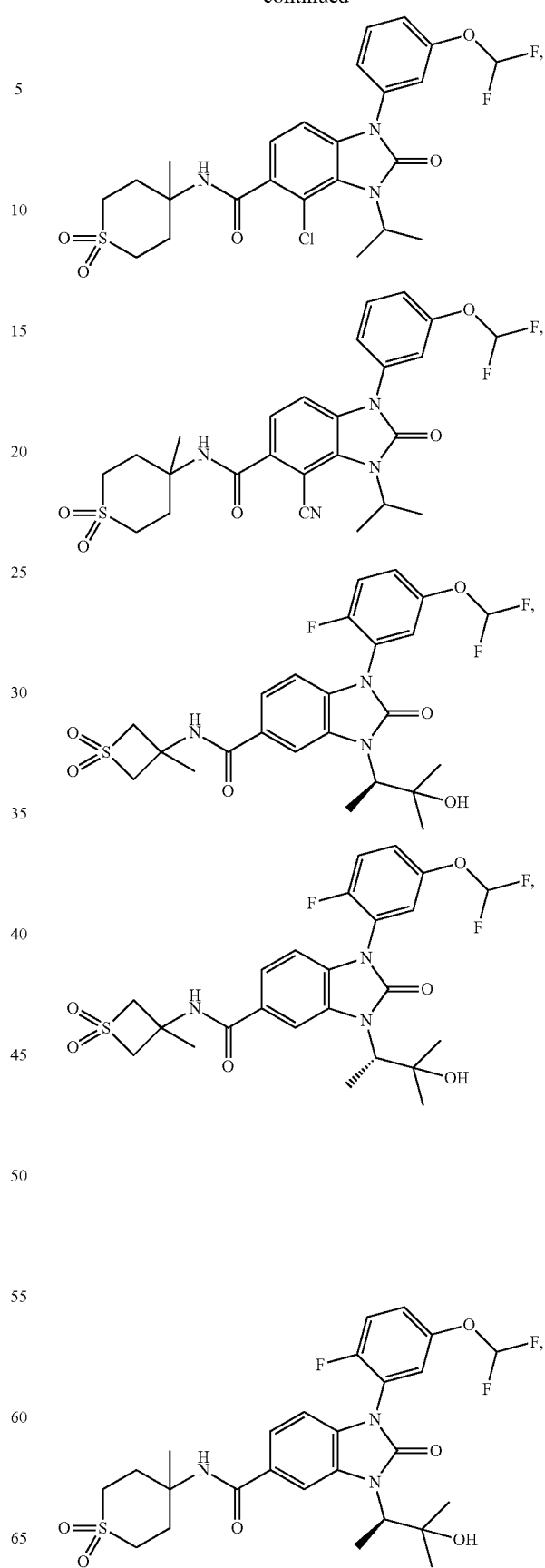

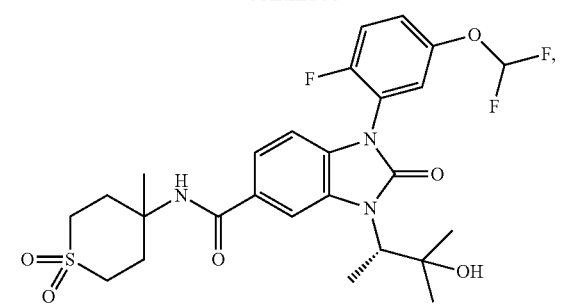
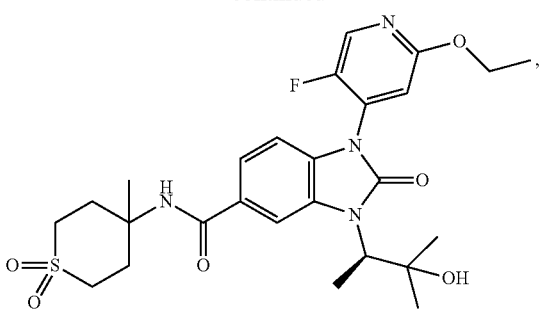
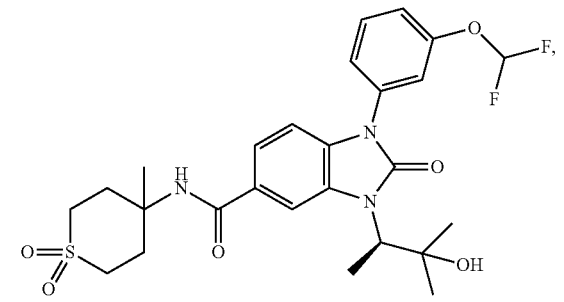
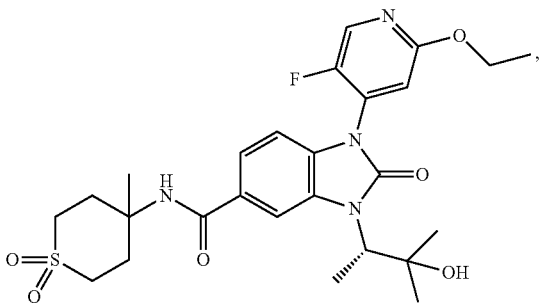
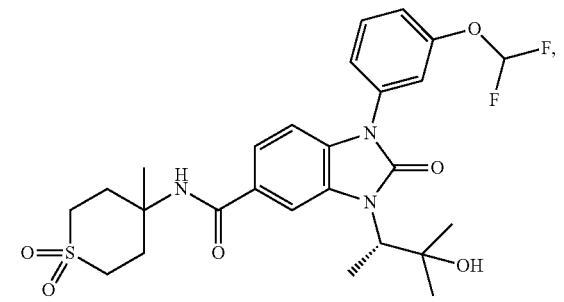
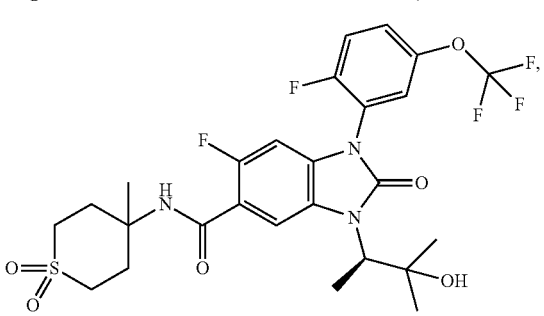
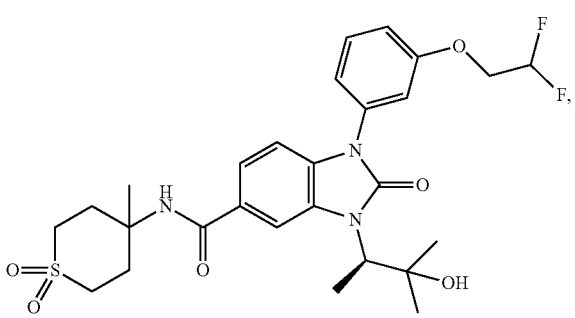
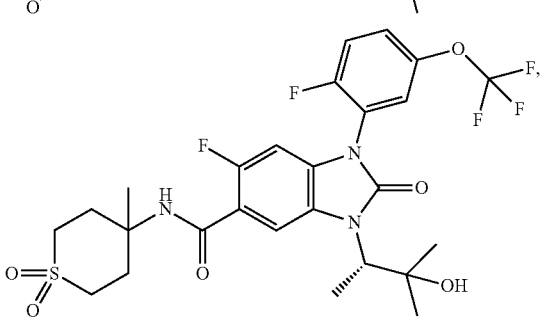
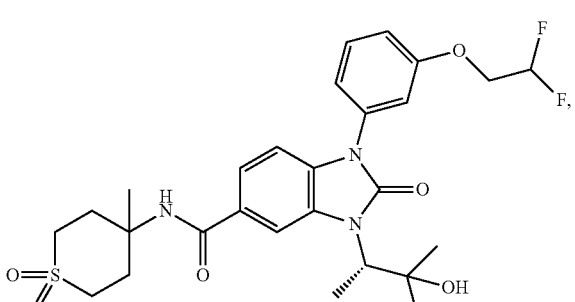
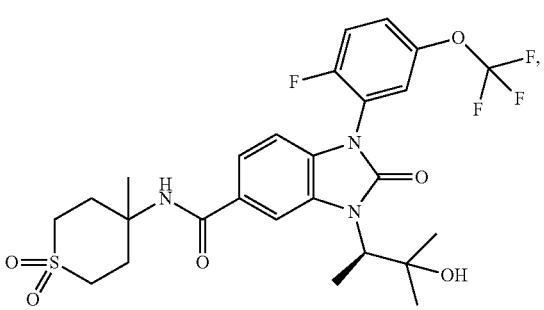

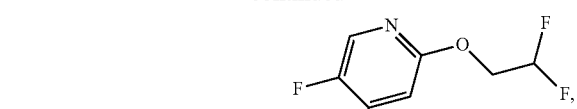
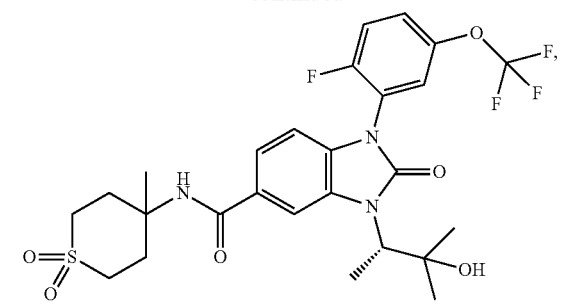
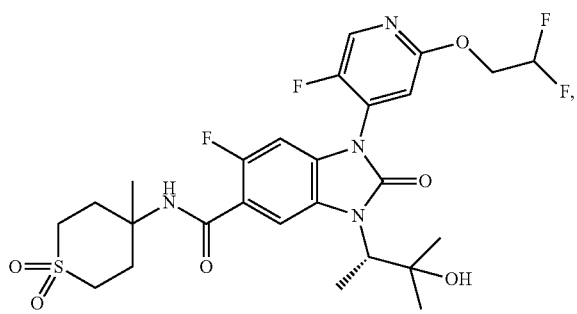
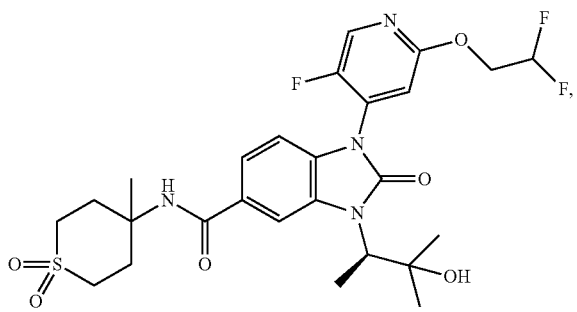
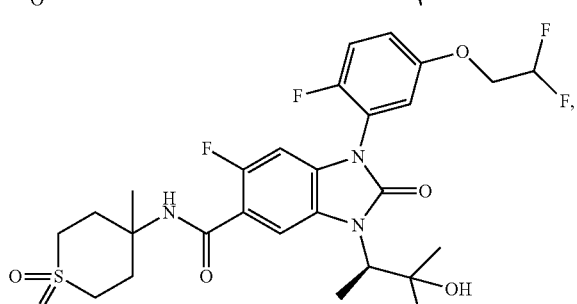

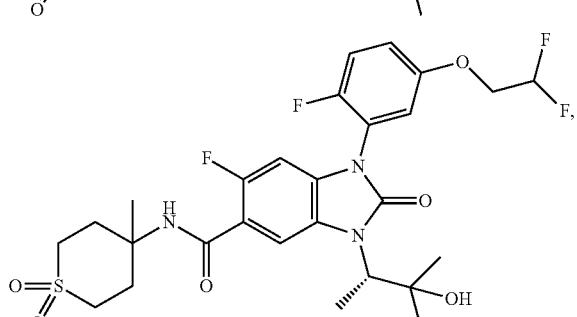
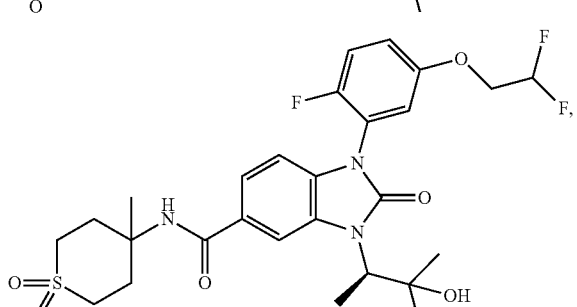
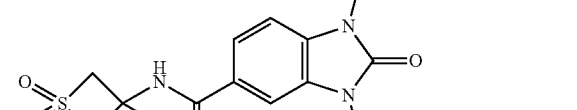
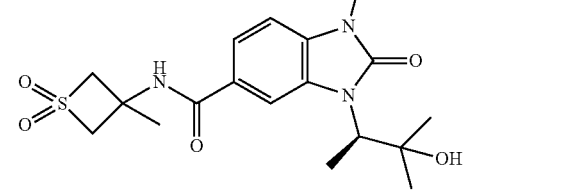

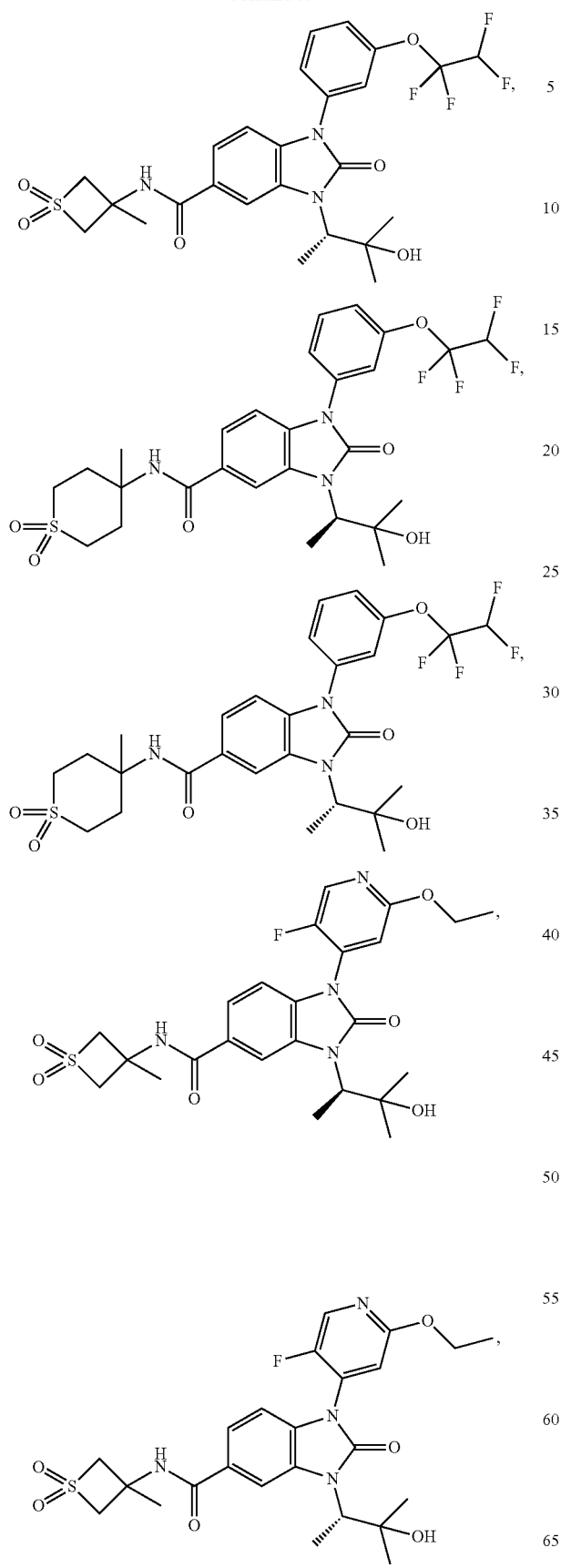
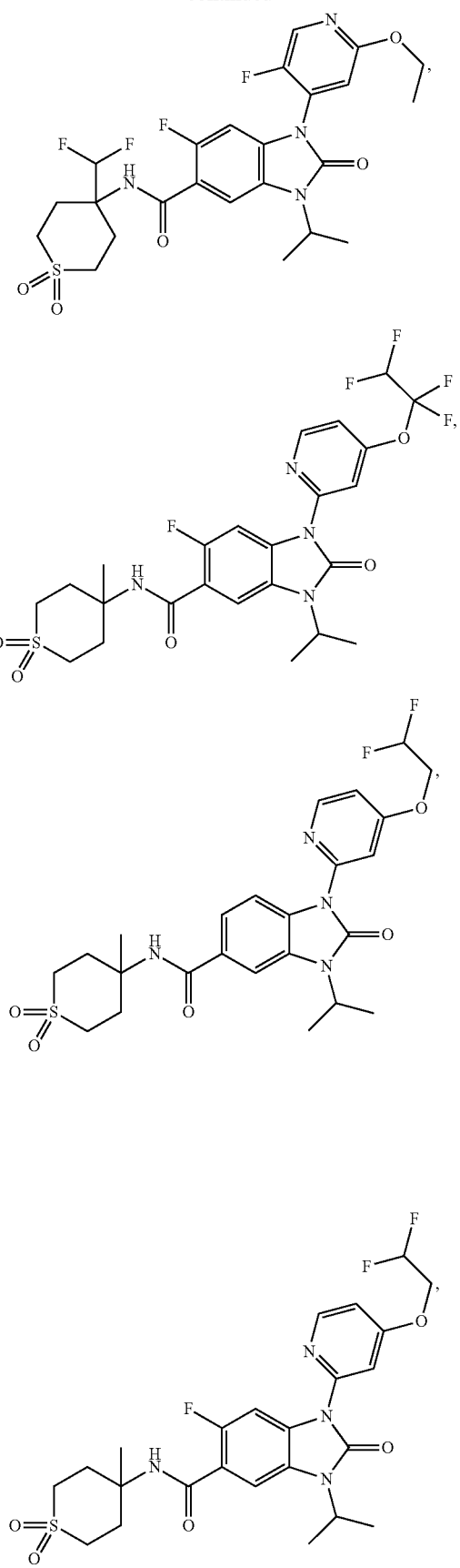

55
-continued
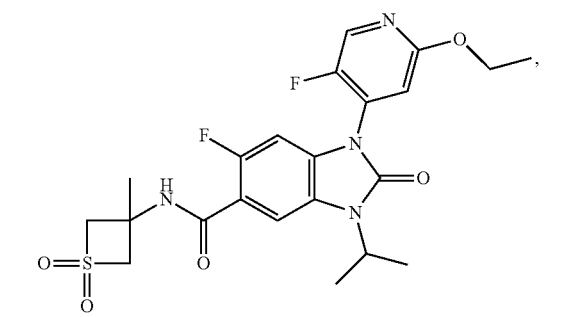
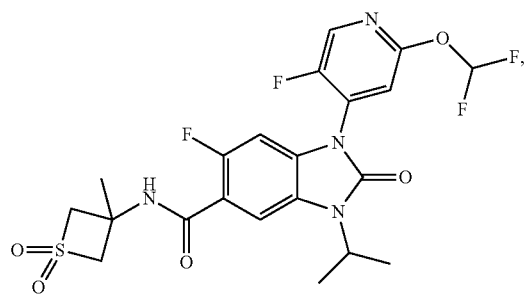
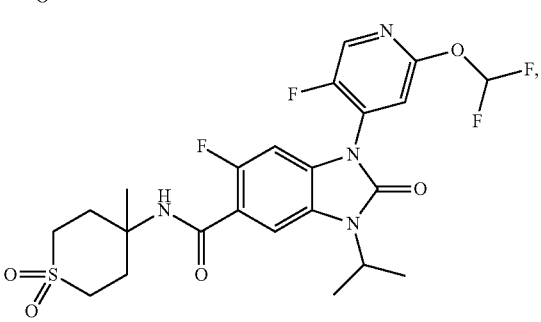
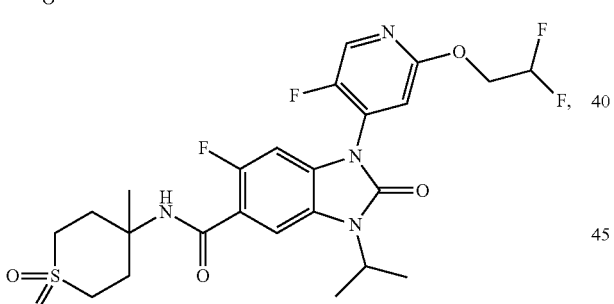
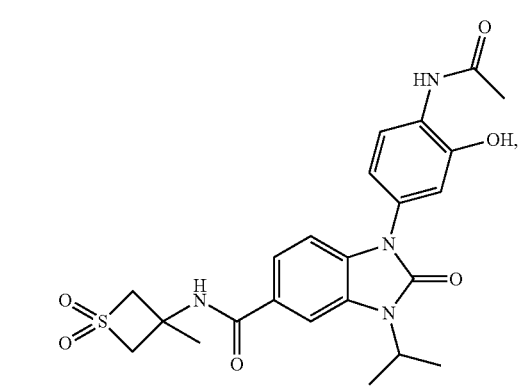
56
-continued
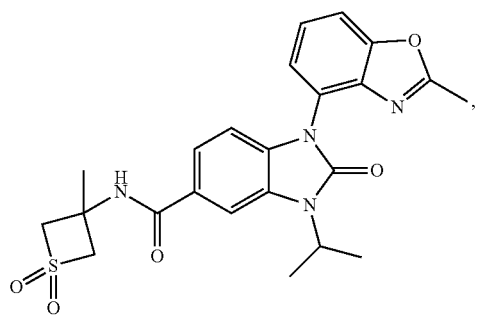
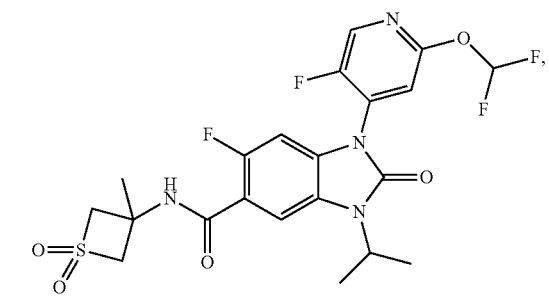
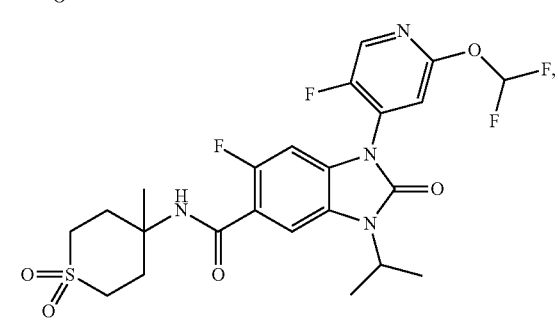
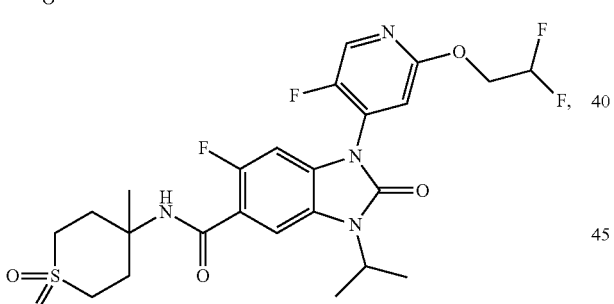
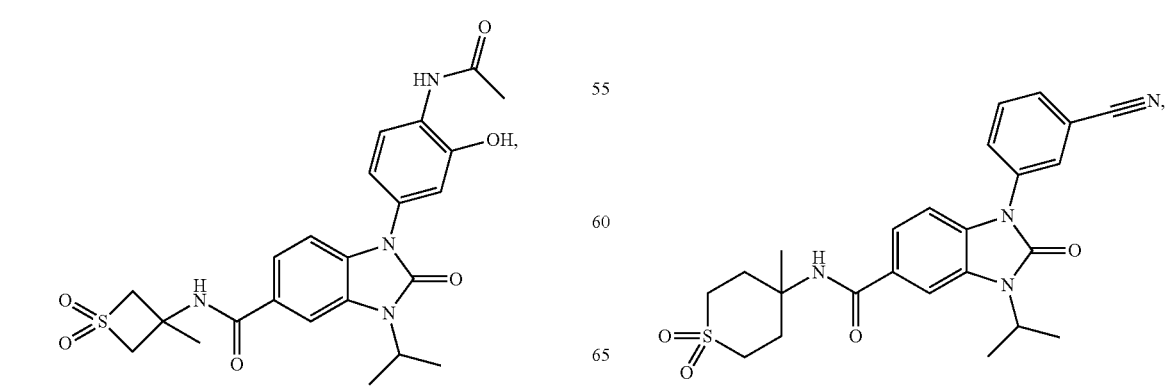

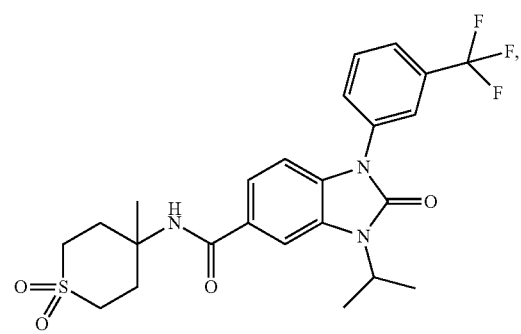
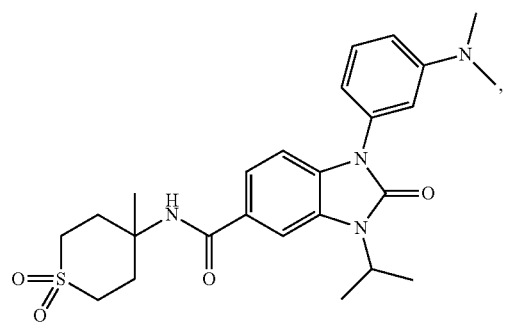
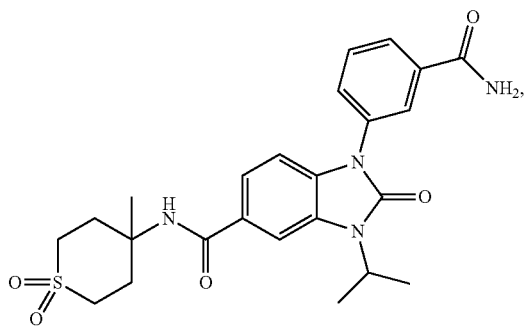
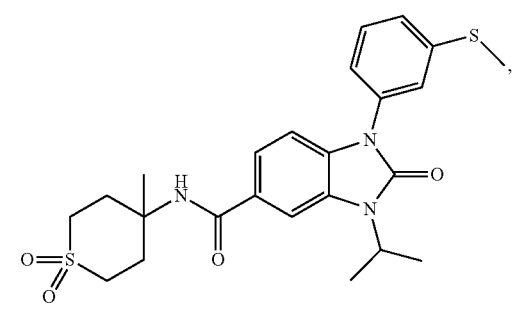
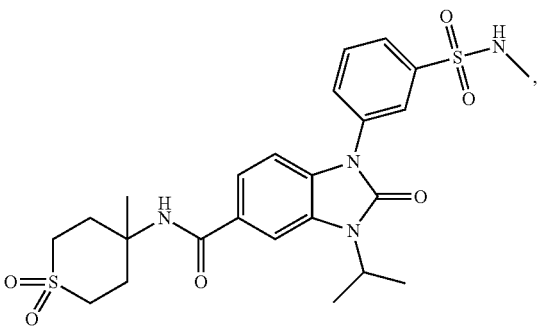
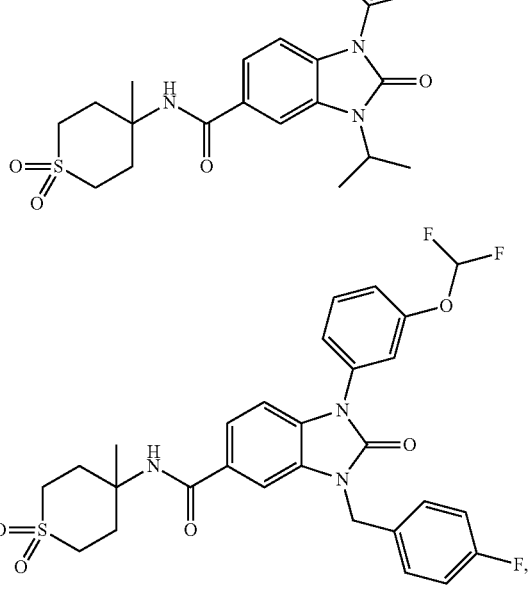
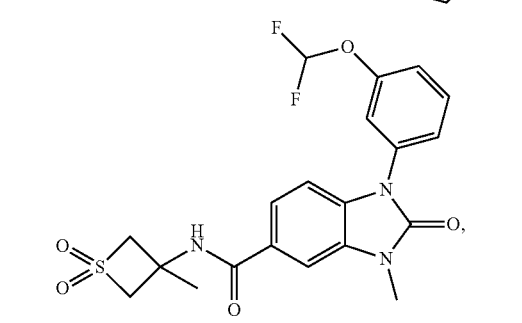
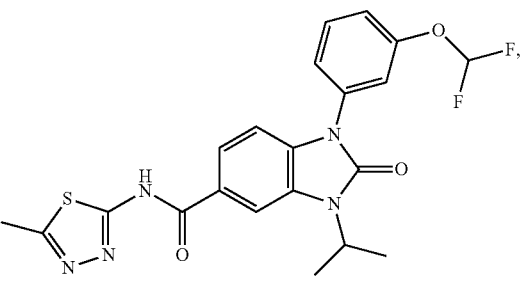
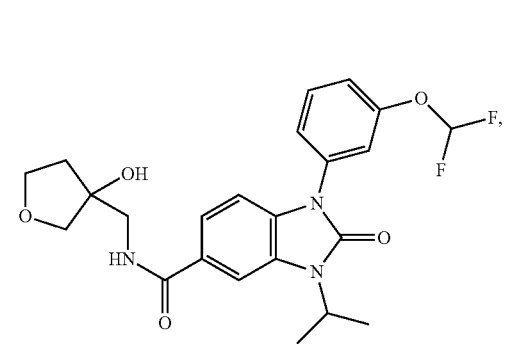

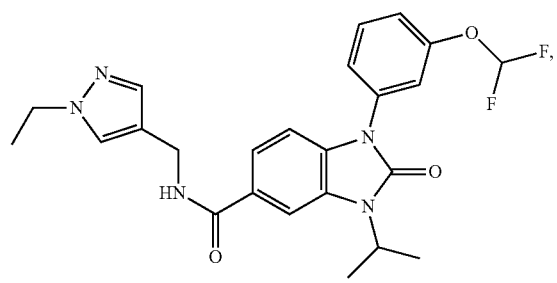

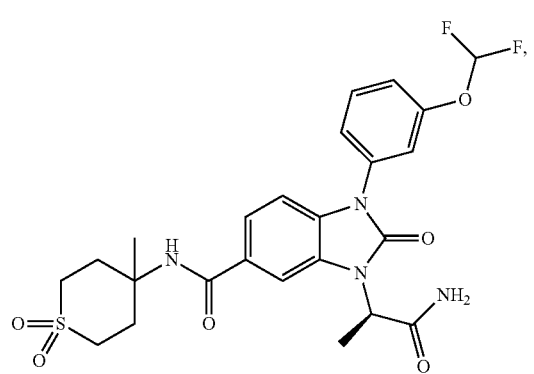

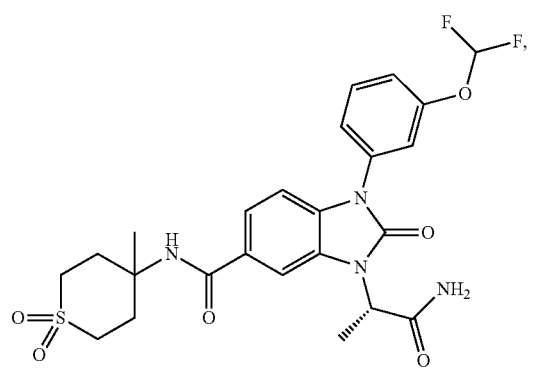

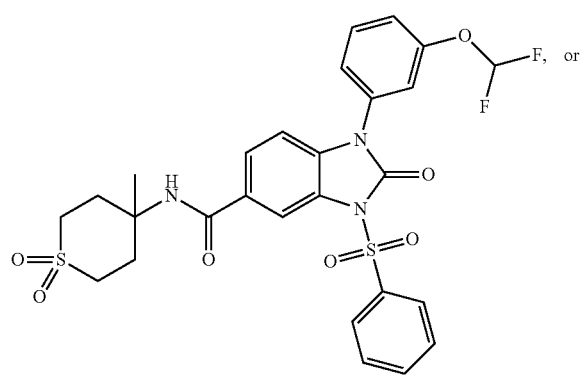

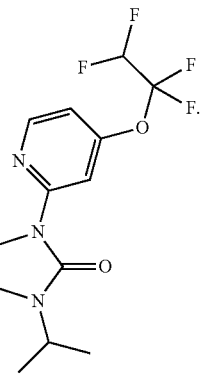

In Embodiment 80 of the invention, the compound of formula I, or a pharmaceutically acceptable salt thereof, is:

(R)-1,3-bis(4-fluorophenyl)-N-(3-methyl-1,1-dioxidotetrahydrothiophen-3-yl)-2-oxo-2,3-dihydro-1H-benzo[d]imidazole-5-carboxamide, 1-(3-(difluoromethoxy)phenyl)-3-(4-fluorophenyl)-N-(3-methyl-1,1-dioxidothietan-3-yl)-2-oxo-2,3-dihydro-1H-benzo[d]imidazole-5-carboxamide, (R)-1-(3-(difluoromethoxy)phenyl)-3-(4-fluorophenyl)-N-(3-methyl-1,1-dioxidotetrahydrothiophen-3-yl)-2-oxo-2,3-dihydro-1H-benzo[d]imidazole-5-carboxamide, 3-(3-(difluoromethoxy)phenyl)-1-(4-fluorophenyl)-N-(3-methyl-1,1-dioxidothietan-3-yl)-2-oxo-2,3-dihydro-1H-imidazo[4,5-b]pyridine-6-carboxamide, 3-isopropyl-N-(3-methyl-1,1-dioxo-thietan-3-yl)-2-oxo-1-[3-(trifluoromethoxy)phenyl]benzimidazole-5-carboxamide, 1-(3-isopropoxyphenyl)-3-isopropyl-N-(3-methyl-1,1-dioxo-thietan-3-yl)-2-oxo-benzimidazole-5-carboxamide, 3-isopropyl-N-(3-methyl-1,1-dioxo-thietan-3-yl)-2-oxo-1-[3-(1,1,2,2-tetrafluoroethoxy)phenyl]benzimidazole-5-carboxamide, 1-[3-(2,2-difluoroethoxy)phenyl]-3-isopropyl-N-(3-methyl-1,1-dioxo-thietan-3-yl)-2-oxo-benzimidazole-5-carboxamide, 1-(3-ethoxyphenyl)-3-isopropyl-N-(3-methyl-1,1-dioxo-thietan-3-yl)-2-oxo-benzimidazole-5-carboxamide, 3-isopropyl-N-(4-methyl-1,1-dioxo-thian-4-yl)-2-oxo-1-[3-(trifluoromethoxy)phenyl]benzimidazole-5-carboxamide, 1-[3-(2,2-difluoroethoxy)phenyl]-3-isopropyl-N-(4-methyl-1,1-dioxo-thian-4-yl)-2-oxo-benzimidazole-5-carboxamide, 1-[4-(difluoromethoxy)-2-pyridyl]-3-isopropyl-N-(3-methyl-1,1-dioxo-thietan-3-yl)-2-oxo-benzimidazole-5-carboxamide, 1-(3-cyclopropylphenyl)-3-isopropyl-N-(3-methyl-1,1-dioxo-thietan-3-yl)-2-oxo-benzimidazole-5-carboxamide, 1-[3-(cyclopropoxy)phenyl]-3-isopropyl-N-(3-methyl-1,1-dioxo-thietan-3-yl)-2-oxo-benzimidazole-5-carboxamide, 1-(2-Ethoxy-5-fluoropyridin-4-yl)-3-isopropyl-N-(4-methyl-1,1-dioxidotetrahydro-2H-thiopyran-4-yl)-2-oxo-2,3-dihydro-1H-benzo[d]imidazole-5-carboxamide, 1-(2-ethoxy-5-fluoropyridin-4-yl)-3-isopropyl-N-(3-methyl-1,1-dioxidothietan-3-yl)-2-oxo-2,3-dihydro-1H-benzo[d]imidazole-5-carboxamide, (S)-1-(2-Ethoxy-5-fluoropyridin-4-yl)-3-isopropyl-N-(3-methyl-1,1-dioxidotetrahydrothiophen-3-yl)-2-oxo-2,3-dihydro-1H-benzo[d]imidazole-5-carboxamide, (R)-1-(2-Ethoxy-5-fluoropyridin-4-yl)-3-isopropyl-N-(3-methyl-1,1-dioxidotetrahydrothiophen-3-yl)-2-oxo-2,3-dihydro-1H-benzo[d]imidazole-5-carboxamide, 1-(2-(Difluoromethoxy)-5-fluoropyridin-4-yl)-3-isopropyl-N-(4-methyl-1,1-dioxidotetrahydro-2H-thiopyran-4-yl)-2-oxo-2,3-dihydro-1H-benzo[d]imidazole-5-carboxamide, 1-(2-(difluoromethoxy)-5-fluoropyridin-4-yl)-3-isopropyl-N-(3-methyl-1,1-dioxidothietan-3-yl)-2-oxo-2,3-dihydro-1H-benzo[d]imidazole-5-carboxamide, 1-(2-Ethoxy-5-fluoropyridin-4-yl)-6-fluoro-3-isopropyl-N-(3-methyl-1,1-dioxidothietan-3-yl)-2-oxo-2,3-dihydro-1H-benzo[d]imidazole-5-carboxamide, 1-(3-(2,2-Difluorocyclopropyl)phenyl)-3-isopropyl-N-(3-methyl-1,1-dioxidothietan-3-yl)-2-oxo-2,3-dihydro-1H-benzo[d]imidazole-5-carboxamide, (R)-1-(3-(Difluoromethoxy)phenyl)-3-isopropyl-N-(3-methyl-1,1-dioxidotetrahydrothiophen-3-yl)-2-oxo-2,3-dihydro-1H-benzo[d]imidazole-5-carboxamide, 1-(2-(Difluoromethoxy)-5-fluoropyridin-4-yl)-6-fluoro-3-isopropyl-N-(3-methyl-1,1-dioxidothietan-3-yl)-2-oxo-2,3-dihydro-1H-benzo[d]imidazole-5-carboxamide, 1-[3-(difluoromethoxy)phenyl]-3-isopropyl-N-(4-methyl-1,1-dioxo-thian-4-yl)-2-oxo-benzimidazole-5-carboxamide, 1-[3-(difluoromethoxy)phenyl]-3-isopropyl-N-(3-methyl-1,1-dioxo-thietan-3-yl)-2-oxo-benzimidazole-5-carboxamide, 1-[3-(difluoromethoxy)phenyl]-N-(2-hydroxy-1,2-dimethyl-propyl)-3-isopropyl-2-oxo-benzimidazole-5-carboxamide, 1-[3-(difluoromethoxy)phenyl]-N-[(1S,2S)-2-hydroxycyclopentyl]-3-isopropyl-2-oxo-benzimidazole-5-carboxamide, 1-[3-(difluoromethoxy)phenyl]-N-[(3R,4S)-3-hydroxytetrahydropyran-4-yl]-3-isopropyl-2-oxo-benzimidazole-5-carboxamide, N-[(1S,2R)-3,3-difluoro-2-hydroxy-cyclohexyl]-1-[3-(difluoromethoxy)phenyl]-3-isopropyl-2-oxo-benzimidazole-5-carboxamide, 1-[3-(difluoromethoxy)phenyl]-N-[(1R,2R)-2-hydroxycyclohexyl]-3-isopropyl-2-oxo-benzimidazole-5-carboxamide, 1-[3-(difluoromethoxy)phenyl]-3-isopropyl-N-[(3S)-3-methyl-1,1-dioxo-thiolan-3-yl]-2-oxo-benzimidazole-5-carboxamide, 1-[3-(difluoromethoxy)phenyl]-N-(3,3-difluoro-1-methylcyclobutyl)-3-isopropyl-2-oxo-benzimidazole-5-carboxamide, 1-[3-(difluoromethoxy)phenyl]-N-[(1S)-1-(hydroxymethyl)-2-methyl-propyl]-3-isopropyl-2-oxo-benzimidazole-5-carboxamide, 1-[3-(difluoromethoxy)phenyl]-N-[(1S,2S)-2-hydroxycyclohexyl]-3-isopropyl-2-oxo-benzimidazole-5-carboxamide, 1-(3-(difluoromethoxy)phenyl)-N-(3-methyl-1,1-dioxidothietan-3-yl)-2-oxo-3-(tetrahydro-2H-pyran-4-yl)-2,3-dihydro-1H-benzo[d]imidazole-5-carboxamide, (R)-3-Cyclobutyl-1-(3-(difluoromethoxy)phenyl)-N-(3-methyl-1,1-dioxidotetrahydrothiophen-3-yl)-2-oxo-2,3-dihydro-1H-benzo[d]imidazole-5-carboxamide, (R)-3-Cyclopentyl-1-(3-(difluoromethoxy)phenyl)-N-(3-methyl-1,1-dioxidotetrahydrothiophen-3-yl)-2-oxo-2,3-dihydro-1H-benzo[d]imidazole-5-carboxamide, 1-(3-(Difluoromethoxy)phenyl)-3-ethyl-N-(4-methyl-1,1-dioxidotetrahydro-2H-thiopyran-4-yl)-2-oxo-2,3-dihydro-1H-benzo[d]imidazole-5-carboxamide, 1-(3-(Difluoromethoxy)phenyl)-3-ethyl-N-(3-methyl-1,1-dioxidothietan-3-yl)-2-oxo-2,3-dihydro-1H-benzo[d]imidazole-5-carboxamide, 3-Cyclopropyl-1-(3-(difluoromethoxy)phenyl)-N-(4-methyl-1,1-dioxidotetrahydro-2H-thiopyran-4-yl)-2-oxo-2,3-dihydro-1H-benzo[d]imidazole-5-carboxamide, 1-(3-(Difluoromethoxy)phenyl)-N-(4-methyl-1,1-dioxidotetrahydro-2H-thiopyran-4-yl)-2-oxo-3-(3,3,3-trifluoropropyl)-2,3-dihydro-1H-benzo[d]imidazole-5-carboxamide, 1-(3-(Difluoromethoxy)phenyl)-N-(3-methyl-1,1-dioxidothietan-3-yl)-2-oxo-3-(2,2,2-trifluoroethyl)-2,3-dihydro-1H-benzo[d]imidazole-5-carboxamide, 1-(3-(difluoromethoxy)phenyl)-N-(4-methyl-1,1-dioxidotetrahydro-2H-thiopyran-4-yl)-2-oxo-3-(2,2,2-trifluoroethyl)-2,3-dihydro-1H-benzo[d]imidazole-5-carboxamide, (R)-1-(3-(difluoromethoxy)phenyl)-3-(1,1-difluoropropan-2-yl)-N-(4-methyl-1,1-dioxidotetrahydro-2H-thiopyran-4-yl)-2-oxo-2,3-dihydro-1H-benzo[d]imidazole-5-carboxamide, (S)-1-(3-(difluoromethoxy)phenyl)-3-(1,1-difluoropropan-2-yl)-N-(4-methyl-1,1-dioxidotetrahydro-2H-thiopyran-4-yl)-2-oxo-2,3-dihydro-1H-benzo[d]imidazole-5-carboxamide, 3-(sec-butyl)-1-(3-(difluoromethoxy)phenyl)-N-(3-methyl-1,1-dioxidothietan-3-yl)-2-oxo-2,3-dihydro-1H-benzo[d]imidazole-5-carboxamide, (R)-3-(sec-butyl)-1-(3-(difluoromethoxy)phenyl)-N-(3-methyl-1,1-dioxidothietan-3-yl)-2-oxo-2,3-dihydro-1H-benzo[d]imidazole-5-carboxamide, (S)-3-(sec-butyl)-1-(3-(difluoromethoxy)phenyl)-N-(3-methyl-1,1-dioxidothietan-3-yl)-2-oxo-2,3-dihydro-1H-benzo[d]imidazole-5-carboxamide, 1-(3-(difluoromethoxy)phenyl)-3-(2-hydroxy-2-methylpropyl)-N-(3-methyl-1,1-dioxidothietan-3-yl)-2-oxo-2,3-dihydro-1H-benzo[d]imidazole-5-carboxamide, 1-(5-(Difluoromethoxy)-2-fluorophenyl)-3-isopropyl-N-(4-methyl-1,1-dioxidotetrahydro-2H-thiopyran-4-yl)-2-oxo-2,3-dihydro-1H-benzo[d]imidazole-5-carboxamide, 1-(5-(Difluoromethoxy)-2-fluorophenyl)-3-isopropyl-N-(3-methyl-1,1-dioxidothietan-3-yl)-2-oxo-2,3-dihydro-1H-benzo[d]imidazole-5-carboxamide, (S)-1-(5-(Difluoromethoxy)-2-fluorophenyl)-3-isopropyl-N-(3-methyl-1,1-dioxidotetrahydrothiophen-3-yl)-2-oxo-2,3-dihydro-1H-benzo[d]imidazole-5-carboxamide, (R)-1-(5-(Difluoromethoxy)-2-fluorophenyl)-3-isopropyl-N-(3-methyl-1,1-dioxidotetrahydrothiophen-3-yl)-2-oxo-2,3-dihydro-1H-benzo[d]imidazole-5-carboxamide, 1-(5-(Difluoromethoxy)pyridin-3-yl)-3-isopropyl-N-(3-methyl-1,1-dioxidothietan-3-yl)-2-oxo-2,3-dihydro-1H-benzo[d]imidazole-5-carboxamide, 1-(5-Cyclopropylpyridin-3-yl)-3-isopropyl-N-(3-methyl-1,1-dioxidothietan-3-yl)-2-oxo-2,3-dihydro-1H-benzo[d]imidazole-5-carboxamide, 1-isopropyl-N-(4-methyl-1,1-dioxo-thian-4-yl)-2-oxo-3-[3-(1,1,2,2-tetrafluoroethoxy)phenyl]imidazo[4,5-b]pyridine-6-carboxamide, 3-[3-(difluoromethoxy)phenyl]-1-isopropyl-N-(4-methyl-1,1-dioxo-thian-4-yl)-2-oxo-imidazo[4,5-b]pyridine-6-carboxamide, 3-[3-(difluoromethoxy)phenyl]-1-isopropyl-N-[(3S)-3-methyl-1,1-dioxo-thiolan-3-yl]-2-oxo-imidazo[4,5-b]pyridine-6-carboxamide, 3-[3-(difluoromethoxy)phenyl]-1-isopropyl-N-[(3R)-3-methyl-1,1-dioxo-thiolan-3-yl]-2-oxo-imidazo[4,5-b]pyridine-6-carboxamide, 1-isopropyl-N-(3-methyl-1,1-dioxo-thietan-3-yl)-2-oxo-3-[3-(trifluoromethoxy)phenyl]imidazo[4,5-b]pyridine-6-carboxamide, 1-isopropyl-N-(4-methyl-1,1-dioxo-thian-4-yl)-2-oxo-3-[3-(trifluoromethoxy)phenyl]imidazo[4,5-b]pyridine-6-carboxamide, 1-isopropyl-N-(3-methyl-1,1-dioxo-thietan-3-yl)-2-oxo-3-[3-(1,1,2,2-tetrafluoroethoxy)phenyl]imidazo[4,5-b]pyridine-6-carboxamide, 1-isopropyl-N-[(3S)-3-methyl-1,1-dioxo-thiolan-3-yl]-2-oxo-3-[3-(1,1,2,2-tetrafluoroethoxy)phenyl]imidazo[4,5-b]pyridine-6-carboxamide, 1-isopropyl-N-[(3R)-3-methyl-1,1-dioxo-thiolan-3-yl]-2-oxo-3-[3-(1,1,2,2-tetrafluoroethoxy)phenyl]imidazo[4,5-b]pyridine-6-carboxamide, 3-(3-ethoxyphenyl)-1-isopropyl-N-(3-methyl-1,1-dioxo-thietan-3-yl)-2-oxo-imidazo[4,5-b]pyridine-6-carboxamide, 3-(3-ethoxyphenyl)-1-isopropyl-N-[(3S)-3-methyl-1,1-dioxo-thiolan-3-yl]-2-oxo-imidazo[4,5-b]pyridine-6-carboxamide, 3-(3-ethoxyphenyl)-1-isopropyl-N-[(3R)-3-methyl-1,1-dioxo-thiolan-3-yl]-2-oxo-imidazo[4,5-b]pyridine-6-carboxamide, 3-(3-ethoxyphenyl)-1-isopropyl-N-(4-methyl-1,1-dioxo-thian-4-yl)-2-oxo-imidazo[4,5-b]pyridine-6-carboxamide, 3-(3-isopropoxyphenyl)-1-isopropyl-N-(3-methyl-1,1-dioxo-thietan-3-yl)-2-oxo-imidazo[4,5-b]pyridine-6-carboxamide, 3-(3-isopropoxyphenyl)-1-isopropyl-N-(4-methyl-1,1-dioxo-thian-4-yl)-2-oxo-imidazo[4,5-b]pyridine-6-carboxamide, 3-[5-(difluoromethoxy)-2-fluoro-phenyl]-1-isopropyl-N-(3-methyl-1,1-dioxo-thietan-3-yl)-2-oxo-imidazo[4,5-b]pyridine-6-carboxamide, 3-[5-(difluoromethoxy)-2-fluoro-phenyl]-1-isopropyl-N-(4-methyl-1,1-dioxo-thian-4-yl)-2-oxo-imidazo[4,5-b]pyridine-6-carboxamide, 3-[3-(difluoromethoxy)phenyl]-1-isopropyl-N-(3-methyl-1,1-dioxo-thietan-3-yl)-2-oxo-imidazo[4,5-b]pyridine-6-carboxamide, 3-(3-(difluoromethoxy)phenyl)-1-isopropyl-N-(3-methyl-1,1-dioxidothietan-3-yl)-2-oxo-2,3-dihydro-1H-imidazo[4,5-c]pyridine-6-carboxamide, 3-(3-(difluoromethoxy)phenyl)-1-isopropyl-N-(4-methyl-1,1-dioxidotetrahydro-2H-thiopyran-4-yl)-2-oxo-2,3-dihydro-1H-imidazo[4,5-c]pyridine-6-carboxamide, 1-(3-(difluoromethoxy)phenyl)-3-isopropyl-N-(3-methyl-1,1-dioxidothietan-3-yl)-2-oxo-2,3-dihydro-1H-imidazo[4,5-b]pyridine-5-carboxamide, 1-[3-(difluoromethoxy)phenyl]-7-fluoro-3-isopropyl-N-(3-methyl-1,1-dioxo-thietan-3-yl)-2-oxo-benzimidazole-5-carboxamide, 1-[3-(difluoromethoxy)phenyl]-7-fluoro-3-isopropyl-N-[(3S)-3-methyl-1,1-dioxo-thiolan-3-yl]-2-oxo-benzimidazole-5-carboxamide, 1-[3-(difluoromethoxy)phenyl]-7-fluoro-3-isopropyl-N-[(3R)-3-methyl-1,1-dioxo-thiolan-3-yl]-2-oxo-benzimidazole-5-carboxamide, 1-[3-(difluoromethoxy)phenyl]-7-fluoro-3-isopropyl-N-(4-methyl-1,1-dioxo-thian-4-yl)-2-oxo-benzimidazole-5-carboxamide, (S)-1-(3-(Difluoromethoxy)phenyl)-6-fluoro-3-isopropyl-N-(3-methyl-1,1-dioxidotetrahydrothiophen-3-yl)-2-oxo-2,3-dihydro-1H-benzo[d]imidazole-5-carboxamide, (R)-1-(3-(Difluoromethoxy)phenyl)-6-fluoro-3-isopropyl-N-(3-methyl-1,1-dioxidotetrahydrothiophen-3-yl)-2-oxo-2,3-dihydro-1H-benzo[d]imidazole-5-carboxamide, 1-(3-(Difluoromethoxy)phenyl)-6-fluoro-3-isopropyl-N-(4-methyl-1,1-dioxidotetrahydro-2H-thiopyran-4-yl)-2-oxo-2,3-dihydro-1H-benzo[d]imidazole-5-carboxamide, (S)-1-(3-(Difluoromethoxy)phenyl)-4-fluoro-3-isopropyl-N-(3-methyl-1,1-dioxidotetrahydrothiophen-3-yl)-2-oxo-2,3-dihydro-1H-benzo[d]imidazole-5-carboxamide, (R)-1-(3-(Difluoromethoxy)phenyl)-4-fluoro-3-isopropyl-N-(3-methyl-1,1-dioxidotetrahydrothiophen-3-yl)-2-oxo-2,3-dihydro-1H-benzo[d]imidazole-5-carboxamide, 1-(3-(Difluoromethoxy)phenyl)-4-fluoro-3-isopropyl-N-(4-methyl-1,1-dioxidotetrahydro-2H-thiopyran-4-yl)-2-oxo-2,3-dihydro-1H-benzo[d]imidazole-5-carboxamide, (S)-6-Chloro-1-(3-(difluoromethoxy)phenyl)-3-isopropyl-N-(3-methyl-1,1-dioxidotetrahydrothiophen-3-yl)-2-oxo-2,3-dihydro-1H-benzo[d]imidazole-5-carboxamide, 4-chloro-1-(3-(difluoromethoxy)phenyl)-3-isopropyl-N-(4-methyl-1,1-dioxidotetrahydro-2H-thiopyran-4-yl)-2-oxo-2,3-dihydro-1H-benzo[d]imidazole-5-carboxamide, 4-cyano-1-(3-(difluoromethoxy)phenyl)-3-isopropyl-N-(4-methyl-1,1-dioxidotetrahydro-2H-thiopyran-4-yl)-2-oxo-2,3-dihydro-1H-benzo[d]imidazole-5-carboxamide, (R)-1-(5-(difluoromethoxy)-2-fluorophenyl)-3-(3-hydroxy-3-methylbutan-2-yl)-N-(3-methyl-1,1-dioxidothietan-3-yl)-2-oxo-2,3-dihydro-1H-benzo[d]imidazole-5-carboxamide, (S)-1-(5-(difluoromethoxy)-2-fluorophenyl)-3-(3-hydroxy-3-methylbutan-2-yl)-N-(3-methyl-1,1-dioxidothietan-3-yl)-2-oxo-2,3-dihydro-1H-benzo[d]imidazole-5-carboxamide, (R)-1-(5-(difluoromethoxy)-2-fluorophenyl)-3-(3-hydroxy-3-methylbutan-2-yl)-N-(4-methyl-1,1-dioxidotetrahydro-2H-thiopyran-4-yl)-2-oxo-2,3-dihydro-1H-benzo[d]imidazole-5-carboxamide, (S)-1-(5-(difluoromethoxy)-2-fluorophenyl)-3-(3-hydroxy-3-methylbutan-2-yl)-N-(4-methyl-1,1-dioxidotetrahydro-2H-thiopyran-4-yl)-2-oxo-2,3-dihydro-1H-benzo[d]imidazole-5-carboxamide, (R)-1-(3-(difluoromethoxy)phenyl)-3-(3-hydroxy-3-methylbutan-2-yl)-N-(4-methyl-1,1-dioxidotetrahydro-2H-thiopyran-4-yl)-2-oxo-2,3-dihydro-1H-benzo[d]imidazole-5-carboxamide, (S)-1-(3-(difluoromethoxy)phenyl)-3-(3-hydroxy-3-methylbutan-2-yl)-N-(4-methyl-1,1-dioxidotetrahydro-2H-thiopyran-4-yl)-2-oxo-2,3-dihydro-1H-benzo[d]imidazole-5-carboxamide, (R)-1-(3-(2,2-difluoroethoxy)phenyl)-3-(3-hydroxy-3-methylbutan-2-yl)-N-(4-methyl-1,1-dioxidotetrahydro-2H-thiopyran-4-yl)-2-oxo-2,3-dihydro-1H-benzo[d]imidazole-5-carboxamide, (S)-1-(3-(2,2-difluoroethoxy)phenyl)-3-(3-hydroxy-3-methylbutan-2-yl)-N-(4-methyl-1,1-dioxidotetrahydro-2H-thiopyran-4-yl)-2-oxo-2,3-dihydro-1H-benzo[d]imidazole-5-carboxamide, (R)-1-(2-ethoxy-5-fluoropyridin-4-yl)-3-(3-hydroxy-3-methylbutan-2-yl)-N-(4-methyl-1,1-dioxidotetrahydro-2H-thiopyran-4-yl)-2-oxo-2,3-dihydro-1H-benzo[d]imidazole-5-carboxamide, (S)-1-(2-ethoxy-5-fluoropyridin-4-yl)-3-(3-hydroxy-3-methylbutan-2-yl)-N-(4-methyl-1,1-dioxidotetrahydro-2H-thiopyran-4-yl)-2-oxo-2,3-dihydro-1H-benzo[d]imidazole-5-carboxamide, (R)-6-fluoro-1-(2-fluoro-5-(trifluoromethoxy)phenyl)-3-(3-hydroxy-3-methylbutan-2-yl)-N-(4-methyl-1,1-dioxidotetrahydro-2H-thiopyran-4-yl)-2-oxo-2,3-dihydro-1H-benzo[d]imidazole-5-carboxamide,
(S)-6-fluoro-1-(2-fluoro-5-(trifluoromethoxy)phenyl)-3-(3-hydroxy-3-methylbutan-2-yl)-N-(4-methyl-1,1-dioxido-tetrahydro-2H-thiopyran-4-yl)-2-oxo-2,3-dihydro-1H-benzo[d]imidazole-5-carboxamide,
(R)-1-(2-fluoro-5-(trifluoromethoxy)phenyl)-3-(3-hydroxy-3-methylbutan-2-yl)-N-(4-methyl-1,1-dioxidotetrahydro-2H-thiopyran-4-yl)-2-oxo-2,3-dihydro-1H-benzo[d]imidazole-5-carboxamide,
(S)-1-(2-fluoro-5-(trifluoromethoxy)phenyl)-3-(3-hydroxy-3-methylbutan-2-yl)-N-(4-methyl-1,1-dioxidotetrahydro-2H-thiopyran-4-yl)-2-oxo-2,3-dihydro-1H-benzo[d]imidazole-5-carboxamide,
(R)-1-(2-(2,2-difluoroethoxy)-5-fluoropyridin-4-yl)-3-(3-hydroxy-3-methylbutan-2-yl)-N-(4-methyl-1,1-dioxido-tetrahydro-2H-thiopyran-4-yl)-2-oxo-2,3-dihydro-1H-benzo[d]imidazole-5-carboxamide,
(S)-1-(2-(2,2-difluoroethoxy)-5-fluoropyridin-4-yl)-3-(3-hydroxy-3-methylbutan-2-yl)-N-(4-methyl-1,1-dioxidotetrahydro-2H-thiopyran-4-yl)-2-oxo-2,3-dihydro-1H-benzo[d]imidazole-5-carboxamide,
(R)-1-(5-(2,2-difluoroethoxy)-2-fluorophenyl)-3-(3-hydroxy-3-methylbutan-2-yl)-N-(4-methyl-1,1-dioxidotetrahydro-2H-thiopyran-4-yl)-2-oxo-2,3-dihydro-1H-benzo[d]imidazole-5-carboxamide,
(S)-1-(5-(2,2-difluoroethoxy)-2-fluorophenyl)-6-fluoro-3-(3-hydroxy-3-methylbutan-2-yl)-N-(4-methyl-1,1-dioxidotetrahydro-2H-thiopyran-4-yl)-2-oxo-2,3-dihydro-1H-benzo[d]imidazole-5-carboxamide,
(R)-1-(2-(2,2-difluoroethoxy)-5-fluoropyridin-4-yl)-6-fluoro-3-(3-hydroxy-3-methylbutan-2-yl)-N-(4-methyl-1,1-dioxidotetrahydro-2H-thiopyran-4-yl)-2-oxo-2,3-dihydro-1H-benzo[d]imidazole-5-carboxamide,
(S)-1-(2-(2,2-difluoroethoxy)-5-fluoropyridin-4-yl)-6-fluoro-3-(3-hydroxy-3-methylbutan-2-yl)-N-(4-methyl-1,1-dioxidotetrahydro-2H-thiopyran-4-yl)-2-oxo-2,3-dihydro-1H-benzo[d]imidazole-5-carboxamide,
(R)-1-(5-(2,2-difluoroethoxy)-2-fluorophenyl)-6-fluoro-3-(3-hydroxy-3-methylbutan-2-yl)-N-(4-methyl-1,1-dioxidotetrahydro-2H-thiopyran-4-yl)-2-oxo-2,3-dihydro-1H-benzo[d]imidazole-5-carboxamide,
(S)-1-(5-(2,2-difluoroethoxy)-2-fluorophenyl)-6-fluoro-3-(3-hydroxy-3-methylbutan-2-yl)-N-(4-methyl-1,1-dioxidotetrahydro-2H-thiopyran-4-yl)-2-oxo-2,3-dihydro-1H-benzo[d]imidazole-5-carboxamide,
(R)-3-(3-hydroxy-3-methylbutan-2-yl)-N-(3-methyl-1,1-dioxidothietan-3-yl)-2-oxo-1-(3-(1,1,2,2-tetrafluoroethoxy)phenyl)-2,3-dihydro-1H-benzo[d]imidazole-5-carboxamide,
(S)-3-(3-hydroxy-3-methylbutan-2-yl)-N-(3-methyl-1,1-dioxidothietan-3-yl)-2-oxo-1-(3-(1,1,2,2-tetrafluoroethoxy)phenyl)-2,3-dihydro-1H-benzo[d]imidazole-5-carboxamide,
(R)-3-(3-hydroxy-3-methylbutan-2-yl)-N-(4-methyl-1,1-dioxidotetrahydro-2H-thiopyran-4-yl)-2-oxo-1-(3-(1,1,2,2-tetrafluoroethoxy)phenyl)-2,3-dihydro-1H-benzo[d]imidazole-5-carboxamide,
(S)-3-(3-hydroxy-3-methylbutan-2-yl)-N-(4-methyl-1,1-dioxidotetrahydro-2H-thiopyran-4-yl)-2-oxo-1-(3-(1,1,2,2-tetrafluoroethoxy)phenyl)-2,3-dihydro-1H-benzo[d]imidazole-5-carboxamide,
(R)-1-(2-ethoxy-5-fluoropyridin-4-yl)-3-(3-hydroxy-3-methylbutan-2-yl)-N-(3-methyl-1,1-dioxidothietan-3-yl)-2-oxo-2,3-dihydro-1H-benzo[d]imidazole-5-carboxamide,
(S)-1-(2-ethoxy-5-fluoropyridin-4-yl)-3-(3-hydroxy-3-methylbutan-2-yl)-N-(3-methyl-1,1-dioxidothietan-3-yl)-2-oxo-2,3-dihydro-1H-benzo[d]imidazole-5-carboxamide,
N-(4-(difluoromethyl)-1,1-dioxidotetrahydro-2H-thiopyran-4-yl)-1-(2-ethoxy-5-fluoropyridin-4-yl)-6-fluoro-3-isopropyl-2-oxo-2,3-dihydro-1H-benzo[d]imidazole-5-carboxamide,
6-fluoro-3-isopropyl-N-(4-methyl-1,1-dioxidotetrahydro-2H-thiopyran-4-yl)-2-oxo-1-(4-(1,1,2,2-tetrafluoroethoxy)pyridin-2-yl)-2,3-dihydro-1H-benzo[d]imidazole-5-carboxamide,
1-(4-(2,2-difluoroethoxy)pyridin-2-yl)-3-isopropyl-N-(4-methyl-1,1-dioxidotetrahydro-2H-thiopyran-4-yl)-2-oxo-2,3-dihydro-1H-benzo[d]imidazole-5-carboxamide,
3-isopropyl-N-(4-methyl-1,1-dioxidotetrahydro-2H-thiopyran-4-yl)-2-oxo-1-(4-(1,1,2,2-tetrafluoroethoxy)pyridin-2-yl)-2,3-dihydro-1H-benzo[d]imidazole-5-carboxamide,
1-(4-(2,2-difluoroethoxy)pyridin-2-yl)-6-fluoro-3-isopropyl-N-(4-methyl-1,1-dioxidotetrahydro-2H-thiopyran-4-yl)-2-oxo-2,3-dihydro-1H-benzo[d]imidazole-5-carboxamide,
1-(2-ethoxy-5-fluoropyridin-4-yl)-6-fluoro-3-isopropyl-N-(3-methyl-1,1-dioxidothietan-3-yl)-2-oxo-2,3-dihydro-1H-benzo[d]imidazole-5-carboxamide,
1-(2-(difluoromethoxy)-5-fluoropyridin-4-yl)-6-fluoro-3-isopropyl-N-(3-methyl-1,1-dioxidothietan-3-yl)-2-oxo-2,3-dihydro-1H-benzo[d]imidazole-5-carboxamide,
1-(2-(difluoromethoxy)-5-fluoropyridin-4-yl)-6-fluoro-3-isopropyl-N-(4-methyl-1,1-dioxidotetrahydro-2H-thiopyran-4-yl)-2-oxo-2,3-dihydro-1H-benzo[d]imidazole-5-carboxamide,
1-(2-(2,2-difluoroethoxy)-5-fluoropyridin-4-yl)-6-fluoro-3-isopropyl-N-(4-methyl-1,1-dioxidotetrahydro-2H-thiopyran-4-yl)-2-oxo-2,3-dihydro-1H-benzo[d]imidazole-5-carboxamide,
1-(4-acetamido-3-hydroxyphenyl)-3-isopropyl-N-(3-methyl-1,1-dioxidothietan-3-yl)-2-oxo-2,3-dihydro-1H-benzo[d]imidazole-5-carboxamide,
3-isopropyl-N-(3-methyl-1,1-dioxidothietan-3-yl)-1-(2-methylbenzo[d]oxazol-4-yl)-2-oxo-2,3-dihydro-1H-benzo[d]imidazole-5-carboxamide,
3-isopropyl-N-(3-methyl-1,1-dioxidothietan-3-yl)-1-(2-methylbenzo[d]oxazol-6-yl)-2-oxo-2,3-dihydro-1H-benzo[d]imidazole-5-carboxamide,
1-(3-fluorophenyl)-3-isopropyl-N-(4-methyl-1,1-dioxidotetrahydro-2H-thiopyran-4-yl)-2-oxo-2,3-dihydro-1H-benzo[d]imidazole-5-carboxamide,
1-(5-fluoro-2-isopropoxypyridin-4-yl)-3-isopropyl-N-(4-methyl-1,1-dioxidotetrahydro-2H-thiopyran-4-yl)-2-oxo-2,3-dihydro-1H-benzo[d]imidazole-5-carboxamide,
1-(3-cyanophenyl)-3-isopropyl-N-(4-methyl-1,1-dioxidotetrahydro-2H-thiopyran-4-yl)-2-oxo-2,3-dihydro-1H-benzo[d]imidazole-5-carboxamide,
3-isopropyl-N-(4-methyl-1,1-dioxidotetrahydro-2H-thiopyran-4-yl)-2-oxo-1-(3-(trifluoromethyl)phenyl)-2,3-dihydro-1H-benzo[d]imidazole-5-carboxamide,
1-(3-(dimethylamino)phenyl)-3-isopropyl-N-(4-methyl-1,1-dioxidotetrahydro-2H-thiopyran-4-yl)-2-oxo-2,3-dihydro-1H-benzo[d]imidazole-5-carboxamide,
1-(3-carbamoylphenyl)-3-isopropyl-N-(4-methyl-1,1-dioxidotetrahydro-2H-thiopyran-4-yl)-2-oxo-2,3-dihydro-1H-benzo[d]imidazole-5-carboxamide,
3-isopropyl-N-(4-methyl-1,1-dioxidotetrahydro-2H-thiopyran-4-yl)-1-(3-(methylthio)phenyl)-2-oxo-2,3-dihydro-1H-benzo[d]imidazole-5-carboxamide, 3-isopropyl-N-(4-methyl-1,1-dioxidotetrahydro-2H-thiopyran-4-yl)-1-(3-(N-methylsulfamoyl)phenyl)-2-oxo-2,3-dihydro-1H-benzo[d]imidazole-5-carboxamide, 3-isopropyl-N-(4-methyl-1,1-dioxidotetrahydro-2H-thiopyran-4-yl)-1-(3-(methylsulfonyl)phenyl)-2-oxo-2,3-dihydro-1H-benzo[d]imidazole-5-carboxamide, 1-(3-(difluoromethoxy)phenyl)-3-(4-fluorobenzyl)-N-(4-methyl-1,1-dioxidotetrahydro-2H-thiopyran-4-yl)-2-oxo-2,3-dihydro-1H-benzo[d]imidazole-5-carboxamide, 1-(3-(difluoromethoxy)phenyl)-3-methyl-N-(3-methyl-1,1-dioxidothietan-3-yl)-2-oxo-2,3-dihydro-1H-benzo[d]imidazole-5-carboxamide, 1-(3-(difluoromethoxy)phenyl)-3-isopropyl-N-(5-methyl-1,3,4-thiadiazol-2-yl)-2-oxo-2,3-dihydro-1H-benzo[d]imidazole-5-carboxamide, 1-(3-(difluoromethoxy)phenyl)-N-((3-hydroxytetrahydrofuran-3-yl)methyl)-3-isopropyl-2-oxo-2,3-dihydro-1H-benzo[d]imidazole-5-carboxamide, 1-(3-(difluoromethoxy)phenyl)-N-((1-ethyl-1H-pyrazol-4-yl)methyl)-3-isopropyl-2-oxo-2,3-dihydro-1H-benzo[d]imidazole-5-carboxamide, (R)-3-(1-amino-1-oxopropan-2-yl)-1-(3-(difluoromethoxy)phenyl)-N-(4-methyl-1,1-dioxidotetrahydro-2H-thiopyran-4-yl)-2-oxo-2,3-dihydro-1H-benzo[d]imidazole-5-carboxamide, (S)-3-(1-amino-1-oxopropan-2-yl)-1-(3-(difluoromethoxy)phenyl)-N-(4-methyl-1,1-dioxidotetrahydro-2H-thiopyran-4-yl)-2-oxo-2,3-dihydro-1H-benzo[d]imidazole-5-carboxamide, or 1-(3-(difluoromethoxy)phenyl)-N-(4-methyl-1,1-dioxidotetrahydro-2H-thiopyran-4-yl)-2-oxo-3-(phenylsulfonyl)-2,3-dihydro-1H-benzo[d]imidazole-5-carboxamide.

The present invention includes the pharmaceutically acceptable salts of the compounds defined therein.

In one embodiment, the present invention is a composition comprising a therapeutically effective amount of at least one compound of formula I, or a pharmaceutically acceptable salt thereof.

The invention also provides a pharmaceutical composition comprising a therapeutically effective amount of at least one compound of Formula I, or a pharmaceutically acceptable salt thereof, and a pharmaceutically acceptable carrier.

The invention also provides a pharmaceutical composition comprising a therapeutically effective amount of at least one compound of formula I, or a pharmaceutically acceptable salt thereof, and a therapeutically effective amount of at least one other pharmaceutically active ingredient (such as, for example, a chemotherapeutic agent).

The invention also provides a pharmaceutical composition comprising a therapeutically effective amount of at least one compound of formula I, or a pharmaceutically acceptable salt thereof, and a therapeutically effective amount of at least one other pharmaceutically active ingredient (such as, for example, a chemotherapeutic agent), and a pharmaceutically acceptable carrier.

In one embodiment, the present invention provides a composition for treating hepatic steatosis, nonalcoholic steatohepatitis (NASH), fibrosis, type-2 diabetes mellitus, obesity, hyperlipidemia, hypercholesterolemia, atherosclerosis, cognitive decline, dementia, cardiorenal diseases such as chronic kidney diseases or heart failure comprising an acceptable carrier and a compound of formula I or a pharmaceutically acceptable salt thereof.

In one embodiment, the present invention provides a composition for treating hepatic steatosis, nonalcoholic steatohepatitis (NASH), fibrosis, type-2 diabetes mellitus, obesity, hyperlipidemia, hypercholesterolemia, atherosclerosis, cognitive decline, dementia, cardiorenal diseases such as chronic kidney diseases or heart failure, comprising a compound of formula I, or a pharmaceutically acceptable salt thereof.

In one embodiment, the present invention provides a composition for treating hepatic steatosis, nonalcoholic steatohepatitis (NASH), fibrosis, type-2 diabetes mellitus, obesity, hyperlipidemia, hypercholesterolemia, atherosclerosis, cognitive decline, dementia, cardiorenal diseases such as chronic kidney diseases or heart failure, comprising a compound of formula I, or a pharmaceutically acceptable salt thereof, and a pharmaceutically acceptable carrier.

In one embodiment, the present invention provides a method of treating hepatic steatosis, nonalcoholic steatohepatitis (NASH), fibrosis, type-2 diabetes mellitus, obesity, hyperlipidemia, hypercholesterolemia, atherosclerosis, cognitive decline, dementia, cardiorenal diseases such as chronic kidney diseases or heart failure in a subject in need of such treatment, comprising a administering to said subject a therapeutically effective amount of at least one compound of formula I, or a pharmaceutically acceptable salt thereof.

In one embodiment, the present invention provides a method of treating hepatic steatosis, nonalcoholic steatohepatitis (NASH), fibrosis, type-2 diabetes mellitus, obesity, hyperlipidemia, hypercholesterolemia, atherosclerosis, cognitive decline, dementia, cardiorenal diseases such as chronic kidney diseases or heart failure in a patient in need thereof, comprising administering to said patient a therapeutically effective amount of at least one compound of formula I, or a pharmaceutically acceptable salt thereof, and a pharmaceutically acceptable carrier.

The methods of the invention include the administration of a pharmaceutical composition comprising at least one compound of the invention, or a pharmaceutically acceptable salt thereof, and a pharmaceutically acceptable carrier.

In another embodiment, the present invention includes a method of treating NASH and/or fibrosis, comprising administering to a patient in need thereof a compound of formula I, or a pharmaceutically acceptable salt thereof.

In another embodiment, the present invention includes a method of treating NASH and/or fibrosis, comprising administering to a patient in need thereof a compound of formula I, or a pharmaceutically acceptable salt thereof, and a pharmaceutically acceptable carrier.

In another embodiment, the present invention includes a method of treating NASH and/or fibrosis, comprising administering to a patient in need thereof a composition comprising a compound of formula I, or a pharmaceutically acceptable salt thereof.

In another embodiment, the present invention includes a method of treating NASH and/or fibrosis, comprising administering to a patient in need thereof a composition comprising a compound of formula I, or a pharmaceutically acceptable salt thereof, and a pharmaceutically acceptable carrier.

In another embodiment, the present invention provides for the use of a compound of formula I, or a pharmaceutically acceptable salt thereof, in the manufacture of a medicament for treating NASH and/or fibrosis, In another embodiment, the present invention includes the use of a compound of formula I, or a pharmaceutically acceptable salt thereof, for the preparation of a medicament for the treatment of NASH and/or fibrosis, "Alkyl" means branched- and straight-chain saturated aliphatic hydrocarbon groups having the specified number of carbon atoms when noted. If no number is specified, 1-6 carbon atoms are intended for linear and 3-7 carbon atoms for branched alkyl groups. Examples of alkyl groups include methyl, ethyl, propyl, isopropyl, cyclopropyl, butyl, sec- and tert-butyl, pentyl, hexyl, octyl, nonyl, and the like. For example, the term "$C_{1-6}$alkyl" includes all of "$C_{1-4}$alkyl" defined as follows, plus the linear or branched chain alkyl groups, including all possible isomers, having 5 or 6 carbon atoms. "$C_{1-6}$alkyl" means linear or branched chain alkyl groups, including all possible isomers, having 1, 2, 3, 4, 5 or 6 carbon atoms, and includes each of the alkyl groups within $C_{1-6}$alkyl including each of the hexyl and pentyl isomers as well as n-, iso-, sec- and tert-butyl (butyl, i-butyl, s-butyl, t-butyl, collectively "$C_4$alkyl"; Bu=butyl), n- and i-propyl (propyl, i-propyl, collectively "$C_3$alkyl"; Pr=propyl), ethyl (Et) and methyl (Me). Commonly used abbreviations for alkyl groups are used throughout the specification, e.g. methyl may be represented by conventional abbreviations including "Me" or $CH_3$ or a symbol that is an extended bond as the terminal group, e.g.

ethyl may be represented by "Et" or $CH_2CH_3$, propyl may be represented by "Pr" or $CH_2CH_2CH_3$, butyl may be represented by "Bu" or $CH_2CH_2CH_2CH_3$, etc. For example, the structures

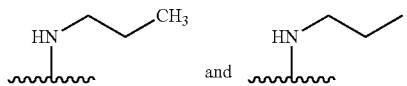

have equivalent meanings. $C_{1-6}$ alkyl includes n-, iso-, sec- and t-butyl, n- and isopropyl, ethyl and methyl. If no number is specified, 1-6 carbon atoms are intended for linear or branched alkyl groups.

"Alkoxy" refers to an alkyl group linked to oxygen. Examples of alkoxy groups include methoxy, ethoxy, propoxy and the like.

"Aryl" refers to an aromatic monocyclic or multicyclic ring moiety comprising 6 to 14 ring carbon atoms. In one embodiment, an aryl group contains from about 6 to 10 ring carbon atoms. Monocyclic aryl rings include, but are not limited to, phenyl. Multicyclic rings include, but are not limited to, naphthyl and bicyclic rings wherein phenyl is fused to a $C_{5-7}$cycloalkyl or $C_{5-7}$cycloalkenyl ring. Aryl groups may be optionally substituted with one or more substituents as defined herein. Bonding can be through any of the carbon atoms of any ring.

"Fused Aryl" refers to an aryl ring fused with heterocyclyl or cycloalkyl.

"Halogen" or "Halo" includes fluorine, chlorine, bromine and iodine.

"Cycloalkyl" refers to a non-aromatic mono- or multicyclic ring system comprising about 3 to 10 ring carbon atoms. If no number of atoms is specified, 3-10 carbon atoms are intended. Cycloalkyl may also be fused, forming 1-3 carbocyclic rings. Non-limiting examples of monocyclic cycloalkyls include cyclopropyl, cyclobutyl, cyclopentyl, cyclohexyl, cycloheptyl and cyclooctyl. A cycloalkyl group is unsubstituted or substituted with one or more ring system substituents which may be the same or different, and are as defined within. The term "$C_{3-6}$cycloalkyl" refers to a cycloalkyl group having 3 to 6 ring carbon atoms. Thus, for example, "$C_{3-6}$ cycloalkyl" includes each of cyclopropyl, cyclobutyl, cyclopentyl, and cyclohexyl. When cycloalkyl is a substituent on an alkyl group, the cycloalkyl substituent can be bonded to any available carbon in the alkyl group. The following are illustrations of —$C_{3-6}$cycloalkyl substituents on an alkyl group wherein the substituent is cyclopropyl in bold:

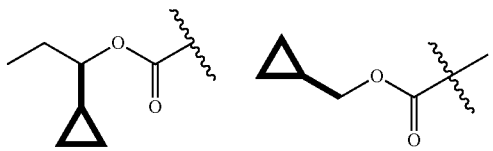

"Haloalkyl" refers to an alkyl group as defined within, wherein one or more of the alkyl group's hydrogen atoms has been replaced with a halogen. In one embodiment, a haloalkyl group has from 1 to 6 carbon atoms. Non-limiting examples of haloalkyl groups include $CH_2F$, $CHF_2$, $CF_3$, $CH_2CF_3$, $CH_2CHF_2$, $CF_2CF_3$, $CF_2CHF_2$, $CH_2Cl$ and $CCl_3$. The term "$C_{1-6}$haloalkyl" or "halo$C_{1-6}$alkyl" refers to a haloalkyl group having from 1 to 6 carbons.

"Haloalkoxy," "haloalkyl-O" and derivatives such as "halo($C_{1-6}$)alkoxy" are used interchangeably and refer to halo substituted alkyl groups linked through the oxygen atom. Haloalkoxy include mono-substituted as well as multiple halo substituted alkoxy groups. For example, trifluoromethoxy, chloromethoxy, and bromomethoxy are included as well as $OCH_2CF_3$, $OCH_2CHF_2$, $OCF_2CF_3$, and $OCF_2CHF_2$.

"Heterocyclyl," "heterocycle" or "heterocyclic" refers to monocyclic ring structures in which one or more atoms in the ring, the heteroatom(s), is an element other than carbon. Heteroatoms are typically O, S or N atoms. A heterocycle containing more than one heteroatom may contain different heteroatoms. Bicyclic ring moieties include fused, spirocyclic and bridged bicyclic rings and may comprise one or more heteroatoms in either of the rings. The ring attached to the remainder of the molecule may or may not contain a heteroatom. Either ring of a bicyclic heterocycle may be saturated, partially unsaturated or unsaturated. The heterocycle may be attached to the rest of the molecule via a ring carbon atom, a ring oxygen atom or a ring nitrogen atom. Examples of heterocyclyl groups include: piperidine, piperazine, morpholine, pyrrolidine, tetrahydrofuran, azetidine, oxirane, or aziridine, and the like.

"Bicyclic heterocyclyl," "bicyclic heterocycle" or "bicyclic heterocyclic" refers to a heterocyclic ring fused to another ring system. The fusion may be bridged or unbridged.

Except where noted, the term "Heteroaryl", as used herein, represents a stable monocyclic, bicyclic or tricyclic ring of up to 10 atoms in each ring, wherein at least one ring is aromatic and contains from 1 to 4 heteroatoms selected from the group consisting of O, N and S. Heteroaryl groups within the scope of this definition include but are not limited to: benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, pyranyl, pyrazinyl, pyrazolyl, pyridazinyl, pyridopyridinyl, pyridyl, pyrimidinyl, pyrrolyl, quinazolinyl, quinolyl, quinoxalinyl, tetrazolyl, tetrazolopyridyl, thiadiazolyl, thiazolyl, thienyl, triazolyl, dihydrobenzoimidazolyl, dihydrobenzofuranyl, dihydrobenzothiophenyl, dihydrobenzoxazolyl, dihydroindolyl, dihydroquinolinyl, methylenedioxybenzene, benzothiazolyl, benzothienyl, quinolinyl, isoquinolinyl, oxazolyl, and tetra-hydroquinoline.

"Fused heteroaryl" is heteroaryl fused with an aryl or heteroaryl.

"Oxo" means an oxygen linked to an atom by a double bond. An example of an oxo group is a doubly bonded oxygen in a ketone, sulfoxide, sulfone and sulfate.

"Hydroxyalkyl" or "hydroxy($C_{1-3}$)alkyl" means an alkyl group having one or more hydrogen atoms replaced by hydroxyl (—OH) groups "Cyanoalkyl" means an alkyl group having one or more hydrogen atoms replaced by cyano (—CN) groups.

"Hydroxyhaloalkyl" means an alkyl group having one or more hydrogen atoms replaced by hydroxyl (—OH) groups, and one or more hydrogen atoms replaced by a halogen.

"Hydroxycycloalkyl" means a cyclic alkyl group having one or more hydrogen atoms replaced by hydroxyl (—OH) groups.

The term "composition" is intended to encompass a product comprising the specified ingredients in the specified amounts, as well as any product which results, directly or indirectly, from combination of the specified ingredients in the specified amounts.

The term "at least one" means one or more than one. The meaning of "at least one" with reference to the number of compounds of the invention is independent of the meaning with reference to the number of chemotherapeutic agents.

The term "chemotherapeutic agent" means a drug (medicament or pharmaceutically active ingredient) for treating cancer (i.e., an antineoplastic agent).

The term "effective amount" means a "therapeutically effective amount". The term "therapeutically effective amount" means that amount of active compound or pharmaceutical agent that elicits the biological or medicinal response in a tissue, system, animal or human that is being sought by a researcher, veterinarian, medical doctor or other clinician.

The term "treating cancer" or "treatment of cancer" refers to administration to a mammal afflicted with a cancerous condition and refers to an effect that alleviates the cancerous condition by killing the cancerous cells, and also refers to an effect that results in the inhibition of growth and/or metastasis of the cancer.

Except where noted herein, the term "carbocycle" (and variations thereof such as "carbocyclic" or "carbocyclyl") as used herein, unless otherwise indicated, refers to a $C_3$ to $C_6$ monocyclic ring, e.g., $C_{3-6}$ monocyclic carbocycle. The carbocycle may be attached to the rest of the molecule at any carbon atom which results in a stable compound. Saturated carbocyclic rings include, for example, "cycloalkyl" rings, e.g., cyclopropyl, cyclobutyl, etc. Unsaturated carbocyclic rings include, for example

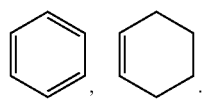

Except where noted, the term "saturated heterocycle" refers to a stable 4- to 7-membered mono-cyclic heteroatom-containing ring system, and which consists of carbon atoms and from one to four heteroatoms independently selected from the group consisting of N, O and S, and wherein the nitrogen and sulfur heteroatoms may optionally be oxidized, and the nitrogen heteroatom may optionally be quaternized. Especially useful are rings containing one oxygen or sulfur, one to four nitrogen atoms, or one oxygen or sulfur combined with one or two nitrogen atoms. The heterocyclic ring may be attached at any heteroatom or carbon atom which results in the creation of a stable structure. Representative examples include azetidine, oxetane, thietane, diazetidine, dioxetane, dithietane, pyrrolidine, tetrahydrofuran, thiolane, imidazolidine, pyrazolidine, oxazolidine, isoxazolidine, thiazolidine, isothiazolidine, dioxolane, dithiolane, piperidine, oxane, thiane, piperazine, morpholine, thiomorpholine, dioxane, dithiane, trioxane, trithiane, azepane, oxepane, thiepane and homopiperazine. For example, a "saturated 6 membered heterocycle" is a stable 6-membered mono-cyclic heteroatom-containing ring system. An example of a saturated 6 membered heterocycle is piperidine. Likewise, but not limiting, a "saturated 4 membered heterocycle" is a stable 4-membered mono-cyclic heteroatom-containing ring system.

Except where noted herein, the term "unsaturated heterocycle" refers to a monocyclic unsaturated heterocycle having a specified number of atom members (e.g., 5 membered), including a specified number of heteroatoms (e.g., 1, 2, 3 or 4 heteroatoms independently selected from N, O or S), e.g., 5-membered rings containing one nitrogen (pyrrole), one oxygen (furan) or one sulfur (thiophene) atom, 5-membered rings containing one nitrogen and one sulfur (thiazole) atom, 5-membered rings containing one nitrogen and one oxygen (oxazole or isoxazole) atom, 5-membered rings containing two nitrogen (imidazole or pyrazole) atoms, five-membered aromatic rings containing three nitrogen (triazole) atoms, five-membered aromatic rings containing one oxygen, one nitrogen or one sulfur atom, five-membered aromatic rings containing two heteroatoms independently selected from oxygen, nitrogen and sulfur (e.g., oxazole), Additional examples are thiophene, imidazole, isothiazole, oxadiazole, and isoxazole. For example, a "unsaturated 6 membered heterocycle" is a 6 membered ring containing 6 atom members including at least one heteroatom. Likewise, an "unsaturated 5 membered heterocycle" is a 5 membered ring containing 5 atom members including at least one heteroatom.

A "stable" compound is a compound which can be prepared and isolated and whose structure and properties remain or can be caused to remain essentially unchanged for a period of time sufficient to allow use of the compound for the purposes described herein (e.g., therapeutic or prophylactic administration to a subject).

The compounds of the present disclosure are limited to stable compounds embraced by Formula I and its embodiments. For example, certain moieties as defined in Formula I, may be unsubstituted or substituted, and the latter is intended to encompass substitution patterns (i.e., number and kind of substituents) that are chemically possible for the moiety and that result in a stable compound.

The term "substituted" means that one or more hydrogens on the designated atom is replaced with a selected from the indicated group, provided that the designated atom's normal valency under the existing circumstances is not exceeded, and that the substitution results in a stable compound. Where multiple substituent moieties are disclosed or claimed, the substituted compound can be independently substituted by one or more of the disclosed or claimed substituent moieties, singly or plurally. By independently substituted, it is meant that the (two or more) substituents can be the same or different. Combinations of substituents and/or variables are permissible only if such combinations result in stable compounds. If a substituent is itself substituted with more than one group, it is understood that these multiple groups may be on the same carbon or on different carbons, so long as a stable structure result. By optionally substituted, it is meant that compounds containing the specified optional substituent(s) as well as compounds that do not contain the optional substituent(s).

The wavy line , as used herein, indicates a point of attachment to the rest of the compound.

Where ring atoms are represented by variables such as "X", e.g.,

the variables are defined by indicating the atom located at the variable ring position without depicting the ring bonds associated with the atom. For example, when X in the above ring is nitrogen, the definition will show "N" and will not depict the bonds associated with it, e.g., will not show "=N—". Likewise, when X is a carbon atom that is substituted with bromide, the definition will show "C—Br" and will not depict the bonds associated with it, e.g., will not show

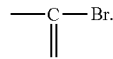

The invention also includes derivatives of the compound of formula I, acting as prodrugs and solvates. Any pharmaceutically acceptable pro-drug modification of a compound of the invention which results in conversion in vivo to a compound within the scope of the invention is also within the scope of the invention. Prodrugs, following administration to the patient, are converted in the body by normal metabolic or chemical processes, such as through hydrolysis in the blood, to the compound of formula I. Such prodrugs include those that demonstrate enhanced bioavailability, tissue specificity, and/or cellular delivery, to improve drug absorption of the compound of I. The effect of such prodrugs may result from modification of physicochemical properties such as lipophilicity, molecular weight, charge, and other physicochemical properties that determine the permeation properties of the drug.

For example, esters can optionally be made by esterification of an available carboxylic acid group or by formation of an ester on an available hydroxy group in a compound. Similarly, labile amides can be made. Pharmaceutically acceptable esters or amides of the compounds of the invention may be prepared to act as pro-drugs which can be hydrolyzed back to an acid (or —COO— depending on the pH of the fluid or tissue where conversion takes place) or hydroxy form particularly in vivo and as such are encompassed within the scope of the invention. Included are those esters and acyl groups known in the art for modifying the solubility or hydrolysis characteristics for use as sustained-release or prodrug formulations. Examples of pharmaceutically acceptable pro-drug modifications include, but are not limited to, —$C_{1-6}$alkyl esters and —$C_{1-6}$alkyl substituted with phenyl esters.

"Celite®" (Fluka) diatomite is diatomaceous earth, and can be referred to as "celite". When any variable (e.g., $R^1$ etc.) occurs more than one time in any constituent or in Formula I or other generic Formula herein, its definition on each occurrence is independent of its definition at every other occurrence. Combinations of substituents and/or variables are permissible only if such combinations result in stable compounds. In choosing compounds of the present invention, one of ordinary skill in the art will recognize that the various substituents, i.e. $R^1$ etc., are to be chosen in conformity with well-known principles of chemical structure connectivity and stability. Unless expressly stated to the contrary, substitution by a named substituent is permitted on any atom in a ring (e.g., aryl, a heteroaryl ring, or a saturated heterocyclic ring) provided such ring substitution is chemically allowed and results in a stable compound.

It should be noted that, if a discrepancy between the chemical name and structure exists, the structure is understood to dominate.

Compounds of structural Formula I may contain one or more asymmetric centers and can thus occur as racemates and racemic mixtures, single enantiomers, diastereoisomeric mixtures and individual diastereoisomers. Centers of asymmetry that are present in the compounds of Formula I can all independently of one another have S configuration or R configuration. When bonds to the chiral carbon are depicted as straight lines in the structural Formula of the invention, it is understood that both the (R) and (S) configurations of the chiral carbon, and hence both enantiomers and mixtures thereof, are embraced within the Formula. Similarly, when a compound name is recited without a chiral designation for a chiral carbon, it is understood that both the (R) and (S) configurations of the chiral carbon, and hence individual enantiomers and mixtures thereof, are embraced by the name. The production of specific stereoisomers or mixtures thereof may be identified in the Examples where such stereoisomers or mixtures were obtained, but this in no way limits the inclusion of all stereoisomers and mixtures thereof from being within the scope of the invention.

The compounds of this invention include all possible enantiomers and diastereomers and mixtures of two or more stereoisomers, for example mixtures of enantiomers and/or diastereomers, in all ratios. Thus, enantiomers are a subject of the invention in enantiomerically pure form, both as levorotatory and as dextrorotatory antipodes, in the form of racemates and in the form of mixtures of the two enantiomers in all ratios. In the case of a cis/trans isomerism the invention includes both the cis form and the trans form as well as mixtures of these forms in all ratios. The present invention is meant to comprehend all such stereo-isomeric forms of the compounds of structural Formula I.

Compounds of structural Formula I may be separated into their individual diastereoisomers by, for example, fractional crystallization from a suitable solvent, for example MeOH or EtOAc or a mixture thereof, or via chiral chromatography using an optically active stationary phase. Optionally a derivatization can be carried out before a separation of stereoisomers. The separation of a mixture of stereoisomers can be carried out at an intermediate step during the synthesis of a compound of formula I, or it can be done on a final racemic product. Absolute stereochemistry may be determined by X-ray crystallography of crystalline products or crystalline intermediates which are derivatized, if necessary, with a reagent containing an asymmetric center of known absolute configuration. Alternatively, any stereoisomer or isomers of a compound of Formula I may be obtained by stereospecific synthesis using optically pure starting materials or reagents of known absolute configuration. The present invention includes all such isomers, as well as salts, solvates (including hydrates) and solvated salts of such racemates, enantiomers, diastereomers and tautomers and mixtures thereof.

If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereoisomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art.

For compounds of Formula I described herein which contain olefinic double bonds, unless specified otherwise, they are meant to include both E and Z geometric isomers.

Some of the compounds described herein may exist as tautomers which have different points of attachment of hydrogen accompanied by one or more double bond shifts. For example, a ketone and its enol form are keto-enol tautomers. The individual tautomers as well as mixtures thereof are encompassed with compounds of Formula I of the present invention.

In the compounds of structural Formula I, the atoms may exhibit their natural isotopic abundances, or one or more of the atoms may be artificially enriched in a particular isotope having the same atomic number, but an atomic mass or mass number different from the atomic mass or mass number predominately found in nature. The present invention as described and claimed herein is meant to include all suitable isotopic variations of the compounds of structural Formula I and embodiments thereof. For example, different isotopic forms of hydrogen (H) include protium ($^1$H) and deuterium ($^2$H, also denoted herein as D). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within structural Formula I, can be prepared without undue experimentation by conventional techniques well known to those skilled in the art or by processes analogous to those described in the Schemes and Examples herein using appropriate isotopically-enriched reagents and/or intermediates.

It will be understood that the compounds of structural Formula I may be prepared as pharmaceutically acceptable salts or as salts that are not pharmaceutically acceptable when they are used as precursors to the free compounds or their pharmaceutically acceptable salts or in other synthetic manipulations. The compounds of the present invention, including the compounds of the Examples, may also include all salts of the compounds of Formula I which, owing to low physiological compatibility, are not directly suitable for use in pharmaceuticals but which can be used, for example, as intermediates for chemical reactions or for the preparation of physiologically acceptable salts.

The compounds of the present invention may be administered in the form of a pharmaceutically acceptable salt. The term "pharmaceutically acceptable salt" refers to salts prepared from pharmaceutically acceptable non-toxic bases or acids including inorganic or organic bases and inorganic or organic acids.

Salts of basic compounds encompassed within the term "pharmaceutically acceptable salt" refer to non-toxic salts of the compounds of this invention which are generally prepared by reacting the free base with a suitable organic or inorganic acid. Representative salts of basic compounds of the present invention include, but are not limited to, the following: acetate, ascorbate, benzenesulfonate, benzoate, bicarbonate, bisulfate, bitartrate, borate, bromide, butyrate, camphorate, camphorsulfonate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, methanesulfonate, mucate, napsylate, nitrate, N-methylglucamine ammonium salt, oleate, oxalate, pamoate (embonate), palmitate, pantothenate, phosphate/diphosphate, polygalacturonate, propionate, salicylate, stearate, sulfate, subacetate, succinate, tannate, tartrate, teoclate, thiocyanate, tosylate, triethiodide, valerate and the like. Furthermore, where the compounds of the invention carry an acidic moiety, suitable pharmaceutically acceptable salts thereof include, but are not limited to, salts derived from inorganic bases including aluminum, ammonium, calcium, copper, ferric, ferrous, lithium, magnesium, manganic, mangamous, potassium, sodium, zinc, and the like. In one embodiment, the salts of acidic compounds are as follows, the ammonium, calcium, magnesium, potassium, and sodium salts.

With basic reagents such as hydroxides, carbonates, hydrogencarbonates, alkoxides and ammonia, organic bases or alternatively basic amino acids the compounds of the formula I, form stable alkali metal, alkaline earth metal or optionally substituted ammonium salts.

Salts derived from pharmaceutically acceptable organic non-toxic bases include salts of primary, secondary, and tertiary amines, cyclic amines, dicyclohexyl amines and basic ion-exchange resins, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. Also, included are the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others.

The preparation of pharmacologically acceptable salts from compounds of the formula I, capable of salt formation, including their stereoisomeric forms is carried out known methods, for example, by mixing a compound of the present invention with an equivalent amount and a solution containing a desired acid, base, or the like, and then collecting the desired salt by filtering the salt or distilling off the solvent. The compounds of the present invention and salts thereof may form solvates with a solvent such as water, ethanol, or glycerol. The compounds of the present invention may form an acid addition salt and a salt with a base at the same time according to the type of substituent of the side chain.

If the compounds of Formula I simultaneously contain acidic and basic groups in the molecule the invention also includes, in addition to the salt forms mentioned, inner salts or betaines (zwitterions). Salts can be obtained from the compounds of Formula I by customary methods which are known to the person skilled in the art, for example by combination with an organic or inorganic acid or base in a solvent or dispersant, or by anion exchange or cation exchange from other salts.

The present invention includes compounds of structural formula I, as well as salts thereof, particularly pharmaceutically acceptable salts, solvates of such compounds and solvated salt forms thereof, where such forms are possible unless specified otherwise.

Furthermore, compounds of the present invention may exist in amorphous form and/or one or more crystalline forms, and as such all amorphous and crystalline forms and mixtures thereof of the compounds of Formula I, including the Examples, are intended to be included within the scope of the present invention. In addition, some of the compounds of the instant invention may form solvates with water (i.e., a hydrate) or common organic solvents such as but not limited to EtOAc. Such solvates and hydrates, particularly the pharmaceutically acceptable solvates and hydrates, of the instant compounds are likewise encompassed within the scope of this invention, along with un-solvated and anhydrous forms.

Accordingly, the compounds within the generic structural Formula, embodiments and specific compounds described in the Examples and claimed herein encompass salts, all possible stereoisomers and tautomers, physical forms (e.g., amorphous and crystalline forms), solvate and hydrate forms thereof and any combination of these forms, as well as the salts, pro-drug forms thereof, and salts of pro-drug forms thereof, where such forms are possible unless specified otherwise.

The invention also relates to medicaments containing at least one compound of the Formula I and/or of a pharmaceutically acceptable salt of the compound of the Formula I and/or an optionally stereoisomeric form of the compound of the Formula I or a pharmaceutically acceptable salt of the stereoisomeric form of the compound of Formula I, together with a pharmaceutically acceptable vehicle, carrier, additive and/or other active substances and auxiliaries.

The medicaments according to the invention can be administered by oral, inhalative, rectal or transdermal administration or by subcutaneous, intraarticular, intraperitoneal or intravenous injection. Oral administration is preferred. Coating of stents with compounds of the Formula I and other surfaces which come into contact with blood in the body is possible.

The invention also relates to a process for the production of a medicament, which comprises bringing at least one compound of the Formula I into a suitable administration form using a pharmaceutically acceptable carrier and optionally further suitable active substances, additives or auxiliaries.

The present invention also relates to processes for the preparation of the compounds of Formula I which are described in the following and by which the compounds of the invention are obtainable.

The terms "therapeutically effective (or efficacious) amount" and similar descriptions such as "an amount efficacious for treatment" are intended to mean that amount of a pharmaceutical drug that will alleviate the symptoms of the disorder, condition or disease being treated (i.e., disorder, condition or disease associated with DGAT2 activity) in an animal or human. The terms "prophylactically effective (or efficacious) amount" and similar descriptions such as "an amount efficacious for prevention" are intended to mean that amount of a pharmaceutical drug that will prevent or reduce the symptoms or occurrence of the disorder, condition or disease being treated (i.e., disorder, condition or disease associated with DGAT2 activity) in an animal or human. The dosage regimen utilizing a compound of the instant invention is selected in accordance with a variety of factors including type, species, age, weight, sex and medical condition of the patient; the severity of the condition to be treated; the potency of the compound chosen to be administered; the route of administration; and the renal and hepatic function of the patient. A consideration of these factors is well within the purview of the ordinarily skilled clinician for the purpose of determining the therapeutically effective or prophylactically effective dosage amount needed to prevent, counter, or arrest the progress of the condition. It is understood that a specific daily dosage amount can simultaneously be both a therapeutically effective amount, e.g., for treatment of hepatic steatosis, diabetes mellitus, obesity, hyperlipidemia, hypercholesterolemia, and a prophylactically effective amount, e.g., for treatment of NASH.

Disorders, conditions and diseases which can be treated or prevented by inhibiting DGAT2 by using the compounds of Formula I are, for example, diseases such as non-alcoholic steatohepatitis (NASH), fibrosis, hyperlipidemia, type I diabetes, type II diabetes mellitus, cognitive decline, dementia, coronary heart disease, ischemic stroke, restenosis, peripheral vascular disease, intermittent claudication, myocardial infarction, dyslipidemia, post-prandial lipemia, obesity, osteoporosis, hypertension, congestive heart failure, left ventricular hypertrophy, peripheral arterial disease, diabetic retinopathy, diabetic nephropathy, glomerulosclerosis, chronic renal failure, diabetic neuropathy, metabolic syndrome, syndrome X, coronary heart disease, angina pectoris, thrombosis, atherosclerosis, myocardial infarction, transient ischemic attacks, stroke, hyperglycemia, hyperinsulinemia, hypertriglyceridemia, hypertriglyceridemia, insulin resistance, impaired glucose tolerance, erectile dysfunction, skin and connective tissue disorders, hyper-apo B lipoproteinemia, non-alcoholic fatty liver disease, cardiorenal diseases such as chronic kidney diseases and heart failure, and related diseases and conditions.

The compounds of Formula I and their pharmaceutically acceptable salts can be administered to animals, preferably to mammals, and in particular to humans, as pharmaceuticals by themselves, in mixtures with one another or in the form of pharmaceutical preparations. The term "patient" includes animals, preferably mammals and especially humans, who use the instant active agents for the prevention or treatment of a medical condition. Administering of the drug to the patient includes both self-administration and administration to the patient by another person. The patient may need, or desire, treatment for an existing disease or medical condition, or may be in need of or desire prophylactic treatment to prevent or reduce the risk of occurrence of said disease or medical condition. As used herein, a patient "in need" of treatment of an existing condition or of prophylactic treatment encompasses both a determination of need by a medical professional as well as the desire of a patient for such treatment.

Furthermore, a subject of the present invention are pharmaceutical preparations (or pharmaceutical compositions) which comprise as active component a therapeutically effective dose of at least one compound of Formula I and/or a pharmaceutically acceptable salt thereof and a customary pharmaceutically acceptable carrier, i.e., one or more pharmaceutically acceptable carrier substances and/or additives.

Thus, a subject of the invention is, for example, said compound and its pharmaceutically acceptable salts for use as a pharmaceutical, pharmaceutical preparations which comprise as active component a therapeutically effective dose of said compound and/or a pharmaceutically acceptable salt thereof and a customary pharmaceutically acceptable carrier, and the uses of said compound and/or a pharmaceutically acceptable salt thereof in the therapy or prophylaxis of the above mentioned syndromes as well as their use for preparing medicaments for these purposes.

The pharmaceuticals according to the invention can be administered orally, for example in the form of pills, tablets, lacquered tablets, sugar-coated tablets, granules, hard and soft gelatin capsules, aqueous, alcoholic or oily solutions, syrups, emulsions or suspensions, or rectally, for example in the form of suppositories. Administration can also be carried out parenterally, for example subcutaneously, intramuscularly or intravenously in the form of solutions for injection or infusion. Other suitable administration forms are, for example, percutaneous or topical administration, for example in the form of ointments, tinctures, sprays or transdermal therapeutic systems, or the inhalative administration in the form of nasal sprays or aerosol mixtures, or, for example, microcapsules, implants or rods. The preferred administration form depends, for example, on the disease to be treated and on its severity.

For the production of pills, tablets, sugar-coated tablets and hard gelatin capsules it is possible to use, for example, lactose, starch, for example maize starch, or starch derivatives, talc, stearic acid or its salts, etc. Carriers for soft gelatin capsules and suppositories are, for example, fats, waxes, semisolid and liquid polyols, natural or hardened oils, etc. Suitable carriers for the preparation of solutions, for example of solutions for injection, or of emulsions or syrups are, for example, water, physiologically sodium chloride solution, alcohols such as ethanol, glycerol, polyols, sucrose, invert sugar, glucose, mannitol, vegetable oils, etc. It is also possible to lyophilize the compounds of Formula I and their pharmaceutically acceptable salts and to use the resulting lyophilisates, for example, for preparing preparations for injection or infusion. Suitable carriers for microcapsules, implants or rods are, for example, copolymers of glycolic acid and lactic acid.

Suitable solid or galenical preparation forms are, for example, granules, powders, coated tablets, tablets, (micro) capsules, suppositories, syrups, juices, suspensions, emulsions, drops or injectable solutions and preparations having prolonged release of active substance, in whose preparation customary excipients such as vehicles, disintegrants, binders, coating agents, swelling agents, glidants or lubricants, flavorings, sweeteners and solubilizers are used. Frequently used auxiliaries which may be mentioned are magnesium carbonate, titanium dioxide, lactose, mannitol and other sugars, talc, lactose, gelatin, starch, cellulose and its derivatives, animal and plant oils such as cod liver oil, sunflower, peanut or sesame oil, polyethylene glycol and solvents such as, for example, sterile water and mono- or polyhydric alcohols such as glycerol.

Besides the active compounds and carriers, the pharmaceutical preparations can also contain customary additives, for example fillers, disintegrants, binders, lubricants, wetting agents, stabilizers, emulsifiers, dispersants, preservatives, sweeteners, colorants, flavorings, aromatizers, thickeners, diluents, buffer substances, solvents, solubilizers, agents for achieving a depot effect, salts for altering the osmotic pressure, coating agents or antioxidants.

The dosage of the active compound of Formula I and/or of a pharmaceutically acceptable salt thereof to be administered depends on the individual case and is, as is customary, to be adapted to the individual circumstances to achieve an optimum effect. Thus, it depends on the nature and the severity of the disorder, condition or disease to be treated, and also on the sex, age, weight and individual responsiveness of the human or animal to be treated, on the efficacy and duration of action of the compounds used, on whether the therapy is acute or chronic or prophylactic, or on whether other active compounds are administered in addition to compounds of Formula I.

Combination Agents

The compounds of the present invention can be administered alone or in combination with one or more additional therapeutic agents disclosed herein or other suitable agents, depending on the condition being treated. Hence, in some embodiments the one or more compounds of the invention will be co-administered with other agents as described above. When used in combination therapy, the compounds described herein are administered with the second agent simultaneously or separately. This administration in combination can include simultaneous administration of the two agents in the same dosage form, simultaneous administration in separate dosage forms, and separate administration. That is, a compound of Formula (I) and any of the agents described above can be formulated together in the same dosage form and administered simultaneously. Alternatively, a compound of Formula (I) and any of the agents described above can be simultaneously administered, wherein both the agents are present in separate formulations. In another alternative, a compound of Formula (I) can be administered just followed by and any of the agents described above, or vice versa. In some embodiments of the separate administration protocol, a compound of Formula (I) and any of the agents described above are administered a few minutes apart, or a few hours apart, or a few days apart.

As one aspect of the present invention contemplates the treatment of the disease/conditions with a combination of pharmaceutically active compounds that may be administered separately, the invention further relates to combining separate pharmaceutical compositions in kit form. The kit comprises two separate pharmaceutical compositions: a compound of Formula (I), and a second pharmaceutical compound. The kit comprises a container for containing the separate compositions such as a divided bottle or a divided foil packet. Additional examples of containers include syringes, boxes, and bags. In some embodiments, the kit comprises directions for the use of the separate components. The kit form is particularly advantageous when the separate components are preferably administered in different dosage forms (e.g., oral, parenteral; IV, transdermal and subcutaneous), are administered at different dosage intervals, or when titration of the individual components of the combination is desired by the prescribing health care professional.

One or more additional pharmacologically active agents may be administered in combination with a compound of Formula I. An additional active agent (or agents) is intended to mean a pharmaceutically active agent (or agents) that is active in the body, including pro-drugs that convert to pharmaceutically active form after administration, which are different from the compound of Formula I, and also includes free-acid, free-base and pharmaceutically acceptable salts of said additional active agents. Generally, any suitable additional active agent or agents, including but not limited to anti-hypertensive agents, anti-obetic, anti-inflammatory, anti-fibrotic, and anti-atherosclerotic agents such as a lipid modifying compound, anti-diabetic agents and/or anti-obesity agents may be used in any combination with the compound of Formula I in a single dosage formulation (a fixed dose drug combination), or may be administered to the patient in one or more separate dosage formulations which allows for concurrent or sequential administration of the active agents (co-administration of the separate active agents).

Examples of additional active agents which may be employed include but are not limited to angiotensin converting enzyme inhibitors (e.g., alacepril, benazepril, captopril, ceronapril, cilazapril, delapril, enalapril, enalaprilat, fosinopril, imidapril, lisinopril, moveltipril, perindopril, quinapril, ramipril, spirapril, temocapril, or trandolapril), angiotensin II receptor antagonists (e.g., losartan i.e., COZAAR®, valsartan, candesartan, olmesartan, telmesartan and any of these drugs used in combination with hydrochlorothiazide such as HYZAAR®); neutral endopeptidase inhibitors (e.g., thiorphan and phosphoramidon), aldosterone antagonists, aldosterone synthase inhibitors, renin inhibitors (e.g. urea derivatives of di- and tri-peptides, amino acids and derivatives, amino acid chains linked by non-peptidic bonds, di- and tri-peptide derivatives, peptidyl amino diols and peptidyl beta-aminoacyl aminodiol carbamates; also, and small molecule renin inhibitors including diol sulfonamides and, N-morpholino derivatives, N-heterocyclic alcohols and pyrolimidazolones; also, pepstatin derivatives and fluoro- and chloro-derivatives of statone-containing peptides, enalkrein, RO 42-5892, A 65317, CP 80794, ES 1005, ES 8891, SQ 34017, aliskiren (2(S),4(S),5(S),7(S)-N-(2-carbamoyl-2-methylpropyl)-5-amino-4-hydroxy-2,7-diisopropyl-8-[4-methoxy-3-(3-methoxypropoxy)-phenyl]-octanamid hemifumarate) SPP600, SPP630 and SPP635), endothelin receptor antagonists, phosphodiesterase-5 inhibitors (e.g. sildenafil, tadalfil and vardenafil), vasodilators, calcium channel blockers (e.g., amlodipine, nifedipine, veraparmil, diltiazem, gallopamil, niludipine, nimodipins, nicardipine), potassium channel activators (e.g., nicorandil, pinacidil, cromakalim, minoxidil, aprilkalim, loprazolam), diuretics (e.g., hydrochlorothiazide), sympatholitics, beta-adrenergic blocking drugs (e.g., propranolol, atenolol, bisoprolol, carvedilol, metoprolol, or metoprolol tartate), alpha adrenergic blocking drugs (e.g., doxazosin, prazosin or alpha methyldopa) central alpha adrenergic agonists, peripheral vasodilators (e.g. hydralazine); lipid lowering agents e.g., HMG-CoA reductase inhibitors such as simvastatin and lovastatin which are marketed as ZOCOR® and MEVACOR® in lactone prodrug form and function as inhibitors after administration, and pharmaceutically acceptable salts of dihydroxy open ring acid HMG-CoA reductase inhibitors such as atorvastatin (particularly the calcium salt sold in LIPITOR®), rosuvastatin (particularly the calcium salt sold in CRESTOR®), pravastatin (particularly the sodium salt sold in PRAVACHOL®), fluvastatin (particularly the sodium salt sold in LESCOL®), cerivastatin, and pitavastatin; a cholesterol absorption inhibitor such as ezetimibe (ZETIA®) and ezetimibe in combination with any other lipid lowering agents such as the HMG-CoA reductase inhibitors noted above and particularly with simvastatin (VYTORIN®) or with atorvastatin calcium; niacin in immediate-release or controlled release forms, and/or with an HMG-CoA reductase inhibitor; niacin receptor agonists such as acipimox and acifran, as well as niacin receptor partial agonists; anti-cholesterol agents such as PCSK9 inhibitors (alirocumab, evolocumab), Nexletol™ (bempedoic acid, ACL inhibitor), and Vascepa® (Icosapent ethyl); metabolic altering agents including insulin and insulin mimetics (e.g., insulin degludec, insulin glargine, insulin lispro), dipeptidyl peptidase-IV (DPP-4) inhibitors (e.g., sitagliptin, alogliptin, omarigliptin, linagliptin, vildagliptin); insulin sensitizers, including (i) β-klotho/FGFR1 activating monoclonal antibody (e.g. MK-3655), pan FGFR1-4/KLB modulators, FGF19 analogue (e.g. Aldafermin) (ii) PPARγ agonists, such as the glitazones (e.g. pioglitazone, AMG 131, CHS 131, MBX2044, mitoglitazone, lobeglitazone, IDR-105, rosiglitazone, and balaglitazone), and other PPAR ligands, including (1) PPARα/γ dual agonists (e.g. ZYH2, ZYH1, GFT505, chiglitazar, muraglitazar, aleglitazar, sodelglitazar, and naveglitazar); (2) PPARα agonists such as fenofibric acid derivatives (e.g., gemfibrozil, clofibrate, ciprofibrate, fenofibrate, bezafibrate), (3) selective PPARγ modulators (SPPARγM's), (e.g., such as those disclosed in WO 02/060388, WO 02/08188, WO 2004/019869, WO 2004/020409, WO 2004/020408, and WO 2004/066963); (4) PPARγ partial agonists, (5) PPAR α/δ dual agonists (e.g. Elafibranor); (iii) biguanides, such as metformin and its pharmaceutically acceptable salts, in particular, metformin hydrochloride, and extended-release formulations thereof, such as Glumetza™, Fortamet™, and GlucophageXR™; and (iv) protein tyrosine phosphatase-1B (PTP-1B) inhibitors (e.g., ISIS-113715 and TTP814); insulin or insulin analogs (e.g., insulin detemir, insulin glulisine, insulin degludec, insulin glargine, insulin lispro and inhalable formulations of each); leptin and leptin derivatives and agonists; amylin and amylin analogs (e.g., pramlintide); sulfonylurea and non-sulfonylurea insulin secretagogues (e.g., tolbutamide, glyburide, glipizide, glimepiride, mitiglinide, meglitinides, nateglinide and repaglinide); α-glucosidase inhibitors (e.g., acarbose, voglibose and miglitol); glucagon receptor antagonists (e.g., MK-3577, MK-0893, LY-2409021 and KT6-971); incretin mimetics, such as GLP-1, GLP-1 analogs, derivatives, and mimetics; and GLP-1 receptor agonists (e.g., dulaglutide, semaglutide, albiglutide, exenatide, liraglutide, lixisenatide, taspoglutide, CJC-1131, and BIM-51077, including intranasal, transdermal, and once-weekly formulations thereof), bile acid sequestering agents (e.g., colestilan, colestimide, colesevalam hydrochloride, colestipol, cholestyramine, and dialkylaminoalkyl derivatives of a cross-linked dextran), acyl CoA:cholesterol acyltransferase inhibitors, (e.g., avasimibe); antiobesity compounds; agents intended for use in inflammatory conditions, such as aspirin, non-steroidal anti-inflammatory drugs or NSAIDs, glucocorticoids, and selective cyclooxygenase-2 or COX-2 inhibitors; glucokinase activators (GKAs) (e.g., AZD6370); inhibitors of 11β-hydroxysteroid dehydrogenase type 1, (e.g., such as those disclosed in U.S. Pat. No. 6,730,690, and LY-2523199); CETP inhibitors (e.g., anacetrapib, torcetrapib, and evacetrapib); inhibitors of fructose 1,6-bisphosphatase, (e.g., such as those disclosed in U.S. Pat. Nos. 6,054,587; 6,110,903; 6,284,748; 6,399,782; and 6,489,476); inhibitors of acetyl CoA carboxylase-1 or 2 (ACC1 or ACC2); AMP-activated Protein Kinase (AMPK) activators; other agonists of the G-protein-coupled receptors: (i) GPR-109, (ii) GPR-119 (e.g., MBX2982 and PSN821), and (iii) GPR-40 (e.g., TAK875); SSTR3 antagonists (e.g., such as those disclosed in WO 2009/001836); neuromedin U receptor agonists (e.g., such as those disclosed in WO 2009/042053, including, but not limited to, neuromedin S (NMS)); SCD modulators (e.g. Aramchol); GPR-105 antagonists (e.g., such as those disclosed in WO 2009/000087); SGLT inhibitors (e.g., ASP1941, SGLT-3, SGLT-2 such as empagliflozin, dapagliflozin, canagliflozin, and ertugliflozin, BI-10773, remogliflozin, TS-071, tofogliflozin, ipragliflozin, and LX-4211); inhibitors of acyl coenzyme A carboxylase (ACC, MK-4074); inhibitors of diacylglycerol acyltransferase 1 and 2 (DGAT-1 and DGAT-2); inhibitors of fatty acid synthase; inhibitors of acyl coenzyme A:monoacylglycerol acyltransferase 1 and 2 (MGAT-1 and MGAT-2); agonists of the TGR5 receptor (also known as GPBAR1, BG37, GPCR19, GPR131, and M-BAR); ileal bile acid transporter inhibitors; bile acid modulators; PACAP, PACAP mimetics, and PACAP receptor 3 agonists; IL-1b antibodies, (e.g., XOMA052 and canakinumab); antifibrotic and/or anti-inflammatory agents (CCR2/CCR5 dual receptor antagonist (e.g. cenicriviroc); galectin 3 inhibitor (e.g. belapectin, GB-1107, GB-1211), siRNA against HSP 47 (e.g. BMS-986263); NSAID derived from pirfenidone (e.g. hydronidone), A3AR agonist (e.g. namodenoson, FM101); TGFTX4 (e.g. nitazoxanide); 5-lipoxygenase inhibitor (e.g. tipelukast), Bifunctional urate inhibitor (e.g. ACQT1127), adiponectin receptor agonist (e.g. ALY688), TNF receptor antagonist (e.g. atrosimab), Autotaxin inhibitor (e.g. BLD-0409, TJC 0265, TJC 0316), CCL24 blocking monoclonal antibody (e.g. CM101), IL-11 inhibitor (e.g. ENx 108A), LPA1 receptor antagonist (e.g. EPGN 696), Dual JAK1/2 inhibitor (e.g. EX 76545), GPR antagonist (e.g. GPR91 antagonist), Integrin avβ1, avβ3 and avβ6 inhibitor (e.g. IDL 2965), NLRP3 antagonist (e.g. IFM-514), inflammasome inhibitors (e.g. JT194, JT349), Cell membrane permeability inhibitor (e.g. Larazotide), CCR5 antagonist (e.g. Ieronlimab), TNF inhibitor (e.g. LIVNate), integrin avP6 inhibitor (e.g. MORF beta6), NLRP inflammasome antagonists, siRNA (e.g. OLX 701), dual TFGD/Hedgehog inhibitor (e.g. Oxy 200), GPR40 agonist/GPR84 antagonist (e.g. PBI-4547), neutrophil elastase inhibitor (e.g. PHP-303), integrin inhibitor (e.g. PLN-1474), TGFβ1 modulator (e.g. PRM-151), CCK receptor antagonist (e.g. proglumide), LOXL2 inhibitor (e.g. PXS-5338K, PXS-5382A), IL-11 inhibitors, MPYS protein inhibitor (e.g. cGAS/STING antagonists), kinase inhibiting RNase, membrane protein mAbs, tumor necrosis factor inhibitor, NRF2 activator (e.g. SCO 116), SSAO inhibitor (e.g. TERN 201), TRATL2 agonist (e.g. TLY012), IL-6 receptor antagonist (e.g. TZLS 501), AOC3 inhibitor (e.g. UD-014), SSAO/VAP-1 inhibitor, TREM2); anti-oxidant (e.g. vitamin E); anti-inflammatory agents (e.g. norfloxacin, ciprofloxacin, ceftriaxone); coagulation modifiers (e.g. anti-coagulants, anti-platelet agents, pentoxifylline, vitamin K, DDAVP); dual GIP and GLP-1 receptor agonist (e.g. tirzepetide); dual GLP-1/GRA (e.g. cotadutide, ALT-801, DD 01, G49, PB-718); dual GLP-1 (e.g. CT 868); GLP-1/GRA/GIP triple agonist (e.g. HM15211); GRP120 stimulant/inflammasome modulator/PPARγ dual agonist (e.g. KDT501); GLP-1/FGF21 (e.g. YH25724); GLP-1 agonist (e.g. Ozempic (semaglutide sc), XW 003); selective thyroid hormone receptor-β agonist (e.g. resmetirom); apoptosis modulators (JNK-1 inhibitor (e.g. CC-90001), Peroxidase inhibitor (e.g. AZM198), ASK-1 inhibitor (e.g. CS-17919, SRT 015)); erythropoietin-stimulating agents (erythropoietin receptor agonist (e.g. cibinetide)); glucose pathway modulators (SGLT-2 inhibitor (e.g. Forxiga, Farxiga (dapagliflozin)); dual SGLT-1/2 inhibitor (e.g. licogliflozin), Glucose-6-P dehydrogenase inhibitor (e.g. fluasterone) LAPS glucagon combo (e.g. HM14320), SGLT-1 inhibitor (e.g. SGL5213)); immune modulators (TLR4 inhibitor (e.g. GBK-233), immunomodulatory polyclonal antibody (e.g. IMM-124E), TLR4 antagonist (e.g. JKB-122), CD3 monoclonal antibody (e.g.foralumab), TLR4 antagonist (e.g. JKB 133), TLR4 inhibitor (e.g. mosedipimod), Macrophage inhibitor via CD206 targeting (e.g. MT2002), TLR2/4 antagonist (e.g. VB-201, VB-703), immunomodulatory polyclonal antibody (e.g. IMM-124E)); incretin-based therapies (GLP-1 agonist (e.g. Ozempic (semaglutide sc), XW 003), GLP-1/glucagon dual receptor agonist (e.g. HM12525A), prandial insulin (e.g. ORMD 0801)); lipid modulators (AMPK Activator/Glutathione transferase (e.g. oltipraz), THR-beta agonist (e.g. resmetirom, VK2809, MGL-3745, ALG-009, ASC41, CNPT-101101, TERN 501), BAT inhibitor (e.g. elobixibat, CJ 14199), omega-6-fatty acid (e.g. epeleuton), FASN inhibitor (e.g. TVB2640, FT 4101, FT 8225), ANGPTL3 inhibitor (e.g. vupanorsen), PNPLA3 inhibitor (e.g. AZD2693), RAS domain kinase inhibitor (e.g. BioE1115), NTCP inhibitor (e.g. bulevirtide), P2Y13 receptor agonist (e.g. CER-209), omega-3 fatty acid, HSD17013 inhibitor; metabolism modulators (FXR agonist (e.g. Ocaliva (obeticholic acid), IOT022), recombinant variant of FGF19 (e.g. aldafermin), bi-specific FGFR1/KLB antibody (e.g. BFKB8488A), mTOT modulator (e.g. MSDC-0602K), pegylated analog of FGF21 (e.g. pegbelfermin, BMS-986171), non-bile FXR agonist (e.g. cilofexor, EDP-305, EYP 001, tropifexor, MET409, AGN-242256, AGN-242266, EDP 297, HPG 1860, MET642, RDX023, TERN 101), ACC inhibitor (e.g. firsocostat, PF-05221304), ketohexokinase inhibitor (e.g. PF-06835919), AMPK activator (e.g. PXL770, MSTM 101, O304), bile acid modulator (e.g. Albiero), FGF21 analog (e.g. BIO89-100), MOTSc analog (e.g. CB4211), cyclophilin inhibitor (e.g. CRV 431), FGF19 (e.g. DEL 30), mitochondrial uncoupler (e.g. GEN 3026), FXR/GPCR dual agonist (e.g. INT-767), Cysteamine derivative (e.g. KB-GE-001), dual amylin and calcitonin receptor agonist (e.g. KBP-089), transient FXR agonist (e.g. M 1217), anti-beta-klotho (KLB)-FGFR1c receptor complex mAb (e.g. MK3655), GDF15 analog (e.g. NGM395), cyclophilin inhibitor (e.g. NV556), LXR modulator (e.g. PX 329, PX 655, PX 788), LXR inverse agonist (e.g. PX016), deuterated obeticholic acid (e.g. ZG 5216)); PPAR modulators (dual PPARα/γ agonist (e.g. elafibranor), PPAR pan agonist (e.g. lanifibranor), PPARα agonists (e.g. Parmodia), PPARγ agonist (e.g. CHS 131), MPC inhibitor (e.g. PXL065), PPAR δ/γ agonist (e.g. T3D 959)); RAAS mIM-Modulators (mineralocorticoid receptor antagonist (e.g. apararenone, eplerenone, spironolactone), angiotensin receptor blocker (e.g. losartan potassium)); neurotransmitter modulators (cannabinoid receptor modulator, CB1 receptor antagonist (e.g. CRB-4001, IM-102, nimacimab), TPH1 inhibitor (e.g. CU 02), GPR120 agonist (e.g. KBR2001), combination of cannabinoid and botanical anti-inflammatory compound (e.g. SCN 002)); PDE Modulator (PDE4 inhibitor (e.g. ART 648)); CYP2E1 inhibitor (e.g. SNP-610); cell therapies (e.g. HepaStem) and bromocriptine mesylate and rapid-release formulations thereof, or with other drugs beneficial for the prevention or the treatment of the above-mentioned diseases including nitroprusside and diazoxide the free-acid, free-base, and pharmaceutically acceptable salt forms of the above active agents where chemically possible.

The present invention includes the pharmaceutically acceptable salts of the compounds defined herein, including the pharmaceutically acceptable salts of all structural formulas, embodiments and classes defined herein.

Dosages of the Compounds of Formula (I)

If the patient is responding, or is stable, after completion of the therapy cycle, the therapy cycle can be repeated according to the judgment of the skilled clinician. Upon completion of the therapy cycles, the patient can be continued on the compounds of the invention at the same dose that was administered in the treatment protocol. This maintenance dose can be continued until the patient progresses or can no longer tolerate the dose (in which case the dose can be reduced and the patient can be continued on the reduced dose).

Those skilled in the art will recognize that the actual dosages and protocols for administration employed in the methods of the invention may be varied according to the judgment of the skilled clinician. The actual dosage employed may be varied depending upon the requirements of the patient and the severity of the condition being treated. Determination of the proper dosage for a particular situation is within the skill of the art. A determination to vary the dosages and protocols for administration may be made after the skilled clinician considers such factors as the patient's age, condition and size, as well as the severity of the condition being treated and the response of the patient to the treatment.

The dosage regimen utilizing a compound of the instant invention is selected in accordance with a variety of factors including type, species, age, weight, sex and medical condition of the patient; the severity of the condition to be treated; the potency of the compound chosen to be administered; the route of administration; and the renal and hepatic function of the patient. A consideration of these factors is well within the purview of the ordinarily skilled clinician for the purpose of determining the therapeutically effective or prophylactically effective dosage amount needed to prevent, counter, or arrest the progress of the condition. It is understood that a specific daily dosage amount can simultaneously be both a therapeutically effective amount, e.g., for treatment of an oncological condition, and a prophylactically effective amount, e.g., for prevention of an oncological condition.

While individual needs vary, determination of optimal ranges of effective amounts of the compound of the invention is within the skill of the art. For administration to a human in the curative or prophylactic treatment of the conditions and disorders identified herein, for example, typical dosages of the compounds of the present invention can be about 0.05 mg/kg/day to about 50 mg/kg/day, for example at least 0.05 mg/kg, at least 0.08 mg/kg, at least 0.1 mg/kg, at least 0.2 mg/kg, at least 0.3 mg/kg, at least 0.4 mg/kg, or at least 0.5 mg/kg, and preferably 50 mg/kg or less, 40 mg/kg or less, 30 mg/kg or less, 20 mg/kg or less, or 10 mg/kg or less, which can be about 2.5 mg/day (0.5 mg/kg×5 kg) to about 5000 mg/day (50 mg/kg×100 kg), for example. For example, dosages of the compounds can be about 0.1 mg/kg/day to about 50 mg/kg/day, about 0.05 mg/kg/day to about 10 mg/kg/day, about 0.05 mg/kg/day to about 5 mg/kg/day, about 0.05 mg/kg/day to about 3 mg/kg/day, about 0.07 mg/kg/day to about 3 mg/kg/day, about 0.09 mg/kg/day to about 3 mg/kg/day, about 0.05 mg/kg/day to about 0.1 mg/kg/day, about 0.1 mg/kg/day to about 1 mg/kg/day, about 1 mg/kg/day to about 10 mg/kg/day, about 1 mg/kg/day to about 5 mg/kg/day, about 1 mg/kg/day to about 3 mg/kg/day, about 3 mg/kg/day to about 500 mg/day, about 5 mg/day to about 250 mg/day, about 10 mg/day to about 100 mg/day, about 3 mg/day to about 10 mg/day, or about 100 mg/day to about 250 mg/day. Such doses may be administered in a single dose or may be divided into multiple doses.

Pharmaceutical Compositions

The compounds of Formula I and their pharmaceutically acceptable salts can be administered to animals, preferably to mammals, and in particular to humans, as pharmaceuticals by themselves, in mixtures with one another or in the form of pharmaceutical compositions. The term "subject" or "patient" includes animals, preferably mammals and especially humans, who use the instant active agents for the prevention or treatment of a medical condition.

Administering of the compound of Formula I to the subject includes both self-administration and administration to the patient by another person. The subject may need, or desire, treatment for an existing disease or medical condition, or may be in need of or desire prophylactic treatment to prevent or reduce the risk of occurrence of said disease or medical condition. As used herein, a subject "in need" of treatment of an existing condition or of prophylactic treatment encompasses both a determination of need by a medical professional as well as the desire of a patient for such treatment.

Methods for the safe and effective administration of most of these agents are known to those skilled in the art. In addition, their administration is described in the standard literature.

If the patient is responding, or is stable, after completion of the therapy cycle, the therapy cycle can be repeated according to the judgment of the skilled clinician. Upon completion of the therapy cycles, the patient can be continued on the compounds of the invention at the same dose that was administered in the treatment protocol. This maintenance dose can be continued until the patient progresses or can no longer tolerate the dose (in which case the dose can be reduced and the patient can be continued on the reduced dose).

Those skilled in the art will recognize that the actual dosages and protocols for administration employed in the methods of the invention may be varied according to the judgment of the skilled clinician. The actual dosage employed may be varied depending upon the requirements of the patient and the severity of the condition being treated. Determination of the proper dosage for a particular situation is within the skill of the art. A determination to vary the dosages and protocols for administration may be made after the skilled clinician takes into account such factors as the patient's age, condition and size, as well as the severity of the condition being treated and the response of the patient to the treatment.

The amount and frequency of administration of the compound of formula I, and any additional agents will be regulated according to the judgment of the attending clinician (physician) considering such factors as age, condition and size of the patient as well as severity of the condition being treated.

The compounds of the invention are also useful in preparing a medicament that is useful in treating NASH and fibrosis.

The instant compounds are also useful in combination with therapeutic, chemotherapeutic and anti-cancer agents for the treatment of hepatic cellular carcinoma. Combinations of the presently disclosed compounds with therapeutic, chemotherapeutic and anti-cancer agents are within the scope of the invention. Examples of such agents can be found in Cancer Principles and Practice of Oncology by V. T. Devita and S. Hellman (editors), $9^{th}$ edition (May 16, 2011), Lippincott Williams & Wilkins Publishers. A person of ordinary skill in the art would be able to discern which combinations of agents would be useful based on the particular characteristics of the drugs and the cancer involved. Such agents include the following: estrogen receptor modulators, programmed cell death protein 1 (PD-1) inhibitors, programmed death-ligand 1 (PD-L1) inhibitors, androgen receptor modulators, retinoid receptor modulators, cytotoxic/cytostatic agents, antiproliferative agents, prenyl-protein transferase inhibitors, HMG-CoA reductase inhibitors and other angiogenesis inhibitors, HIV protease inhibitors, reverse transcriptase inhibitors, inhibitors of cell proliferation and survival signaling, bisphosphonates, aromatase inhibitors, siRNA therapeutics, γ-secretase inhibitors, agents that interfere with receptor tyrosine kinases (RTKs) and agents that interfere with cell cycle checkpoints.

The chemotherapeutic agent can be administered according to therapeutic protocols well known in the art. It will be apparent to those skilled in the art that the administration of the chemotherapeutic agent can be varied depending on the cancer being treated and the known effects of the chemotherapeutic agent on that disease. Also, in accordance with the knowledge of the skilled clinician, the therapeutic protocols (e.g., dosage amounts and times of administration) can be varied in view of the observed effects of the administered therapeutic agents on the patient, and in view of the observed responses of the cancer to the administered therapeutic agents. The particular choice of chemotherapeutic agent will depend upon the diagnosis of the attending physicians and their judgment of the condition of the patient and the appropriate treatment protocol.

The initial administration can be made according to established protocols known in the art, and then, based upon the observed effects, the dosage, modes of administration and times of administration can be modified by the skilled clinician.

The determination of the order of administration, and the number of repetitions of administration of the chemotherapeutic agent during a treatment protocol, is well within the knowledge of the skilled physician after evaluation of the condition being treated and the condition of the patient.

Thus, in accordance with experience and knowledge, the practicing physician can modify each protocol for the administration of a chemotherapeutic agent according to the individual patient's needs, as the treatment proceeds. All such modifications are within the scope of the present invention.

The agent can be administered according to therapeutic protocols well known in the art. It will be apparent to those skilled in the art that the administration of the anti-cancer agent can be varied depending on the cancer being treated and the known effects of the anti-cancer agent on that disease.

The initial administration can be made according to established protocols known in the art, and then, based upon the observed effects, the dosage, modes of administration and times of administration can be modified by the skilled clinician.

The particular choice of agent will depend upon the diagnosis of the attending physicians and their judgment of the condition of the patient and the appropriate treatment protocol.

The determination of the order of administration, and the number of repetitions of administration of the agent during a treatment protocol, is well within the knowledge of the skilled physician after evaluation of the cancer being treated and the condition of the patient.

Thus, in accordance with experience and knowledge, the practicing physician can modify each protocol for the administration of an anti-cancer agent according to the individual patient's needs, as the treatment proceeds. All such modifications are within the scope of the present invention.

The attending clinician, in judging whether treatment is effective at the dosage administered, will consider the general well-being of the patient as well as more definite signs such as relief of cancer-related symptoms (e.g., pain), inhibition of tumor growth, actual shrinkage of the tumor, or inhibition of metastasis. Size of the tumor can be measured by standard methods such as radiological studies, e.g., CAT or MRI scan, and successive measurements can be used to judge whether or not growth of the tumor has been retarded or even reversed. Relief of disease-related symptoms such as pain, and improvement in overall condition can also be used to help judge effectiveness of treatment.

The compounds, compositions and methods provided herein are useful for the treatment of cancer. Cancers that may be treated by the compounds, compositions and methods disclosed herein include, but are not limited to: Liver: hepatoma (hepatocellular carcinoma), cholangiocarcinoma, hepatoblastoma, angiosarcoma, hepatocellular adenoma, hemangioma.

PD-1 inhibitors include pembrolizumab (lambrolizumab), nivolumab and MPDL3280A. PDL-inhibitors include atezolizumab, avelumab, and durvalumab.

The invention further relates to a method of treating hepatic cellular carcinoma in a human patient comprising administration of a compound of the invention (i.e., a compound of Formula I) and a PD-1 antagonist to the patient. The compound of the invention and the PD-1 antagonist may be administered concurrently or sequentially.

In particular embodiments, the PD-1 antagonist is an anti-PD-1 antibody, or antigen binding fragment thereof. In alternative embodiments, the PD-1 antagonist is an anti-PD-L1 antibody, or antigen binding fragment thereof. In some embodiments, the PD-1 antagonist is pembrolizumab (KEYTRUDA™, Merck & Co., Inc., Kenilworth, NJ, USA), nivolumab (OPDIVO™, Bristol-Myers Squibb Company, Princeton, NJ, USA), cemiplimab (LIBTAYO™ Regeneron Pharmaceuticals, Inc., Tarrytown, NY, USA), atezolizumab (TECENTRIQ™ Genentech, San Francisco, CA, USA), durvalumab (IMFINZI™, AstraZeneca Pharmaceuticals LP, Wilmington, DE), or avelumab (BAVENCIO™, Merck KGaA, Darmstadt, Germany).

In some embodiments, the PD-1 antagonist is pembrolizumab. In particular sub-embodiments, the method comprises administering 200 mg of pembrolizumab to the patient about every three weeks. In other sub-embodiments, the method comprises administering 400 mg of pembrolizumab to the patient about every six weeks.

In further sub-embodiments, the method comprises administering 2 mg/kg of pembrolizumab to the patient about every three weeks. In particular sub-embodiments, the patient is a pediatric patient.

In some embodiments, the PD-1 antagonist is nivolumab. In particular sub-embodiments, the method comprises administering 240 mg of nivolumab to the patient about every two weeks. In other sub-embodiments, the method comprises administering 480 mg of nivolumab to the patient about every four weeks.

In some embodiments, the PD-1 antagonist is cemiplimab. In particular embodiments, the method comprises administering 350 mg of cemiplimab to the patient about every 3 weeks.

In some embodiments, the PD-1 antagonist is atezolizumab. In particular sub-embodiments, the method comprises administering 1200 mg of atezolizumab to the patient about every three weeks.

In some embodiments, the PD-1 antagonist is durvalumab. In particular sub-embodiments, the method comprises administering 10 mg/kg of durvalumab to the patient about every two weeks.

In some embodiments, the PD-1 antagonist is avelumab. In particular sub-embodiments, the method comprises administering 800 mg of avelumab to the patient about every two weeks.

A compound of the instant invention, or a pharmaceutically acceptable salt thereof, may also be useful for treating cancer in combination with the following therapeutic agents: pembrolizumab (Keytruda®), abarelix (Plenaxis Depot®); aldesleukin (Prokine®); Aldesleukin (Proleukin®); Alemtuzumabb (Campath®); alitretinoin (Panretin®); allopurinol (Zyloprim®); altretamine (Hexalen®); amifostine (Ethyol®); anastrozole (Arimidex®); arsenic trioxide (Trisenox®); asparaginase (Elspar®); azacitidine (Vidaza®); bevacuzimab (Avastin®); bexarotene capsules (Targretin®); bexarotene gel (Targretin®); bleomycin (Blenoxane®); bortezomib (Velcade®); busulfan intravenous (Busulfex®); busulfan oral (Myleran®); calusterone (Methosarb®); capecitabine (Xeloda®); carboplatin (Paraplatin®); carmustine (BCNU®, BiCNU®); carmustine (Gliadel®); carmustine with Polifeprosan 20 Implant (Gliadel Wafer®); celecoxib (Celebrex®); cetuximab (Erbitux®); chlorambucil (Leukeran®); cisplatin (Platinol®); cladribine (Leustatin®, 2-CdA®); clofarabine (Clolar®); cyclophosphamide (Cytoxan®, Neosar®); cyclophosphamide (Cytoxan Injection®); cyclophosphamide (Cytoxan Tablet®); cytarabine (Cytosar-U®); cytarabine liposomal (DepoCyt®); dacarbazine (DTIC-Dome®); dactinomycin, actinomycin D (Cosmegen®); Darbepoetin alfa (Aranesp®); daunorubicin liposomal (DanuoXome®); daunorubicin, daunomycin (Daunorubicin®); daunorubicin, daunomycin (Cerubidine®); Denileukin diftitox (Ontak®); dexrazoxane (Zinecard®); docetaxel (Taxotere®); doxorubicin (Adriamycin PFS®); doxorubicin (Adriamycin®, Rubex®); doxorubicin (Adriamycin PFS Injection®); doxorubicin liposomal (Doxil®); dromostanolone propionate (Dromostanolone®); dromostanolone propionate (Masterone Injection®); Elliott's B Solution (Elliott's B Solution®); epirubicin (Ellence®); Epoetin alfa (Epogen®); erlotinib (Tarceva®); estramustine (Emcyt®); etoposide phosphate (Etopophos®); etoposide, VP-16 (Vepesid®); exemestane (Aromasin®); Filgrastim (Neupogen®); floxuridine (intraarterial) (FUDR®); fludarabine (Fludara®); fluorouracil, 5-FU (Adrucil®); fulvestrant (Faslodex®); gefitinib (Iressa®); gemcitabine (Gemzar®); gemtuzumab ozogamicin (Mylotarg®); goserelin acetate (Zoladex Implant®); goserelin acetate (Zoladex®); histrelin acetate (Histrelin Implant®); hydroxyurea (Hydrea®); Ibritumomab Tiuxetan (Zevalin®); idarubicin (Idamycin®); ifosfamide (IFEX®); imatinib mesylate (Gleevec®); interferon alfa 2a (Roferon A®); Interferon alfa-2b (Intron A®); irinotecan (Camptosar®); lenalidomide (Revlimid®); letrozole (Femara®); leucovorin (Wellcovorin®, Leucovorin®); Leuprolide Acetate (Eligard®); levamisole (Ergamisol®); lomustine, CCNU (CeeBU®); meclorethamine, nitrogen mustard (Mustargen®); megestrol acetate (Megace®); melphalan, L-PAM (Alkeran®); mercaptopurine, 6-MP (Purinethol®); mesna (Mesnex®); mesna (Mesnex Tabs®); methotrexate (Methotrexate®); methoxsalen (Uvadex®); mitomycin C (Mutamycin®); mitotane (Lysodren®); mitoxantrone (Novantrone®); nandrolone phenpropionate (Durabolin-50®); nelarabine (Arranon®); Nofetumomab (Verluma®); Oprelvekin (Neumega®); oxaliplatin (Eloxatin®); paclitaxel (Paxene®); paclitaxel (Taxol®); paclitaxel protein-bound particles (Abraxane®); palifermin (Kepivance®); pamidronate (Aredia®); pegademase (Adagen (Pegademase Bovine)®); pegaspargase (Oncaspar®); Pegfilgrastim (Neulasta®); pemetrexed disodium (Alimta®); pentostatin (Nipent®); pipobroman (Vercyte®); plicamycin, mithramycin (Mithracin®); porfimer sodium (Photofrin®); procarbazine (Matulane®); quinacrine (Atabrine®); Rasburicase (Elitek®); Rituximab (Rituxan®); Ridaforolimus; sargramostim (Leukine®); Sargramostim (Prokine®); sorafenib (Nexavar®); streptozocin (Zanosar®); sunitinib maleate (Sutent®); talc (Sclerosol®); tamoxifen (Nolvadex®); temozolomide (Temodar®); teniposide, VM-26 (Vumon®); testolactone (Teslac®); thioguanine, 6-TG (Thioguanine®); thiotepa (Thioplex®); topotecan (Hycamtin®); toremifene (Fareston®); Tositumomab (Bexxar®); Tositumomab/I-131 tositumomab (Bexxar®); Trastuzumab (Herceptin®); tretinoin, ATRA (Vesanoid®); Uracil Mustard (Uracil Mustard Capsules®); valrubicin (Valstar®); vinblastine (Velban®); vincristine (Oncovin®); vinorelbine (Navelbine®); vorinostat (Zolinza®) and zoledronate (Zometa®), or a pharmaceutically acceptable salt thereof.

Methods for Making the Compounds of Present Invention

The following examples are provided so that the invention might be more fully understood. Unless otherwise indicated, the starting materials are commercially available. They should not be construed as limiting the invention in any way.

Several methods for preparing the compounds of this invention are described in the following Schemes and Examples. Starting materials and intermediates are purchased, made from known procedures, or as otherwise illustrated. Some frequently applied routes to the compounds of Formula I are also described by the Schemes as follows. In some cases, the order of carrying out the steps of reaction schemes may be varied to facilitate the reaction or to avoid unwanted reaction products. For stereoisomers, enantiomer A refers to the faster/earlier eluting enantiomer and enantiomer B refers to the slower/later eluting enantiomer at the point of separation and this nomenclature is maintained through the remainder of a synthetic sequence for a given enantiomeric series regardless of the possibility that subsequent intermediates and final compounds may have the same or opposite orders of elution.

Throughout the synthetic schemes and examples, abbreviations and acronyms may be used with the following meanings unless otherwise indicated:
ACN=acetonitrile
BPO=Benzoyl peroxide
Brett phos Pd G3
CDI=1,1'-Carbonyldiimidazole
Cu(OAc)$_2$=copper acetate
DMF=dimethylformamide
DMS=dimethyl sulfide
DCM=dichloromethane
DIPEA=N,N-Diisopropylethylamine
DPPA=Diphenylphosphoryl azide
dppf=1,1'-bis(diphenylphosphino)ferrocene Et=ethyl
EtOAc=ethyl acetate
EDC=N-(3-Dimethylaminopropyl)-N'-ethylcarbodiimide hydrochloride
DCE=1,2-dichloroethane
RP HPLC=Reverse Phase High Pressure Liquid Chromatography
h or hrs=hour or hours
HATU=1-[bis(dimethylamino)methylene]-1H-1,2,3-triazolo[4,5-b]pyridinium 3-oxid-hexafluorophosphate
Hex=hexanes
HOBT=Hydroxybenzotriazole
IPA=iso-Propanol
Me=methyl
mCPBA=meta-chloroperoxybenzoic acid
MgSO$_4$=magnesium sulfate
MP-cyanoborohydride=macroporous polymer-supported cyanoborohydride
rt or RT=room temperature
nBu$_4$LI=Tetra-n-butylammonium iodide
NBS=N-bromosuccinimide
NCS=N-Chlorosuccinimide
NIS=N-Iodosuccinimide
PdCl$_2$(dppf)=bis(diphenylphosphino)ferrocene]dichloropalladium(II)
SFC=supercritical fluid chromatography
SM=Starting material
tBuBrettPhos=2-(Di-tert-butylphosphino)-2',4',6'-triisopropyl-3,6-dimethoxy-1,1'-biphenyl
THF=tetrahydrofuran
TCMS=Methyltrichlorosilane
TFA=Trifluoroacetic acid
Xphos=2-Dicyclohexylphosphino-2',4',6'-triisopropylbiphenyl
XPhos Pd G2=chloro(2-dicyclohexylphosphino-2',4',6'-triisopropyl-1,1'-biphenyl)[2-(2'-amino-1,1'-biphenyl)]palladium(II)

Also, aq. is aqueous, TLC is thin layer chromatography; Ts is tosyl; UV is ultraviolet; W is watts; wt. % is percentage by weight; xg is times gravity; [$_D$] is the specific rotation of polarized light at 589 nm; ° C. is degrees Celsius; % w/v is percentage in weight of the former agent relative to the volume of the latter agent.

LCMS conditions: column: SUPELCO Ascentis Express C18 3×100 mm, 2.7 um. Solvent system: A—0.05% TFA in water and B—0.05% TFA in Acetonitrile.

Gradient condition: 10-99% B in 3.5 min.

General Synthetic Schemes

While the present invention has been described in conjunction with the specific examples set forth above, many alternatives, modifications and variations thereof will be apparent to those of ordinary skill in the art. In some cases, the order of carrying out the steps of the reaction schemes may be varied to facilitate the reaction or to avoid unwanted reaction products. All such alternatives, modifications and variations are intended to fall within the spirit and scope of the present invention.

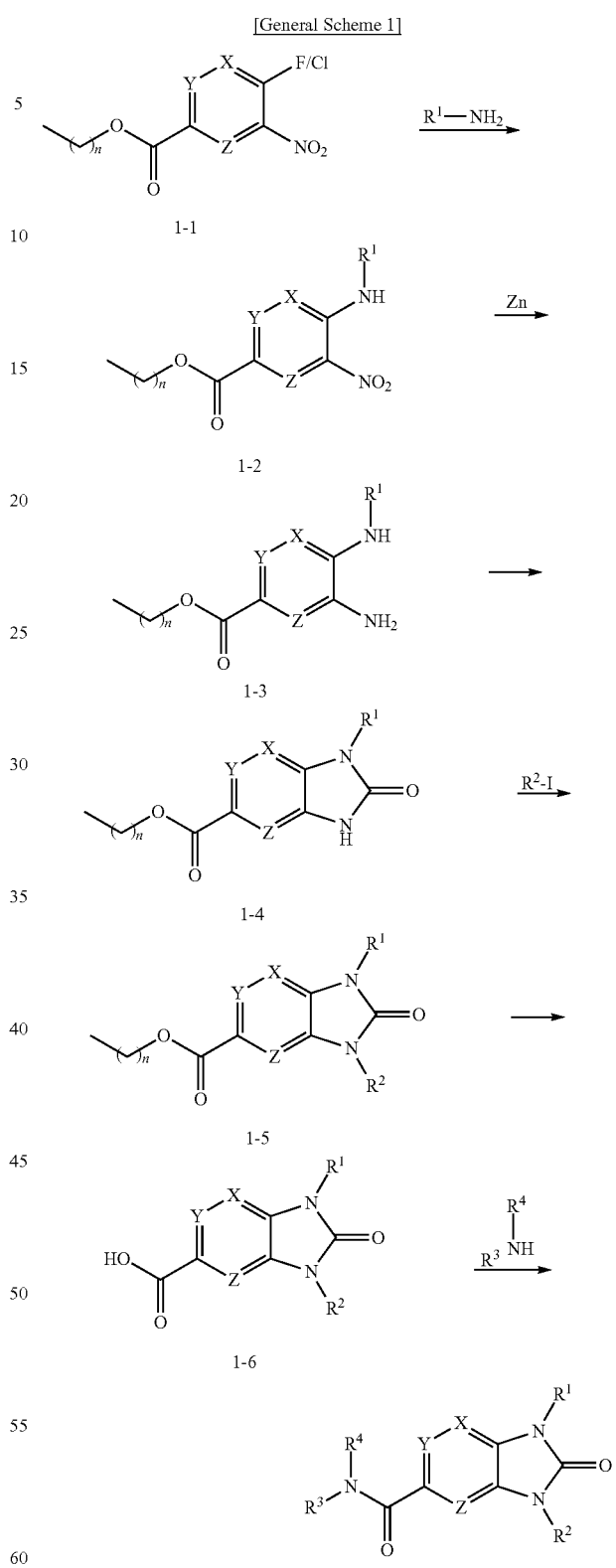

[General Scheme 1]

Compounds of formula I were prepared from 1-1 with R$^1$—NH$_2$ via SN$_{Ar}$, followed by reduction of the nitro group to the amino group to yield 1-3. Cyclization with carbonyldiimidazole provided 1-4, and subsequent SN$_2$ with R$_2$—I yielded 1-5. Saponification of 1-5 provided the corresponding carboxylic acid (1-5), and subsequent amide coupling with the appropriate amines provided compounds of formula (I) as described by the general scheme. The order of steps for some examples may be varied to facilitate the syntheses.

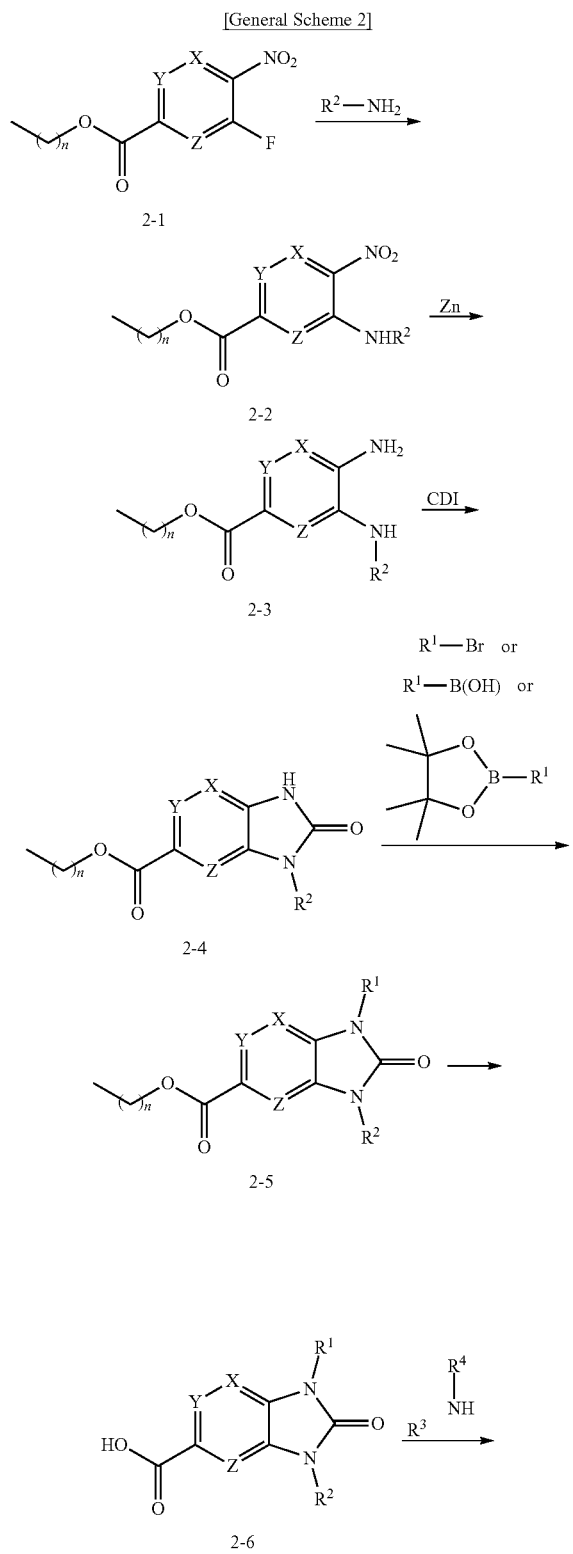

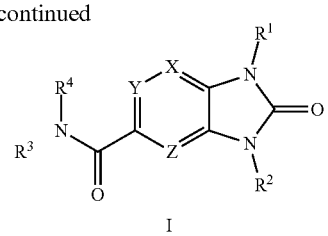

Compounds of formula I were also prepared from 2-1 with $R^2$—$NH_2$ via $SN_{Ar}$, followed by reduction of the nitro group to the amino group to yield 2-3. Reaction with carbodiimidazole (CDI) formed the cyclized product 2-4, and C—C coupling with the corresponding $R^1$-bromide, $R^1$-boronic acid, or $R^1$-boronic ester species afforded 2-5. Hydrolysis of the ester in 2-5 to the carboxylic acid provided 2-6, which was then coupled to the requisite amine to form the compounds of formula (I) as described by the general scheme. The order of steps for some examples may be varied to facilitate the syntheses.

Intermediates

Intermediate-1: Methyl 3-isopropyl-2-oxo-2,3-dihydro-1H-benzo[d]imidazole-5-carboxylate

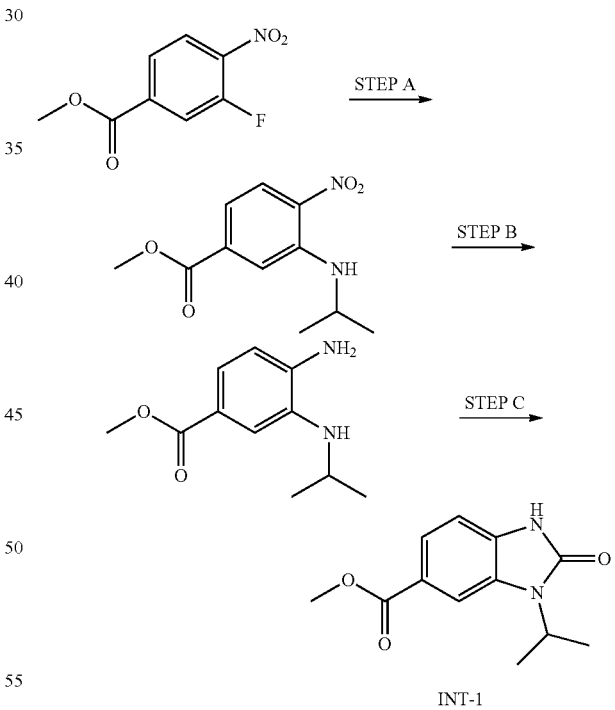

Step A: Methyl 3-(isopropylamino)-4-nitrobenzoate

To a stirred solution of methyl 3-fluoro-4-nitrobenzoate (4 g, 20.09 mmol) in DMSO (50 mL) was added propan-2-amine (1.140 g, 19.28 mmol) and DIPEA (7.02 mL, 40.2 mmol). The reaction mixture was stirred at 100° C. for 12 h, then diluted with water and EtOAc. The layers were separated, and the aqueous layer was extracted EtOAc. The combined organic extracts were washed with brine, dried over Na$_2$SO$_4$ (s) and concentrated in vacuo. The residue was purified by flash silica gel column chromatography eluting with 5% EtOAc/PE to give the title compound. LC/MS=239.2 [M+1].

Step B: 4-Amino-3-(isopropylamino)benzoate

To a stirred solution of methyl 3-(isopropylamino)-4-nitrobenzoate (4.4 g, 18.47 mmol) in MeOH (60 mL) was added Pd/C (0.983 g, 9.23 mmol). The reaction mixture was stirred at 25° C. for 12 h under 1 atm of hydrogen, then filtered and washed with DCM\MeOH (V\V=10:1). The filtrate was concentrated under reduced pressure to give the title compound. LC/MS=209.3 [M+1].

Step C: Methyl 3-isopropyl-2-oxo-2,3-dihydro-1H-benzo[d]imidazole-5-carboxylate

To a stirred solution of methyl 4-amino-3-(isopropylamino)benzoate (3.9 g, 18.73 mmol) in THF (50 mL) was added Et$_3$N (7.83 mL, 56.2 mmol) and CDI (21.26 g, 131 mmol). The reaction mixture was stirred at 25° C. for 12 hours under a nitrogen atmosphere, then diluted with water and EtOAc. The layers were separated, and the aqueous layer was extracted with EtOAc. The combined organic extracts were concentrated in vacuo. The residue was diluted with water. The mixture was stirred at RT for thirty minutes, then filtered, and the filter cake was concentrated under reduced pressure to afford the title compound. 1H NMR (500 MHz, Chloroform-d) δ 10.09 (s, 1H), 7.86-7.79 (m, 2H), 7.18-7.08 (m, 1H), 4.76 (hept, J=7.0 Hz, 1H), 3.93 (s, 3H), 1.59 (d, J=7.0 Hz, 6H). LC/MS=235.2 [M+1].

EXAMPLES

The following experimental procedures detail the preparation of specific examples of the instant disclosure. The examples are for illustrative purposes only and are not intended to limit the scope of the instant disclosure in any way.

Example 1: (R)-1,3-bis(4-fluorophenyl)-N-(3-methyl-1,1-dioxidotetrahydrothiophen-3-yl)-2-oxo-2,3-dihydro-1H-benzo[d]imidazole-5-carboxamide

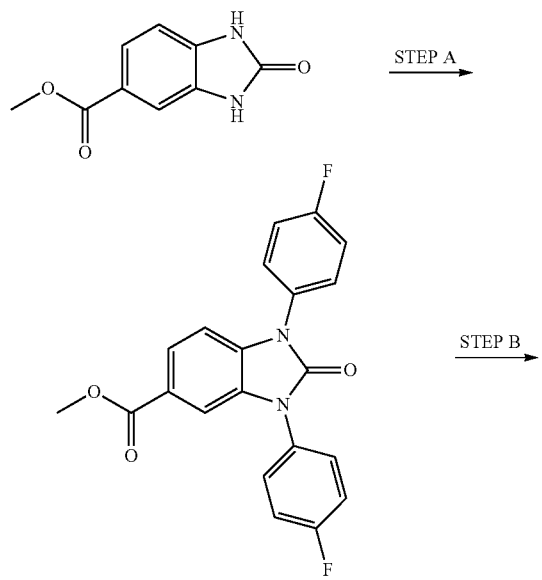

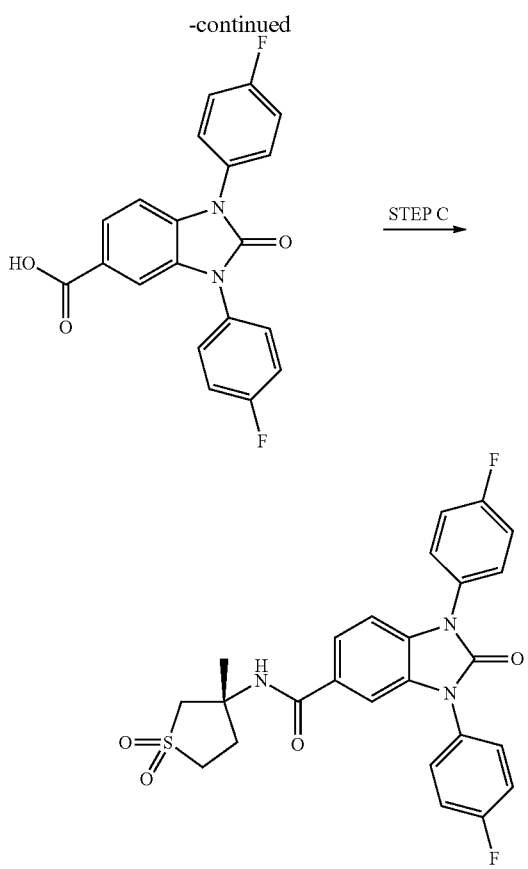

EX-1

Step A: methyl 1,3-bis(4-fluorophenyl)-2-oxo-2,3-dihydro-1H-benzo[d]imidazole-5-carboxylate To a stirred solution of methyl 2-oxo-2,3-dihydro-1H-benzo[d]imidazole-5-carboxylate (470 mg, 2.446 mmol) and (4-fluorophenyl)boronic acid (5133 mg, 36.7 mmol) in DMF (20 mL) was added Cu(OAc)$_2$ (533 mg, 2.93 mmol) and pyridine (2 mL, 2.446 mmol) at 15° C. After the addition was finished, the reaction mixture was stirred at 15° C. for 16 h, then poured into H$_2$O and was extracted with DCM. The combined organic layers were washed with brine, dried over Na$_2$SO$_4$, filtered and concentrated in vacuo. The residue was purified by column chromatography on silica (0-100% EtOAc/hexanes) to afford the title compound. LC/MS=381 [M+1].

Step B: 1,3-bis(4-fluorophenyl)-2-oxo-2,3-dihydro-1H-benzo[d]imidazole-5-carboxylic acid To a stirred solution of methyl 1,3-bis(4-fluorophenyl)-2-oxo-2,3-dihydro-1H-benzo[d]imidazole-5-carboxylate (60 mg, 0.158 mmol) in MeOH (1 mL), THF (3 mL) and water (1 mL) was added lithium hydroxide hydrate (10 mg, 0.238 mmol) at 15° C. After the addition was finished, the reaction mixture was stirred at 50° C. for 2 h, then concentrated in vacuo. The residue was dissolved in H$_2$O and 1N HCl was added to adjust the solution to pH=4. The mixture was extracted with DCM, and combined organic layers were washed with brine, dried over Na$_2$SO$_4$, filtered and concentrated in vacuo to afford the title compound. LC/MS=367 [M+1].

Step C: (R)-1,3-bis(4-fluorophenyl)-N-(3-methyl-1,1-dioxidotetrahydrothiophen-3-yl)-2-oxo-2,3-dihydro-1H-benzo[d]imidazole-5-carboxamide To a stirred solution of 1,3-bis(4-fluorophenyl)-2-oxo-2,3-dihydro-1H-benzo[d]imidazole-5-carboxylic acid (50 mg, 0.136 mmol) and (R)-3-amino-3-methyltetrahydrothiophene 1,1-dioxide (25 mg, 0.168 mmol) in DMF (1.5 mL) was added N-ethyl-N-isopropylpropan-2-amine (53 mg, 0.410 mmol) and 2-(3H-[1,2,3]triazolo[4,5-b]pyridin-3-yl)-1,1,3,3-tetramethylisouronium hexafluorophosphate(V) (78 mg, 0.205 mmol) at 15° C. After the addition was finished, the reaction mixture was stirred at 15° C. for 16 h. The crude was purified directly by mass triggered reverse phase HPLC (ACN/water with 0.1% TFA modifier) to afford the title compound. LC/MS=498 [M+1]. $^1$H NMR (400 MHz, DMSO-d6, ppm) δ 8.31 (s, 1H), 7.68 (dt, J=5.0, 8.5 Hz, 5H), 7.51-7.41 (m, 5H), 7.11 (d, J=8.0 Hz, 1H), 3.90 (m, 1H), 3.27 (br d, J=9.0 Hz, 2H), 3.16 (m, 1H), 2.80-2.60 (m, 1H), 2.17 (m, 1H), 1.53 (s, 3H). Human DGAT2 IC$_{50}$=573 nM Example 2: 1-(3-(difluoromethoxy)phenyl)-3-(4-fluorophenyl)-N-(3-methyl-1,1-dioxidothietan-3-yl)-2-oxo-2,3-dihydro-1H-benzo[d]imidazole-5-carboxamide

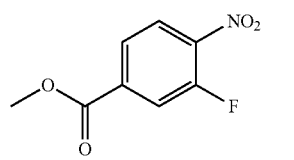

STEP A →

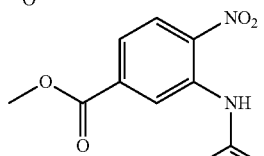

STEP B →

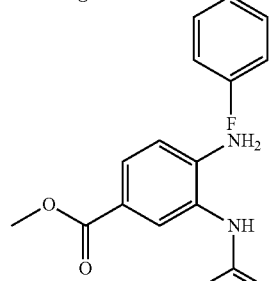

STEP C →

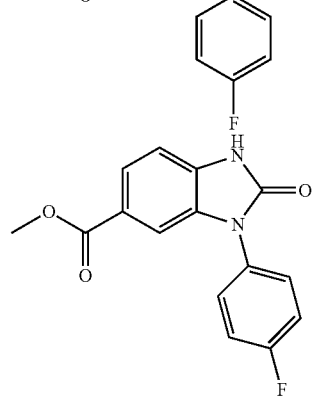

STEP D →

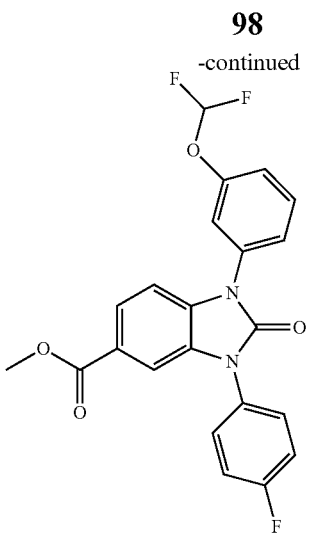

STEP E →

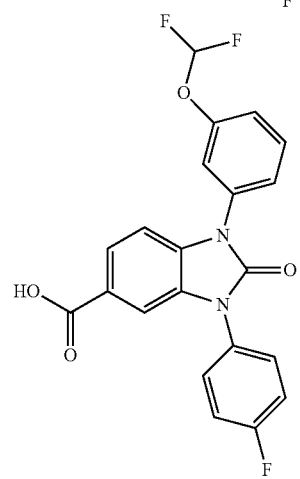

STEP F →

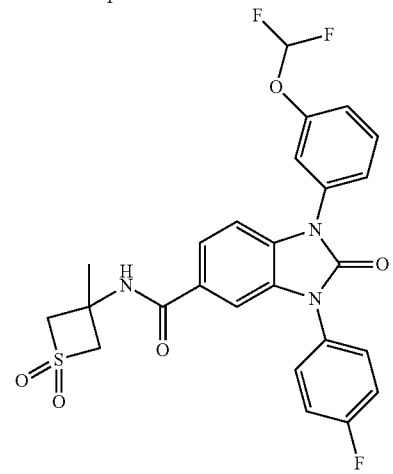

EX-2

Step A: methyl 3-((4-fluorophenyl)amino)-4-nitrobenzoate

To a stirred solution of methyl 3-fluoro-4-nitrobenzoate (4.8 g, 24.10 mmol) in DMSO (150 mL) was added 4-fluoroaniline (2.68 g, 24.10 mmol) and DIEA (8.42 mL, 48.2 mmol) at 15° C. After the addition was finished, the reaction mixture was stirred at 100° C. for 16 h. The mixture was poured into H$_2$O and filtered. The filter cake was dissolved in ethyl acetate and concentrated in vacuo to afford the title compound. LC/MS=291 [M+1].

Step B: methyl 4-amino-3-((4-fluorophenyl)amino)benzoate

To a solution of Pd—C (600 mg, 5.64 mmol) in MeOH (150 mL) was added methyl 3-((4-fluorophenyl)amino)-4-nitrobenzoate (5.4 g, 18.60 mmol) at 15° C. The mixture was purged with $H_2$ stirred under 1 atm of $H_2$ at 15° C. for 16 h, then filtered and concentrated in vacuo. The residue was purified by column chromatography on silica (0-100% EtOAc/hexanes) to afford the title compound. LC/MS=261 [M+1].

Step C: methyl 3-(4-fluorophenyl)-2-oxo-2,3-dihydro-1H-benzo[d]imidazole-5-carboxylate To a stirred solution of methyl 4-amino-3-((4-fluorophenyl)amino)benzoate (2 g, 7.68 mmol) in THF (80 mL) was added CDI (4.98 g, 30.7 mmol) at 15° C. After the addition was finished, the reaction mixture was stirred at 15° C. for 16 h, then poured into $H_2O$ and extracted with DCM. The combined organic layers were washed with brine, dried over $Na_2SO_4$, filtered and concentrated in vacuo. The residue was purified by column chromatography on silica (0-100% EtOAc/hexanes) to afford the title compound (1.37 g). LC/MS=287 [M+1].

Step D: methyl 1-(3-(difluoromethoxy)phenyl)-3-(4-fluorophenyl)-2-oxo-2,3-dihydro-1H-benzo[d]imidazole-5-carboxylate To a stirred solution of methyl 3-(4-fluorophenyl)-2-oxo-2,3-dihydro-1H-benzo[d]imidazole-5-carboxylate (400 mg, 1.397 mmol) and 2-(3-(difluoromethoxy)phenyl)-4,4,5,5-tetramethyl-1,3,2-dioxaborolane (4 g, 14.81 mmol) in DMF (20 mL) was added $Cu(OAc)_2$ (305 mg, 1.677 mmol) and pyridine (3 mL, 37.2 mmol) at 15° C. After the addition was finished, the reaction mixture was stirred at 75° C. for 48 h, then poured into $H_2O$ and extracted with DCM. The combined organic layers were washed with brine, dried over $Na_2SO_4$, then filtered and concentrated in vacuo. The residue was purified by column chromatography on silica (0-100% EtOAc/hexanes) to afford the title compound (200 mg). LC/MS=429 [M+1].

Step E: 1-(3-(difluoromethoxy)phenyl)-3-(4-fluorophenyl)-2-oxo-2,3-dihydro-1H-benzo[d]imidazole-5-carboxylic acid To a stirred solution of methyl 1-(3-(difluoromethoxy)phenyl)-3-(4-fluorophenyl)-2-oxo-2,3-dihydro-1H-benzo[d]imidazole-5-carboxylate (200 mg, 0.467 mmol) in THF (6 mL) and water (2 mL) was added lithium hydroxide hydrate (78 mg, 1.868 mmol) at 15° C. The reaction mixture was stirred at 15° C. for 16 h, then concentrated in vacuo and dissolved in $H_2O$. HCl (1N in water) was added to the mixture until pH=4. The mixture was extracted with DCM. The combined organic layers were washed with brine, dried over $Na_2SO_4$, filtered and concentrated in vacuo to afford the title compound. LC/MS=415 [M+1].

Step F: 1-(3-(difluoromethoxy)phenyl)-3-(4-fluorophenyl)-N-(3-methyl-1,1-dioxidothietan-3-yl)-2-oxo-2,3-dihydro-1H-benzo[d]imidazole-5-carboxamide To a stirred solution of 1-(3-(difluoromethoxy)phenyl)-3-(4-fluorophenyl)-2-oxo-2,3-dihydro-1H-benzo[d]imidazole-5-carboxylic acid (35 mg, 0.084 mmol) and 2-(3H-[1,2,3]triazolo[4,5-b]pyridin-3-yl)-1,1,3,3-tetramethylisouronium hexafluorophosphate(V) (64 mg, 0.168 mmol) in DMF (1.5 mL) was added N-ethyl-N-isopropylpropan-2-amine (0.070 mL, 0.422 mmol) at 15° C. After the mixture was stirred for 15 min, 3-amino-3-methylthietane 1,1-dioxide (14 mg, 0.104 mmol) was added to the mixture. After the addition was finished, the reaction mixture was stirred at 15° C. for 2 h. The crude mixture was purified by mass triggered reverse phase HPLC (ACN/water with 0.1% TFA modifier) to afford the title compound. LC/MS=532 [M+1]. 1H NMR (400 MHz, DMSO-d6, ppm) δ 7.60-7.53 (m, 4H), 7.51-7.45 (m, 2H), 7.40 (t, J=2.0 Hz, 1H), 7.30-7.26 (m, 2H), 7.26-7.21 (m, 2H), 7.18-7.14 (m, 1H), 6.76-6.49 (m, 1H), 4.62-4.50 (m, 2H), 4.21-4.09 (m, 2H), 1.25 (br d, J=3.5 Hz, 3H). Human DGAT2 $IC_{50}$=1.8 nM By using procedures similar to those described in Example 2 with appropriate amine and (hetero)arylhalide reagents, the following compound was synthesized. These compounds were characterized by LC/MS.

| Example | Structure | Name | LCMS [M + 1] | Human DGAT2 $IC_{50}$ (nM) |
|---|---|---|---|---|
| 3 | 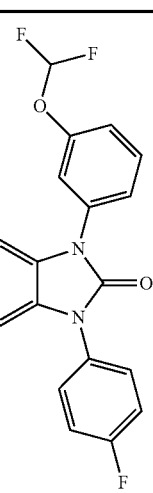 | (R)-1-(3-(difluoromethoxy)phenyl)-3-(4-fluorophenyl)-N-(3-methyl-1,1-dioxidotetrahydrothiophen-3-yl)-2-oxo-2,3-dihydro-1H-benzo[d]imidazole-5-carboxamide | 546 | 2.4 |

101

Example 4: 3-(3-(difluoromethoxy)phenyl)-1-(4-fluorophenyl)-N-(3-methyl-1,1-dioxidothietan-3-yl)-2-oxo-2,3-dihydro-1H-imidazo[4,5-b]pyridine-6-carboxamide

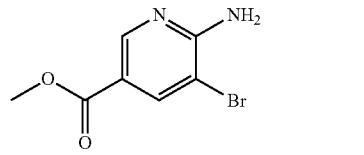

STEP A →

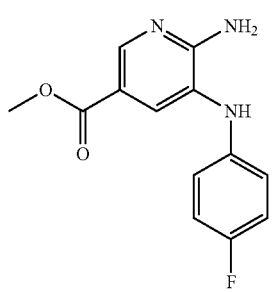

STEP B →

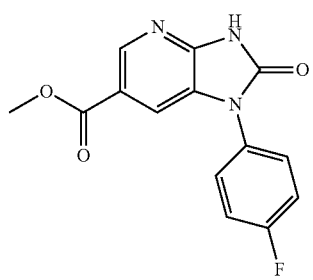

STEP C →

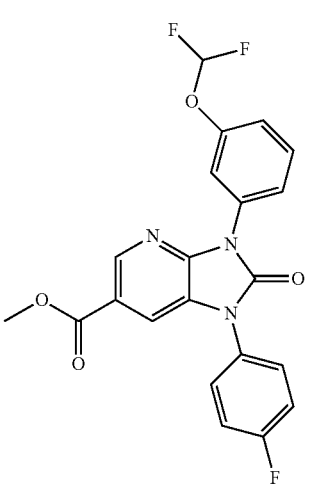

STEP D →

102

-continued

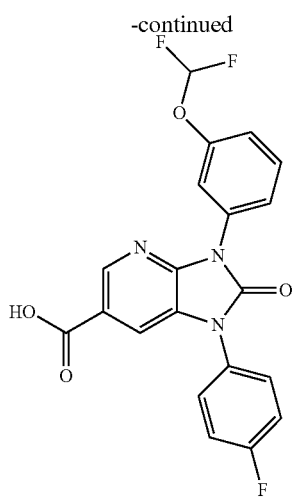

STEP E →

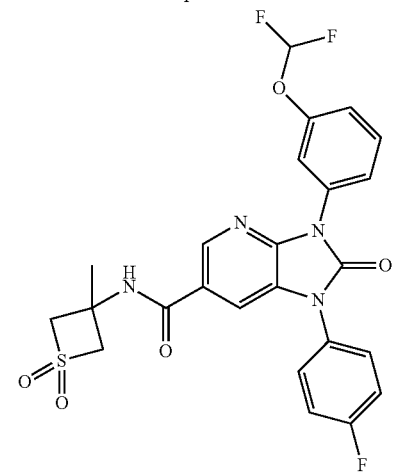

EX-4

Step A: methyl 6-amino-5-((4-fluorophenyl)amino)nicotinate

To a stirred solution of methyl 6-amino-5-bromonicotinate (300 mg, 1.298 mmol) in THF (8 mL) were added 4-fluoroaniline (1443 mg, 12.98 mmol), Cs$_2$CO$_3$ (1269 mg, 3.90 mmol) and Brettphos Pd G3 (118 mg, 0.130 mmol) in glovebox at 25° C. The reaction mixture was stirred at 70° C. for 16 h, then poured into H$_2$O and extracted with DCM (×3). The combined organic layers were washed with brine, dried over Na$_2$SO$_4$, filtered and concentrated in vacuo. The residue was purified by column chromatography on silica (0-100% EtOAc/hexanes) to afford the title compound. LC/MS=262 [M+1].

Step B: methyl 1-(4-fluorophenyl)-2-oxo-2,3-dihydro-1H-imidazo[4,5-b]pyridine-6-carboxylate To a stirred solution of methyl 6-amino-5-((4-fluorophenyl)amino)nicotinate (822 mg, 3.15 mmol) in THF (30 mL) was added CDI (2041 mg, 12.59 mmol) at 25° C. The reaction mixture was stirred at 25° C. for 16 h, then poured into H$_2$O and extracted with DCM. The combined organic layers were washed with brine, dried over Na$_2$SO$_4$, filtered and concentrated in vacuo. The residue was purified by column chromatography on silica (0-100% EtOAc/hexanes) to afford the title compound. LC/MS=288 [M+1].

Step C: methyl 3-(3-(difluoromethoxy)phenyl)-1-(4-fluorophenyl)-2-oxo-2,3-dihydro-1H-imidazo[4,5-b]pyridine-6-carboxylate To a stirred solution of methyl 1-(4-fluorophenyl)-2-oxo-2,3-dihydro-1H-imidazo[4,5-b]pyridine-6-carboxylate (720 mg, 2.507 mmol) and 2-(3-(difluoromethoxy)phenyl)-4,4,5,5-tetramethyl-1,3,2-dioxaborolane (5416 mg, 20.05 mmol) in DMF (15 mL) were added Cu(OAc)$_2$ (683 mg, 3.76 mmol) and pyridine (4.04 mL, 50.1 mmol) at 25° C. The reaction mixture was stirred at 80° C. for 16 h (open to air with a drying tube), then poured into H$_2$O and extracted with DCM. The combined organic layers were washed with brine, dried over Na$_2$SO$_4$, filtered and concentrated in vacuo. The residue was purified by column chromatography on silica (0-100% EtOAc/hexanes) to afford the title compound. LC/MS=430 [M+1].

Step D: 3-(3-(difluoromethoxy)phenyl)-1-(4-fluorophenyl)-2-oxo-2,3-dihydro-1H-imidazo[4,5-b]pyridine-6-carboxylic acid To a stirred solution of methyl 3-(3-(difluoromethoxy) phenyl)-1-(4-fluorophenyl)-2-oxo-2,3-dihydro-1H-imidazo [4,5-b]pyridine-6-carboxylate (100 mg, 0.233 mmol) in THF (1 mL) was added lithium hydroxide hydrate (30 mg, 0.715 mmol) at 25° C. The reaction mixture was stirred at 25° C. for 0.5 h, then concentrated in vacuo and dissolved in H$_2$O. HCl (1N in water) was added to the mixture until pH=4. Then, the mixture was extracted with DCM (×3). The combined organic layers were washed with brine, dried over Na$_2$SO$_4$, then filtered and concentrated in vacuo to afford the title compound. LC/MS=416 [M+1].

Step E: 3-(3-(difluoromethoxy)phenyl)-1-(4-fluorophenyl)-N-(3-methyl-1,1-dioxidothietan-3-yl)-2-oxo-2,3-dihydro-1H-imidazo[4,5-b]pyridine-6-carboxamide To a stirred solution of 3-(3-(difluoromethoxy)phenyl)-1-(4-fluorophenyl)-2-oxo-2,3-dihydro-1H-imidazo[4,5-b] pyridine-6-carboxylic acid (95 mg, 0.229 mmol) and 2-(3H-[1,2,3]triazolo[4,5-b]pyridin-3-yl)-1,1,3,3-tetramethylisouronium hexafluorophosphate(V) (130 mg, 0.343 mmol) in DMF (2 ml) was added N-ethyl-N-isopropylpropan-2-amine (0.114 ml, 0.686 mmol) at 25° C. After the addition was finished, the reaction mixture was stirred at 25° C. for 5 mins, followed by addition of 3-amino-3-methylthietane 1,1-dioxide (38 mg, 0.281 mmol). The reaction mixture was stirred at 25° C. for 1.5 h. The crude mixture was purified directly by mass triggered reverse phase HPLC (ACN/water with 0.1% TFA modifier) to afford the title compound as the TFA salt. LC/MS=533 [M+1]. $^1$H NMR (500 MHz, METHANOL-d4, ppm) δ=8.64 (d, J=1.8 Hz, 1H), 7.86 (d, J=1.8 Hz, 1H), 7.76-7.61 (m, 5H), 7.45-7.37 (m, 2H), 7.34-7.28 (m, 1H), 7.12-6.78 (m, 1H), 4.58 (d, J=14.6 Hz, 2H), 4.27-4.19 (m, 2H), 1.83 (s, 3H). Human DGAT2 IC$_{50}$=8.5 nM Example 5: 1-(2-(Difluoromethoxy)-5-fluoropyridin-4-yl)-3-isopropyl-N-(4-methyl-1,1-dioxidotetrahydro-2H-thiopyran-4-yl)-2-oxo-2,3-dihydro-1H-benzo[d]imidazole-5-carboxamide

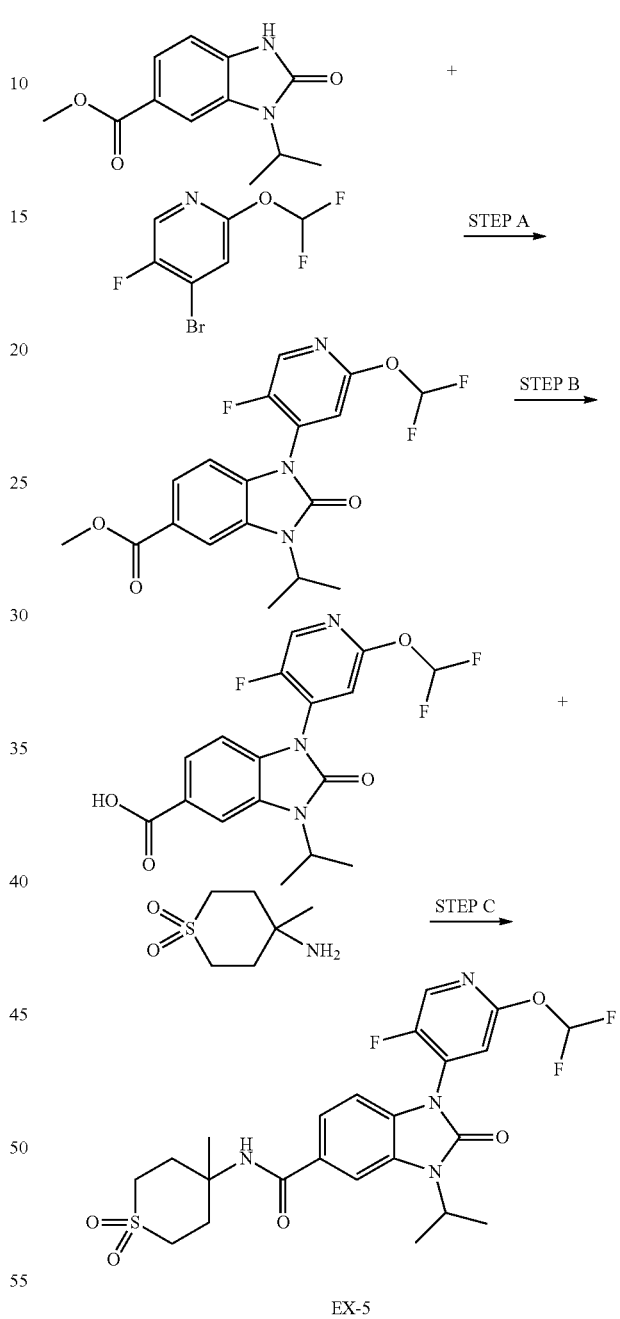

Step A: methyl 1-(2-(difluoromethoxy)-5-fluoropyridin-4-yl)-3-isopropyl-2-oxo-2,3-dihydro-1H-benzo[d]imidazole-5-carboxylate At 20° C., to 20-mL vial was charged 4-bromo-2-(difluoromethoxy)-5-fluoropyridine (279 mg, 1.15 mmol), methyl 3-isopropyl-2-oxo-2,3-dihydro-1H-benzo[d]imidazole-5-carboxylate (150 mg, 0.640 mmol), copper(I) iodide (122 mg, 0.640 mmol), (1R,2R)-N1,N2-dimethylcyclohexane-1,2-diamine (182 mg, 1.28 mmol), tripotassium phosphate (408 mg, 1.92 mmol), and 1,4-dioxane (6.4 mL) was added. The vial was evacuated and refilled with $N_2$ thrice, and the mixture was stirred at 100° C. for 7 h. Then, the volatiles were evaporated, and the residue was purified by flash silica gel chromatography (0 to 80% EtOAc in hexanes) to afford the title compound. LC/MS=396 [M+1].

Step B: 1-(2-(difluoromethoxy)-5-fluoropyridin-4-yl)-3-isopropyl-2-oxo-2,3-dihydro-1H-benzo[d]imidazole-5-carboxylic acid At 20° C., to a stirred mixture of methyl 1-(2-(difluoromethoxy)-5-fluoropyridin-4-yl)-3-isopropyl-2-oxo-2,3-dihydro-1H-benzo[d]imidazole-5-carboxylate (39 mg, 0.099 mmol) in THF (0.4 mL) and MeOH (0.1 mL) was added lithium hydroxide hydrate (33.1 mg, 0.789 mmol) in Water (0.4 mL), and the mixture was stirred at 50° C. for 1 h. Then, HCl (1 N solution in water) (0.79 mL, 0.79 mmol) was added, and the mixture stirred vigorously. The volatiles were evaporated to afford the title compound. LC/MS=382 [M+1].

Step C: 1-(2-(Difluoromethoxy)-5-fluoropyridin-4-yl)-3-isopropyl-N-(4-methyl-1,1-dioxidotetrahydro-2H-thiopyran-4-yl)-2-oxo-2,3-dihydro-1H-benzo[d]imidazole-5-carboxamide At 20° C., to a stirred mixture of 1-(2-(difluoromethoxy)-5-fluoropyridin-4-yl)-3-isopropyl-2-oxo-2,3-dihydro-1H-benzo[d]imidazole-5-carboxylic acid (19 mg, 0.050 mmol) and HATU (37.9 mg, 0.100 mmol) in DMF (1.0 mL) was added DIPEA (44 µl, 0.25 mmol), followed by 4-amino-4-methyltetrahydro-2H-thiopyran 1,1-dioxide (12 mg, 0.075 mmol). The mixture was stirred at 20° C. for 2 h, then purified directly by reverse phase HPLC (55 to 95% MeCN in water) to afford the title compound. $^1$H NMR (500 MHz, DMSO-$d_6$) δ 8.61 (s, 1H), 7.89 (s, 1H), 7.80 (s, 1H), 7.73 (t, J=72.4 Hz, 1H), 7.68 (d, J=8.4 Hz, 1H), 7.55 (d, J=4.8 Hz, 1H), 7.14 (dd, J=8.3, 2.4 Hz, 1H), 4.71 (hept, J=6.6 Hz, 1H), 3.21-3.11 (m, 2H), 3.10-3.03 (m, 2H), 2.85-2.76 (m, 2H), 2.08-1.96 (m, 2H), 1.55 (d, J=6.9 Hz, 6H), 1.44 (s, 3H). LC/MS=527 [M+1]. Human DGAT2 IC$_{50}$=34 nM.

By using procedures similar to those described in Example 5 with appropriate aryl bromide and amine reagents, the following compounds were synthesized. These compounds were characterized by LC/MS.

| Example | Structure | Name | LCMS [M + 1] | Human DGAT2 IC$_{50}$ (nM) |
|---|---|---|---|---|
| 6 | 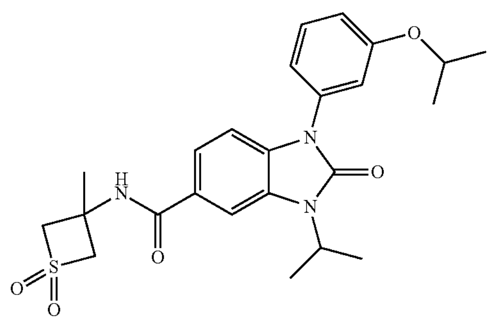 [SMILES: CC(C)Oc1cccc(-n2c(=O)n(C(C)C)c3cc(C(=O)NC4(C)CS(=O)(=O)C4)ccc32)c1] | 1-(3-isopropoxyphenyl)-3-isopropyl-N-(3-methyl-1,1-dioxo-thietan-3-yl)-2-oxo-benzimidazole-5-carboxamide | 473 | 88 |
| 7 | 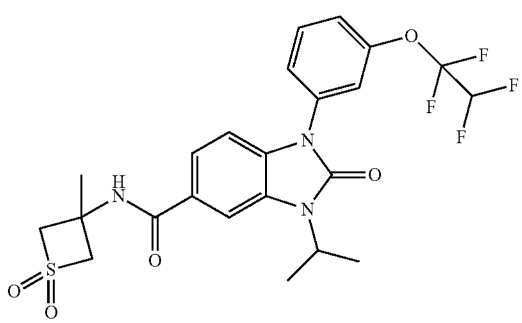 [SMILES: CC(C)n1c(=O)n(-c2cccc(OC(F)(F)C(F)F)c2)c2ccc(C(=O)NC3(C)CS(=O)(=O)C3)cc21] | 3-isopropyl-N-(3-methyl-1,1-dioxo-thietan-3-yl)-2-oxo-1-[3-(1,1,2,2-tetrafluoroethoxy)phenyl]benzimidazole-5-carboxamide | 531 | 16 |
| 8 | 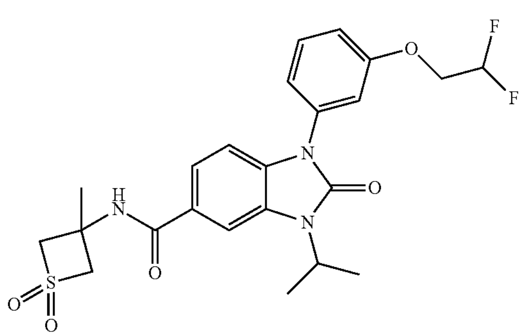 [SMILES: CC(C)n1c(=O)n(-c2cccc(OCC(F)F)c2)c2ccc(C(=O)NC3(C)CS(=O)(=O)C3)cc21] | 1-[3-(2,2-difluoroethoxy)phenyl]-3-isopropyl-N-(3-methyl-1,1-dioxo-thietan-3-yl)-2-oxo-benzimidazole-5-carboxamide | 495 | 43 |

-continued

| Example | Structure | Name | LCMS [M + 1] | Human DGAT2 IC$_{50}$ (nM) |
|---|---|---|---|---|
| 9 | 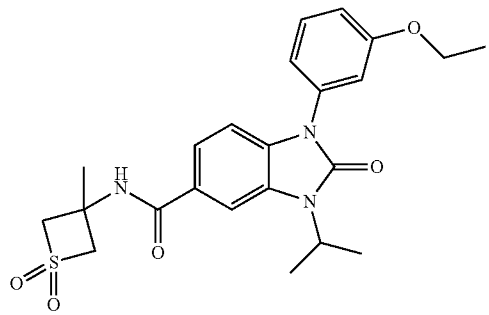 [SMILES: CCOc1cccc(-n2c(=O)n(C(C)C)c3cc(C(=O)NC4(C)CS(=O)(=O)C4)ccc32)c1] | 1-(3-ethoxyphenyl)-3-isopropyl-N-(3-methyl-1,1-dioxo-thietan-3-yl)-2-oxo-benzimidazole-5-carboxamide | 459 | 4.3 |
| 10 | 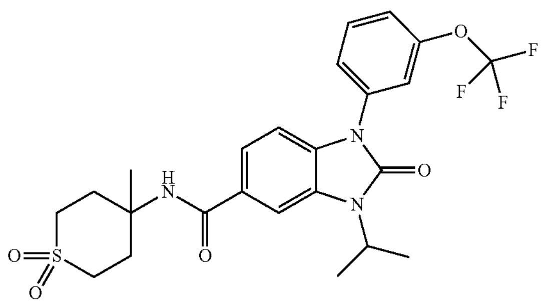 [SMILES: CC(C)n1c(=O)n(-c2cccc(OC(F)(F)F)c2)c2ccc(C(=O)NC3(C)CCS(=O)(=O)CC3)cc21] | 3-isopropyl-N-(4-methyl-1,1-dioxo-thian-4-yl)-2-oxo-1-[3-(trifluoromethoxy)phenyl]benzimidazole-5-carboxamide | 527 | 153 |
| 11 | 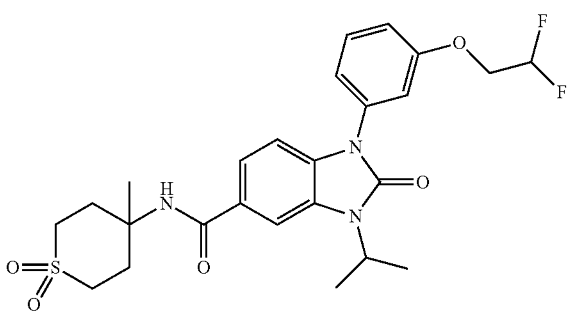 [SMILES: CC(C)n1c(=O)n(-c2cccc(OCC(F)F)c2)c2ccc(C(=O)NC3(C)CCS(=O)(=O)CC3)cc21] | 1-[3-(2,2-difluoroethoxy)phenyl]-3-isopropyl-N-(4-methyl-1,1-dioxo-thian-4-yl)-2-oxo-benzimidazole-5-carboxamide | 523 | 15 |
| 12 | 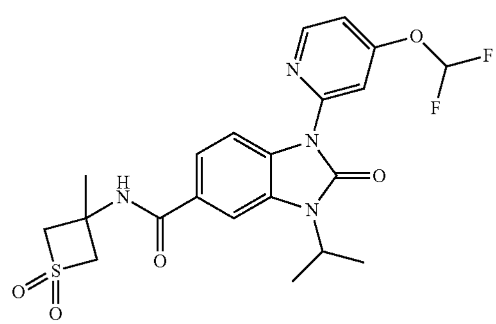 [SMILES: CC(C)n1c(=O)n(-c2cc(OC(F)F)ccn2)c2ccc(C(=O)NC3(C)CS(=O)(=O)C3)cc21] | 1-[4-(difluoromethoxy)-2-pyridyl]-3-isopropyl-N-(3-methyl-1,1-dioxo-thietan-3-yl)-2-oxo-benzimidazole-5-carboxamide | 481 | 122 |
| 13 | 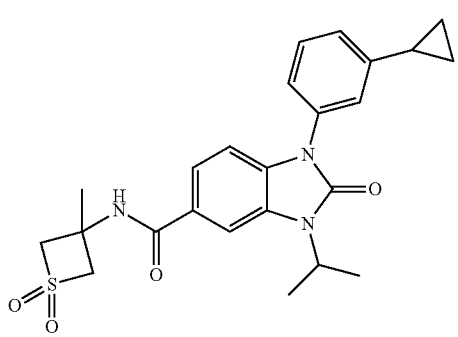 [SMILES: CC(C)n1c(=O)n(-c2cccc(C3CC3)c2)c2ccc(C(=O)NC3(C)CS(=O)(=O)C3)cc21] | 1-(3-cyclopropylphenyl)-3-isopropyl-N-(3-methyl-1,1-dioxo-thietan-3-yl)-2-oxo-benzimidazole-5-carboxamide | 455 | 17 |

-continued

| Example | Structure | Name | LCMS [M + 1] | Human DGAT2 IC$_{50}$ (nM) |
|---|---|---|---|---|
| 14 | 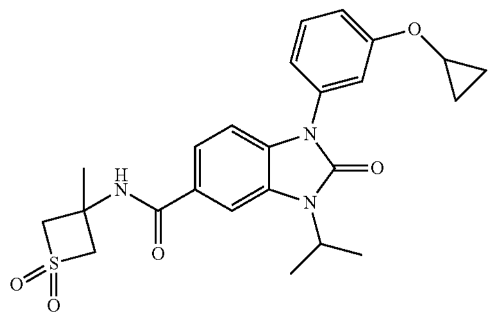 [SMILES: CC(C)n1c(=O)n(-c2cccc(OC3CC3)c2)c2ccc(C(=O)NC3(C)CS(=O)(=O)C3)cc21] | 1-[3-(cyclopropoxy)phenyl]-3-isopropyl-N-(3-methyl-1,1-dioxo-thietan-3-yl)-2-oxo-benzimidazole-5-carboxamide | 471 | 15 |
| 15 | 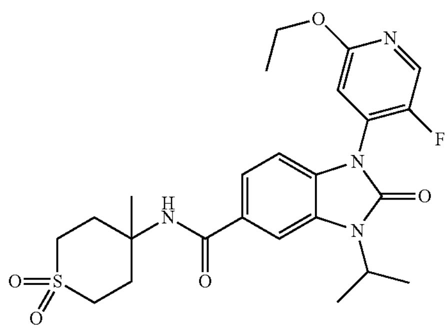 [SMILES: CCOc1cc(-n2c(=O)n(C(C)C)c3cc(C(=O)NC4(C)CCS(=O)(=O)CC4)ccc32)c(F)cn1] | 1-(2-Ethoxy-5-fluoropyridin-4-yl)-3-isopropyl-N-(4-methyl-1,1-dioxidotetrahydro-2H-thiopyran-4-yl)-2-oxo-2,3-dihydro-1H-benzo[d]imidazole-5-carboxamide | 505 | 6.7 |
| 16 | 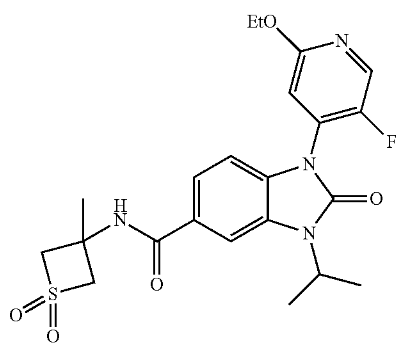 [SMILES: CCOc1cc(-n2c(=O)n(C(C)C)c3cc(C(=O)NC4(C)CS(=O)(=O)C4)ccc32)c(F)cn1] | 1-(2-ethoxy-5-fluoropyridin-4-yl)-3-isopropyl-N-(3-methyl-1,1-dioxidothietan-3-yl)-2-oxo-2,3-dihydro-1H-benzo[d]imidazole-5-carboxamide | 477 | 32 |
| 17 | 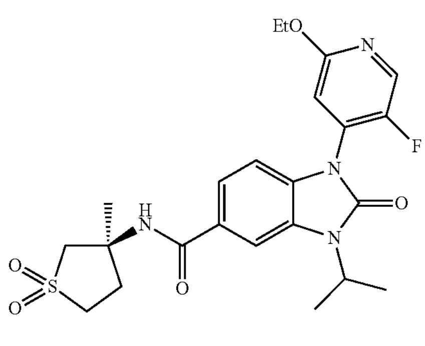 [SMILES: CCOc1cc(-n2c(=O)n(C(C)C)c3cc(C(=O)N[C@@]4(C)CCS(=O)(=O)C4)ccc32)c(F)cn1] | (S)-1-(2-Ethoxy-5-fluoropyridin-4-yl)-3-isopropyl-N-(3-methyl-1,1-dioxidotetrahydrothiophen-3-yl)-2-oxo-2,3-dihydro-1H-benzo[d]imidazole-5-carboxamide | 491 | 122 |

-continued

| Example | Structure | Name | LCMS [M + 1] | Human DGAT2 IC$_{50}$ (nM) |
|---|---|---|---|---|
| 18 | 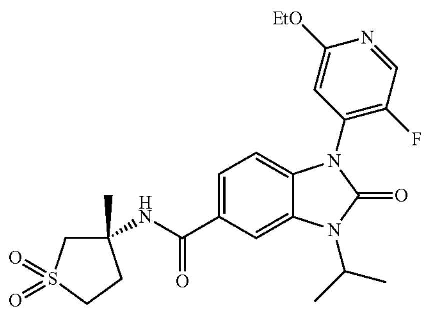 [SMILES: CCOc1cc(-n2c(=O)n(C(C)C)c3cc(C(=O)N[C@]4(C)CCS(=O)(=O)C4)ccc32)c(F)cn1] | (R)-1-(2-Ethoxy-5-fluoropyridin-4-yl)-3-isopropyl-N-(3-methyl-1,1-dioxidotetrahydrothiophen-3-yl)-2-oxo-2,3-dihydro-1H-benzo[d]imidazole-5-carboxamide | 491 | 28 |
| 19 | 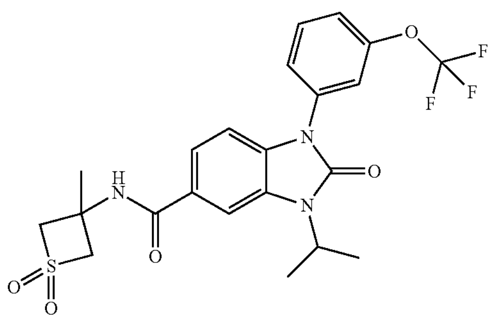 [SMILES: CC(C)n1c(=O)n(-c2cccc(OC(F)(F)F)c2)c2ccc(C(=O)NC3(C)CS(=O)(=O)C3)cc21] | 3-isopropyl-N-(3-methyl-1,1-dioxo-thietan-3-yl)-2-oxo-1-[3-(trifluoromethoxy)phenyl]benz-imidazole-5-carboxamide | 498 | 100 |
| 20 | 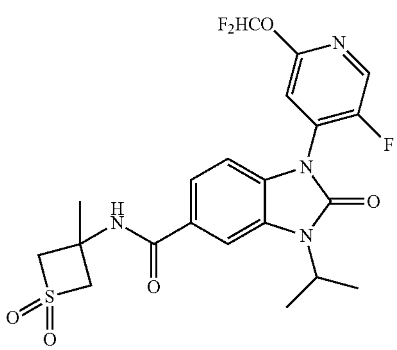 [SMILES: CC(C)n1c(=O)n(-c2cc(OC(F)F)ncc2F)c2ccc(C(=O)NC3(C)CS(=O)(=O)C3)cc21] | 1-(2-(difluoromethoxy)-5-fluoropyridin-4-yl)-3-isopropyl-N-(3-methyl-1,1-dioxidothietan-3-yl)-2-oxo-2,3-dihydro-1H-benzo[d]imidazole-5-carboxamide | 499 | 76 |
| 21 | 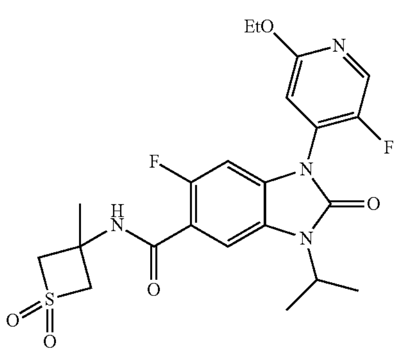 [SMILES: CCOc1cc(-n2c(=O)n(C(C)C)c3cc(C(=O)NC4(C)CS(=O)(=O)C4)c(F)cc32)c(F)cn1] | 1-(2-Ethoxy-5-fluoropyridin-4-yl)-6-fluoro-3-isopropyl-N-(3-methyl-1,1-dioxidothietan-3-yl)-2-oxo-2,3-dihydro-1H-benzo[d]imidazole-5-carboxamide | 495 | 31 |

-continued

| Example | Structure | Name | LCMS [M + 1] | Human DGAT2 IC$_{50}$ (nM) |
|---|---|---|---|---|
| 22 | 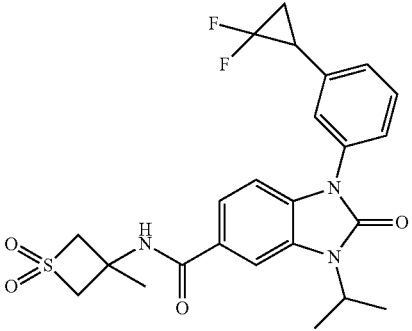 [SMILES: CC(C)n1c(=O)n(-c2cccc(C3CC3(F)F)c2)c2ccc(C(=O)NC3(C)CS(=O)(=O)C3)cc21] | 1-(3-(2,2-Difluorocyclopropyl)phenyl)-3-isopropyl-N-(3-methyl-1,1-dioxidothietan-3-yl)-2-oxo-2,3-dihydro-1H-benzo[d]imidazole-5-carboxamide | 490 | 66 |
| 23 | 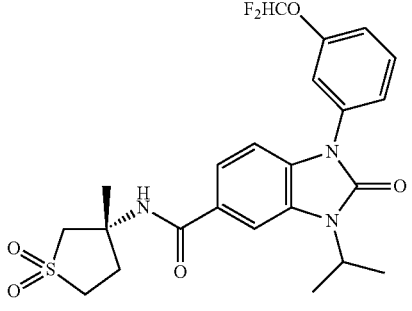 [SMILES: CC(C)n1c(=O)n(-c2cccc(OC(F)F)c2)c2ccc(C(=O)N[C@]3(C)CCS(=O)(=O)C3)cc21] | (R)-1-(3-(Difluoromethoxy)phenyl)-3-isopropyl-N-(3-methyl-1,1-dioxidotetrahydrothiophen-3-yl)-2-oxo-2,3-dihydro-1H-benzo[d]imidazole-5-carboxamide | 494 | 63 |
| 24 | 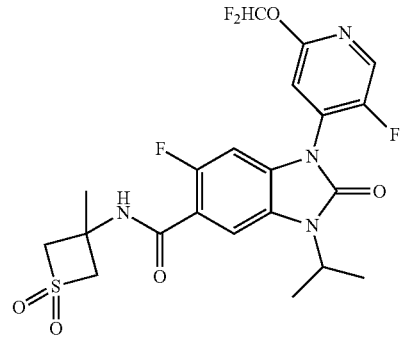 [SMILES: CC(C)n1c(=O)n(-c2cc(OC(F)F)ncc2F)c2cc(F)c(C(=O)NC3(C)CS(=O)(=O)C3)cc21] | 1-(2-(Difluoromethoxy)-5-fluoropyridin-4-yl)-6-fluoro-3-isopropyl-N-(3-methyl-1,1-dioxidothietan-3-yl)-2-oxo-2,3-dihydro-1H-benzo[d]imidazole-5-carboxamide | 517 | 66 |

Example 25: 1-(3-(difluoromethoxy)phenyl)-3-isopropyl-N-(4-methyl-1,1-dioxidotetrahydro-2H-thiopyran-4-yl)-2-oxo-2,3-dihydro-1H-benzo[d]imidazole-5-carboxamide

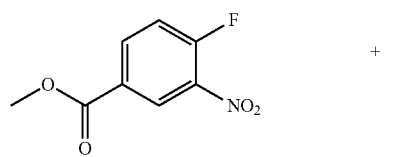

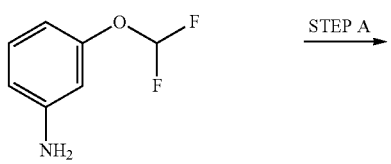

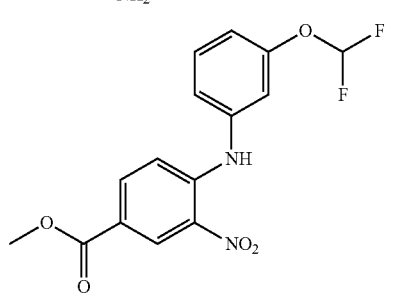

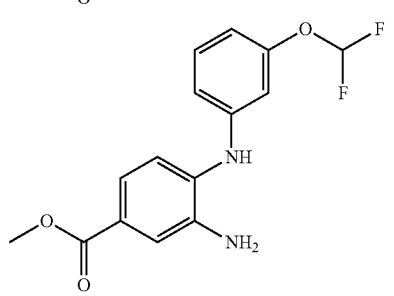

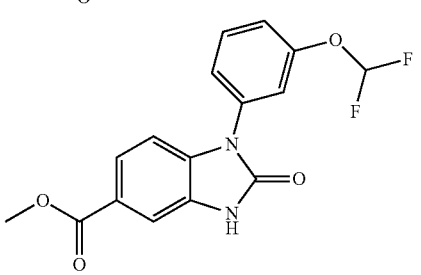

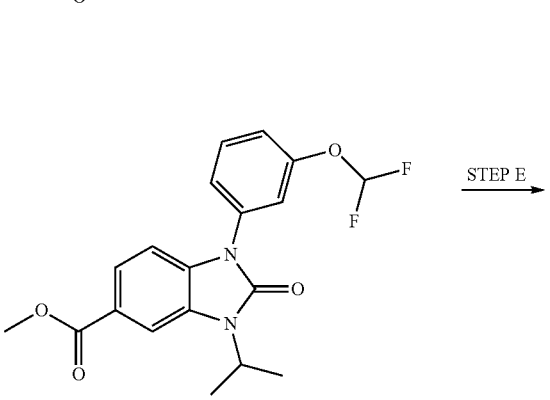

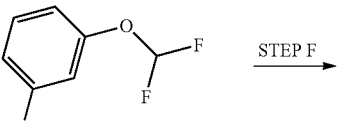

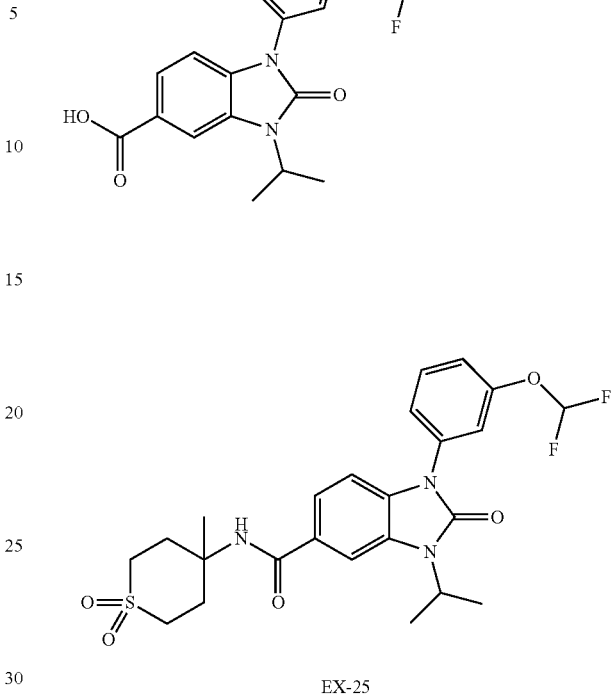

EX-25

Step A: Methyl 4-((3-(difluoromethoxy)phenyl)amino)-3-nitrobenzoate

To a stirred solution of methyl 4-fluoro-3-nitrobenzoate (7.0 g, 35.2 mmol) in DMSO (176 ml) were added 3-(difluoromethoxy)aniline (4.34 ml, 35.2 mmol) and DIPEA (12.28 ml, 70.3 mmol) at RT. The reaction was heated to 100° C. and stirred overnight. The reaction was cooled to RT. Water was added, and the resulting solid was collected by vacuum filtration and dissolved in ethyl acetate. The aqueous fraction was extracted three times with ethyl acetate. The combined organic fractions were washed with brine, dried over $Na_2SO_4$ (s), filtered, and concentrated under reduced pressure to afford the title compound. LC/MS=339 [M+1].

Step B: Methyl 3-amino-4-((3-(difluoromethoxy)phenyl)amino)benzoate

At RT, zinc (10.44 g, 160 mmol) was added to a stirred mixture of methyl 4-((3-(difluoromethoxy)phenyl)amino)-3-nitrobenzoate (10.8 g, 31.9 mmol) in methanol (106 ml), THF (53.2 ml), and saturated aqueous ammonium chloride (53.2 ml). The reaction was stirred for two hours at RT, then filtered over Celite. The celite was washed with methanol. The mixture was concentrated, EtOAc was added, and the water layer was separated. The organic layer was dried with $Na_2SO_4$ (s), filtered, and concentrated under reduced pressure. The crude residue was purified by flash silica gel column chromatography (0 to 100% EtOAc in hexanes) to afford the title compound. LC/MS=309 [M+1].

Step C: 1-(3-(difluoromethoxy)phenyl)-2-oxo-2,3-dihydro-1H-benzo[d]imidazole-5-carboxylate At RT, methyl 3-amino-4-((3-(difluoromethoxy)phenyl)amino)benzoate (5.90 g, 19.14 mmol) was dissolved in THF (191 ml). CDI (15.52 g, 96 mmol) was added, and the reaction was stirred at RT for 16 hrs. Water and EtOAc were added, the layers were separated, and the aqueous layer was extracted three times with EtOAc. The combined organic layers were dried with $Na_2SO_4$ (s), filtered, and concentrated under reduced pressure. The crude residue was purified by flash silica gel column chromatography (0 to 100% EtOAc in hexanes) to afford the title compound. LC/MS=335 [M+1].

Step D: 1-(3-(difluoromethoxy)phenyl)-3-isopropyl-2-oxo-2,3-dihydro-1H-benzo[d]imidazole-5-carboxylate At RT, methyl 1-(3-(difluoromethoxy)phenyl)-2-oxo-2,3-dihydro-1H-benzo[d]imidazole-5-carboxylate (0.93 g, 2.78 mmol) was dissolved in DMF (27.8 ml) and cesium carbonate (2.72 g, 8.35 mmol) was added. 2-iodopropane (0.833 ml, 8.35 mmol) was added, and the mixture was stirred under a nitrogen atmosphere, heated to 80° C., and stirred at that temperature overnight. Water and ethyl acetate were added, the layers were separated, and the aqueous layer was extracted three times with EtOAc. The combined organic layers were washed with brine, dried with $MgSO_4$ (s), filtered, and concentrated under reduced pressure. The crude residue was purified by flash silica gel column chromatography (0 to 100% EtOAc in hexanes) to afford the title compound. LC/MS=377 [M+1].

Step E: 1-(3-(difluoromethoxy)phenyl)-3-isopropyl-2-oxo-2,3-dihydro-1H-benzo[d]imidazole-5-carboxylic acid To a stirred solution of methyl 1-(3-(difluoromethoxy)phenyl)-3-isopropyl-2-oxo-2,3-dihydro-1H-benzo[d]imidazole-5-carboxylate (937 mg, 2.490 mmol) in THF (4.15 ml) and methanol (4.15 ml) at RT was added a solution of lithium hydroxide (298 mg, 12.45 mmol) in water (4.15 ml). The reaction was stirred at RT, then, the reaction mixture was acidified to pH=1 with 1 N aqueous HCl. EtOAc was added, and the layers were separated. The aqueous layer was extracted with EtOAc three times, and the combined organic layers were dried with $MgSO_4$ (s), filtered, and concentrated under reduced pressure to afford the title compound. LC/MS=363 [M+1].

Step F 1-(3-(difluoromethoxy)phenyl)-3-isopropyl-N-(4-methyl-1,1-dioxidotetrahydro-2H-thiopyran-4-yl)-2-oxo-2,3-dihydro-1H-benzo[d]imidazole-5-carboxamide At RT, to a stirred solution of -(3-(difluoromethoxy)phenyl)-3-isopropyl-2-oxo-2,3-dihydro-1H-benzo[d]imidazole-5-carboxylic acid (36 mg, 0.099 mmol), HATU (41.6 mg, 0.109 mmol), and 4-amino-4-methyltetrahydro-2H-thiopyran 1,1-dioxide (17.84 mg, 0.109 mmol) in DMF (0.994 ml) was added DIPEA (0.052 ml, 0.298 mmol. The reaction was stirred at RT for 16 hrs. The next morning, the reaction was complete as determined by LCMS, and the DMF was evaporated under reduced pressure. The crude residue was purified by flash silica gel column chromatography (0 to 100% EtOAc in hexanes followed by 0 to 30% Acetone in DCM) to afford the title compound. 1H NMR (500 MHz, Methanol-$d_4$) δ 7.82 (d, J=1.4 Hz, 1H), 7.66-7.60 (m, 2H), 7.42 (dd, J=8.0, 1.1 Hz, 1H), 7.36 (t, J=2.0 Hz, 1H), 7.28 (dd, J=8.2, 2.0 Hz, 1H), 7.15 (d, J=8.2 Hz, 1H), 6.94 (t, J=73.6 Hz, 1H), 4.84-4.75 (m, 1H), 3.29-3.21 (m, 2H), 3.02 (d, J=13.7 Hz, 2H), 2.91 (d, J=14.7 Hz, 2H), 2.25-2.14 (m, 2H), 1.64 (d, J=7.0 Hz, 6H), 1.55 (s, 3H). LC/MS=508 [M+1]. Human DGAT2 $IC_{50}$=23 nM.

By using procedures similar to those described in Example 25 with appropriate reagents, the following compounds were synthesized. These compounds were characterized by LC/MS.

| Example | Structure | Name | LCMS [M + 1] | DGAT2 IC50 (nM) |
|---|---|---|---|---|
| 26 | 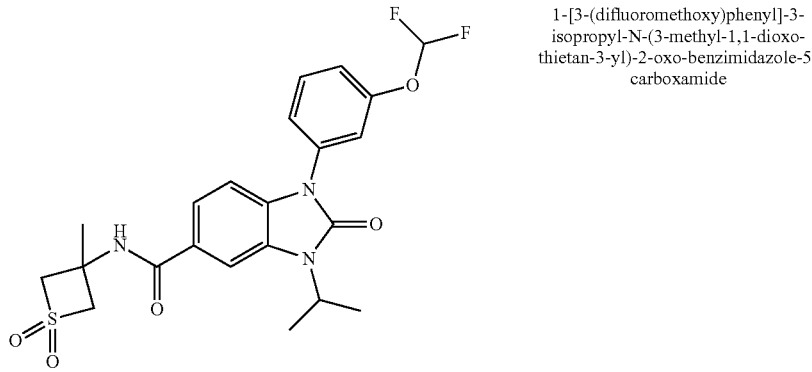 | 1-[3-(difluoromethoxy)phenyl]-3-isopropyl-N-(3-methyl-1,1-dioxo-thietan-3-yl)-2-oxo-benzimidazole-5-carboxamide | 481 | 54 |

-continued

| Example | Structure | Name | LCMS [M + 1] | DGAT2 IC50 (nM) |
|---------|-----------|------|--------------|-----------------|
| 27 | 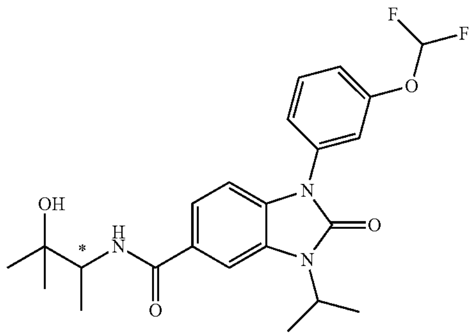 [SMILES: CC(C)n1c(=O)n(-c2cccc(OC(F)F)c2)c2ccc(C(=O)NC(C)C(C)(C)O)cc21] | 1-[3-(difluoromethoxy)phenyl]-N-(2-hydroxy-1,2-dimethyl-propyl)-3-isopropyl-2-oxo-benzimidazole-5-carboxamide | 448 | >10000 |
| 28 | 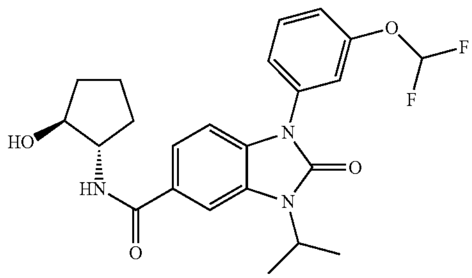 [SMILES: CC(C)n1c(=O)n(-c2cccc(OC(F)F)c2)c2ccc(C(=O)N[C@H]3CCC[C@@H]3O)cc21] | 1-[3-(difluoromethoxy)phenyl]-N-[(1S,2S)-2-hydroxycyclopentyl]-3-isopropyl-2-oxo-benzimidazole-5-carboxamide | 446 | 779 |
| 29 | 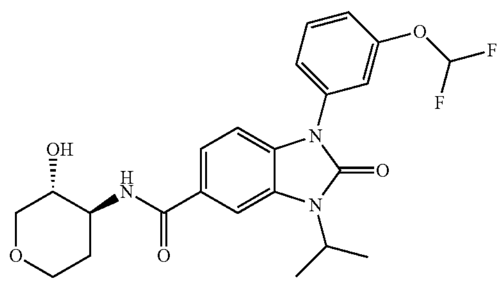 [SMILES: CC(C)n1c(=O)n(-c2cccc(OC(F)F)c2)c2ccc(C(=O)N[C@H]3CCOC[C@@H]3O)cc21] | 1-[3-(difluoromethoxy)phenyl]-N-[(3R,4S)-3-hydroxytetrahydropyran-4-yl]-3-isopropyl-2-oxo-benzimidazole-5-carboxamide | 462 | 1256 |
| 30 | 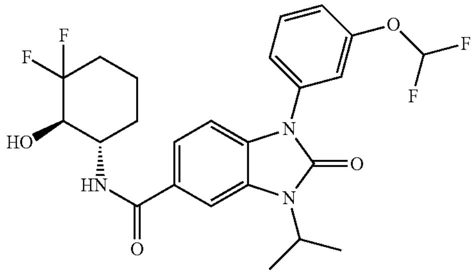 [SMILES: CC(C)n1c(=O)n(-c2cccc(OC(F)F)c2)c2ccc(C(=O)N[C@H]3CCCC(F)(F)[C@@H]3O)cc21] | N-[(1S,2R)-3,3-difluoro-2-hydroxy-cyclohexyl]-1-[3-(difluoromethoxy)phenyl]-3-isopropyl-2-oxo-benzimidazole-5-carboxamide | 496 | 31 |
| 31 | 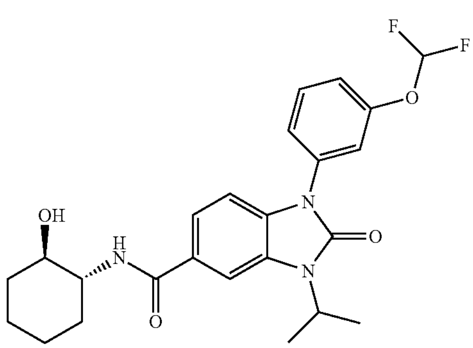 [SMILES: CC(C)n1c(=O)n(-c2cccc(OC(F)F)c2)c2ccc(C(=O)N[C@@H]3CCCC[C@H]3O)cc21] | 1-[3-(difluoromethoxy)phenyl]-N-[(1R,2R)-2-hydroxycyclohexyl]-3-isopropyl-2-oxo-benzimidazole-5-carboxamide | 460 | 106 |

| Example | Structure | Name | LCMS [M + 1] | DGAT2 IC50 (nM) |
|---|---|---|---|---|
| 32 | 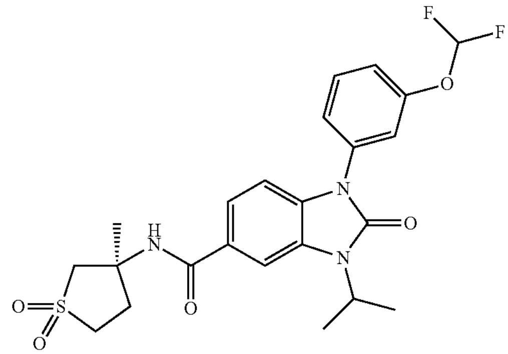 [SMILES: CC(C)n1c(=O)n(-c2cccc(OC(F)F)c2)c2ccc(C(=O)N[C@@]3(C)CCS(=O)(=O)C3)cc21] | 1-[3-(difluoromethoxy)phenyl]-3-isopropyl-N-[(3S)-3-methyl-1,1-dioxo-thiolan-3-yl]-2-oxo-benzimidazole-5-carboxamide | 494 | 96 |
| 33 | 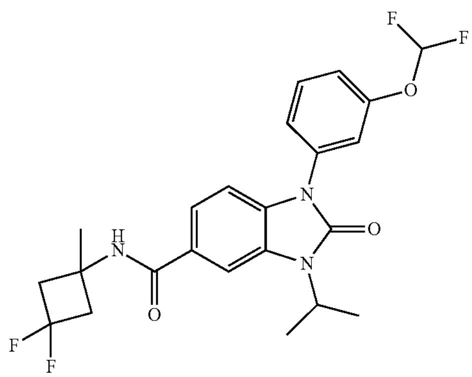 [SMILES: CC(C)n1c(=O)n(-c2cccc(OC(F)F)c2)c2ccc(C(=O)NC3(C)CC(F)(F)C3)cc21] | 1-[3-(difluoromethoxy)phenyl]-N-(3,3-difluoro-1-methyl-cyclobutyl)-3-isopropyl-2-oxo-benzimidazole-5-carboxamide | 466 | 182 |
| 34 | 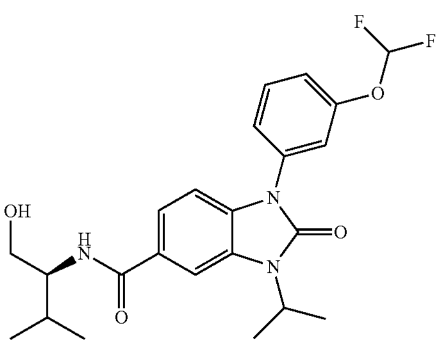 [SMILES: CC(C)[C@@H](CO)NC(=O)c1ccc2c(c1)n(C(C)C)c(=O)n2-c1cccc(OC(F)F)c1] | 1-[3-(difluoromethoxy)phenyl]-N-[(1S)-1-(hydroxymethyl)-2-methyl-propyl]-3-isopropyl-2-oxo-benzimidazole-5-carboxamide | 448 | 62 |
| 35 | 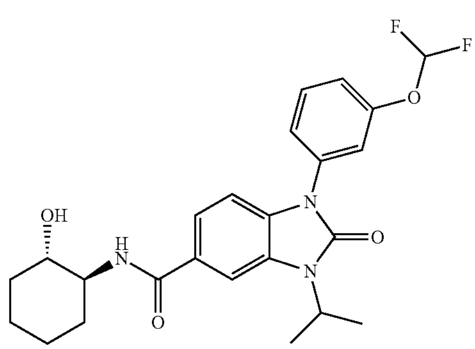 [SMILES: CC(C)n1c(=O)n(-c2cccc(OC(F)F)c2)c2ccc(C(=O)N[C@H]3CCCC[C@@H]3O)cc21] | 1-[3-(difluoromethoxy)phenyl]-N-[(1S,2S)-2-hydroxycyclohexyl]-3-isopropyl-2-oxo-benzimidazole-5-carboxamide | 460 | 71 |

-continued

| Example | Structure | Name | LCMS [M + 1] | DGAT2 IC50 (nM) |
|---|---|---|---|---|
| 36 | 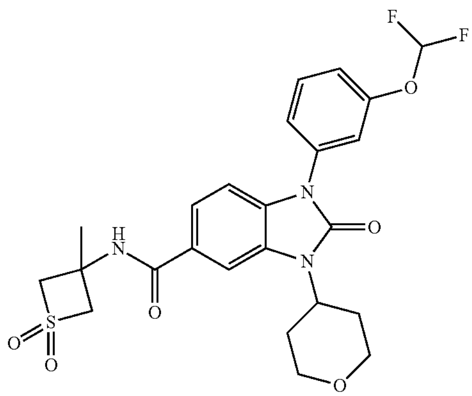 [SMILES: CC1(NC(=O)c2ccc3c(c2)n(C2CCOCC2)c(=O)n3-c2cccc(OC(F)F)c2)CS(=O)(=O)C1] | 1-(3-(difluoromethoxy)phenyl)-N-(3-methyl-1,1-dioxidothietan-3-yl)-2-oxo-3-(tetrahydro-2H-pyran-4-yl)-2,3-dihydro-1H-benzo[d]imidazole-5-carboxamide | 522 | 19.4 |
| 37 | 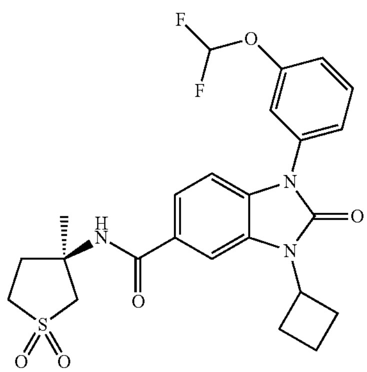 [SMILES: C[C@@]1(NC(=O)c2ccc3c(c2)n(C2CCC2)c(=O)n3-c2cccc(OC(F)F)c2)CCS(=O)(=O)C1] | (R)-3-Cyclobutyl-1-(3-(difluoromethoxy)phenyl)-N-(3-methyl-1,1-dioxidotetrahydrothiophen-3-yl)-2-oxo-2,3-dihydro-1H-benzo[d]imidazole-5-carboxamide | 506 | 64 |
| 38 | 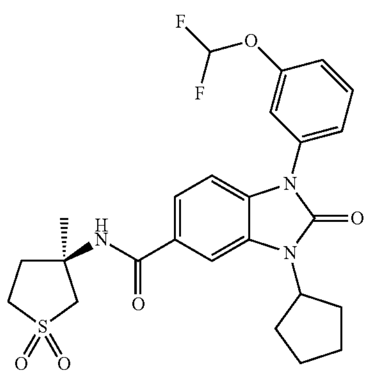 [SMILES: C[C@@]1(NC(=O)c2ccc3c(c2)n(C2CCCC2)c(=O)n3-c2cccc(OC(F)F)c2)CCS(=O)(=O)C1] | (R)-3-Cyclopentyl-1-(3-(difluoromethoxy)phenyl)-N-(3-methyl-1,1-dioxidotetrahydrothiophen-3-yl)-2-oxo-2,3-dihydro-1H-benzo[d]imidazole-5-carboxamide | 520 | 24 |
| 39 | 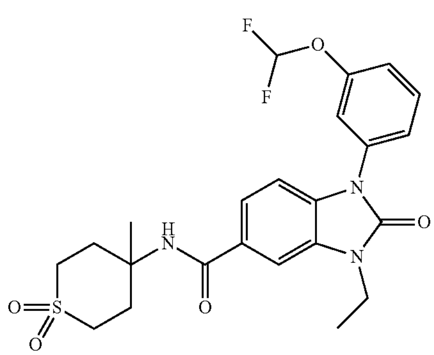 [SMILES: CCn1c(=O)n(-c2cccc(OC(F)F)c2)c2ccc(C(=O)NC3(C)CCS(=O)(=O)CC3)cc21] | 1-(3-(Difluoromethoxy)phenyl)-3-ethyl-N-(4-methyl-1,1-dioxidotetrahydro-2H-thiopyran-4-yl)-2-oxo-2,3-dihydro-1H-benzo[d]imidazole-5-carboxamide | 494 | 109 |

-continued

| Example | Name | LCMS [M + 1] | DGAT2 IC50 (nM) |
|---|---|---|---|
| 40 | 1-(3-(Difluoromethoxy)phenyl)-3-ethyl-N-(3-methyl-1,1-dioxidothietan-3-yl)-2-oxo-2,3-dihydro-1H-benzo[d]imidazole-5-carboxamide | 466 | 194 |
| 41 | 3-Cyclopropyl-1-(3-(difluoromethoxy)phenyl)-N-(4-methyl-1,1-dioxidotetrahydro-2H-thiopyran-4-yl)-2-oxo-2,3-dihydro-1H-benzo[d]imidazole-5-carboxamide | 506 | 211.4 |
| 42 | 1-(3-(Difluoromethoxy)phenyl)-N-(4-methyl-1,1-dioxidotetrahydro-2H-thiopyran-4-yl)-2-oxo-3-(3,3,3-trifluoropropyl)-2,3-dihydro-1H-benzo[d]imidazole-5-carboxamide | 562 | 404.9 |
| 43 | 1-(3-(Difluoromethoxy)phenyl)-N-(3-methyl-1,1-dioxidothietan-3-yl)-2-oxo-3-(2,2,2-trifluoroethyl)-2,3-dihydro-1H-benzo[d]imidazole-5-carboxamide | 520 | 202 |

-continued

| Example | Structure | Name | LCMS [M + 1] | DGAT2 IC50 (nM) |
|---|---|---|---|---|
| 44 | 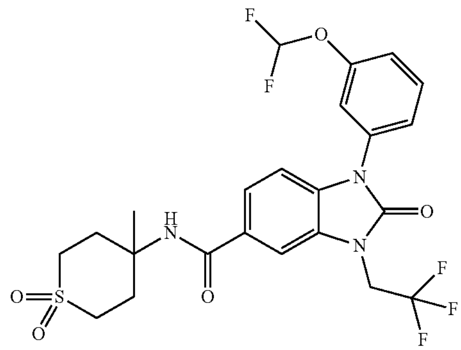 [SMILES: CC1(NC(=O)c2ccc3c(c2)n(CC(F)(F)F)c(=O)n3-c2cccc(OC(F)F)c2)CCS(=O)(=O)CC1] | 1-(3-(difluoromethoxy)phenyl)-N-(4-methyl-1,1-dioxidotetrahydro-2H-thiopyran-4-yl)-2-oxo-3-(2,2,2-trifluoroethyl)-2,3-dihydro-1H-benzo[d]imidazole-5-carboxamide | 548 | 87 |
| 45a | 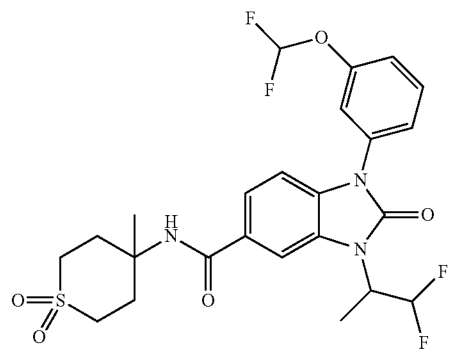 [SMILES: CC(C(F)F)n1c(=O)n(-c2cccc(OC(F)F)c2)c2ccc(C(=O)NC3(C)CCS(=O)(=O)CC3)cc21] | 1-(3-(Difluoromethoxy)phenyl)-3-(1,1-difluoropropan-2-yl)-N-(4-methyl-1,1-dioxidotetrahydro-2H-thiopyran-4-yl)-2-oxo-2,3-dihydro-1H-benzo[d]imidazole-5-carboxamide (faster eluting on AD-H column, 15% EtOH/CO$_2$) | 544 | 12 |
| 45b | 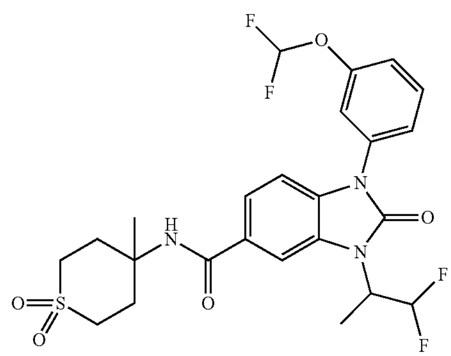 [SMILES: CC(C(F)F)n1c(=O)n(-c2cccc(OC(F)F)c2)c2ccc(C(=O)NC3(C)CCS(=O)(=O)CC3)cc21] | 1-(3-(Difluoromethoxy)phenyl)-3-(1,1-difluoropropan-2-yl)-N-(4-methyl-1,1-dioxidotetrahydro-2H-thiopyran-4-yl)-2-oxo-2,3-dihydro-1H-benzo[d]imidazole-5-carboxamide (slower eluting on AD-H column, 15% EtOH/CO$_2$) | 544 | 101 |
| 46a | 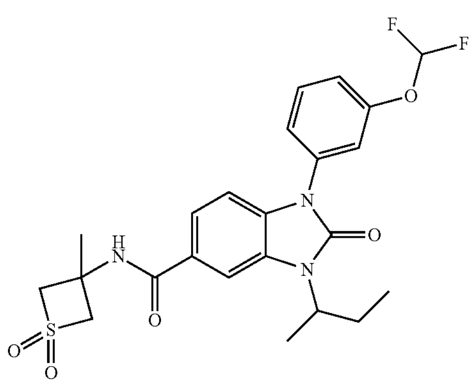 [SMILES: CCC(C)n1c(=O)n(-c2cccc(OC(F)F)c2)c2ccc(C(=O)NC3(C)CS(=O)(=O)C3)cc21] | 3-(sec-butyl)-1-(3-(difluoromethoxy)phenyl)-N-(3-methyl-1,1-dioxidothietan-3-yl)-2-oxo-2,3-dihydro-1H-benzo[d]imidazole-5-carboxamide (Faster eluting on IC-H column, 40%/60% ethanol/CO$_2$) | 494 | 81 |

-continued

| Example | Structure | Name | LCMS [M + 1] | DGAT2 IC50 (nM) |
|---|---|---|---|---|
| 46b | 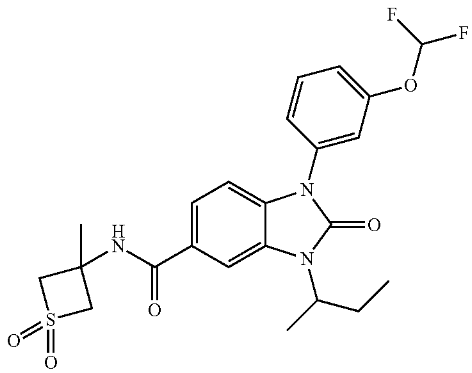 [SMILES: CCC(C)n1c(=O)n(-c2cccc(OC(F)F)c2)c2ccc(C(=O)NC3(C)CS(=O)(=O)C3)cc21] | 3-(sec-butyl)-1-(3-(difluoromethoxy)phenyl)-N-(3-methyl-1,1-dioxidothietan-3-yl)-2-oxo-2,3-dihydro-1H-benzo[d]imidazole-5-carboxamide (slower eluting on IC-H column, 40%/60% ethanol/CO$_2$) | 494 | 92 |
| 47 | 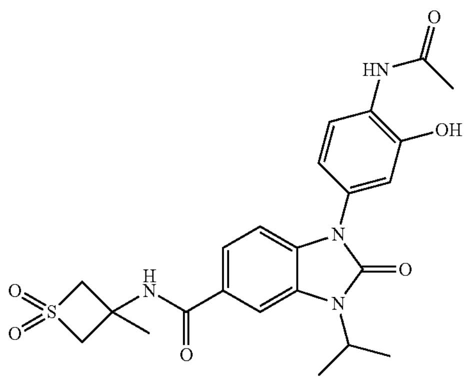 [SMILES: CC(=O)Nc1ccc(-n2c(=O)n(C(C)C)c3cc(C(=O)NC4(C)CS(=O)(=O)C4)ccc32)cc1O] | 1-(4-acetamido-3-hydroxyphenyl)-3-isopropyl-N-(3-methyl-1,1-dioxidothietan-3-yl)-2-oxo-2,3-dihydro-1H-benzo[d]imidazole-5-carboxamide | 487 | >10000 |
| 48 | 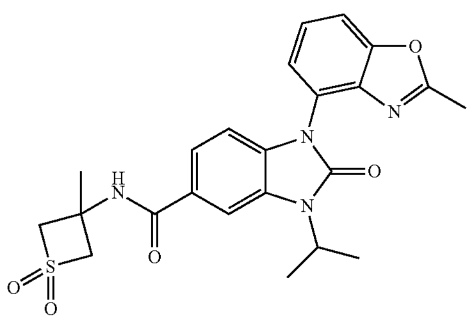 [SMILES: Cc1nc2c(-n3c(=O)n(C(C)C)c4cc(C(=O)NC5(C)CS(=O)(=O)C5)ccc43)cccc2o1] | 3-isopropyl-N-(3-methyl-1,1-dioxidothietan-3-yl)-1-(2-methylbenzo[d]oxazol-4-yl)-2-oxo-2,3-dihydro-1H-benzo[d]imidazole-5-carboxamide | 469 | >10000 |
| 49 | 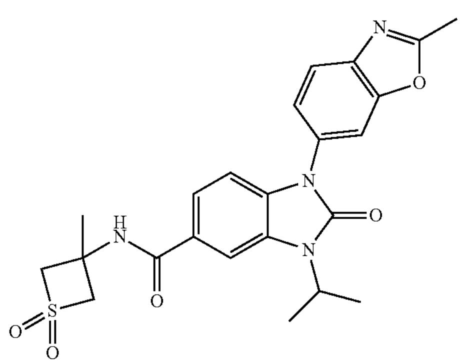 [SMILES: Cc1nc2ccc(-n3c(=O)n(C(C)C)c4cc(C(=O)NC5(C)CS(=O)(=O)C5)ccc43)cc2o1] | 3-isopropyl-N-(3-methyl-1,1-dioxidothietan-3-yl)-1-(2-methylbenzo[d]oxazol-6-yl)-2-oxo-2,3-dihydro-1H-benzo[d]imidazole-5-carboxamide | 469 | >10000 |

| Example | Structure | Name | LCMS [M + 1] | DGAT2 IC50 (nM) |
|---|---|---|---|---|
| 50 | 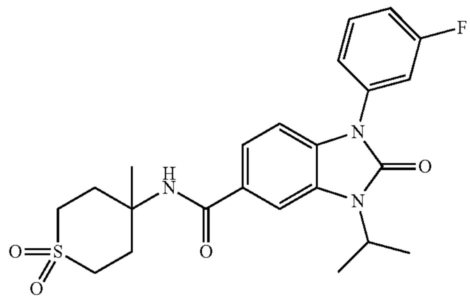 [SMILES: CC(C)n1c(=O)n(-c2cccc(F)c2)c2ccc(C(=O)NC3(C)CCS(=O)(=O)CC3)cc21] | 1-(3-fluorophenyl)-3-isopropyl-N-(4-methyl-1,1-dioxidotetrahydro-2H-thiopyran-4-yl)-2-oxo-2,3-dihydro-1H-benzo[d]imidazole-5-carboxamide | 460 | >9990 |
| 51 | 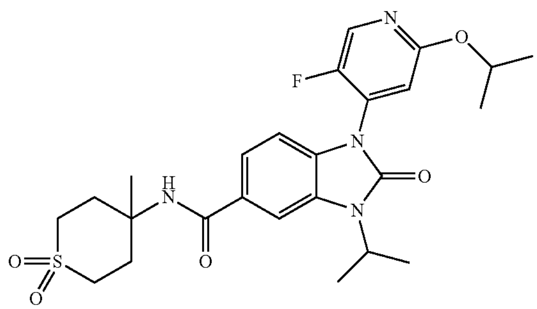 [SMILES: CC(C)Oc1cc(-n2c(=O)n(C(C)C)c3cc(C(=O)NC4(C)CCS(=O)(=O)CC4)ccc32)c(F)cn1] | 1-(5-fluoro-2-isopropoxypyridin-4-yl)-3-isopropyl-N-(4-methyl-1,1-dioxidotetrahydro-2H-thiopyran-4-yl)-2-oxo-2,3-dihydro-1H-benzo[d]imidazole-5-carboxamide | 519 | 251 |
| 52 | 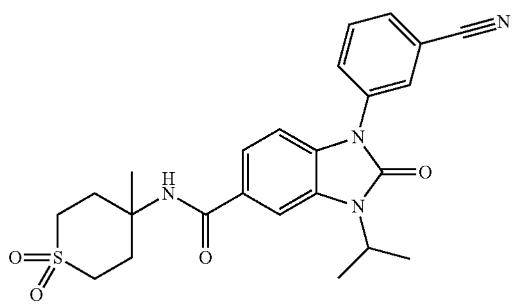 [SMILES: CC(C)n1c(=O)n(-c2cccc(C#N)c2)c2ccc(C(=O)NC3(C)CCS(=O)(=O)CC3)cc21] | 1-(3-cyanophenyl)-3-isopropyl-N-(4-methyl-1,1-dioxidotetrahydro-2H-thiopyran-4-yl)-2-oxo-2,3-dihydro-1H-benzo[d]imidazole-5-carboxamide | 467 | >9990 |
| 53 | 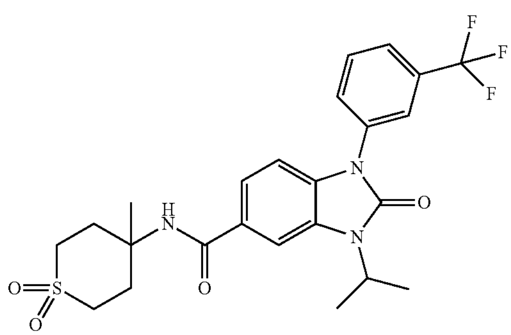 [SMILES: CC(C)n1c(=O)n(-c2cccc(C(F)(F)F)c2)c2ccc(C(=O)NC3(C)CCS(=O)(=O)CC3)cc21] | 3-isopropyl-N-(4-methyl-1,1-dioxidotetrahydro-2H-thiopyran-4-yl)-2-oxo-1-(3-(trifluoromethyl)phenyl)-2,3-dihydro-1H-benzo[d]imidazole-5-carboxamide | 510 | 1834 |
| 54 | 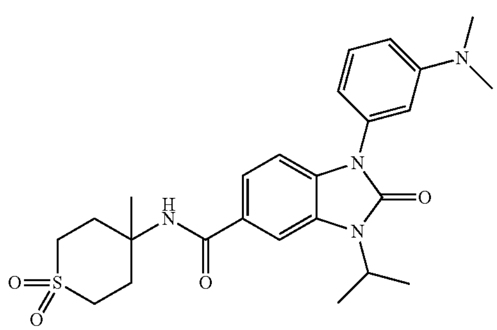 [SMILES: CC(C)n1c(=O)n(-c2cccc(N(C)C)c2)c2ccc(C(=O)NC3(C)CCS(=O)(=O)CC3)cc21] | 1-(3-(dimethylamino)phenyl)-3-isopropyl-N-(4-methyl-1,1-dioxidotetrahydro-2H-thiopyran-4-yl)-2-oxo-2,3-dihydro-1H-benzo[d]imidazole-5-carboxamide | 485 | 1324 |

-continued

| Example | Structure | Name | LCMS [M + 1] | DGAT2 IC50 (nM) |
|---|---|---|---|---|
| 55 | 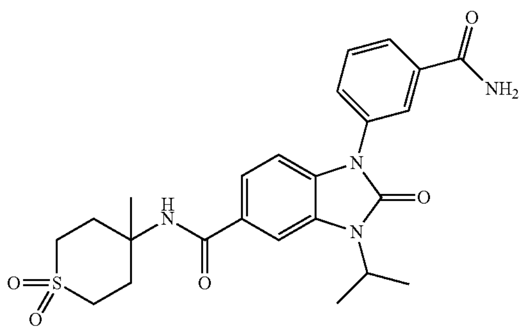 [SMILES: CC(C)n1c(=O)n(-c2cccc(C(N)=O)c2)c2ccc(C(=O)NC3(C)CCS(=O)(=O)CC3)cc21] | 1-(3-carbamoylphenyl)-3-isopropyl-N-(4-methyl-1,1-dioxidotetrahydro-2H-thiopyran-4-yl)-2-oxo-2,3-dihydro-1H-benzo[d]imidazole-5-carboxamide | 485 | >9990 |
| 56 | 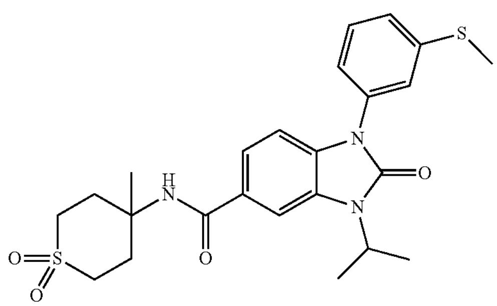 [SMILES: CSc1cccc(-n2c(=O)n(C(C)C)c3cc(C(=O)NC4(C)CCS(=O)(=O)CC4)ccc32)c1] | 3-isopropyl-N-(4-methyl-1,1-dioxidotetrahydro-2H-thiopyran-4-yl)-1-(3-(methylthio)phenyl)-2-oxo-2,3-dihydro-1H-benzo[d]imidazole-5-carboxamide | 488 | 367 |
| 57 | 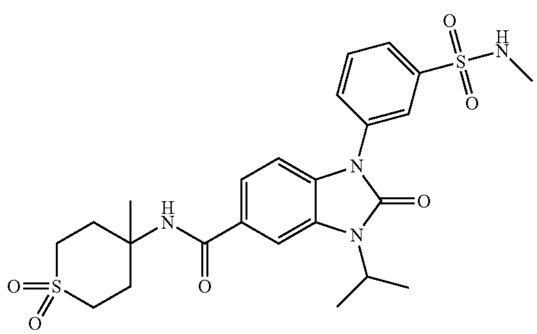 [SMILES: CNS(=O)(=O)c1cccc(-n2c(=O)n(C(C)C)c3cc(C(=O)NC4(C)CCS(=O)(=O)CC4)ccc32)c1] | 3-isopropyl-N-(4-methyl-1,1-dioxidotetrahydro-2H-thiopyran-4-yl)-1-(3-(N-methylsulfamoyl)phenyl)-2-oxo-2,3-dihydro-1H-benzo[d]imidazole-5-carboxamide | 535 | >9990 |
| 58 | 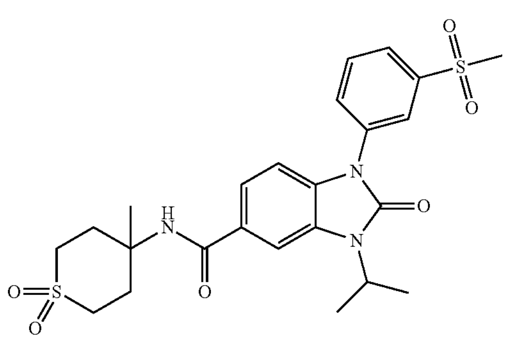 [SMILES: CC(C)n1c(=O)n(-c2cccc(S(C)(=O)=O)c2)c2ccc(C(=O)NC3(C)CCS(=O)(=O)CC3)cc21] | 3-isopropyl-N-(4-methyl-1,1-dioxidotetrahydro-2H-thiopyran-4-yl)-1-(3-(methylsulfonyl)phenyl)-2-oxo-2,3-dihydro-1H-benzo[d]imidazole-5-carboxamide | 520 | >9990 |

| Example | Structure | Name | LCMS [M + 1] | DGAT2 IC50 (nM) |
|---|---|---|---|---|
| 59 | 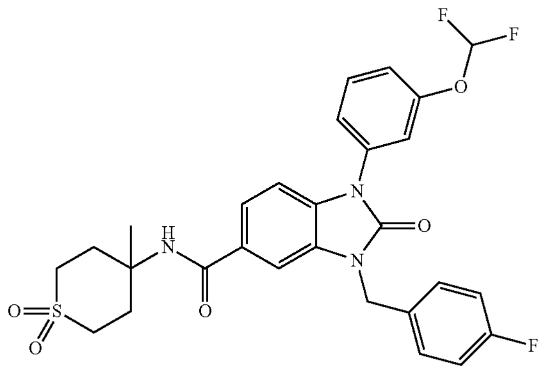 [SMILES: CC1(NC(=O)c2ccc3c(c2)n(Cc2ccc(F)cc2)c(=O)n3-c2cccc(OC(F)F)c2)CCS(=O)(=O)CC1] | 1-(3-(difluoromethoxy)phenyl)-3-(4-fluorobenzyl)-N-(4-methyl-1,1-dioxidotetrahydro-2H-thiopyran-4-yl)-2-oxo-2,3-dihydro-1H-benzo[d]imidazole-5-carboxamide | 574 | 38 |
| 60 | 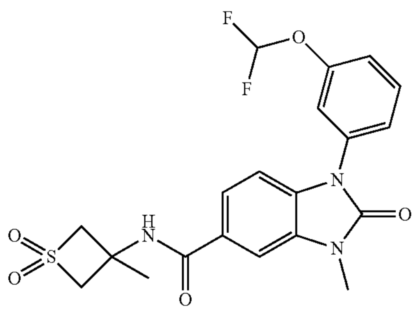 [SMILES: Cn1c(=O)n(-c2cccc(OC(F)F)c2)c2ccc(C(=O)NC3(C)CS(=O)(=O)C3)cc21] | 1-(3-(difluoromethoxy)phenyl)-3-methyl-N-(3-methyl-1,1-dioxidothietan-3-yl)-2-oxo-2,3-dihydro-1H-benzo[d]imidazole-5-carboxamide | 452 | 1086 |
| 61 | 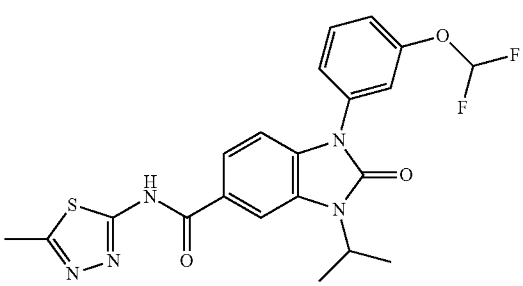 [SMILES: Cc1nnc(NC(=O)c2ccc3c(c2)n(C(C)C)c(=O)n3-c2cccc(OC(F)F)c2)s1] | 1-(3-(difluoromethoxy)phenyl)-3-isopropyl-N-(5-methyl-1,3,4-thiadiazol-2-yl)-2-oxo-2,3-dihydro-1H-benzo[d]imidazole-5-carboxamide | 460 | >9990 |
| 62 | 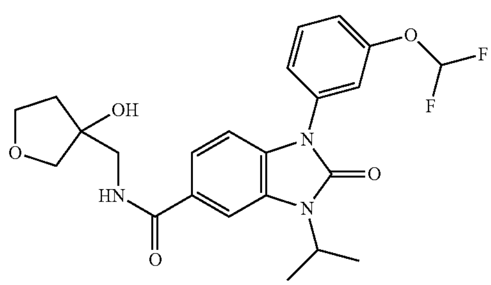 [SMILES: CC(C)n1c(=O)n(-c2cccc(OC(F)F)c2)c2ccc(C(=O)NCC3(O)CCOC3)cc21] | 1-(3-(difluoromethoxy)phenyl)-N-((3-hydroxytetrahydrofuran-3-yl)methyl)-3-isopropyl-2-oxo-2,3-dihydro-1H-benzo[d]imidazole-5-carboxamide | 462 | >9990 |
| 63 | 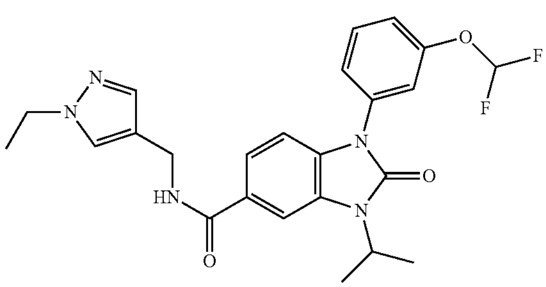 [SMILES: CCn1cc(CNC(=O)c2ccc3c(c2)n(C(C)C)c(=O)n3-c2cccc(OC(F)F)c2)cn1] | 1-(3-(difluoromethoxy)phenyl)-N-((1-ethyl-1H-pyrazol-4-yl)methyl)-3-isopropyl-2-oxo-2,3-dihydro-1H-benzo[d]imidazole-5-carboxamide | 470 | >9990 |

Example 64: 1-(3-(difluoromethoxy)phenyl)-3-(2-hydroxy-2-methylpropyl)-N-(3-methyl-1,1-dioxidothietan-3-yl)-2-oxo-2,3-dihydro-1H-benzo[d]imidazole-5-carboxamide

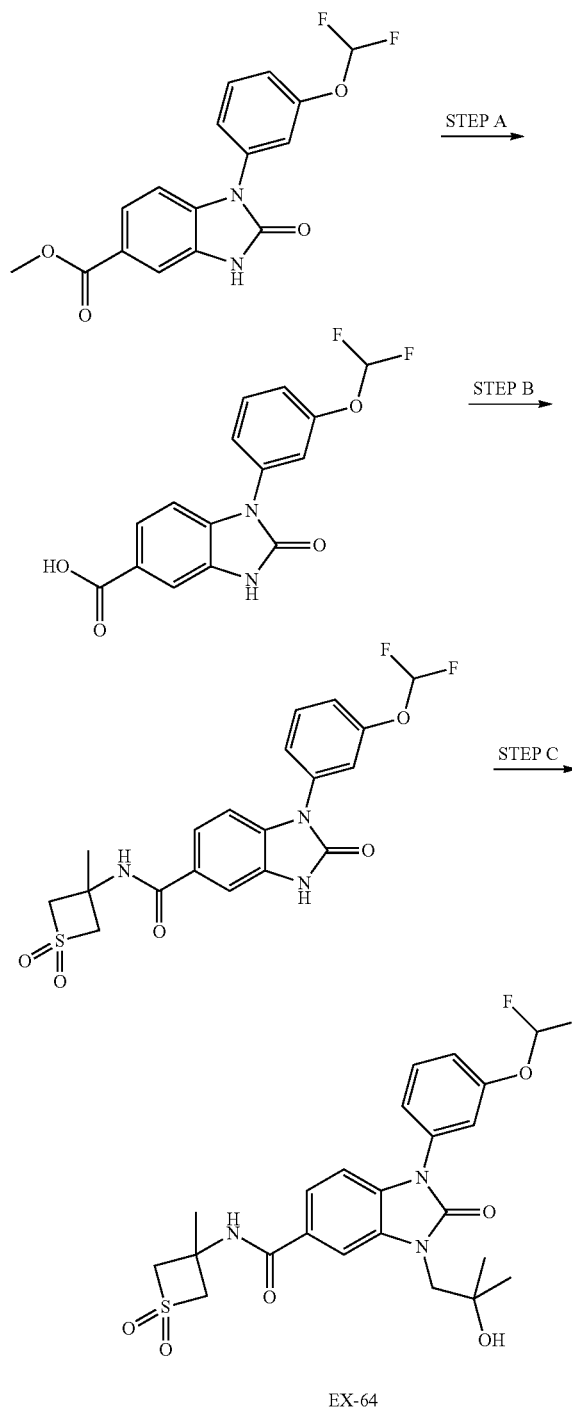

EX-64

Step A: 1-(3-(difluoromethoxy)phenyl)-2-oxo-2,3-dihydro-1H-benzo[d]imidazole-5-carboxylic acid To a stirred solution of methyl 1-(3-(difluoromethoxy)phenyl)-2-oxo-2,3-dihydro-1H-benzo[d]imidazole-5-carboxylate (211 mg, 0.631 mmol) in THF (2 mL), MeOH (2 mL) and water (2 mL) was added lithium hydroxide hydrate (79 mg, 1.894 mmol) at 25° C. After the addition was finished, the reaction mixture was stirred at 50° C. for 5 h, then concentrated in vacuo. The residue was dissolved in H₂O, and HCl (1N in water) was added to the mixture until pH=4. Then the mixture was extracted with DCM (×3). The combined organic layers were washed with brine, dried over Na₂SO₄, then filtered and concentrated in vacuo to afford the title compound. LC/MS=321 [M+1].

Step B: 1-(3-(difluoromethoxy)phenyl)-N-(3-methyl-1,1-dioxidothietan-3-yl)-2-oxo-2,3-dihydro-1H-benzo[d]imidazole-5-carboxamide To a stirred solution of 1-(3-(difluoromethoxy)phenyl)-2-oxo-2,3-dihydro-1H-benzo[d]imidazole-5-carboxylic acid (179 mg, 0.559 mmol) and 2-(3H-[1,2,3]triazolo[4,5-b]pyridin-3-yl)-1,1,3,3-tetramethylisouronium hexafluorophosphate(V) (319 mg, 0.838 mmol) in DMF (5 mL) was added N-ethyl-N-isopropylpropan-2-amine (0.278 ml, 1.677 mmol) at 25° C. After the addition was finished, the reaction mixture was stirred at 25° C. for 5 mins, and 3-amino-3-methylthietane 1,1-dioxide (83 mg, 0.615 mmol) was added. After the addition was finished, the reaction mixture was stirred at 50° C. for 2 h. The crude mixture was purified directly by mass triggered reverse phase HPLC (ACN/water with 0.1% TFA modifier) to afford the title compound. LC/MS=438 [M+1].

Step C: 1-(3-(difluoromethoxy)phenyl)-3-(2-hydroxy-2-methylpropyl)-N-(3-methyl-1,1-dioxidothietan-3-yl)-2-oxo-2,3-dihydro-1H-benzo[d]imidazole-5-carboxamide A flask was charged with 1-(3-(difluoromethoxy)phenyl)-N-(3-methyl-1,1-dioxidothietan-3-yl)-2-oxo-2,3-dihydro-1H-benzo[d]imidazole-5-carboxamide (39 mg, 0.089 mmol), 1-chloro-2-methylpropan-2-ol (48.4 mg, 0.446 mmol), and cesium carbonate (87 mg, 0.267 mmol) in DMF (2 mL). The reaction mixture was bubbled with a stream of N₂ for 2 mins, then was stirred at 90° C. for 16 h under N₂ atmosphere. The crude mixture was directly purified by mass triggered reverse phase HPLC (ACN/water with 0.1% TFA modifier) to afford the title compound. LC/MS=510 [M+1]. ¹H NMR (500 MHz, METHANOL-d4, ppm) δ 7.90 (s, 1H), 7.71-7.62 (m, 2H), 7.47 (d, J=7.5 Hz, 1H), 7.41 (s, 1H), 7.32 (br d, J=8.5 Hz, 1H), 7.18 (d, J=8.5 Hz, 1H), 7.13-6.79 (m, 1H), 4.61 (m, 2H), 4.27 (m, 2H), 4.01 (s, 2H), 1.87 (s, 3H), 1.37 (s, 6H). Human DGAT2 IC₅₀=35.6 nM Example 65: 1-(5-(difluoromethoxy)-2-fluorophenyl)-3-(3-hydroxy-3-methylbutan-2-yl)-N-(3-methyl-1,1-dioxidothietan-3-yl)-2-oxo-2,3-dihydro-1H-benzo[d]imidazole-5-carboxamide

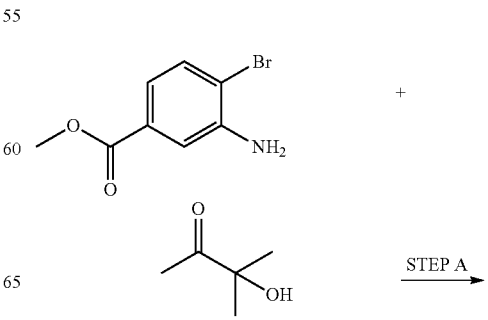

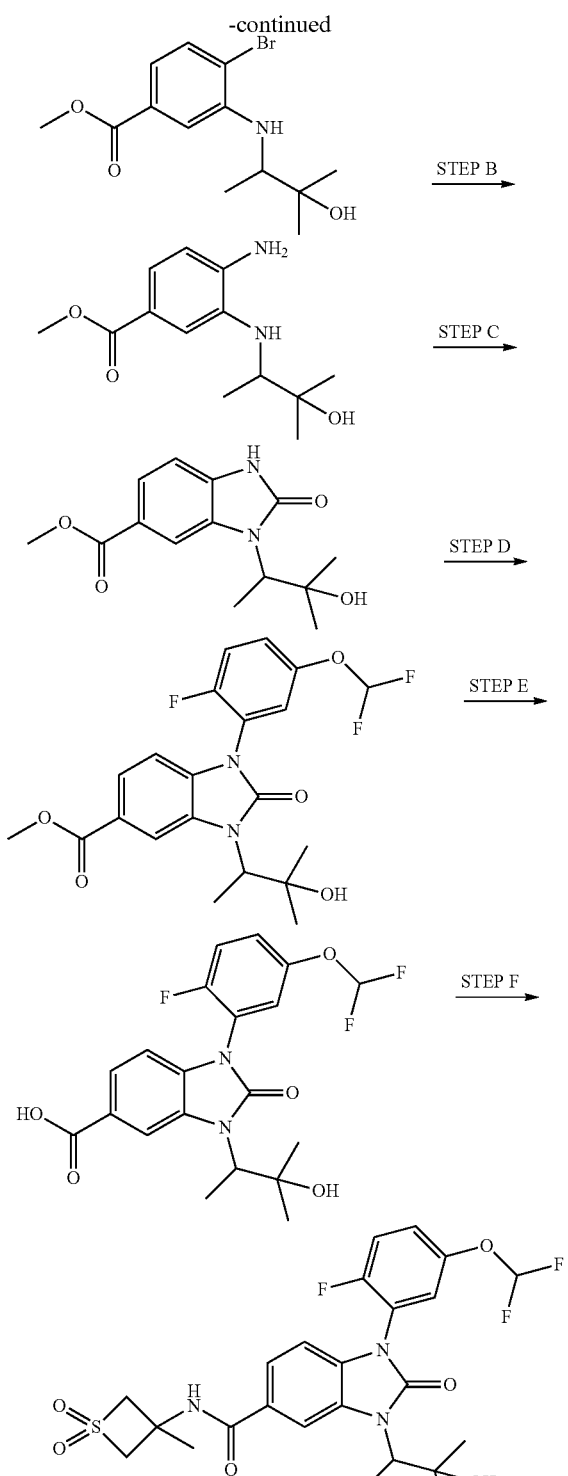

EX-65a and 65b

Step A: methyl 4-bromo-3-((3-hydroxy-3-methylbutan-2-yl)amino)benzoate

To a mixture of methyl 3-amino-4-bromobenzoate (1 g, 4.35 mmol) in DMF (15 mL) was added 3-hydroxy-3-methylbutan-2-one (0.666 g, 6.52 mmol) at 20° C. The resulting mixture was degassed and backfilled with N₂ (three times), followed by addition of TMCS (1.161 ml, 13.04 mmol) and sodium cyanoborohydride (0.410 g, 6.52 mmol) at 0° C. under N₂. The resulting mixture was stirred under N₂ at 20° C. for 1 h, then poured into H₂O and extracted with EtOAc (×3). The combined organic layers were washed with brine, dried over Na₂SO₄, then filtered and concentrated under reduced pressure. The residue was purified by flash column chromatography on silica (0-100% EtOAc/hexanes) to afford the title compound. LC/MS=316 [M+1].

Step B: methyl 4-amino-3-((3-hydroxy-3-methylbutan-2-yl)amino)benzoate

A 8 mL of tube was charged with methyl 4-bromo-3-((3-hydroxy-3-methylbutan-2-yl)amino)benzoate (300 mg, 0.949 mmol), ammonia hydrate (66.5 mg, 1.898 mmol), K₃PO₄ (242 mg, 1.139 mmol), BPPO (37.2 mg, 0.095 mmol), copper(I) iodide (18.07 mg, 0.095 mmol) and DMSO (4 mL) in glovebox at 20° C. Then the reaction was sealed and stirred at 90° C. for 24 h. The mixture was poured into H₂O, then extracted with EtOAc (×3). The combined organic layers were washed with brine, dried over Na₂SO₄, then filtered and concentrated under reduced pressure. The residue was purified by flash column chromatography on silica (0-100% EtOAc/hexanes) to afford the title compound. LC/MS=253 [M+1].

Step C: methyl 3-(3-hydroxy-3-methylbutan-2-yl)-2-oxo-2,3-dihydro-1H-benzo[d]imidazole-5-carboxylate A mixture of methyl 4-amino-3-((3-hydroxy-3-methylbutan-2-yl)amino)benzoate (110 mg, 0.436 mmol) and di(1H-imidazol-1-yl)methanone (353 mg, 2.180 mmol) in THF (3 mL) was stirred at 30° C. for 12 h. The mixture was poured into H₂O, then extracted with EtOAc (×3). The combined organic layers were washed with brine, dried over Na₂SO₄, then filtered and concentrated under reduced pressure. The residue was purified by flash column chromatography on silica (0-100% EtOAc/hexanes) to afford the title compound. LC/MS=279 [M+1].

Step D: methyl 1-(5-(difluoromethoxy)-2-fluorophenyl)-3-(3-hydroxy-3-methylbutan-2-yl)-2-oxo-2,3-dihydro-1H-benzo[d]imidazole-5-carboxylate To a mixture of 2-(5-(difluoromethoxy)-2-fluorophenyl)-4,4,5,5-tetramethyl-1,3,2-dioxaborolane (279 mg, 0.970 mmol) in DMF (5 mL) was added pyridine (0.521 ml, 6.47 mmol), methyl 3-(3-hydroxy-3-methylbutan-2-yl)-2-oxo-2,3-dihydro-1H-benzo[d]imidazole-5-carboxylate (90 mg, 0.323 mmol), copper(ii) acetate (70.5 mg, 0.388 mmol). The mixture was stirred at 80° C. for 16 h open to air under a drying tube. The mixture was poured into H₂O, then extracted with EtOAc (×3). The combined organic layers were washed with brine, dried over Na₂SO₄, filtered and concentrated under reduced pressure. The residue was purified by flash column chromatography on silica (0-100% EtOAc/hexanes) to afford the title compound. LC/MS=439 [M+1].

Step E: 1-(5-(difluoromethoxy)-2-fluorophenyl)-3-(3-hydroxy-3-methylbutan-2-yl)-2-oxo-2,3-dihydro-1H-benzo[d]imidazole-5-carboxylic acid To a solution of methyl 1-(5-(difluoromethoxy)-2-fluorophenyl)-3-(3-hydroxy-3-methylbutan-2-yl)-2-oxo-2,3-dihydro-1H-benzo[d]imidazole-5-carboxylate (90 mg, 0.205 mmol) in MeOH (3 mL)/Water (1.00 mL) was added lithium hydroxide hydrate (17.23 mg, 0.411 mmol). The reaction mixture was stirred at 40° C. for 3 h, then concentrated under reduced pressure. The concentrated mixture was dissolved in H$_2$O. HCl (1N in water) was added to the mixture until pH=4. Then the mixture was extracted with EtOAc (×3). The combined organic layers were washed with brine, dried over Na$_2$SO$_4$, then filtered and concentrated under reduced pressure to afford the title compound. LC/MS=425[M+1].

Step F: 1-(5-(difluoromethoxy)-2-fluorophenyl)-3-(3-hydroxy-3-methylbutan-2-yl)-N-(3-methyl-1,1-dioxidothietan-3-yl)-2-oxo-2,3-dihydro-1H-benzo[d]imidazole-5-carboxamide A 8 mL of tube was charged with 1-(5-(difluoromethoxy)-2-fluorophenyl)-3-(3-hydroxy-3-methylbutan-2-yl)-2-oxo-2,3-dihydro-1H-benzo[d]imidazole-5-carboxylic acid (60 mg, 0.141 mmol), DIEA (0.074 ml, 0.424 mmol), HATU (81 mg, 0.212 mmol), 3-amino-3-methylthietane 1,1-dioxide (28.7 mg, 0.212 mmol) and DMF (1 mL) at 25° C. The mixture was stirred at 25° C. for 0.5 h, then poured into H$_2$O and extracted with EtOAc (×3). The combined organic layers were washed with brine, dried over Na$_2$SO$_4$, then filtered and concentrated under reduced pressure. The residue was purified by flash column chromatography on silica (0-100% EtOAc/hexanes) to afford the title compound. LC/MS=542 [M+1].

The mixture of the two stereoisomers was purified by chiral SFC (IC-H column, 40%/60% ethanol/CO$_2$). EX-65a (faster eluting): LC/MS=542 [M+1]. 1H NMR (500 MHz, METHANOL-d4) δ 7.99 (br s, 1H), 7.53 (br d, J=7.48 Hz, 1H), 7.21-7.45 (m, 3H), 6.58-7.03 (m, 2H), 4.43-4.56 (m, 3H), 4.13 (br d, J=14.95 Hz, 2H), 1.73 (s, 3H), 1.58 (br d, J=7.02 Hz, 3H), 1.25-1.35 (m, 3H), 1.00-1.21 (m, 3H). Human DGAT2 IC$_{50}$=53 nM. EX-65b (slower eluting): LC/MS=542 [M+1]. 1H NMR (500 MHz, METHANOL-d4) δ 7.96 (br s, 1H), 7.53 (br d, J=7.48 Hz, 1H), 7.23-7.45 (m, 3H), 6.59-6.98 (m, 2H), 4.46-4.54 (m, 3H), 4.13 (br d, J=14.80 Hz, 2H), 1.67-1.82 (m, 3H), 1.58 (br d, J=7.17 Hz, 3H), 1.29 (s, 3H), 1.13 (br s, 3H). Human DGAT2 IC$_{50}$=0.7 nM.

By using procedures similar to those described in Example 65 with appropriate amine reagents, the following compounds were synthesized. These compounds were characterized by LC/MS.

| Example | Structure | Name | LCMS [M+1] | DGAT2 IC50 (nM) |
|---|---|---|---|---|
| 66a | 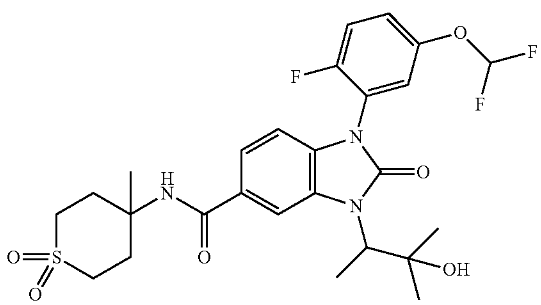 [SMILES: CC(n1c(=O)n(-c2cc(OC(F)F)ccc2F)c2ccc(C(=O)NC3(C)CCS(=O)(=O)CC3)cc21)C(C)(C)O] | 1-(5-(difluoromethoxy)-2-fluorophenyl)-3-(3-hydroxy-3-methylbutan-2-yl)-N-(4-methyl-1,1-dioxidotetrahydro-2H-thiopyran-4-yl)-2-oxo-2,3-dihydro-1H-benzo[d]imidazole-5-carboxamide (faster eluting on Cellulose 2 column, 5-40% EtOH/CO$_2$) | 570 | 1.1 |
| 66b | 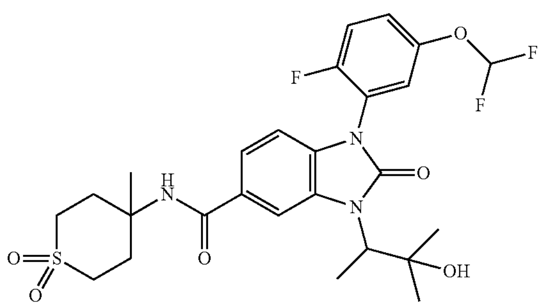 [SMILES: CC(n1c(=O)n(-c2cc(OC(F)F)ccc2F)c2ccc(C(=O)NC3(C)CCS(=O)(=O)CC3)cc21)C(C)(C)O] | 1-(5-(difluoromethoxy)-2-fluorophenyl)-3-(3-hydroxy-3-methylbutan-2-yl)-N-(4-methyl-1,1-dioxidotetrahydro-2H-thiopyran-4-yl)-2-oxo-2,3-dihydro-1H-benzo[d]imidazole-5-carboxamide (slower eluting on Cellulose 2 column, 5-40% EtOH/CO$_2$) | 570 | 16.9 |
| 67a | 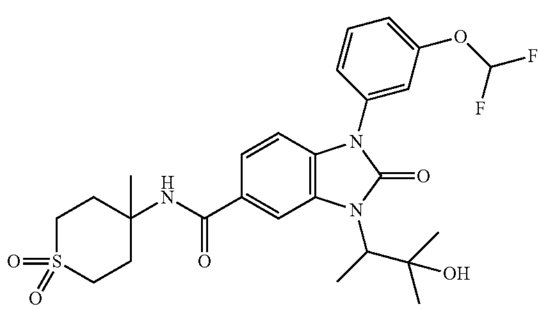 [SMILES: CC(n1c(=O)n(-c2cccc(OC(F)F)c2)c2ccc(C(=O)NC3(C)CCS(=O)(=O)CC3)cc21)C(C)(C)O] | 1-(3-(difluoromethoxy)phenyl)-3-(3-hydroxy-3-methylbutan-2-yl)-N-(4-methyl-1,1-dioxidotetrahydro-2H-thiopyran-4-yl)-2-oxo-2,3-dihydro-1H-benzo[d]imidazole-5-carboxamide (faster eluting on Chiral Pak IC-3 column, 40% iPrOH/CO$_2$) | 552 | 1.6 |

| Example | Structure | Name | LCMS [M + 1] | DGAT2 IC50 (nM) |
|---|---|---|---|---|
| 67b | 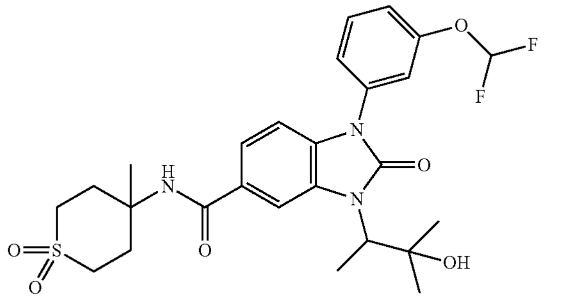 [SMILES: CC(n1c(=O)n(-c2cccc(OC(F)F)c2)c2ccc(C(=O)NC3(C)CCS(=O)(=O)CC3)cc21)C(C)(C)O] | 1-(3-(difluoromethoxy)phenyl)-3-(3-hydroxy-3-methylbutan-2-yl)-N-(4-methyl-1,1-dioxidotetrahydro-2H-thiopyran-4-yl)-2-oxo-2,3-dihydro-1H-benzo[d]imidazole-5-carboxamide (slower eluting on Chiral Pak IC-3 column, 40% iPrOH/CO$_2$) | 552 | 211 |
| 68a | 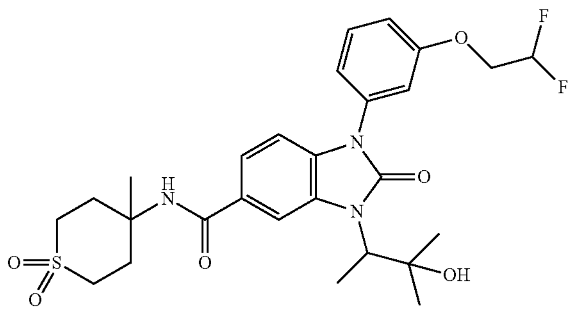 [SMILES: CC(n1c(=O)n(-c2cccc(OCC(F)F)c2)c2ccc(C(=O)NC3(C)CCS(=O)(=O)CC3)cc21)C(C)(C)O] | 1-(3-(2,2-difluoroethoxy)phenyl)-3-(3-hydroxy-3-methylbutan-2-yl)-N-(4-methyl-1,1-dioxidotetrahydro-2H-thiopyran-4-yl)-2-oxo-2,3-dihydro-1H-benzo[d]imidazole-5-carboxamide (faster eluting on Chiral Pak IC-3 column, 40% EtOH/CO$_2$) | 566 | 4.1 |
| 68b | 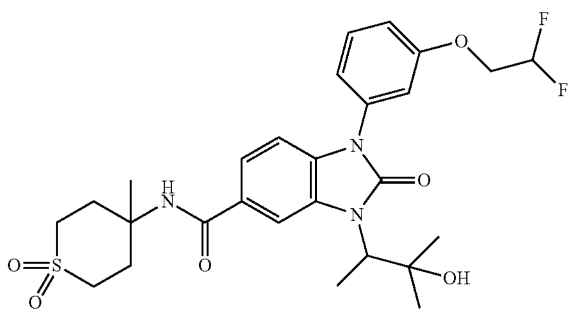 [SMILES: CC(n1c(=O)n(-c2cccc(OCC(F)F)c2)c2ccc(C(=O)NC3(C)CCS(=O)(=O)CC3)cc21)C(C)(C)O] | 1-(3-(2,2-difluoroethoxy)phenyl)-3-(3-hydroxy-3-methylbutan-2-yl)-N-(4-methyl-1,1-dioxidotetrahydro-2H-thiopyran-4-yl)-2-oxo-2,3-dihydro-1H-benzo[d]imidazole-5-carboxamide (slower eluting on Chiral Pak IC-3 column, 40% EtOH/CO$_2$) | 566 | 1.8 |
| 69a | 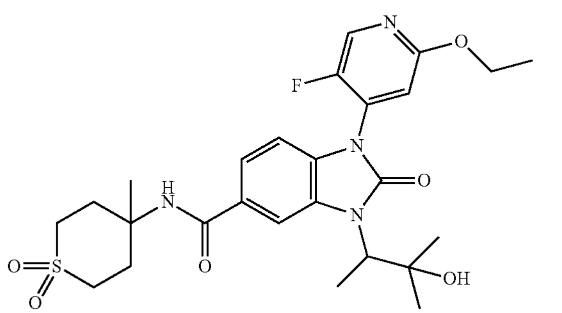 [SMILES: CCOc1cc(-n2c(=O)n(C(C)C(C)(C)O)c3cc(C(=O)NC4(C)CCS(=O)(=O)CC4)ccc32)c(F)cn1] | 1-(2-ethoxy-5-fluoropyridin-4-yl)-3-(3-hydroxy-3-methylbutan-2-yl)-N-(4-methyl-1,1-dioxidotetrahydro-2H-thiopyran-4-yl)-2-oxo-2,3-dihydro-1H-benzo[d]imidazole-5-carboxamide (faster eluting on Chiral Pak AD-3 column, 40% EtOH/CO$_2$) | 549 | 9.7 |
| 69b | 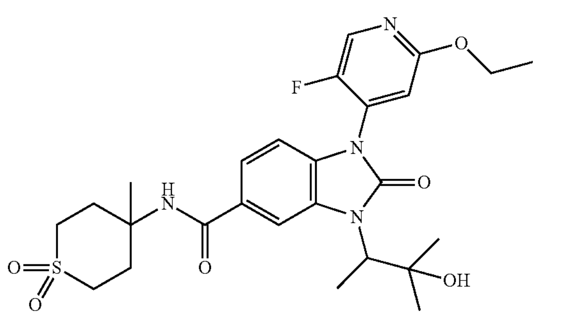 [SMILES: CCOc1cc(-n2c(=O)n(C(C)C(C)(C)O)c3cc(C(=O)NC4(C)CCS(=O)(=O)CC4)ccc32)c(F)cn1] | 1-(2-ethoxy-5-fluoropyridin-4-yl)-3-(3-hydroxy-3-methylbutan-2-yl)-N-(4-methyl-1,1-dioxidotetrahydro-2H-thiopyran-4-yl)-2-oxo-2,3-dihydro-1H-benzo[d]imidazole-5-carboxamide (slower eluting on Chiral Pak AD-3 column, 40% EtOH/CO$_2$) | 549 | 3.9 |

| Example | Structure | Name | LCMS [M + 1] | DGAT2 IC50 (nM) |
|---|---|---|---|---|
| 70a | 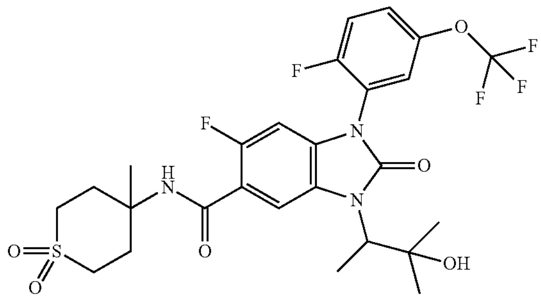 [SMILES: CC(n1c(=O)n(-c2cc(OC(F)(F)F)ccc2F)c2cc(F)c(C(=O)NC3(C)CCS(=O)(=O)CC3)cc21)C(C)(C)O] | 6-fluoro-1-(2-fluoro-5-(trifluoromethoxy)phenyl)-3-(3-hydroxy-3-methylbutan-2-yl)-N-(4-methyl-1,1-dioxidotetrahydro-2H-thiopyran-4-yl)-2-oxo-2,3-dihydro-1H-benzo[d]imidazole-5-carboxamide (slower eluting on Chiral Pak AD-3 column, 40% EtOH/CO$_2$) | 606 | 1.0 |
| 70b | 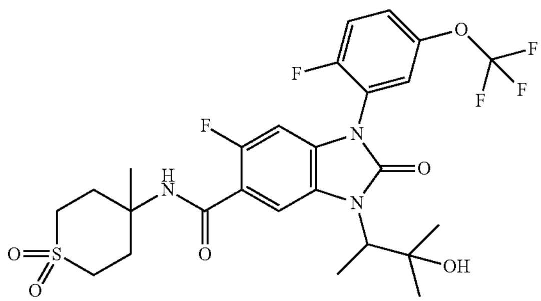 [SMILES: CC(n1c(=O)n(-c2cc(OC(F)(F)F)ccc2F)c2cc(F)c(C(=O)NC3(C)CCS(=O)(=O)CC3)cc21)C(C)(C)O] | 6-fluoro-1-(2-fluoro-5-(trifluoromethoxy)phenyl)-3-(3-hydroxy-3-methylbutan-2-yl)-N-(4-methyl-1,1-dioxidotetrahydro-2H-thiopyran-4-yl)-2-oxo-2,3-dihydro-1H-benzo[d]imidazole-5-carboxamide (faster eluting on Chiral Pak AD-3 column, 40% EtOH/CO$_2$) | 606 | 30.4 |
| 71a | 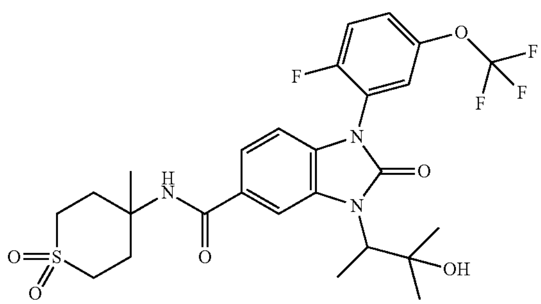 [SMILES: CC(n1c(=O)n(-c2cc(OC(F)(F)F)ccc2F)c2ccc(C(=O)NC3(C)CCS(=O)(=O)CC3)cc21)C(C)(C)O] | 1-(2-fluoro-5-(trifluoromethoxy)phenyl)-3-(3-hydroxy-3-methylbutan-2-yl)-N-(4-methyl-1,1-dioxidotetrahydro-2H-thiopyran-4-yl)-2-oxo-2,3-dihydro-1H-benzo[d]imidazole-5-carboxamide (slower eluting on Cellulose 2 column, 5-40% EtOH/CO$_2$) | 588 | 71 |
| 71b | 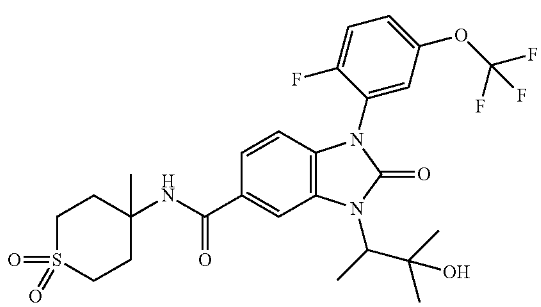 [SMILES: CC(n1c(=O)n(-c2cc(OC(F)(F)F)ccc2F)c2ccc(C(=O)NC3(C)CCS(=O)(=O)CC3)cc21)C(C)(C)O] | 1-(2-fluoro-5-(trifluoromethoxy)phenyl)-3-(3-hydroxy-3-methylbutan-2-yl)-N-(4-methyl-1,1-dioxidotetrahydro-2H-thiopyran-4-yl)-2-oxo-2,3-dihydro-1H-benzo[d]imidazole-5-carboxamide (faster eluting on Cellulose 2 column, 5-40% EtOH/CO$_2$) | 588 | 5.4 |
| 72a | 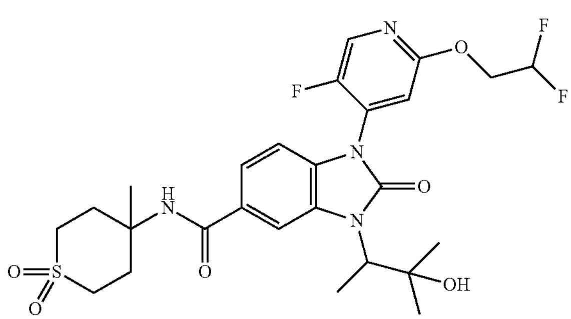 [SMILES: CC(n1c(=O)n(-c2cc(OCC(F)F)ncc2F)c2ccc(C(=O)NC3(C)CCS(=O)(=O)CC3)cc21)C(C)(C)O] | 1-(2-(2,2-difluoroethoxy)-5-fluoropyridin-4-yl)-3-(3-hydroxy-3-methylbutan-2-yl)-N-(4-methyl-1,1-dioxidotetrahydro-2H-thiopyran-4-yl)-2-oxo-2,3-dihydro-1H-benzo[d]imidazole-5-carboxamide (faster eluting on Chiral Pak IG-3 column, 5-40% MeOH/CO$_2$) | 585 | 6.4 |

| Example | Structure | Name | LCMS [M + 1] | DGAT2 IC50 (nM) |
|---|---|---|---|---|
| 72b | 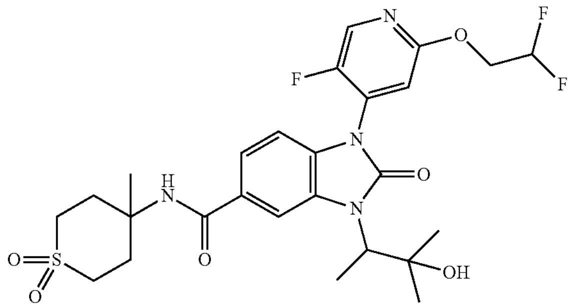 [SMILES: CC(n1c(=O)n(-c2cc(OCC(F)F)ncc2F)c2ccc(C(=O)NC3(C)CCS(=O)(=O)CC3)cc21)C(C)(C)O] | 1-(2-(2,2-difluoroethoxy)-5-fluoropyridin-4-yl)-3-(3-hydroxy-3-methylbutan-2-yl)-N-(4-methyl-1,1-dioxidotetrahydro-2H-thiopyran-4-yl)-2-oxo-2,3-dihydro-1H-benzo[a]imidazole-5-carboxamide (slower eluting on Chiral Pak IG-3 column, 5% MeOH/CO$_2$) | 585 | 6.6 |
| 73a | 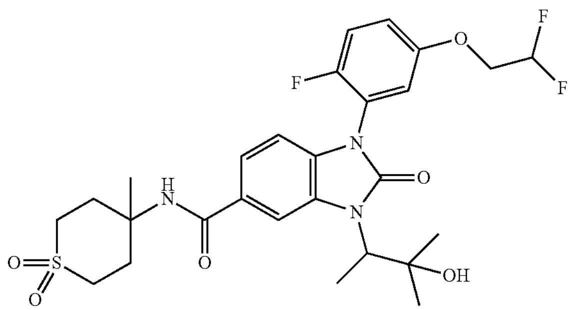 [SMILES: CC(n1c(=O)n(-c2cc(OCC(F)F)ccc2F)c2ccc(C(=O)NC3(C)CCS(=O)(=O)CC3)cc21)C(C)(C)O] | 1-(5-(2,2-difluoroethoxy)-2-fluorophenyl)-3-(3-hydroxy-3-methylbutan-2-yl)-N-(4-methyl-1,1-dioxidotetrahydro-2H-thiopyran-4-yl)-2-oxo-2,3-dihydro-1H-benzo[a]imidazole-5-carboxamide (faster eluting on Chiral Pak IG-3 column, 5-40% EtOH/CO$_2$) | 584 | 2.6 |
| 73b | 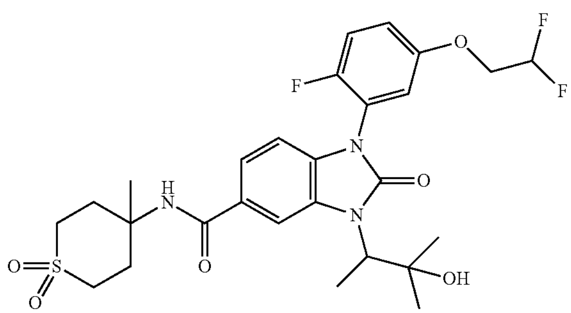 [SMILES: CC(n1c(=O)n(-c2cc(OCC(F)F)ccc2F)c2ccc(C(=O)NC3(C)CCS(=O)(=O)CC3)cc21)C(C)(C)O] | 1-(5-(2,2-difluoroethoxy)-2-fluorophenyl)-6-fluoro-3-(3-hydroxy-3-methylbutan-2-yl)-N-(4-methyl-1,1-dioxidotetrahydro-2H-thiopyran-4-yl)-2-oxo-2,3-dihydro-1H-benzo[d]imidazole-5-carboxamide (slower eluting on Chiral Pak IG-3 column, 5-40% EtOH/CO$_2$) | 584 | 3.3 |
| 74a | 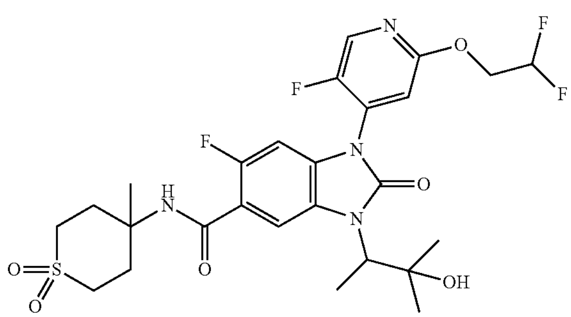 [SMILES: CC(n1c(=O)n(-c2cc(OCC(F)F)ncc2F)c2cc(F)c(C(=O)NC3(C)CCS(=O)(=O)CC3)cc21)C(C)(C)O] | 1-(2-(2,2-difluoroethoxy)-5-fluoropyridin-4-yl)-6-fluoro-3-(3-hydroxy-3-methylbutan-2-yl)-N-(4-methyl-1,1-dioxidotetrahydro-2H-thiopyran-4-yl)-2-oxo-2,3-dihydro-1H-benzo[d]imidazole-5-carboxamide (faster eluting on Chiral Pak AD-3 column, 40% EtOH/CO$_2$) | 603 | 6.1 |
| 74b | 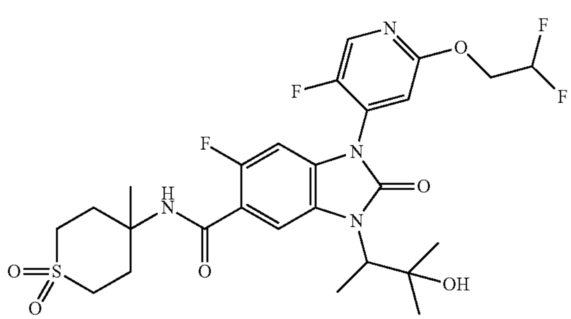 [SMILES: CC(n1c(=O)n(-c2cc(OCC(F)F)ncc2F)c2cc(F)c(C(=O)NC3(C)CCS(=O)(=O)CC3)cc21)C(C)(C)O] | 1-(2-(2,2-difluoroethoxy)-5-fluoropyridin-4-yl)-6-fluoro-3-(3-hydroxy-3-methylbutan-2-yl)-N-(4-methyl-1,1-dioxidotetrahydro-2H-thiopyran-4-yl)-2-oxo-2,3-dihydro-1H-benzo[d]imidazole-5-carboxamide (slower eluting on Chiral Pak AD-3 column, 40% EtOH/CO$_2$) | 603 | 6.5 |

| Example | Structure | Name | LCMS [M+1] | DGAT2 IC50 (nM) |
|---|---|---|---|---|
| 75a | 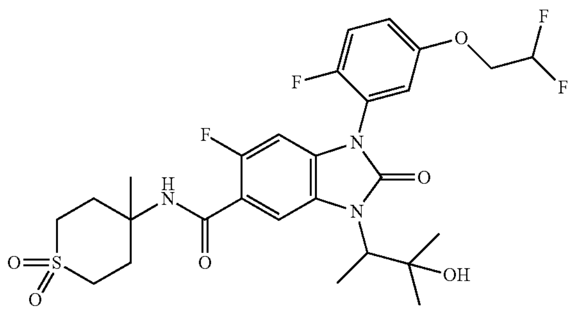 [SMILES: CC(n1c(=O)n(-c2cc(OCC(F)F)ccc2F)c2cc(F)c(C(=O)NC3(C)CCS(=O)(=O)CC3)cc21)C(C)(C)O] | 1-(5-(2,2-difluoroethoxy)-2-fluorophenyl)-6-fluoro-3-(3-hydroxy-3-methylbutan-2-yl)-N-(4-methyl-1,1-dioxidotetrahydro-2H-thiopyran-4-yl)-2-oxo-2,3-dihydro-1H-benzo[d]imidazole-5-carboxamide (faster eluting on Cellulose 2 column, 5-40% EtOH/CO$_2$) | 602 | 1.5 |
| 75b | 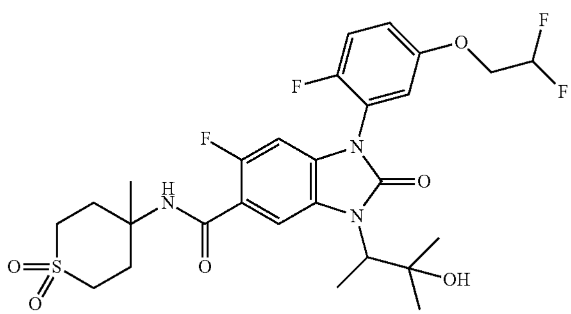 [SMILES: CC(n1c(=O)n(-c2cc(OCC(F)F)ccc2F)c2cc(F)c(C(=O)NC3(C)CCS(=O)(=O)CC3)cc21)C(C)(C)O] | 1-(5-(2,2-difluoroethoxy)-2-fluorophenyl)-6-fluoro-3-(3-hydroxy-3-methylbutan-2-yl)-N-(4-methyl-1,1-dioxidotetrahydro-2H-thiopyran-4-yl)-2-oxo-2,3-dihydro-1H-benzo[d]imidazole-5-carboxamide (slower eluting on Cellulose 2 column, 5-40% EtOH/CO$_2$) | 602 | 2.4 |
| 76a | 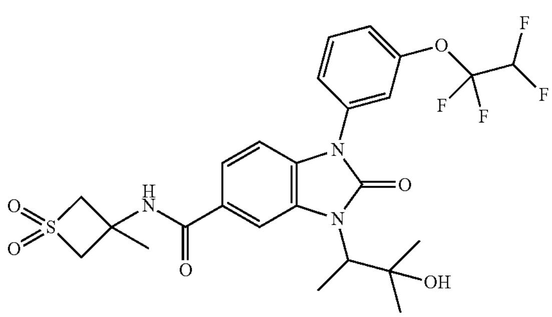 [SMILES: CC(n1c(=O)n(-c2cccc(OC(F)(F)C(F)F)c2)c2ccc(C(=O)NC3(C)CS(=O)(=O)C3)cc21)C(C)(C)O] | 3-(3-hydroxy-3-methylbutan-2-yl)-N-(3-methyl-1,1-dioxidothietan-3-yl)-2-oxo-1-(3-(1,1,2,2-tetrafluoroethoxy)phenyl)-2,3-dihydro-1H-benzo[d]imidazole-5-carboxamide (faster eluting on Chiral Pak AD-3 column, 5-40% EtOH/CO$_2$) | 574 | 80 |
| 76b | 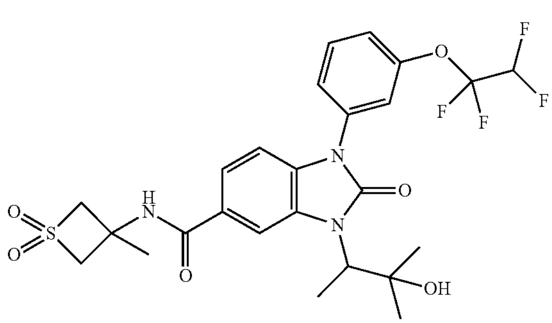 [SMILES: CC(n1c(=O)n(-c2cccc(OC(F)(F)C(F)F)c2)c2ccc(C(=O)NC3(C)CS(=O)(=O)C3)cc21)C(C)(C)O] | 3-(3-hydroxy-3-methylbutan-2-yl)-N-(3-methyl-1,1-dioxidothietan-3-yl)-2-oxo-1-(3-(1,1,2,2-tetrafluoroethoxy)phenyl)-2,3-dihydro-1H-benzo[d]imidazole-5-carboxamide (slower eluting on Chiral Pak AD-3 column, 40% EtOH/CO$_2$) | 574 | 7.9 |

| Example | Structure | Name | LCMS [M + 1] | DGAT2 IC50 (nM) |
|---|---|---|---|---|
| 77a | 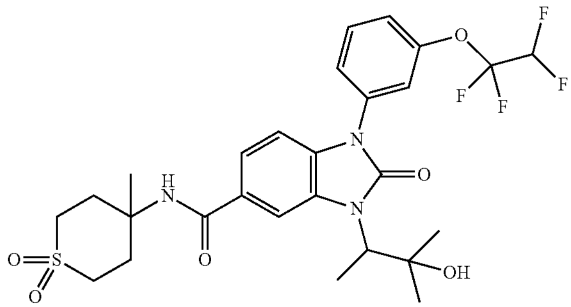 [SMILES: CC(n1c(=O)n(-c2cccc(OC(F)(F)C(F)F)c2)c2ccc(C(=O)NC3(C)CCS(=O)(=O)CC3)cc21)C(C)(C)O] | 3-(3-hydroxy-3-methylbutan-2-yl)-N-(4-methyl-1,1-dioxidotetrahydro-2H-thiopyran-4-yl)-2-oxo-1-(3-(1,1,2,2-tetrafluoroethoxy)phenyl)-2,3-dihydro-1H-benzo[d]imidazole-5-carboxamide (faster eluting on Cellulose 2 column, 5-40% EtOH/CO$_2$) | 602 | 5.6 |
| 77b | 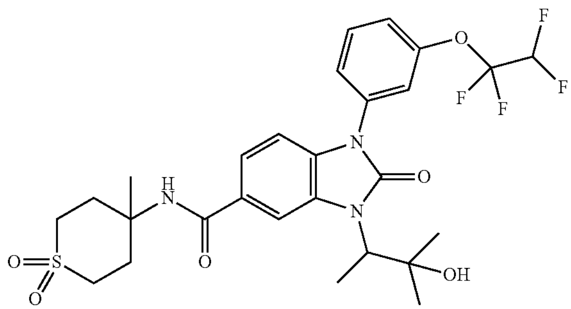 [SMILES: CC(n1c(=O)n(-c2cccc(OC(F)(F)C(F)F)c2)c2ccc(C(=O)NC3(C)CCS(=O)(=O)CC3)cc21)C(C)(C)O] | 3-(3-hydroxy-3-methylbutan-2-yl)-N-(4-methyl-1,1-dioxidotetrahydro-2H-thiopyran-4-yl)-2-oxo-1-(3-(1,1,2,2-tetrafluoroethoxy)phenyl)-2,3-dihydro-1H-benzo[d]imidazole-5-carboxamide (slower eluting on Cellulose 2 column, 5-40% EtOH/CO$_2$) | 602 | 9.8 |
| 78a | 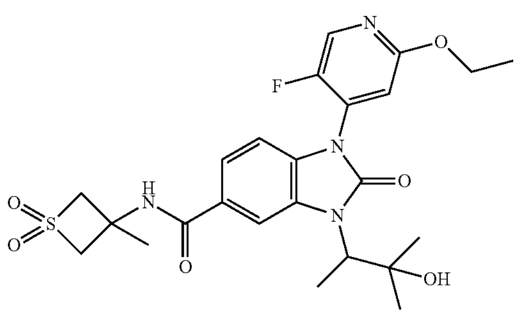 [SMILES: CCOc1cc(-n2c(=O)n(C(C)C(C)(C)O)c3cc(C(=O)NC4(C)CS(=O)(=O)C4)ccc32)c(F)cn1] | 1-(2-ethoxy-5-fluoropyridin-4-yl)-3-(3-hydroxy-3-methylbutan-2-yl)-N-(3-methyl-1,1-dioxidothietan-3-yl)-2-oxo-2,3-dihydro-1H-benzo[d]imidazole-5-carboxamide (faster eluting on Chiral Pak AD-3 column, 40% EtOH/CO$_2$) | 521 | 123 |
| 78b | 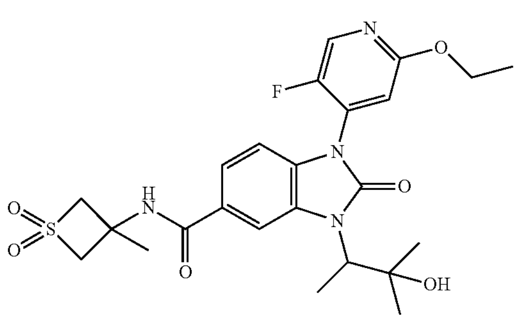 [SMILES: CCOc1cc(-n2c(=O)n(C(C)C(C)(C)O)c3cc(C(=O)NC4(C)CS(=O)(=O)C4)ccc32)c(F)cn1] | 1-(2-ethoxy-5-fluoropyridin-4-yl)-3-(3-hydroxy-3-methylbutan-2-yl)-N-(3-methyl-1,1-dioxidothietan-3-yl)-2-oxo-2,3-dihydro-1H-benzo[d]imidazole-5-carboxamide (slower eluting on Chiral Pak AD-3 column, 40% EtOH/CO$_2$) | 521 | 13 |

Example 79: 1-(5-(Difluoromethoxy)-2-fluorophenyl)-3-isopropyl-N-(4-methyl-1,1-dioxidotetrahydro-2H-thiopyran-4-yl)-2-oxo-2,3-dihydro-1H-benzo[d]imidazole-5-carboxamide

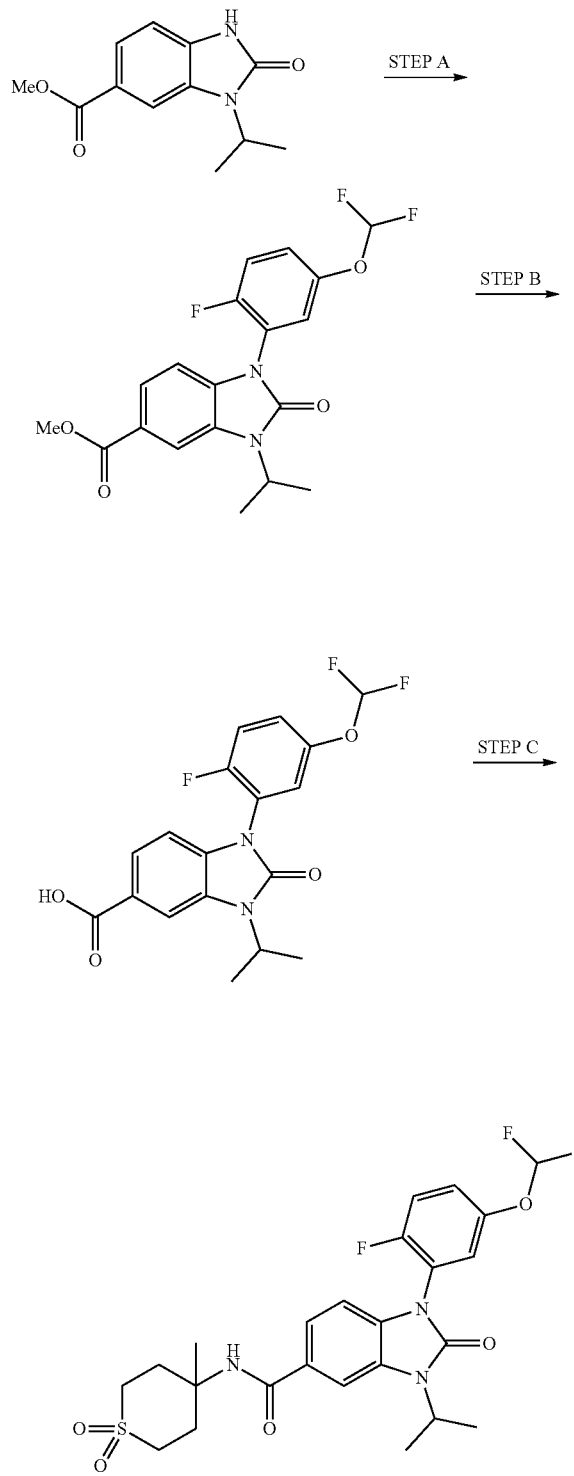

EX-79

Step A: Methyl 1-(5-(difluoromethoxy)-2-fluorophenyl)-3-isopropyl-2-oxo-2,3-dihydro-1H-benzo[d]imidazole-5-carboxylate At 20° C., to a stirred mixture of 2-(5-(difluoromethoxy)-2-fluorophenyl)-4,4,5,5-tetramethyl-1,3,2-dioxaborolane (2.15 g, 7.47 mmol), methyl 3-isopropyl-2-oxo-2,3-dihydro-1H-benzo[d]imidazole-5-carboxylate (0.700 g, 2.99 mmol), and diacetoxycopper (1.09 g, 5.98 mmol) in DCE (14.9 ml) was added triethylamine (1.67 ml, 12.0 mmol), and the mixture was stirred at 95° C. for 32 h. Then, the volatiles were evaporated, and the residue was purified by flash silica gel chromatography (0 to 100% EtOAc in hexanes) to afford the title compound. LC/MS=395 [M+1].

Step B: 1-(5-(difluoromethoxy)-2-fluorophenyl)-3-isopropyl-2-oxo-2,3-dihydro-1H-benzo[d]imidazole-5-carboxylic acid At 20° C., to a stirred mixture of methyl 1-(5-(difluoromethoxy)-2-fluorophenyl)-3-isopropyl-2-oxo-2,3-dihydro-1H-benzo[d]imidazole-5-carboxylate (990 mg, 2.51 mmol) in THF (5.71 mL) and MeOH (1.14 mL) was added lithium hydroxide hydrate (316 mg, 7.53 mmol) in Water (5.71 mL), and the mixture was stirred vigorously at 50° C. for 5 h. Then, the mixture was neutralized to pH 7 with HCl (aqueous, 12 N) (628 µl, 7.53 mmol), the volatiles were evaporated, and the aqueous layer was extracted with EtOAc. The organic layer was washed with brine and dried over $Na_2SO_4$ (s), and the volatiles evaporated to afford the title compound. LC/MS=381 [M+1].

Step C: 1-(5-(difluoromethoxy)-2-fluorophenyl)-3-isopropyl-N-(4-methyl-1,1-dioxidotetrahydro-2H-thiopyran-4-yl)-2-oxo-2,3-dihydro-1H-benzo[d]imidazole-5-carboxamide At 20° C., to a stirred mixture of 1-(5-(difluoromethoxy)-2-fluorophenyl)-3-isopropyl-2-oxo-2,3-dihydro-1H-benzo[d]imidazole-5-carboxylic acid (690 mg, 1.81 mmol) and HATU (1.00 g, 2.63 mmol) in DMF (5.00 mL) and ethyl acetate (3.00 mL) was added 4-amino-4-methyltetrahydro-2H-thiopyran 1,1-dioxide hydrochloride (600 mg, 3.00 mmol), followed by DIPEA (0.951 mL, 5.44 mmol). The mixture was stirred at 20° C. for 1 h, ten partitioned between EtOAc and LiOH (aqueous, 10 wt %). The organic layer was separated, washed with LiOH (aqueous, 10 wt %), brine, dried over $Na_2SO_4$ (s), and the volatiles evaporated. The residue was purified by flash silica gel chromatography (0 to 100% EtOAc in hexanes) to afford the title compound. $^1$H NMR (500 MHz, DMSO-d$_6$) δ 7.85 (s, 1H), 7.79 (s, 1H), 7.66 (d, J=8.3 Hz, 1H), 7.62 (t, J=9.4 Hz, 1H), 7.57 (dd, J=6.0, 3.0 Hz, 1H), 7.46-7.40 (m, 1H), 7.30 (t, J=73.6 Hz, 1H), 6.93 (d, J=8.3 Hz, 1H), 4.71 (hept, J=6.9 Hz, 1H), 3.17 (t, J=13.2 Hz, 2H), 3.06 (d, J=13.6 Hz, 2H), 2.81 (d, J=14.5 Hz, 2H), 2.02 (t, J=12.9 Hz, 2H), 1.55 (d, J=6.9 Hz, 6H), 1.44 (s, 3H). LC/MS=526 [M+1]. Human DGAT2 IC$_{50}$=2.1 nM.

By using procedures slimier to those described in Example 79 with appropriate amine and (hetero)arylhalide reagents, the following compounds were synthesized. These compounds were characterized by LC/MS.

| Example | Structure | Name | LCMS [M + 1] | Human DGAT2 IC$_{50}$ (nM) |
|---|---|---|---|---|
| 80 | 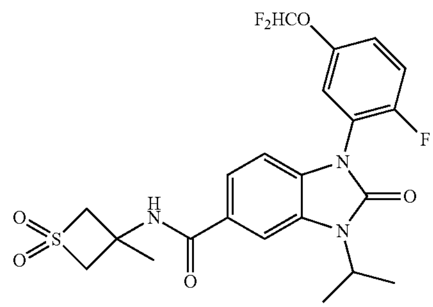 [SMILES: CC(C)n1c(=O)n(-c2cc(OC(F)F)ccc2F)c2ccc(C(=O)NC3(C)CS(=O)(=O)C3)cc21] | 1-(5-(Difluoromethoxy)-2-fluorophenyl)-3-isopropyl-N-(3-methyl-1,1-dioxidothietan-3-yl)-2-oxo-2,3-dihydro-1H-benzo[d]imidazole-5-carboxamide | 498 | 7.7 |
| 81 | 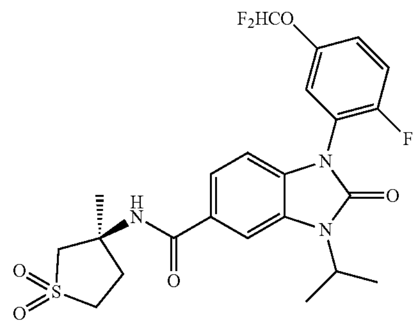 [SMILES: CC(C)n1c(=O)n(-c2cc(OC(F)F)ccc2F)c2ccc(C(=O)N[C@@]3(C)CCS(=O)(=O)C3)cc21] | (S)-1-(5-(Difluoromethoxy)-2-fluorophenyl)-3-isopropyl-N-(3-methyl-1,1-dioxidotetrahydrothiophen-3-yl)-2-oxo-2,3-dihydro-1H-benzo[d]imidazole-5-carboxamide | 512 | 6.3 |
| 82 | 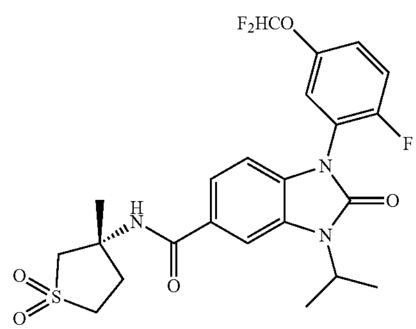 [SMILES: CC(C)n1c(=O)n(-c2cc(OC(F)F)ccc2F)c2ccc(C(=O)N[C@]3(C)CCS(=O)(=O)C3)cc21] | (R)-1-(5-(Difluoromethoxy)-2-fluorophenyl)-3-isopropyl-N-(3-methyl-1,1-dioxidotetrahydrothiophen-3-yl)-2-oxo-2,3-dihydro-1H-benzo[d]imidazole-5-carboxamide | 512 | 5.7 |
| 83 | 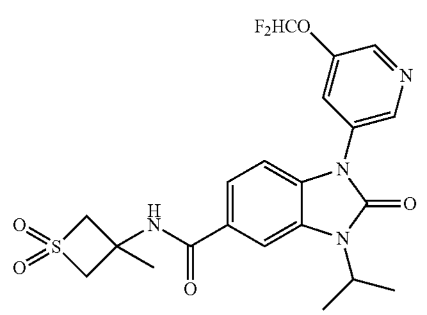 [SMILES: CC(C)n1c(=O)n(-c2cncc(OC(F)F)c2)c2ccc(C(=O)NC3(C)CS(=O)(=O)C3)cc21] | 1-(5-(Difluoromethoxy)pyridin-3-yl)-3-isopropyl-N-(3-methyl-1,1-dioxidothietan-3-yl)-2-oxo-2,3-dihydro-1H-benzo[d]imidazole-5-carboxamide | 481 | 150 |

| Example | Structure | Name | LCMS [M + 1] | Human DGAT2 IC$_{50}$ (nM) |
|---|---|---|---|---|
| 84 | 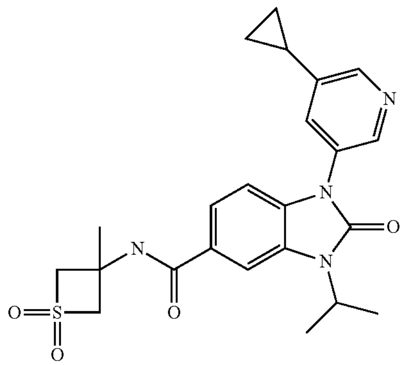 [SMILES: CC(C)n1c(=O)n(-c2cncc(C3CC3)c2)c2ccc(C(=O)NC3(C)CS(=O)(=O)C3)cc21] | 1-(5-Cyclopropylpyridin-3-yl)-3-isopropyl-N-(3-methyl-1,1-dioxidothietan-3-yl)-2-oxo-2,3-dihydro-1H-benzo[d]imidazole-5-carboxamide | 455 | 71 |

Example 85: 3-(1-amino-1-oxopropan-2-yl)-1-(3-(difluoromethoxy)phenyl)-N-(4-methyl-1,1-dioxidotetrahydro-2H-thiopyran-4-yl)-2-oxo-2,3-dihydro-1H-benzo[d]imidazole-5-carboxamide

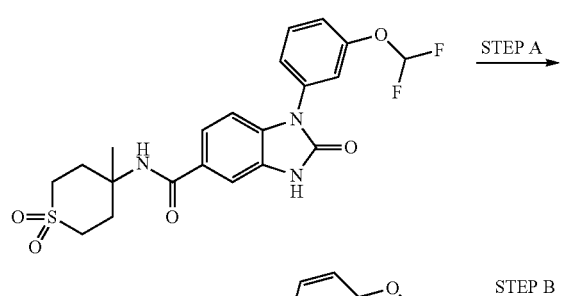

STEP A

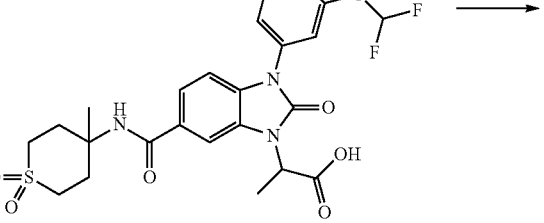

STEP B

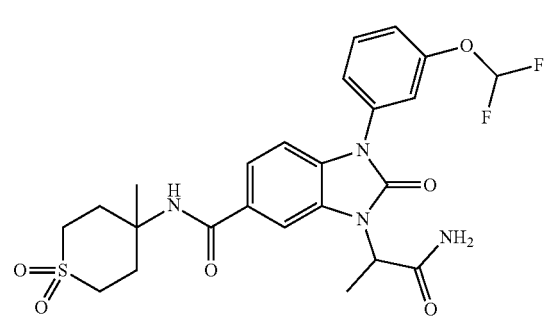

EX-85a and EX-85b

Step A: 2-(3-(3-(difluoromethoxy)phenyl)-6-((4-methyl-1,1-dioxidotetrahydro-2H-thiopyran-4-yl)carbamoyl)-2-oxo-2,3-dihydro-1H-benzo[d]imidazol-1-yl)propanoic acid Sodium hydride (20.62 mg, 0.516 mmol) was added to the mixture of 1-(3-(difluoromethoxy)phenyl)-N-(4-methyl-1,1-dioxidotetrahydro-2H-thiopyran-4-yl)-2-oxo-2,3-dihydro-1H-benzo[d]imidazole-5-carboxamide (160 mg, 0.344 mmol) in DMF (2 ml) at 0° C. under N$_2$. The mixture was stirred at 0° C. for 0.5 h. Then ethyl 2-bromopropanoate (93 mg, 0.516 mmol) was added to the mixture. The mixture was stirred at 15° C. for 12 h under N$_2$. LCMS showed that the desired product was formed. The mixture was poured into NH$_4$Cl, then the mixture was extracted with DCM (×3). The combined organic layers were washed with brine, dried over Na$_2$SO$_4$, then filtered and concentrated under reduced pressure to afford the title compound. LC/MS=538 [M+1].

Step B: 3-(1-amino-1-oxopropan-2-yl)-1-(3-(difluoromethoxy)phenyl)-N-(4-methyl-1,1-dioxidotetrahydro-2H-thiopyran-4-yl)-2-oxo-2,3-dihydro-1H-benzo[d]imidazole-5-carboxamide To a solution of 2-(3-(3-(difluoromethoxy)phenyl)-6-((4-methyl-1,1-dioxidotetrahydro-2H-thiopyran-4-yl)carbamoyl)-2-oxo-2,3-dihydro-1H-benzo[d]imidazol-1-yl)propanoic acid (200 mg, 0.372 mmol), DIEA (0.195 ml, 1.116 mmol), HATU (212 mg, 0.558 mmol) in DMF (3 ml) was added NH$_4$Cl (25 mg, 0.467 mmol). The mixture was stirred at 15° C. for 1 h. LCMS showed that the desired product was formed. The mixture was poured into H$_2$O, then the mixture was extracted with DCM (×3). The combined organic layers were washed with brine, dried over Na$_2$SO$_4$, then filtered and concentrated under reduced pressure. The residue was purified by column chromatography on silica (0-100% EtOAc/hexanes) to afford the title compound. LC/MS=537 [M+1]. The mixture of the two stereoisomers 3-(1-amino-1-oxopropan-2-yl)-1-(3-(difluoromethoxy)phenyl)-N-(4-methyl-1,1-dioxidotetrahydro-2H-thiopyran-4-yl)-2-oxo-2,3-dihydro-1H-benzo[d]imidazole-5-carboxamide (100 mg) was purified by chiral SFC (IC-H column, 40%/60% ethanol/CO$_2$). Isomer EX-85a (faster eluting): LC/MS=537 [M+1]. $^1$H NMR (400 MHz, METHANOL-d$_4$) δ 7.70 (d, J=1.43 Hz, 1H), 7.61-7.67 (m, 2H), 7.44-7.48 (m, 1H), 7.41

(t, J=2.03 Hz, 1H), 7.29 (dd, J=2.09, 8.29 Hz, 1H), 6.75-7.18 (m, 2H), 5.28 (q, J=7.27 Hz, 1H), 3.19-3.28 (m, 2H), 2.99-3.02 (m, 2H), 2.84-2.93 (m, 2H), 2.14-2.23 (m, 2H), 1.79 (d, J=7.39 Hz, 3H), 1.53 (s, 3H). Human DGAT2 IC50=551 nM. Isomer EX-85b (slower eluting): LC/MS=537 [M+1]. ¹H NMR (400 MHz, METHANOL-d₄) δ 7.70 (d, J=1.43 Hz, 1H), 7.61-7.67 (m, 2H), 7.46 (d, J=7.99 Hz, 1H), 7.41 (t, J=1.97 Hz, 1H), 7.29 (dd, J=2.09, 8.29 Hz, 1H), 6.75-7.18 (m, 2H), 5.28 (q, J=7.39 Hz, 1H), 3.19-3.28 (m, 2H), 2.99-3.02 (m, 2H), 2.84-2.94 (m, 2H), 2.15-2.24 (m, 2H), 1.79 (d, J=7.39 Hz, 3H), 1.53 (s, 3H). Human DGAT2 IC50=1752 nM.

Example 86: 1-(3-(difluoromethoxy)phenyl)-N-(4-methyl-1,1-dioxidotetrahydro-2H-thiopyran-4-yl)-2-oxo-3-(phenylsulfonyl)-2,3-dihydro-1H-benzo[d]imidazole-5-carboxamide

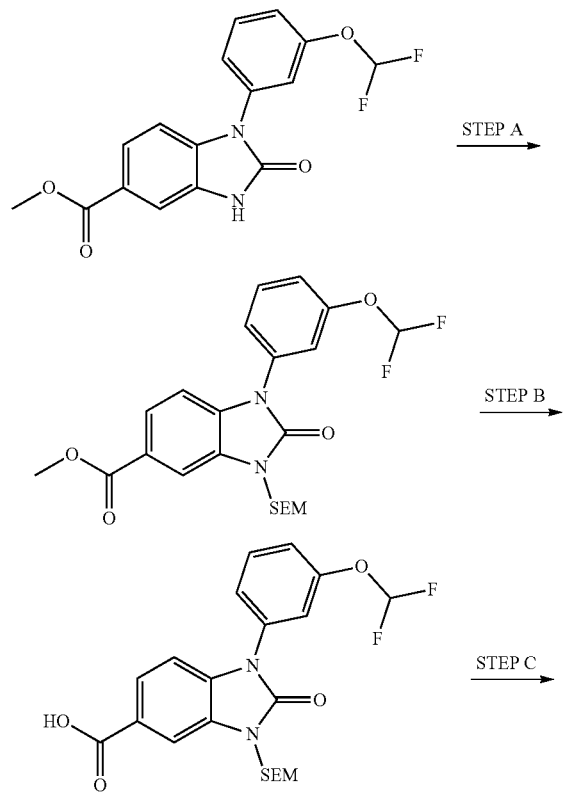

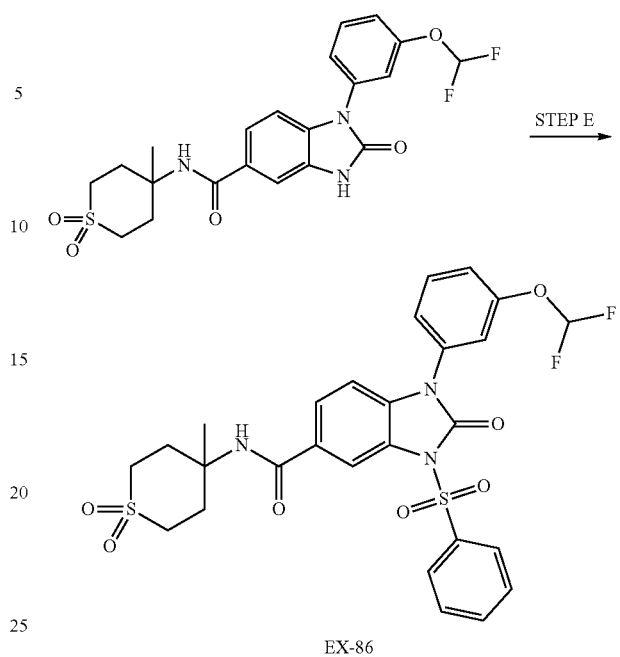

Step A: methyl 1-(3-(difluoromethoxy)phenyl)-2-oxo-3-((2-(trimethylsilyl)ethoxy)methyl)-2,3-dihydro-1H-benzo[d]imidazole-5-carboxylate To a solution of methyl 1-(3-(difluoromethoxy)phenyl)-2-oxo-2,3-dihydro-1H-benzo[d]imidazole-5-carboxylate (500 mg, 1.496 mmol) in THF (10 ml) was added NaH (90 mg, 2.244 mmol) at 0° C. under N₂. The mixture was stirred at 0° C. for 0.5 h. Then 2-(trimethylsilyl)ethoxymethyl chloride (374 mg, 2.244 mmol) was added dropwise to the mixture. The mixture was stirred at 15° C. for 15 h under N₂. LCMS showed that the desired product was formed. The mixture was poured into NH₄Cl, then extracted with DCM (×3). The combined organic layers were washed with brine, dried over Na₂SO₄, then filtered and concentrated under reduced pressure. The residue was purified by column chromatography on silica (0-100% EtOAc/hexanes) to afford the title compound. LC/MS=465 [M+1].

Step B: 1-(3-(difluoromethoxy)phenyl)-2-oxo-3-((2-(trimethylsilyl)ethoxy)methyl)-2,3-dihydro-1H-benzo[d]imidazole-5-carboxylic acid To a solution of methyl 1-(3-(difluoromethoxy)phenyl)-2-oxo-3-((2-(trimethylsilyl)ethoxy)methyl)-2,3-dihydro-1H-benzo[d]imidazole-5-carboxylate (590 mg, 1.270 mmol) in MeOH (2 ml), THF (2 ml) and H₂O (1 ml) was added LiOH H₂O (107 mg, 2.54 mmol). The mixture was stirred at 15° C. for 12 h. LCMS showed that the desired product was formed. The mixture was concentrated under reduced pressure and was dissolved in H₂O. HCl (1N in water) was added to the mixture until pH=4. Then the mixture was extracted with DCM (×3). The combined organic layers were washed with brine, dried over Na₂SO₄, then filtered and concentrated under reduced pressure to afford the title compound. LC/MS=451 [M+1].

Step C: 1-(3-(difluoromethoxy)phenyl)-N-(4-methyl-1,1-dioxidotetrahydro-2H-thiopyran-4-yl)-2-oxo-3-((2-(trimethylsilyl)ethoxy)methyl)-2,3-dihydro-1H-benzo[d]imidazole-5-carboxamide To a solution of 1-(3-(difluoromethoxy)phenyl)-2-oxo-3-((2-(trimethylsilyl)ethoxy)methyl)-2,3-dihydro-1H-benzo[d]imidazole-5-carboxylic acid (500 mg, 1.110 mmol) in DMF (10 ml) was added N-ethyl-N-isopropylpropan-2-amine (430 mg, 3.33 mmol), 2-(3H-[1,2,3]triazolo[4,5-b]pyridin-3-yl)-1,1,3,3-tetramethylisouronium hexafluorophosphate(V) (633 mg, 1.665 mmol) and 4-amino-4-methyltetrahydro-2H-thiopyran 1,1-dioxide hydrochloride (266 mg, 1.332 mmol). The reaction was stirred at 15° C. for 1 h. LCMS showed that the desired product was formed. The mixture was poured into H₂O, then extracted with DCM (×3). The combined organic layers were washed with brine, dried over Na₂SO₄, then filtered and concentrated under reduced pressure. The residue was purified by column chromatography on silica (0-100% EtOAc/hexanes) to afford the title compound. LC/MS=596 [M+1].

Step D: 1-(3-(difluoromethoxy)phenyl)-N-(4-methyl-1,1-dioxidotetrahydro-2H-thiopyran-4-yl)-2-oxo-2,3-dihydro-1H-benzo[d]imidazole-5-carboxamide To a solution of 1-(3-(difluoromethoxy)phenyl)-N-(4-methyl-1,1-dioxidotetrahydro-2H-thiopyran-4-yl)-2-oxo-3-((2-(trimethylsilyl)ethoxy)methyl)-2,3-dihydro-1H-benzo[d]imidazole-5-carboxamide (790 mg, 1.326 mmol) in THF (10 ml) was added TBAF (4 ml, 4.00 mmol). The mixture was stirred at 65° C. for 15 h. LCMS showed that the desired product was formed. The mixture was poured into H₂O, then extracted with DCM (×3). The combined organic layers were washed with brine, dried over Na₂SO₄, then filtered and concentrated under reduced pressure. The residue was purified by column chromatography on silica (0-100% EtOAc/hexanes) to afford the title compound. LC/MS=466 [M+1].

Step E: 1-(3-(difluoromethoxy)phenyl)-N-(4-methyl-1,1-dioxidotetrahydro-2H-thiopyran-4-yl)-2-oxo-3-(phenylsulfonyl)-2,3-dihydro-1H-benzo[d]imidazole-5-carboxamide Sodium hydride (10 mg, 0.250 mmol) was added to the mixture of 1-(3-(difluoromethoxy)phenyl)-N-(4-methyl-1,1-dioxidotetrahydro-2H-thiopyran-4-yl)-2-oxo-2,3-dihydro-1H-benzo[d]imidazole-5-carboxamide (70 mg, 0.150 mmol) in DMF (2 ml) at 0° C. under N₂. The mixture was stirred at 0° C. for 0.5 h. Then benzenesulfonyl chloride (54 mg, 0.306 mmol) was added to the mixture. The mixture was stirred at 15° C. for 12 h under N₂. LCMS showed that the desired product was formed. The mixture was poured into NH₄Cl, then extracted with DCM (×3). The combined organic layers were washed with brine, dried over Na₂SO₄, then filtered and concentrated under reduced pressure. The residue was purified by mass triggered reverse phase HPLC (ACN/water with 0.1% NH₄HCO₃ modifier) to afford the title compound. LC/MS=606 [M+1]. $^1$H NMR (500 MHz, METHANOL-$d_4$) δ 8.44 (d, J=1.53 Hz, 1H), 8.17-8.21 (m, 2H), 7.73-7.79 (m, 2H), 7.58-7.67 (m, 3H), 7.27-7.34 (m, 3H), 6.76-7.09 (m, 2H), 3.23-3.29 (m, 2H), 3.02-3.05 (m, 2H), 2.89-2.92 (m, 2H), 2.18-2.25 (m, 2H), 1.56 (s, 3H). Human DGAT2 IC50=>9990 nM.

Example 87: 1-isopropyl-N-(4-methyl-1,1-dioxothian-4-yl)-2-oxo-3-[3-(1,1,2,2-tetrafluoroethoxy)phenyl]imidazo[4,5-b]pyridine-6-carboxamide

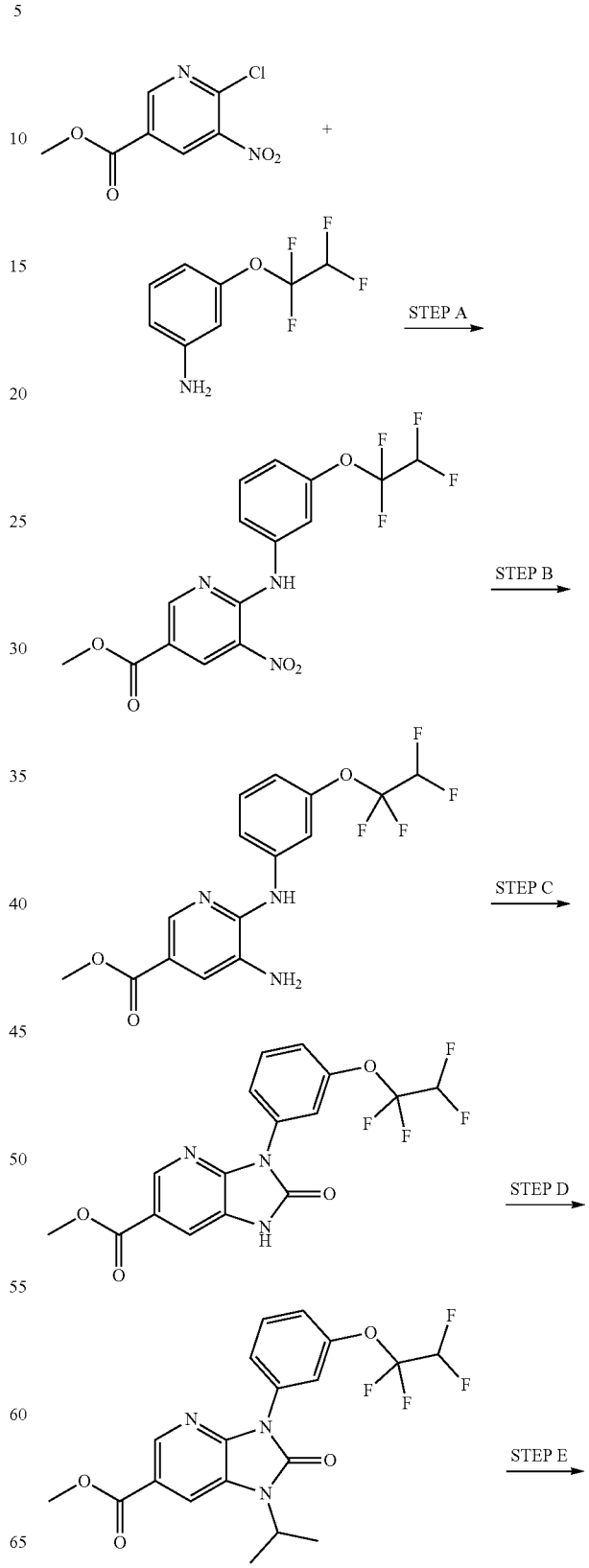

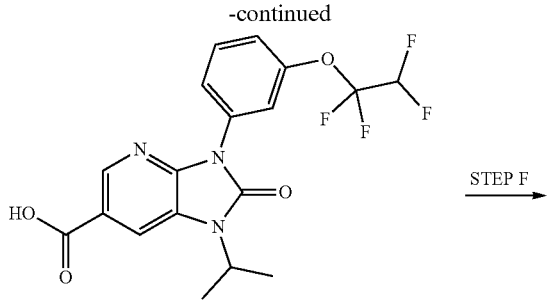

STEP F

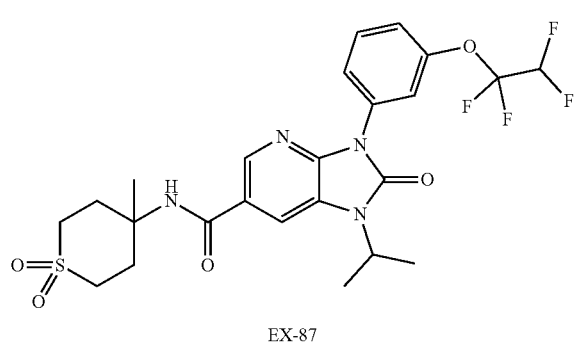

EX-87

Step A: Methyl 5-nitro-6-((3-(1,1,2,2-tetrafluoroethoxy)phenyl)amino)nicotinate

At RT, methyl 6-chloro-5-nitronicotinate (0.206 g, 0.95 mmol) was dissolved in dioxane (4.75 mL), and 3-(1,1,2,2-tetrafluoroethoxy)aniline (0.209 g, 1.00 mmol) and DIPEA (0.199 mL, 1.140 mmol) were added. The reaction was heated to 100° C. for 1 hour. The reaction was then cooled to RT, and the dioxane was removed under reduced pressure to afford the title compound. LC/MS=390 [M+1].

Step B: Methyl 5-amino-6-((3-(1,1,2,2-tetrafluoroethoxy)phenyl)amino)nicotinate

At RT, methyl 5-nitro-6-((3-(1,1,2,2-tetrafluoroethoxy)phenyl)amino)nicotinate (370 mg, 0.951 mmol) was dissolved in THF (3.80 mL), methanol (1.901 mL), and saturated aqueous ammonium chloride (3.80 mL). Zinc (311 mg, 4.75 mmol) was added, and the reaction was stirred at RT for 20 minutes. The reaction was filtered through Celite, and the THF and methanol were evaporated under reduced pressure. EtOAc and water were added, and the layers were separated. The aqueous layer was extracted three times with ethyl acetate. The combined organic layers were washed with brine, dried with MgSO$_4$ (s), filtered, and concentrated under reduced pressure to afford the title compound. LC/MS=360 [M+1].

Step C: Methyl 2-oxo-3-(3-(1,1,2,2-tetrafluoroethoxy)phenyl)-2,3-dihydro-1H-imidazo[4,5-b]pyridine-6-carboxylate At RT, methyl 5-amino-6-((3-(1,1,2,2-tetrafluoroethoxy)phenyl)amino)nicotinate (341 mg, 0.95 mmol) was dissolved in THF (9.50 mL) and di(1H-imidazol-1-yl)methanone (462 mg, 2.85 mmol) was added. The reaction was stirred at RT for 16 hrs. The next morning, water was added, and the THF was removed under reduced pressure. Ethyl acetate was added, and the layers were separated. The aqueous layer was extracted three times with ethyl acetate, and the combined organic layers were washed with brine. The organic fraction was then dried with MgSO$_4$ (s), filtered, and concentrated under reduced pressure. The crude residue was purified by flash silica gel column chromatography (0 to 100% EtOAc in hexanes), then the combined fractions were taken up in EtOAc and washed with 1 N HCl and brine, then dried with MgSO$_4$ (s), filtered, and concentrated to afford the title compound. LC/MS=386 [M+1].

Step D: Methyl 1-isopropyl-2-oxo-3-(3-(1,1,2,2-tetrafluoroethoxy)phenyl)-2,3-dihydro-1H-imidazo[4,5-b]pyridine-6-carboxylate At RT, methyl 2-oxo-3-(3-(1,1,2,2-tetrafluoroethoxy)phenyl)-2,3-dihydro-1H-imidazo[4,5-b]pyridine-6-carboxylate (187.5 mg, 0.487 mmol) and cesium carbonate (634 mg, 1.947 mmol) were suspended in DMF (2.433 ml). 2-iodopropane (0.097 ml, 0.973 mmol) was added, and the reaction was heated to 80° C. and stirred for one hour. Then, the reaction was cooled to RT and water was added, followed by EtOAc. The layers were separated, and the aqueous layer was extracted with EtOAc three times. The combined organic layers were washed with brine, dried with MgSO$_4$ (s), filtered, and concentrated under reduced pressure. The crude residue was purified by flash silica gel column chromatography (0 to 10% EtOAc in DCM) to afford the title compound. LC/MS=428 [M+1].

Step E: 1-isopropyl-2-oxo-3-(3-(1,1,2,2-tetrafluoroethoxy)phenyl)-2,3-dihydro-1H-imidazo[4,5-b]pyridine-6-carboxylic acid At RT, methyl 1-isopropyl-2-oxo-3-(3-(1,1,2,2-tetrafluoroethoxy)phenyl)-2,3-dihydro-1H-imidazo[4,5-b]pyridine-6-carboxylate (144 mg, 0.337 mmol) was dissolved in THF (1.444 mL) and methanol (0.481 mL). A solution of lithium hydroxide (40.3 mg, 1.685 mmol) in Water (1.444 mL) was added. The reaction was stirred overnight at RT. The next morning, 1 N aqueous HCl was added to a pH of 0. Ethyl acetate and water were added, the layers were separated, and the aqueous layer was extracted with ethyl acetate three times. The combined organic layers were washed with brine, dried with MgSO$_4$ (s), filtered, and concentrated under reduced pressure to afford the title compound. LC/MS=414 [M+1].

Step F: 1-isopropyl-N-(4-methyl-1,1-dioxidotetrahydro-2H-thiopyran-4-yl)-2-oxo-3-(3-(1,1,2,2-tetrafluoroethoxy)phenyl)-2,3-dihydro-1H-imidazo[4,5-b]pyridine-6-carboxamide At RT, 1-isopropyl-2-oxo-3-(3-(1,1,2,2-tetrafluoroethoxy)phenyl)-2,3-dihydro-1H-imidazo[4,5-b]pyridine-6-carboxylic acid (31.1 mg, 0.075 mmol), 4-amino-4-methyltetrahydro-2H-thiopyran 1,1-dioxide (13.5 mg, 0.083 mmol), and HATU (31.5 mg, 0.083 mmol) were dissolved in DMF (0.75 mL). DIPEA (0.04 mL, 0.226 mmol) was added, and the reaction was stirred at RT for 6 hrs. The crude residue was purified by mass triggered reverse phase PLC (ACN/water with 0.1% formic acid modifier) to afford the title compound. 1H NMR (500 MHz, Methanol-$d_4$) δ 8.52 (d, J=1.5 Hz, 1H), 8.04 (d, J=1.5 Hz, 1H), 7.75-7.71 (m, 1H), 7.68 (s, 1H), 7.63 (t, J=8.2 Hz, 1H), 7.35 (d, J=7.7 Hz, 1H), 6.36 (t, J=52.6 Hz, 2H), 4.84-4.75 (m, 1H), 3.30-3.25 (m, 2H), 3.08-2.99 (m, 2H), 2.94-2.86 (m, 2H), 2.27-2.17 (m, 2H), 1.63 (d, J=6.9 Hz, 6H), 1.55 (s, 3H). LC/MS=559 [M+1]. Human DGAT2 $IC_{50}$=20 nM.

By using procedures similar to those described in Example 87 with appropriate reagents, the following compounds were synthesized. These compounds were characterized by LC/MS.

| Example | Structure | Name | LCMS [M + 1] | DGAT2 IC50 (nM) |
|---|---|---|---|---|
| 88 | 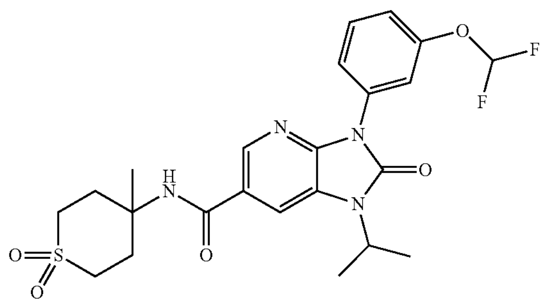 [SMILES: CC(C)n1c(=O)n(-c2cccc(OC(F)F)c2)c2ncc(C(=O)NC3(C)CCS(=O)(=O)CC3)cc21] | 3-[3-(difluoromethoxy)phenyl]-1-isopropyl-N-(4-methyl-1,1-dioxo-thian-4-yl)-2-oxo-imidazo[4,5-b]pyridine-6-carboxamide | 510 | 62 |
| 89 | 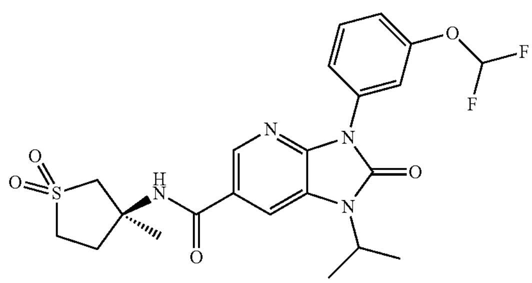 [SMILES: CC(C)n1c(=O)n(-c2cccc(OC(F)F)c2)c2ncc(C(=O)N[C@@]3(C)CCS(=O)(=O)C3)cc21] | 3-[3-(difluoromethoxy)phenyl]-1-isopropyl-N-[(3S)-3-methyl-1,1-dioxo-thiolan-3-yl]-2-oxo-imidazo[4,5-b]pyridine-6-carboxamide | 495 | 288 |
| 90 | 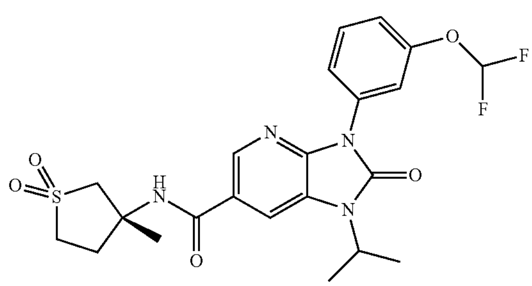 [SMILES: CC(C)n1c(=O)n(-c2cccc(OC(F)F)c2)c2ncc(C(=O)N[C@]3(C)CCS(=O)(=O)C3)cc21] | 3-[3-(difluoromethoxy)phenyl]-1-isopropyl-N-[(3R)-3-methyl-1,1-dioxo-thiolan-3-yl]-2-oxo-imidazo[4,5-b]pyridine-6-carboxamide | 495 | 193 |
| 91 | 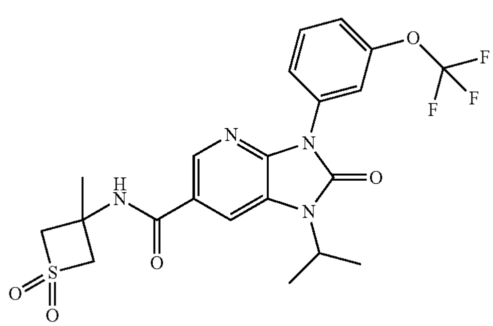 [SMILES: CC(C)n1c(=O)n(-c2cccc(OC(F)(F)F)c2)c2ncc(C(=O)NC3(C)CS(=O)(=O)C3)cc21] | 1-isopropyl-N-(3-methyl-1,1-dioxo-thietan-3-yl)-2-oxo-3-[3-(trifluoromethoxy)phenyl]imidazo[4,5-b]pyridine-6-carboxamide | 499 | 355 |

-continued

| Example | Structure | Name | LCMS [M + 1] | DGAT2 IC50 (nM) |
|---|---|---|---|---|
| 92 | 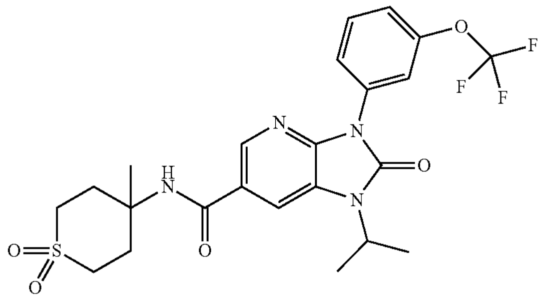 [SMILES: CC(C)n1c(=O)n(-c2cccc(OC(F)(F)F)c2)c2ncc(C(=O)NC3(C)CCS(=O)(=O)CC3)cc21] | 1-isopropyl-N-(4-methyl-1,1-dioxo-thian-4-yl)-2-oxo-3-[3-(trifluoromethoxy)phenyl]imidazo[4,5-b]pyridine-6-carboxamide | 527 | 236 |
| 93 | 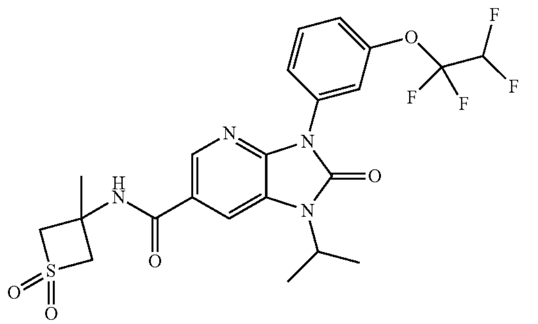 [SMILES: CC(C)n1c(=O)n(-c2cccc(OC(F)(F)C(F)F)c2)c2ncc(C(=O)NC3(C)CS(=O)(=O)C3)cc21] | 1-isopropyl-N-(3-methyl-1,1-dioxo-thietan-3-yl)-2-oxo-3-[3-(1,1,2,2-tetrafluoroethoxy)phenyl]imidazo[4,5-b]pyridine-6-carboxamide | 531 | 24 |
| 94 | 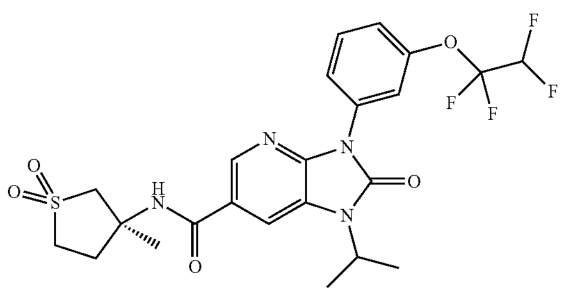 [SMILES: CC(C)n1c(=O)n(-c2cccc(OC(F)(F)C(F)F)c2)c2ncc(C(=O)N[C@@]3(C)CCS(=O)(=O)C3)cc21] | 1-isopropyl-N-[(3S)-3-methyl-1,1-dioxo-thiolan-3-yl]-2-oxo-3-[3-(1,1,2,2-tetrafluoroethoxy)phenyl]imidazo[4,5-b]pyridine-6-carboxamide | 545 | 108 |
| 95 | 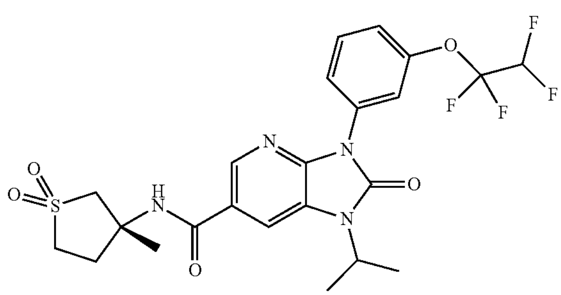 [SMILES: CC(C)n1c(=O)n(-c2cccc(OC(F)(F)C(F)F)c2)c2ncc(C(=O)N[C@]3(C)CCS(=O)(=O)C3)cc21] | 1-isopropyl-N-[(3R)-3-methyl-1,1-dioxo-thiolan-3-yl]-2-oxo-3-[3-(1,1,2,2-tetrafluoroethoxy)phenyl]imidazo[4,5-b]pyridine-6-carboxamide | 545 | 23 |
| 96 | 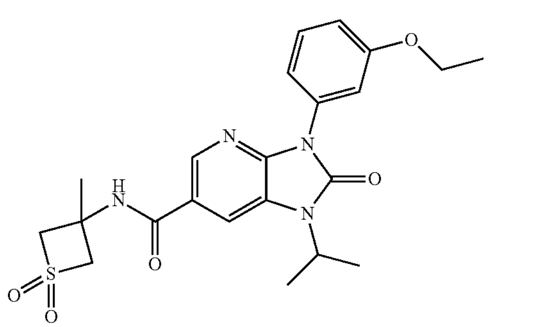 [SMILES: CCOc1cccc(-n2c(=O)n(C(C)C)c3cc(C(=O)NC4(C)CS(=O)(=O)C4)cnc32)c1] | 3-(3-ethoxyphenyl)-1-isopropyl-N-(3-methyl-1,1-dioxo-thietan-3-yl)-2-oxo-imidazo[4,5-b]pyridine-6-carboxamide | 459 | 93 |

-continued

| Example | Name | LCMS [M + 1] | DGAT2 IC50 (nM) |
|---|---|---|---|
| 97 | 3-(3-ethoxyphenyl)-1-isopropyl-N-[(3S)-3-methyl-1,1-dioxo-thiolan-3-yl]-2-oxo-imidazo[4,5-b]pyridine-6-carboxamide | 473 | 154 |
| 98 | 3-(3-ethoxyphenyl)-1-isopropyl-N-[(3R)-3-methyl-1,1-dioxo-thiolan-3-yl]-2-oxo-imidazo[4,5-b]pyridine-6-carboxamide | 473 | 102 |
| 99 | 3-(3-ethoxyphenyl)-1-isopropyl-N-(4-methyl-1,1-dioxo-thian-4-yl)-2-oxo-imidazo[4,5-b]pyridine-6-carboxamide | 487 | 52 |
| 100 | 3-(3-isopropoxyphenyl)-1-isopropyl-N-(3-methyl-1,1-dioxo-thietan-3-yl)-2-oxo-imidazo[4,5-b]pyridine-6-carboxamide | 473 | 692 |
| 101 | 3-(3-isopropoxyphenyl)-1-isopropyl-N-(4-methyl-1,1-dioxo-thian-4-yl)-2-oxo-imidazo[4,5-b]pyridine-6-carboxamide | 501 | 506 |

-continued

| Example | Structure | Name | LCMS [M + 1] | DGAT2 IC50 (nM) |
|---|---|---|---|---|
| 102 | 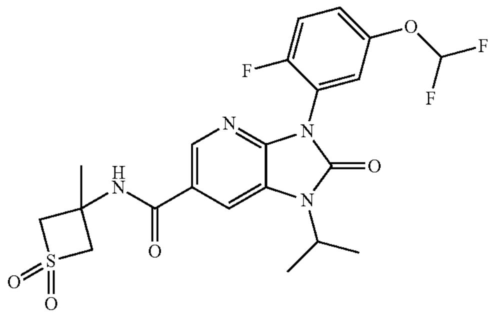 [SMILES: CC(C)n1c(=O)n(-c2cc(OC(F)F)ccc2F)c2ncc(C(=O)NC3(C)CS(=O)(=O)C3)cc21] | 3-[5-(difluoromethoxy)-2-fluoro-phenyl]-1-isopropyl-N-(3-methyl-1,1-dioxo-thietan-3-yl)-2-oxo-imidazo[4,5-b]pyridine-6-carboxamide | 499 | 148 |
| 103 | 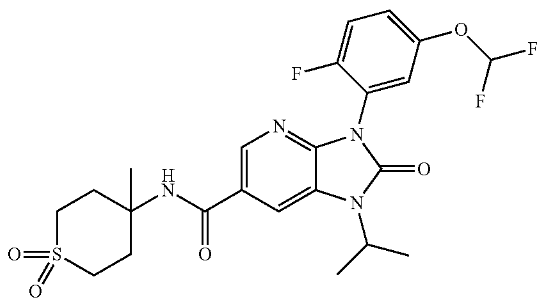 [SMILES: CC(C)n1c(=O)n(-c2cc(OC(F)F)ccc2F)c2ncc(C(=O)NC3(C)CCS(=O)(=O)CC3)cc21] | 3-[5-(difluoromethoxy)-2-fluoro-phenyl]-1-isopropyl-N-(4-methyl-1,1-dioxo-thian-4-yl)-2-oxo-imidazo[4,5-b]pyridine-6-carboxamide | 528 | 74 |
| 104 | 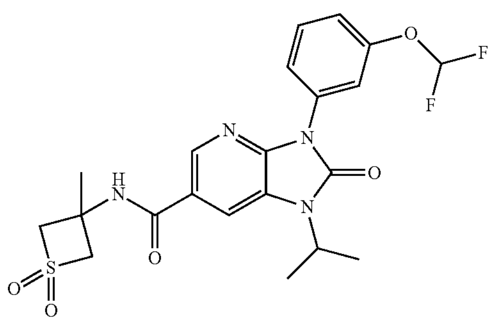 [SMILES: CC(C)n1c(=O)n(-c2cccc(OC(F)F)c2)c2ncc(C(=O)NC3(C)CS(=O)(=O)C3)cc21] | 3-[3-(difluoromethoxy)phenyl]-1-isopropyl-N-(3-methyl-1,1-dioxo-thietan-3-yl)-2-oxo-imidazo[4,5-b]pyridine-6-carboxamide | 481 | 94 |

Example 105: 3-(3-(difluoromethoxy)phenyl)-1-isopropyl-N-(3-methyl-1,1-dioxidothietan-3-yl)-2-oxo-2,3-dihydro-1H-imidazo[4,5-c]pyridine-6-carboxamide

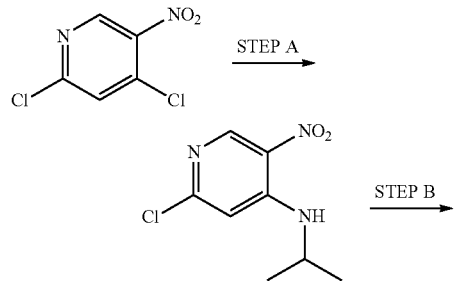

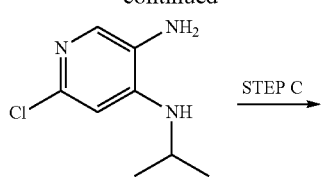

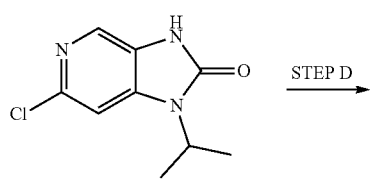

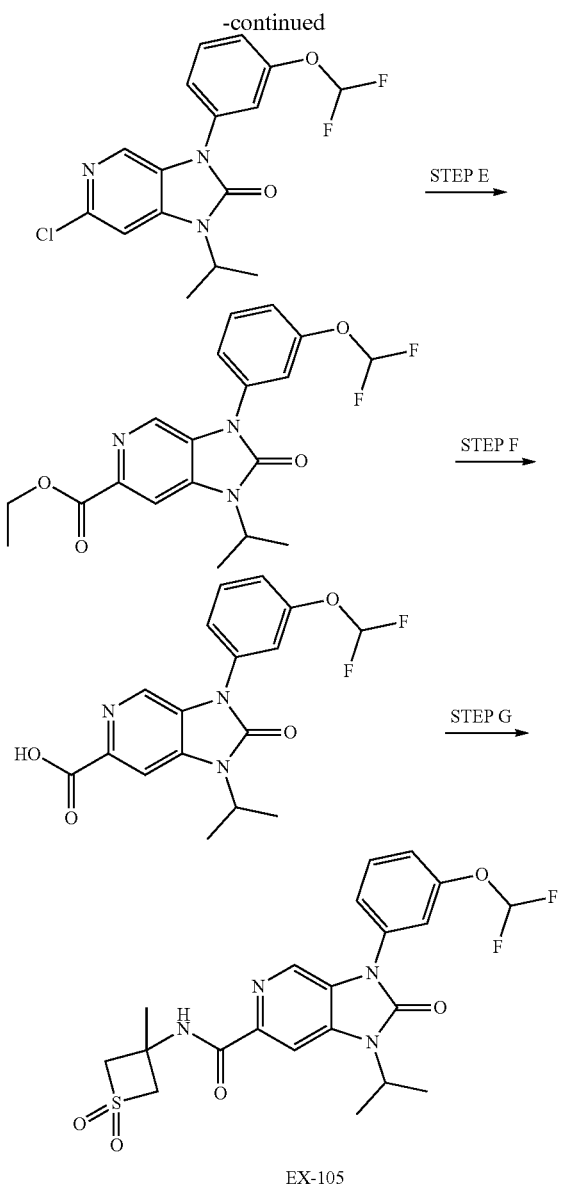

EX-105

Step A:
2-chloro-N-isopropyl-5-nitropyridin-4-amine

To a solution of 2,4-dichloro-5-nitropyridine (300 mg, 1.555 mmol) in THF (6 mL) was added propan-2-amine (110 mg, 1.865 mmol) and Et₃N (0.433 mL, 3.11 mmol). The reaction mixture was stirred at 25° C. for 3 h, then poured into sat. NH₄Cl, and extracted with DCM (×3). The combined organic layers were washed with brine, dried over Na₂SO₄, filtered and concentrated in vacuo. The residue was purified by column chromatography on silica (0-100% EtOAc/hexanes) to afford the title compound. LC/MS=216 [M+1].

Step B: 6-chloro-N-isopropylpyridine-3,4-diamine

To a solution of 2-chloro-N-isopropyl-5-nitropyridin-4-amine (300 mg, 1.391 mmol) in MeOH (4 mL) was added iron (194 mg, 3.48 mmol) and ammonium chloride (0.186 mL, 3.48 mmol). The reaction mixture was stirred at 65° C. for 13 h, then poured into sat. NH₄Cl, and extracted with DCM (×3). The combined organic layers were washed with brine, dried over Na₂SO₄, filtered and concentrated in vacuo. The residue was purified by column chromatography on silica (0-100% EtOAc/hexanes) to afford the title compound. LC/MS=186 [M+1].

Step C: 6-chloro-1-isopropyl-1H-imidazo[4,5-c]pyridin-2(3H)-one

To a solution of 6-chloro-N4-isopropylpyridine-3,4-diamine (200 mg, 1.077 mmol) in THF (5 mL) was added Et₃N (0.450 mL, 3.23 mmol) and CDI (873 mg, 5.39 mmol). The reaction mixture was stirred at 25° C. for 12 h under a N₂ balloon, then poured into sat. NH₄Cl and extracted with DCM (×3). The combined organic layers were washed with brine, dried over Na₂SO₄, filtered and concentrated in vacuo. The residue was purified by column chromatography on silica (0-100% EtOAc/hexanes) to afford the title compound. LC/MS=212 [M+1].

Step D: 6-chloro-3-(3-(difluoromethoxy)phenyl)-1-isopropyl-1H-imidazo[4,5-c]pyridin-2(3H)-one To a solution of 6-chloro-1-isopropyl-1H-imidazo[4,5-c]pyridin-2(3H)-one (190 mg, 0.898 mmol) in DMF (3 mL) was added 2-(3-(difluoromethoxy)phenyl)-4,4,5,5-tetramethyl-1,3,2-dioxaborolane (1212 mg, 4.49 mmol), Pyridine (1.452 mL, 17.95 mmol), 4 A molecular sieve (200 mg) and Cu(OAc)₂ (326 mg, 1.795 mmol). The mixture was stirred at 80° C. for 13 h, open to air with a drying tube, then poured into sat. NH₄Cl and extracted with DCM (×3). The combined organic layers were washed with brine, dried over Na₂SO₄, then filtered and concentrated in vacuo. The residue was purified by column chromatography on silica (0-100% EtOAc/hexanes) to afford the title compound. LC/MS=354 [M+1].

Step E: ethyl 3-(3-(difluoromethoxy)phenyl)-1-isopropyl-2-oxo-2,3-dihydro-1H-imidazo[4,5-c]pyridine-6-carboxylate To a solution of 6-chloro-3-(3-(difluoromethoxy)phenyl)-1-isopropyl-1H-imidazo[4,5-c]pyridin-2(3H)-one (300 mg, 0.848 mmol) in EtOH (20 mL) was added potassium acetate (0.159 mL, 2.54 mmol) and [1,1'-bis(diphenylphosphino)ferrocene]dichloropalladium(II) (124 mg, 0.170 mmol). The mixture was stirred at 100° C. for 16 h under a CO balloon, then poured into sat. NH₄Cl and extracted with DCM (×3). The combined organic layers were washed with brine, dried over Na₂SO₄, filtered and concentrated in vacuo. The residue was purified by column chromatography on silica (0-100% EtOAc/hexanes) to afford the title compound. LC/MS=392 [M+1].

Step F: 3-(3-(difluoromethoxy)phenyl)-1-isopropyl-2-oxo-2,3-dihydro-1H-imidazo[4,5-c]pyridine-6-carboxylic acid To a solution of ethyl 3-(3-(difluoromethoxy)phenyl)-1-isopropyl-2-oxo-2,3-dihydro-1H-imidazo[4,5-c]pyridine-6-carboxylate (217 mg, 0.554 mmol) in MeOH (4 mL) and water (0.4 mL) was added lithium hydroxide monohydrate (46.5 mg, 1.109 mmol). The mixture was stirred at 25° C. for 8 h, then concentrated in vacuo and dissolved in H₂O. HCl (1N in water) was added to the mixture until pH=4. The mixture was extracted with DCM (×3). The combined organic layers were washed with brine, dried over Na$_2$SO$_4$, filtered and concentrated in vacuo to afford the title compound. LC/MS=364 [M+1].

Step G: 3-(3-(difluoromethoxy)phenyl)-1-isopropyl-N-(3-methyl-1,1-dioxidothietan-3-yl)-2-oxo-2,3-dihydro-1H-imidazo[4,5-c]pyridine-6-carboxamide To a solution of 3-(3-(difluoromethoxy)phenyl)-1-isopropyl-2-oxo-2,3-dihydro-1H-imidazo[4,5-c]pyridine-6-carboxylic acid (30 mg, 0.083 mmol) in DMF (2 mL) was added DIEA (0.072 ml, 0.413 mmol) and HATU (47.1 mg, 0.124 mmol). The mixture was stirred at 25° C. for 0.5 h. Then, 3-amino-3-methylthietane 1,1-dioxide (14.51 mg, 0.107 mmol) was added to the mixture followed by stirring at 25° C. for 1 h. The crude mixture was purified directly by mass triggered reverse phase HPLC (ACN/water with 0.1% TFA modifier) to afford the title compound as the TFA salt. LC/MS=481 [M+1]. $^1$H NMR (400 MHz, METHANOL-d4, ppm) δ 8.33 (s, 1H), 8.12 (s, 1H), 7.58-7.71 (m, 1H), 7.42-7.54 (m, 2H), 7.31 (dd, J=1.6, 8.4 Hz, 1H), 6.71-7.14 (m, 1H), 4.76-4.84 (m, 1H), 4.65 (br d, J=14.8 Hz, 2H), 4.18-4.29 (m, 2H), 1.84 (s, 3H), 1.63 (d, J=7.2 Hz, 6H). Human DGAT2 IC$_{50}$=1804 nM.

By using procedures similar to those described in Example 72 with appropriate reagents, the following compounds were synthesized. These compounds were characterized by LC/MS.

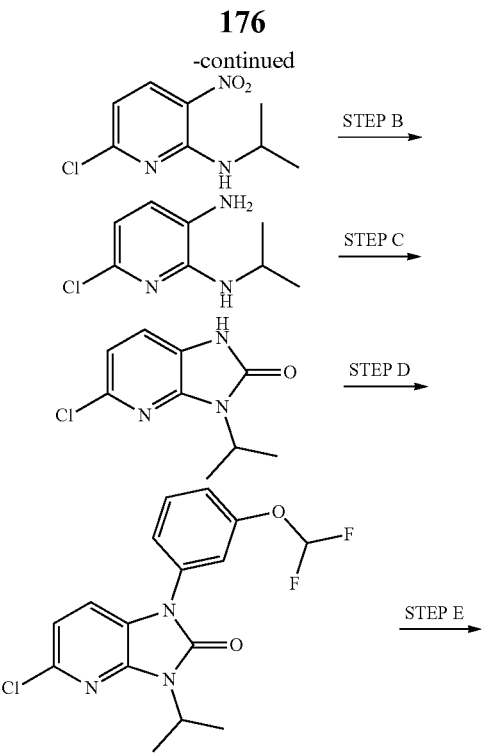

| Example | Structure | Name | LCMS [M + 1] | Human DGAT2 IC50 (nM) |
|---|---|---|---|---|
| 106 | 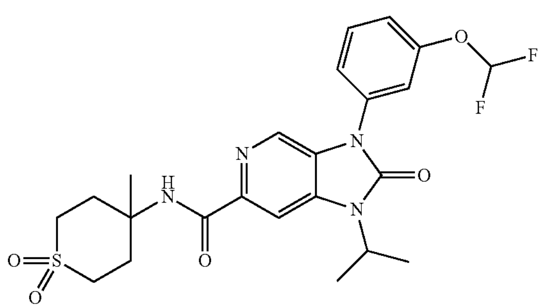 [SMILES: CC(C)n1c(=O)n(-c2cccc(OC(F)F)c2)c2cnc(C(=O)NC3(C)CCS(=O)(=O)CC3)cc21] | 3-(3-(difluoromethoxy)phenyl)-1-isopropyl-N-(4-methyl-1,1-dioxidotetrahydro-2H-thiopyran-4-yl)-2-oxo-2,3-dihydro-1H-imidazo[4,5-c]pyridine-6-carboxamide | 509 | 69.8 |

Example 107: 1-(3-(difluoromethoxy)phenyl)-3-isopropyl-N-(3-methyl-1,1-dioxidothietan-3-yl)-2-oxo-2,3-dihydro-1H-imidazo[4,5-b]pyridine-5-carboxamide

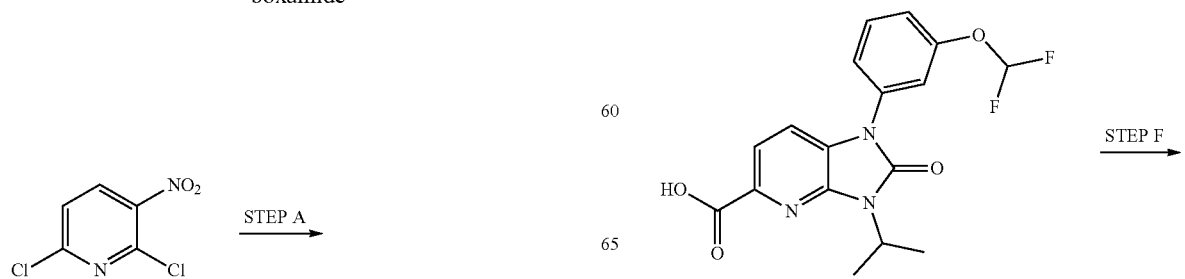

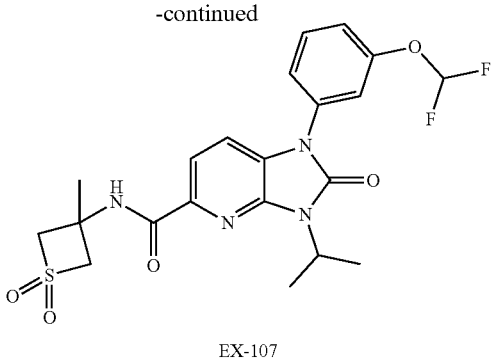

EX-107

Step A: 6-chloro-N-isopropyl-3-nitropyridin-2-amine

Propan-2-amine (2.66 mL, 31.1 mmol) was added to a solution of 2,6-dichloro-3-nitropyridine (3 g, 15.55 mmol) in absolute EtOH (30 mL). The resulting mixture was stirred at 15° C. for 20 min, then concentrated in vacuo. The residue was purified by column chromatography on silica (0-100% EtOAc/hexanes) to afford the title compound. LC/MS=217 [M+1]. $^1$H NMR (400 MHz, METHANOL-d4, ppm) δ 8.41 (d, J=8.61 Hz, 1H), 6.68 (d, J=8.61 Hz, 1H), 4.35-4.51 (m, 1H), 1.31 (d, J=6.26 Hz, 6H).

Step B: 6-chloro-N2-isopropylpyridine-2,3-diamine

The NH$_4$Cl (2.98 g, 55.6 mmol) of H$_2$O (10 mL) was added to 6-chloro-N-isopropyl-3-nitropyridin-2-amine (2 g, 9.27 mmol) in MeOH (20 mL) solution, and then iron (2.59 g, 46.4 mmol) was added to the above mixed solution. The resulting mixture was stirred at 75° C. for 13 h, then poured into sat. NaHCO$_3$ and was extracted with DCM (×3). The combined organic layers were washed with brine, dried over Na$_2$SO$_4$, then filtered and concentrated in vacuo. The residue was purified by column chromatography on silica (0-100% EtOAc/hexanes) to afford the title compound. LC/MS=186 [M+1]. $^1$H NMR (400 MHz, METHANOL-d4, ppm) δ 6.75 (d, J=7.83 Hz, 1H), 6.32 (d, J=7.58 Hz, 1H), 4.11-4.27 (m, 1H), 1.20 (d, J=6.36 Hz, 6H).

Step C: 5-chloro-3-isopropyl-1H-imidazo[4,5-b]pyridin-2(3H)-one

A mixture of 6-chloro-N2-isopropylpyridine-2,3-diamine (400 mg, 2.155 mmol) and CDI (1747 mg, 10.77 mmol) in THF (5 mL) was stirred at 20° C. for 2 h. The mixture was poured into sat. NaHCO$_3$ and extracted with DCM (×3). The combined organic layers were washed with brine, dried over Na$_2$SO$_4$, filtered and concentrated in vacuo. The residue was purified by column chromatography on silica (0-100% EtOAc/hexanes) to afford the title compound. LC/MS=213 [M+1].

Step D: 5-chloro-1-(3-(difluoromethoxy)phenyl)-3-isopropyl-1H-imidazo[4,5-b]pyridin-2(3H)-one To a solution of 5-chloro-3-isopropyl-1H-imidazo[4,5-b]pyridin-2(3H)-one (280 mg, 1.323 mmol) and 2-(3-(difluoromethoxy)phenyl)-4,4,5,5-tetramethyl-1,3,2-dioxaborolane (1787 mg, 6.61 mmol) in DMF (4 mL) was added diacetoxycopper (288 mg, 1.588 mmol) and pyridine (2.131 mL, 26.5 mmol) at 80° C. The mixture was stirred for 5 h, then poured into sat. NaHCO$_3$ and extracted with DCM (×3). The combined organic layers were washed with brine, dried over Na$_2$SO$_4$, then filtered and concentrated in vacuo. The residue was purified by column chromatography on silica (0-100% EtOAc/hexanes) to afford the title compound. LC/MS=355 [M+1].

Step E: 1-(3-(difluoromethoxy)phenyl)-3-isopropyl-2-oxo-2,3-dihydro-1H-imidazo[4,5-b]pyridine-5-carboxylic acid A 50 mL flask was charged with 5-chloro-1-(3-(difluoromethoxy)phenyl)-3-isopropyl-1H-imidazo[4,5-b]pyridin-2(3H)-one (100 mg, 0.283 mmol), K$_2$CO$_3$ (78 mg, 0.565 mmol), diacetoxypalladium (19.04 mg, 0.085 mmol), propane-1,3-diylbis(dicyclohexylphosphonium) (69.2 mg, 0.113 mmol), DMSO (2 ml) and H$_2$O (0.2 mL) at 20° C. The mixture was degassed and backfilled with CO (three times), then stirred under CO (pressure: 15 psi) at 110° C. for 5 h. The mixture was poured into water and extracted with DCM (×3). The combined organic layers were washed with brine, dried over Na$_2$SO$_4$, filtered and concentrated in vacuo to afford the title compound. LC/MS=364 [M+1].

Step F: 1-(3-(difluoromethoxy)phenyl)-3-isopropyl-N-(3-methyl-1,1-dioxidothietan-3-yl)-2-oxo-2,3-dihydro-1H-imidazo[4,5-b]pyridine-5-carboxamide A 8 mL tube was charged with 1-(3-(difluoromethoxy)phenyl)-3-isopropyl-2-oxo-2,3-dihydro-1H-imidazo[4,5-b]pyridine-5-carboxylic acid (30 mg, 0.083 mmol), DIEA (0.043 mL, 0.248 mmol), 3-amino-3-methylthietane 1,1-dioxide (16.74 mg, 0.124 mmol), HATU (47.1 mg, 0.124 mmol) and DMF (0.5 mL) at 20° C. and stirred for 0.5 h. The crude mixture was purified by mass triggered reverse phase HPLC (ACN/water with 0.1% TFA modifier) to afford the title compound as the TFA salt. LC/MS=481 [M+1]. $^1$H NMR (500 MHz, METHANOL-d4, ppm) δ 8.99 (s, 1H), 7.91 (d, J=8.24 Hz, 1H), 7.61-7.70 (m, 1H), 7.55 (d, J=8.09 Hz, 1H), 7.47 (dd, J=0.99, 8.01 Hz, 1H), 7.43 (s, 1H), 7.30 (dd, J=1.75, 8.32 Hz, 1H), 6.80-7.15 (m, 1H), 5.14 (d, J=6.89 Hz, 1H), 4.69 (br d, J=14.50 Hz, 2H), 4.29 (d, J=14.80 Hz, 2H), 1.89 (s, 3H), 1.69 (d, J=6.87 Hz, 6H). Human DGAT2 IC50=1083 nM

Example 108: 1-[3-(difluoromethoxy)phenyl]-7-fluoro-3-isopropyl-N-(3-methyl-1,1-dioxo-thietan-3-yl)-2-oxo-benzimidazole-5-carboxamide

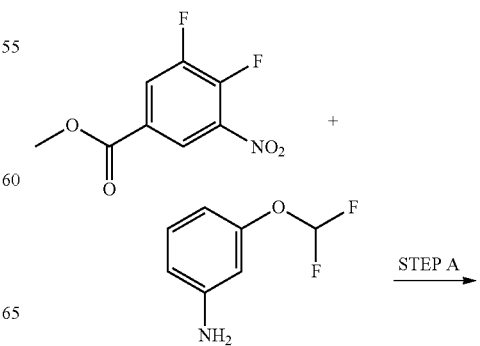

STEP A

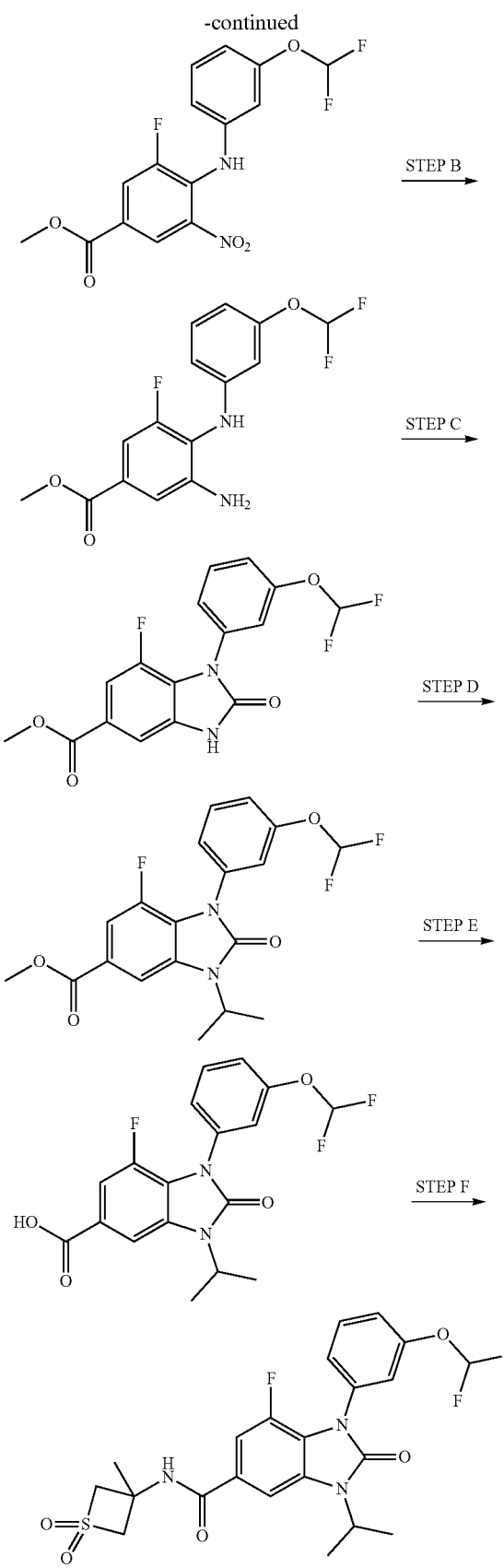

EX-108

Step A: Methyl 4-((3-(difluoromethoxy)phenylamino)-3-fluoro-5-nitrobenzoate

At RT, methyl 3,4-difluoro-5-nitrobenzoate (761 mg, 3.50 mmol), 3-(difluoromethoxy)aniline (0.432 ml, 3.50 mmol), and DIPEA (1.224 ml, 7.01 mmol) were dissolved in DMSO (17.5 mL). The mixture was heated to 100° C. and stirred overnight. The reaction was cooled to RT and water was added. EtOAc was added, and the layers were separated. The aqueous layer was extracted three times with EtOAc. The combined organic layers were washed with brine, dried with $MgSO_4$ (s), filtered, and concentrated under reduced pressure. The crude residue was purified by flash silica gel chromatography (0 to 100% EtOAc) to afford the title compound. LC/MS=357 [M+1].

Step B: Methyl 3-amino-4-((3-(difluoromethoxy)phenyl)amino)-5-fluorobenzoate

At RT, methyl 4-((3-(difluoromethoxy)phenyl)amino)-3-fluoro-5-nitrobenzoate (911 mg, 2.56 mmol) was dissolved in THF (5.11 ml), and methanol (2.56 ml) and saturated aqueous ammonium chloride (5.11 ml). Zinc (836 mg, 12.8 mmol) were added. The reaction was stirred for 30 minutes at RT, then filtered through Celite, and the celite was washed with EtOAc. The mixture was concentrated under reduced pressure. Water and EtOAc were added, and the layers were separated. The aqueous layer was extracted three times with EtOAc. The combined organic layers were washed with brine, dried with $MgSO_4$ (s), filtered, and concentrated under reduced pressure. The crude residue was purified by flash silica gel column chromatography (0 to 100% EtOAc in Hexanes) to afford the title compound. LC/MS=327 [M+1].

Step C: Methyl 1-(3-(difluoromethoxy)phenyl)-7-fluoro-2-oxo-2,3-dihydro-1H-benzo[d]imidazole-5-carboxylate At RT, methyl 3-amino-4-((3-(difluoromethoxy)phenyl)amino)-5-fluorobenzoate (777 mg, 2.381 mmol) was dissolved in THF (23.81 ml). di(1H-imidazol-1-yl)methanone (1545 mg, 9.53 mmol) was added and the reaction was stirred overnight. The next day, water was added and the THF was removed under reduced pressure. EtOAc was added, the layers were separated, and the aqueous layer was extracted three times with EtOAc. The combined organic layers were washed with brine, dried with $MgSO_4$ (s), filtered, and concentrated under reduced pressure. The crude residue was purified by flash silica gel column chromatography (0 to 50% EtOac in DCM) to afford the title compound. LC/MS=353 [M+1].

Step D: Methyl 1-(3-(difluoromethoxy)phenyl)-7-fluoro-3-isopropyl-2-oxo-2,3-dihydro-1H-benzo[d]imidazole-5-carboxylate At RT, methyl 1-(3-(difluoromethoxy)phenyl)-7-fluoro-2-oxo-2,3-dihydro-1H-benzo[d]imidazole-5-carboxylate (176 mg, 0.500 mmol) and cesium carbonate (651 mg, 1.998 mmol) were suspended in DMF (2.5 mL). 2-iodopropane (100 µl, 0.999 mmol) was added, and the reaction was heated to 80° C. for two days. The reaction was cooled to RT, then water and EtOAc were added. The layers were separated and the aqueous layer was extracted with EtOAc three times. The combined organic layers were washed with brine, dried with $MgSO_4$ (s), filtered, and concentrated under reduced pressure. The crude residue was purified by flash silica gel column chromatography (0 to 15% EtOAc in DCM) to afford the title compound. LC/MS=395 [M+1].

Step E: 1-(3-(difluoromethoxy)phenyl)-7-fluoro-3-isopropyl-2-oxo-2,3-dihydro-1H-benzo[d]imidazole-5-carboxylic acid At RT, to a stirred solution of methyl 1-(3-(difluoromethoxy)phenyl)-7-fluoro-3-isopropyl-2-oxo-2,3-dihydro-1H-benzo[d]imidazole-5-carboxylate (0.198 g, 0.500 mmol) dissolved in THF (0.714 ml) and methanol (2.143 ml). was added a solution of lithium hydroxide (0.060 g, 2.500 mmol) in water (2.143 ml). The reaction was stirred at RT for 16 hrs. Aqueous hydrochloric acid (1 N, 10 ml, 10.00 mmol) was added until the pH=1, and EtOAc was added. The layers were separated, and the aqueous layer was extracted three times with EtOAc. The combined organic layers were washed with brine, dried with $MgSO_4$ (s), filtered, and concentrated under reduced pressure to afford the title compound. LC/MS=381 [M+1].

Step F: 1-(3-(difluoromethoxy)phenyl)-7-fluoro-3-isopropyl-N-(3-methyl-1,1-dioxidothietan-3-yl)-2-oxo-2,3-dihydro-1H-benzo[d]imidazole-5-carboxamide At RT, DIPEA (0.262 mL, 1.499 mmol) was added to a stirred solution of 1-(3-(difluoromethoxy)phenyl)-7-fluoro-3-isopropyl-2-oxo-2,3-dihydro-1H-benzo[d]imidazole-5-carboxylic acid (190 mg, 0.500 mmol), 3-amino-3-methyl-thietane 1,1-dioxide hydrochloride (94 mg, 0.550 mmol), and HATU (209 mg, 0.550 mmol in DMF (5.00 mL). DIPEA (0.262 mL, 1.499 mmol) was added, and the reaction was stirred at RT. Then, the DMF was removed under reduced pressure. The crude residue was purified twice by flash silica gel column chromatography (0 to 100% EtOAc in hexanes followed by 0 to 30% Acetone in DCM) to afford the title compound. 1H NMR (500 MHz, Methanol-$d_4$) δ 7.74 (d, J=1.3 Hz, 1H), 7.58 (t, J=8.2 Hz, 1H), 7.49 (dd, J=12.0, 1.3 Hz, 1H), 7.38 (d, J=7.9 Hz, 1H), 7.34 (d, J=1.9 Hz, 1H), 7.29 (dd, J=8.3, 2.1 Hz, 1H), 6.93 (t, J=73.7 Hz, 1H), 4.79 (hept, J=6.9 Hz, 1H), 4.65-4.58 (m, 2H), 4.30-4.22 (m, 2H), 1.86 (s, 3H), 1.65 (d, J=7.0 Hz, 6H). LC/MS=498 [M+1]. Human DGAT2 IC50=12 nM By using procedures similar to those described in Example 108 with appropriate amine reagents, the following compounds were synthesized. These compounds were characterized by LC/MS.

| Example | Structure | Name | LCMS [M + 1] | DGAT2 IC50 (nM) |
|---|---|---|---|---|
| 109 | 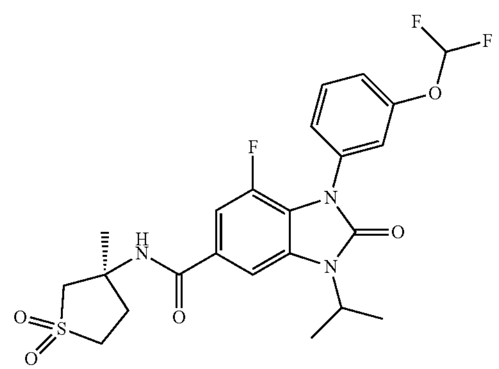 [SMILES: CC(C)n1c(=O)n(-c2cccc(OC(F)F)c2)c2c(F)cc(C(=O)N[C@@]3(C)CCS(=O)(=O)C3)cc21] | 1-[3-(difluoromethoxy)phenyl]-7-fluoro-3-isopropyl-N-[(3S)-3-methyl-1,1-dioxo-thiolan-3-yl]-2-oxo-benzimidazole-5-carboxamide | 513 | 9.0 |
| 110 | 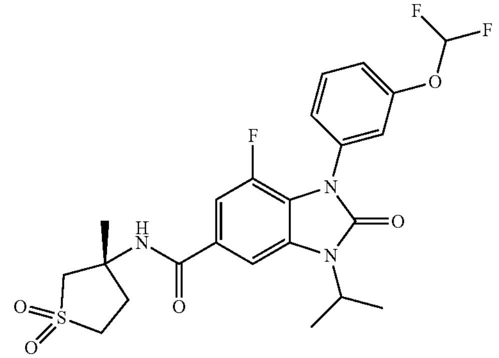 [SMILES: CC(C)n1c(=O)n(-c2cccc(OC(F)F)c2)c2c(F)cc(C(=O)N[C@]3(C)CCS(=O)(=O)C3)cc21] | 1-[3-(difluoromethoxy)phenyl]-7-fluoro-3-isopropyl-N-[(3R)-3-methyl-1,1-dioxo-thiolan-3-yl]-2-oxo-benzimidazole-5-carboxamide | 513 | 7.0 |

| Example | Structure | Name | LCMS [M + 1] | DGAT2 IC50 (nM) |
|---|---|---|---|---|
| 111 | 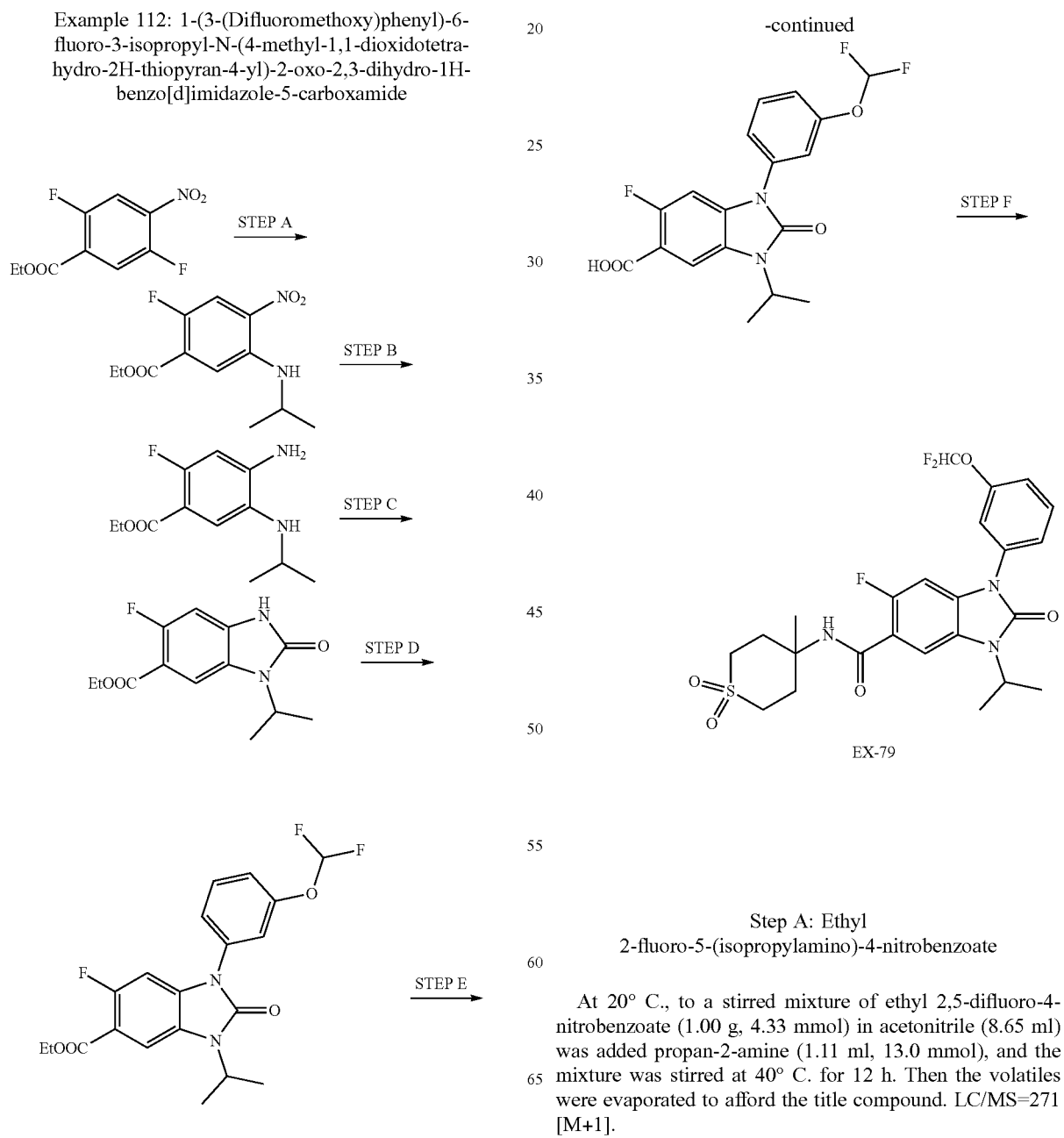 | 1-[3-(difluoromethoxy)phenyl]-7-fluoro-3-isopropyl-N-(4-methyl-1,1-dioxo-thian-4-yl)-2-oxo-benzimidazole-5-carboxamide | 527 | 68 |

Example 112: 1-(3-(Difluoromethoxy)phenyl)-6-fluoro-3-isopropyl-N-(4-methyl-1,1-dioxidotetrahydro-2H-thiopyran-4-yl)-2-oxo-2,3-dihydro-1H-benzo[d]imidazole-5-carboxamide

Step A: Ethyl 2-fluoro-5-(isopropylamino)-4-nitrobenzoate

At 20° C., to a stirred mixture of ethyl 2,5-difluoro-4-nitrobenzoate (1.00 g, 4.33 mmol) in acetonitrile (8.65 ml) was added propan-2-amine (1.11 ml, 13.0 mmol), and the mixture was stirred at 40° C. for 12 h. Then the volatiles were evaporated to afford the title compound. LC/MS=271 [M+1].

Step B: Ethyl 4-amino-2-fluoro-5-(isopropylamino)benzoate

At 0° C., to a stirred mixture of ethyl 2-fluoro-5-(isopropylamino)-4-nitrobenzoate (1.17 g, 4.33 mmol) in THF (8.66 ml). and MeOH (4.33 ml) saturated ammonia hydrochloride aqueous solution (8.66 ml), was added zinc (1.13 g, 17.3 mmol). The mixture was stirred at 20° C. for 1 h, then filtered over sand, and the filtrate concentrated. The residue was partitioned between EtOAc and water. The organic layer was separated, washed with brine, dried over $Na_2SO_4$ (s), and the volatiles evaporated to afford the title compound. LC/MS=241 [M+1].

Step C: Ethyl 6-fluoro-3-isopropyl-2-oxo-2,3-dihydro-1H-benzo[d]imidazole-5-carboxylate At 20° C., to a stirred mixture of ethyl 4-amino-2-fluoro-5-(isopropylamino)benzoate (1040 mg, 4.33 mmol) in THF (8.66 mL) was added 1,1'-carbonyldiimidazole (2.81 g, 17.3 mmol). The mixture was stirred at 20° C. for 16 h, then was filtered, and the volatiles were removed. The residue was purified by flash silica gel chromatography (0 to 100% EtOAc in hexanes) to afford the title compound. LC/MS=267 [M+1].

Step D: Ethyl 1-(3-(difluoromethoxy)phenyl)-6-fluoro-3-isopropyl-2-oxo-2,3-dihydro-1H-benzo[d]imidazole-5-carboxylate At 20° C., to a stirred mixture of ethyl 6-fluoro-3-isopropyl-2-oxo-2,3-dihydro-1H-benzo[d]imidazole-5-carboxylate (100 mg, 0.376 mmol), and (3-(difluoromethoxy)phenyl)boronic acid (85 mg, 0.451 mmol) was added DCE (1.25 mL) and copper (II) acetate (82 mg, 0.451 mmol). The mixture was stirred at 50° C. for 3 d. Then the volatiles were evaporated, and the residue was purified by flash silica gel chromatography (0 to 70% EtOAc in hexanes) to afford the title compound. LC/MS=409 [M+1].

Step E: 1-(3-(Difluoromethoxy)phenyl)-6-fluoro-3-isopropyl-2-oxo-2,3-dihydro-1H-benzo[d]imidazole-5-carboxylic acid At 20° C., to a stirred mixture of ethyl 1-(3-(difluoromethoxy)phenyl)-6-fluoro-3-isopropyl-2-oxo-2,3-dihydro-1H-benzo[d]imidazole-5-carboxylate (58 mg, 0.142 mmol) in THF (1.22 mL) and MeOH (0.40 mL) was added lithium hydroxide hydrate (23.8 mg, 0.568 mmol) in water (1.22 mL). The mixture was stirred at 20° C. for 1 h, then, 1N HCl (1 mL, aqueous) was added, and the mixture was partitioned between EtOAc and water. The organic layer was separated, washed with brine, dried over $Na_2SO_4$ (s), filtered, and the volatiles evaporated to afford the title compound. LC/MS=381 [M+1].

Step F: 1-(3-(Difluoromethoxy)phenyl)-6-fluoro-3-isopropyl-N-(4-methyl-1,1-dioxidotetrahydro-2H-thiopyran-4-yl)-2-oxo-2,3-dihydro-1H-benzo[d]imidazole-5-carboxamide At 20° C., to a stirred mixture of 1-(3-(difluoromethoxy)phenyl)-6-fluoro-3-isopropyl-2-oxo-2,3-dihydro-1H-benzo[d]imidazole-5-carboxylic acid (50 mg, 0.13 mmol) and HATU (65 mg, 0.17 mmol) in DMF (0.9 mL) were added 4-amino-4-methyltetrahydro-2H-thiopyran 1,1-dioxide hydrochloride (53 mg, 0.26 mmol), then DIPEA (92 µl, 0.53 mmol). The mixture was stirred at 20° C. for 1 h, then partitioned between LiCl (10 wt %, aqueous, 10 mL) and EtOAc (10 mL). The organic layer was separated, washed with brine, dried over $Na_2SO_4$ (s), and the volatiles evaporated. The residue was purified by flash silica gel chromatography (0 to 100% EtOAc in hexanes), then lyophilized, to afford the title compound. $^1$H NMR (500 MHz, DMSO-$d_6$) δ 8.08 (s, 1H), 7.64 (t, J=8.2 Hz, 1H), 7.50 (d, J=5.7 Hz, 1H), 7.43 (dd, J=8.0, 1.1 Hz, 1H), 7.38 (t, J=2.1 Hz, 1H), 7.34 (t, J=73.8 Hz, 1H), 7.29 (dd, J=8.3, 2.3 Hz, 1H), 7.06 (d, J=10.0 Hz, 1H), 4.70 (hept, J=7.1 Hz, 1H), 3.18-3.09 (m, 2H), 3.09-3.01 (m, 2H), 2.72-2.65 (m, 2H), 2.03-1.94 (m, 2H), 1.51 (d, J=6.9 Hz, 6H), 1.44 (s, 3H). LC/MS=526 [M+1]. Human DGAT2 $IC_{50}$=73.8 nM.

By using procedures similar to those described in Example 112 with appropriate reagents, the following compounds were synthesized. These compounds were characterized by LC/MS.

| Example | Structure | Name | LCMS [M + 1] | DGAT2 $IC_{50}$ (nM) |
|---|---|---|---|---|
| 113 | 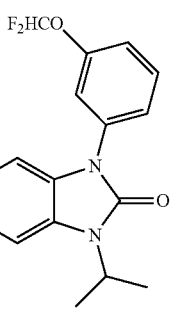 | (R)-1-(3-(Difluoromethoxy)phenyl)-6-fluoro-3-isopropyl-N-(3-methyl-1,1-dioxidotetrahydrothiophen-3-1)-2-oxo-2,3-dihydro-1H-benzo[d]imidazole-5-carboxamide | 512 | 78 |

-continued

| Example | Structure | Name | LCMS [M + 1] | DGAT2 IC$_{50}$ (nM) |
|---|---|---|---|---|
| 114 | 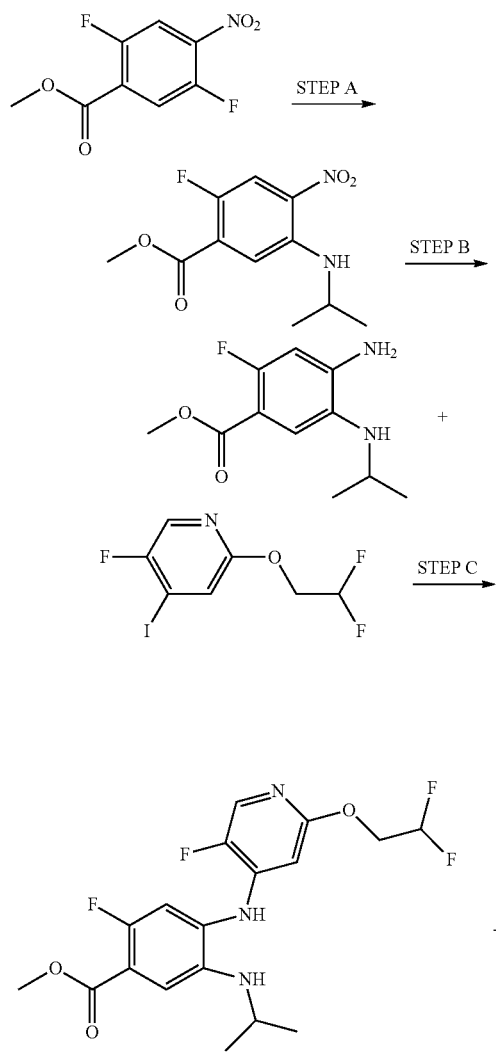 | (S)-1-(3-(Difluoromethoxy)phenyl)-6-fluoro-3-isopropyl-N-(3-methyl-1,1-dioxidotetrahydrothiophen-3-yl)-2-oxo-2,3-dihydro-1H-benzo[d]imidazole-5-carboxamide | 512 | 80 |

Example 115: 1-(2-(2,2-difluoroethoxy)-5-fluoro-pyridin-4-yl)-6-fluoro-3-isopropyl-N-(4-methyl-1,1-dioxidotetrahydro-2H-thiopyran-4-yl)-2-oxo-2,3-dihydro-1H-benzo[d]imidazole-5-carboxamide

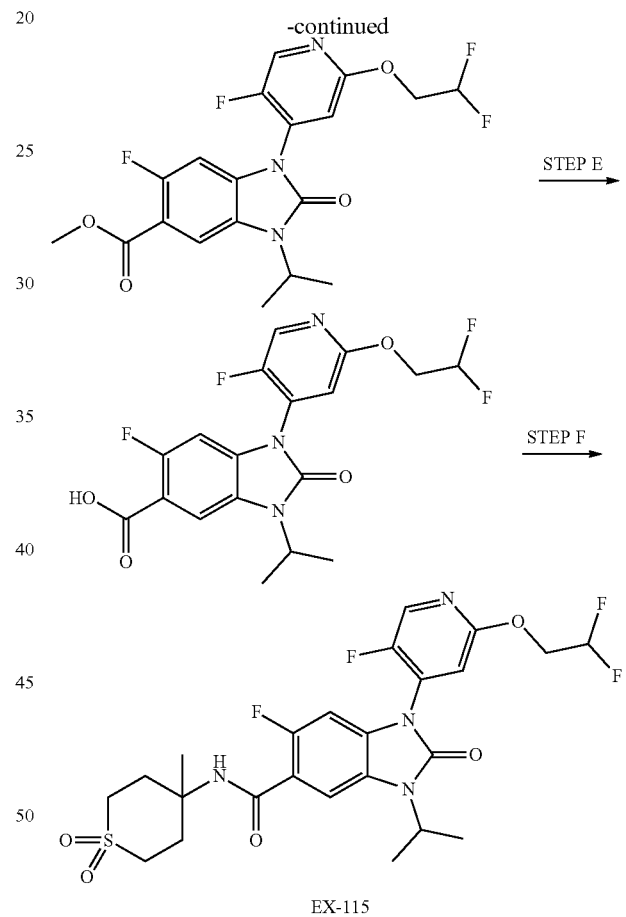

Step A: methyl 2-fluoro-5-(isopropylamino)-4-nitrobenzoate

A mixture of methyl 2,5-difluoro-4-nitrobenzoate (20 g, 92 mmol), propan-2-amine (7.08 g, 120 mmol), and potassium carbonate (12.73 g, 92 mmol) in THF (200 ml) was stirred at 40° C. for 15 h. The mixture was poured into H$_2$O, then extracted with EtOAc (×3). The combined organic layers were washed with brine, dried over Na$_2$SO$_4$, then filtered and concentrated under reduced pressure. The residue was purified by column chromatography on silica (0-100% EtOAc/hexanes) to afford the title compound. LC/MS=257 [M+1].

Step B: methyl 4-amino-2-fluoro-5-(isopropylamino)benzoate

A mixture of methyl 2-fluoro-5-(isopropylamino)-4-nitrobenzoate (13.8 g, 53.9 mmol) and Pd/C (2.5 g, 2.349 mmol) in THF (20 ml) was stirred at 50° C. for 2 h under $H_2$ 15 psi. The suspension was filtered through a pad of Celite and the filter cake was washed with EtOAc (30 mL). The combined filtrates were concentrated. The residue was purified by column chromatography on silica (0-100% EtOAc/hexanes) to afford the title compound. LC/MS=227 [M+1].

Step C: methyl 4-((2-(2,2-difluoroethoxy)-5-fluoropyridin-4-yl)amino)-2-fluoro-5-(isopropylamino)benzoate A mixture of methyl 4-amino-2-fluoro-5-(isopropylamino)benzoate (4.5 g, 19.89 mmol), 2-(2,2-difluoroethoxy)-5-fluoro-4-iodopyridine (7.23 g, 23.87 mmol) in THF (50 mL) was added $Cs_2CO_3$ (19.44 g, 59.7 mmol), Brettphos Pd $G_3$ (1.5 g, 1.655 mmol) at 20° C. Then the mixture was heated to 80° C. under $N_2$ for 15 h then poured into $H_2O$, and extracted with EtOAc (×3). The combined organic layers were washed with brine, dried over $Na_2SO_4$, then filtered and concentrated under reduced pressure. The residue was purified by column chromatography on silica (0-100% EtOAc/hexanes) to afford the title compound. LC/MS=402 [M+1].

Step D: methyl 1-(2-(2,2-difluoroethoxy)-5-fluoropyridin-4-yl)-6-fluoro-3-isopropyl-2-oxo-2,3-dihydro-1H-benzo[d]imidazole-5-carboxylate A mixture of methyl 4-((2-(2,2-difluoroethoxy)-5-fluoropyridin-4-yl)amino)-2-fluoro-5-(isopropylamino)benzoate (6.42 g, 16.00 mmol) and CDI (12.97 g, 80 mmol), DIEA (8.38 ml, 48.0 mmol) in THF (70 mL) was stirred at 70° C. for 40 h, then poured into $H_2O$, and extracted with EtOAc (×3). The combined organic layers were washed with brine, dried over $Na_2SO_4$, then filtered and concentrated under reduced pressure. The residue was purified by column chromatography on silica (0-100% EtOAc/hexanes) to afford the title compound. LC/MS=428 [M+1].

Step E: 1-(2-(2,2-difluoroethoxy)-5-fluoropyridin-4-yl)-6-fluoro-3-isopropyl-2-oxo-2,3-dihydro-1H-benzo[d]imidazole-5-carboxylic acid A mixture of lithium hydroxide hydrate (1.304 g, 31.1 mmol) and methyl 1-(2-(2,2-difluoroethoxy)-5-fluoropyridin-4-yl)-6-fluoro-3-isopropyl-2-oxo-2,3-dihydro-1H-benzo[d]imidazole-5-carboxylate (6.64 g, 15.54 mmol) in THF (15 mL) and water (15 mL) was stirred at 35° C. for 2 h. The mixture was concentrated under reduced pressure and the resulting concentrate was dissolved in $H_2O$ and the pH was adjusted to 4 by addition of HCl (1N in water). Then the mixture was extracted with EtOAc (×3). The combined organic layers were washed with brine, dried over $Na_2SO_4$, then filtered and concentrated under reduced pressure to afford the title compound. LC/MS=414 [M+1].

Step F: 1-(2-(2,2-difluoroethoxy)-5-fluoropyridin-4-yl)-6-fluoro-3-isopropyl-N-(4-methyl-1,1-dioxidotetrahydro-2H-thiopyran-4-yl)-2-oxo-2,3-dihydro-1H-benzo[d]imidazole-5-carboxamide A 100 mL eggplant shaped bottle was charged with 1-(2-(2,2-difluoroethoxy)-5-fluoropyridin-4-yl)-6-fluoro-3-isopropyl-2-oxo-2,3-dihydro-1H-benzo[d]imidazole-5-carboxylic acid (6.62 g, 16.02 mmol), DIEA (8.39 ml, 48.0 mmol), HATU (9.13 g, 24.02 mmol), 4-amino-4-methyltetrahydro-2H-thiopyran 1,1-dioxide (3.92 g, 24.02 mmol) and DMF (40 ml) at 20° C., then the mixture was stirred at 20° C. for 0.5 h. The mixture was poured into $H_2O$, then extracted with EtOAc (×3). The combined organic layers were washed with brine, dried over $Na_2SO_4$, then filtered and concentrated under reduced pressure. The residue was purified by column chromatography on silica (0-100% EtOAc/hexanes) to afford the title compound. LC/MS=559 [M+1]. 1H NMR (400 MHz, METHANOL-d4) δ 8.32 (d, J=1.96 Hz, 1H), 8.05 (br s, 1H), 7.58 (d, J=5.48 Hz, 1H), 7.17 (d, J=4.70 Hz, 1H), 6.95 (dd, J=2.35, 10.17 Hz, 1H), 5.98-6.45 (m, 1H), 4.73 (s, 1H), 4.58 (m, 2H), 3.13-3.27 (m, 2H), 2.99 (m, 2H), 2.81 (m, 2H), 2.11-2.25 (m, 2H), 1.59 (m, 6H), 1.54 (s, 3H). Human DGAT2 $IC_{50}$=4.1 nM.

By using procedures similar to those described in Example 115 with appropriate reagents, the following compounds were synthesized. These compounds were characterized by LC/MS.

| Example | Structure | Name | LCMS [M + 1] | DGAT2 $IC_{50}$ (nM) |
|---|---|---|---|---|
| 116 | 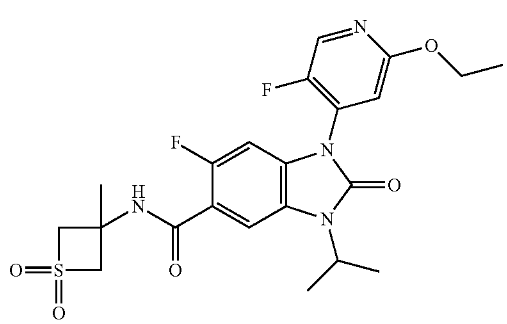 [SMILES: CCOc1cc(-n2c(=O)n(C(C)C)c3cc(C(=O)NC4(C)CS(=O)(=O)C4)c(F)cc32)c(F)cn1] | 1-(2-ethoxy-5-fluoropyridin-4-yl)-6-fluoro-3-isopropyl-N-(3-methyl-1,1-dioxidothietan-3-yl)-2-oxo-2,3-dihydro-1H-benzo[d]imidazole-5-carboxamide | 495 | 93 |

-continued

| Example | Structure | Name | LCMS [M + 1] | DGAT2 IC$_{50}$ (nM) |
|---|---|---|---|---|
| 117 | 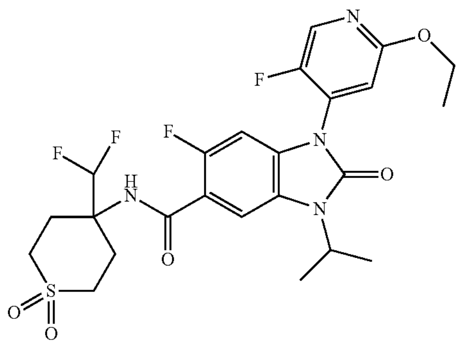 [SMILES: CCOc1cc(-n2c(=O)n(C(C)C)c3cc(C(=O)NC4(C(F)F)CCS(=O)(=O)CC4)c(F)cc32)c(F)cn1] | N-(4-(difluoromethyl)-1,1-dioxidotetrahydro-2H-thiopyran-4-yl)-1-(2-ethoxy-5-fluoropyridin-4-yl)-6-fluoro-3-isopropyl-2-oxo-2,3-dihydro-1H-benzo[d]imidazole-5-carboxamide | 559 | 27 |
| 118 | 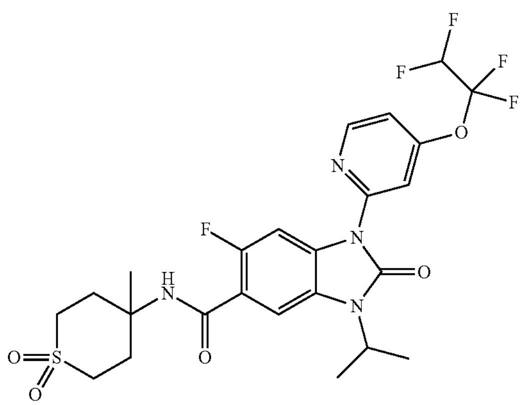 [SMILES: CC(C)n1c(=O)n(-c2cc(OC(F)(F)C(F)F)ccn2)c2cc(F)c(C(=O)NC3(C)CCS(=O)(=O)CC3)cc21] | 6-fluoro-3-isopropyl-N-(4-methyl-1,1-dioxidotetrahydro-2H-thiopyran-4-yl)-2-oxo-1-(4-(1,1,2,2-tetrafluoroethoxy)pyridin-2-yl)-2,3-dihydro-1H-benzo[d]imidazole-5-carboxamide | 577 | 5.5 |
| 119 | 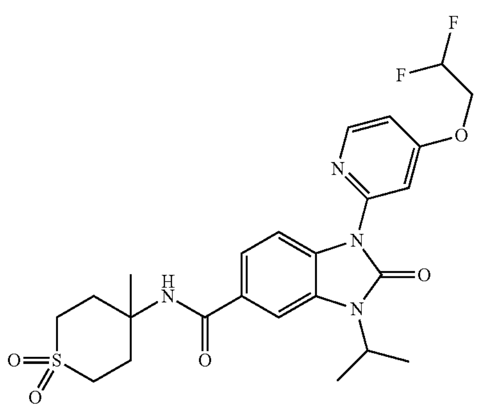 [SMILES: CC(C)n1c(=O)n(-c2cc(OCC(F)F)ccn2)c2ccc(C(=O)NC3(C)CCS(=O)(=O)CC3)cc21] | 1-(4-(2,2-difluoroethoxy)pyridin-2-yl)-3-isopropyl-N-(4-methyl-1,1-dioxidotetrahydro-2H-thiopyran-4-yl)-2-oxo-2,3-dihydro-1H-benzo[d]imidazole-5-carboxamide | 523 | 51 |
| 120 | 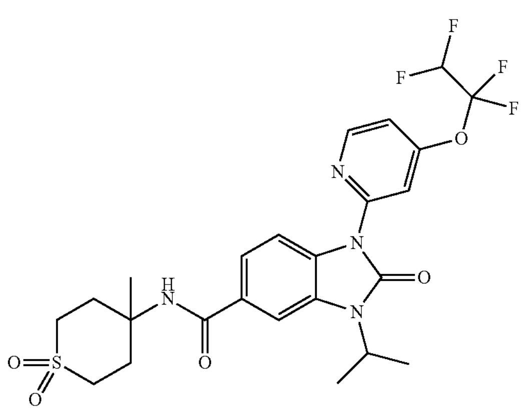 [SMILES: CC(C)n1c(=O)n(-c2cc(OC(F)(F)C(F)F)ccn2)c2ccc(C(=O)NC3(C)CCS(=O)(=O)CC3)cc21] | 3-isopropyl-N-(4-methyl-1,1-dioxidotetrahydro-2H-thiopyran-4-yl)-2-oxo-1-(4-(1,1,2,2-tetrafluoroethoxy)pyridin-2-yl)-2,3-dihydro-1H-benzo[d]imidazole-5-carboxamide | 559 | 3.2 |

| Example | Structure | Name | LCMS [M + 1] | DGAT2 IC$_{50}$ (nM) |
|---|---|---|---|---|
| 121 | 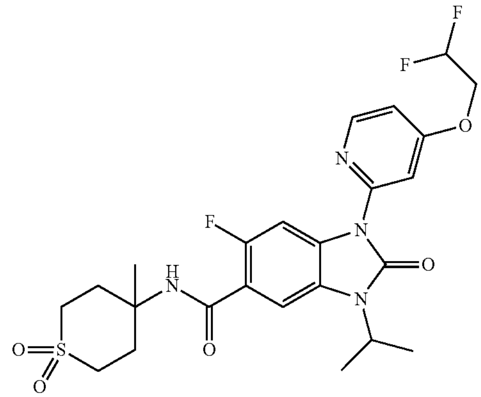 [SMILES: CC(C)n1c(=O)n(-c2cc(OCC(F)F)ccn2)c2cc(F)c(C(=O)NC3(C)CCS(=O)(=O)CC3)cc21] | 1-(4-(2,2-difluoroethoxy)pyridin-2-yl)-6-fluoro-3-isopropyl-N-(4-methyl-1,1-dioxidotetrahydro-2H-thiopyran-4-yl)-2-oxo-2,3-dihydro-1H-benzo[d]imidazole-5-carboxamide | 541 | 92 |

Example 122: 1-(2-(difluoromethoxy)-5-fluoropyridin-4-yl)-6-fluoro-3-isopropyl-N-(4-methyl-1,1-dioxidotetrahydro-2H-thiopyran-4-yl)-2-oxo-2,3-dihydro-1H-benzo[d]imidazole-5-carboxamide

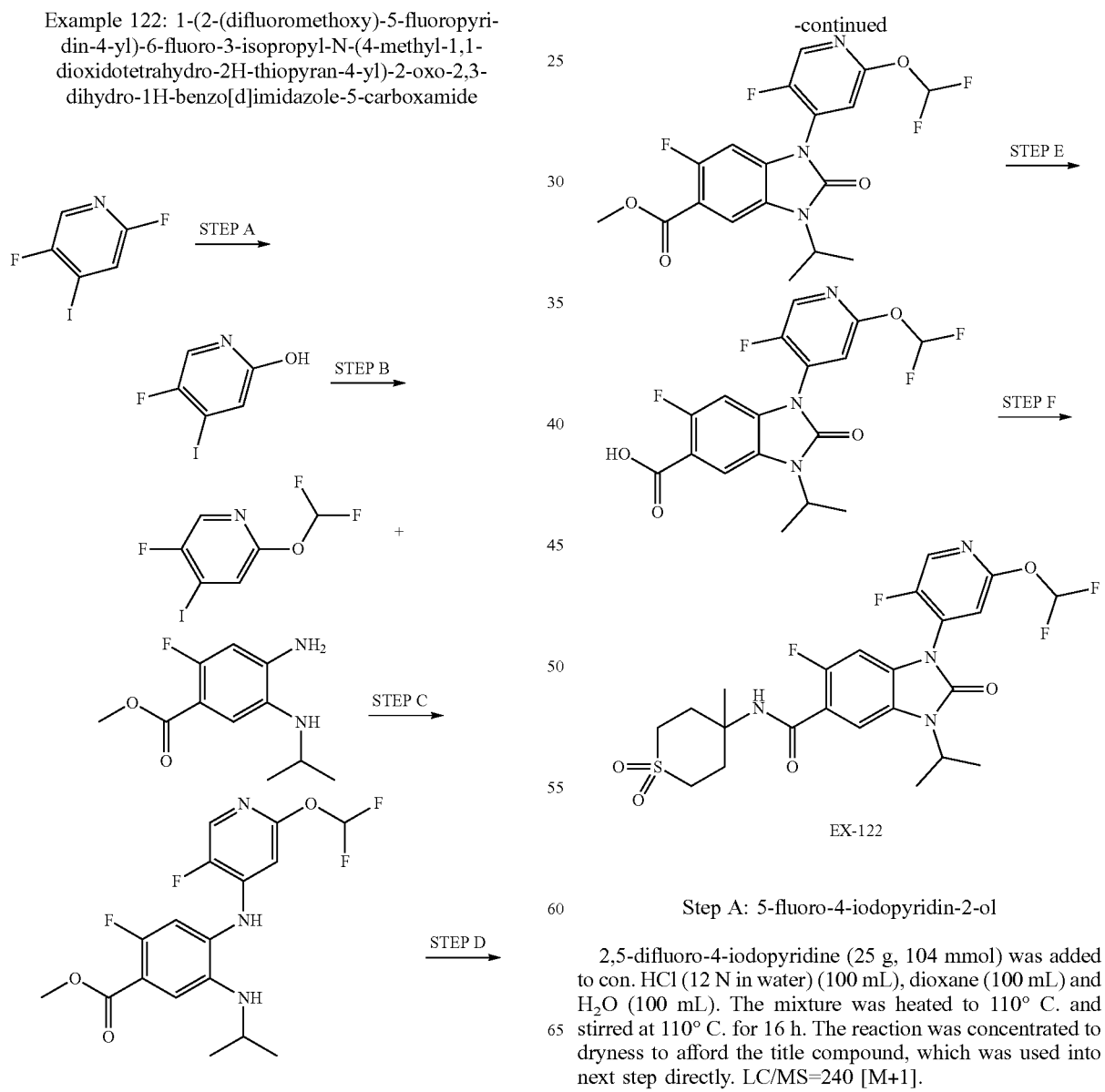

Step A: 5-fluoro-4-iodopyridin-2-ol 2,5-difluoro-4-iodopyridine (25 g, 104 mmol) was added to con. HCl (12 N in water) (100 mL), dioxane (100 mL) and H$_2$O (100 mL). The mixture was heated to 110° C. and stirred at 110° C. for 16 h. The reaction was concentrated to dryness to afford the title compound, which was used into next step directly. LC/MS=240 [M+1].

Step B: 2-(difluoromethoxy)-5-fluoro-4-iodopyridine

Chlorodifluoromethane (43.4 g, 502 mmol) was added to a mixture of 5-fluoro-4-iodopyridin-2-ol (24 g, 100 mmol) and $Cs_2CO_3$ (110 g, 338 mmol) in DMF (300 mL) at 25° C. for 25 min, then the mixture was stirred at 50° C. for 1 h. The mixture was poured into sat. $NH_4Cl$, then extracted with EtOAc (×3). The combined organic layers were washed with brine, dried over $Na_2SO_4$, then filtered and concentrated under reduced pressure. The residue was purified by column chromatography on silica (0-3% EtOAc/hexanes) to afford the title compound. LC/MS=290 [M+1].

Step C: methyl 4-((2-(difluoromethoxy)-5-fluoropyridin-4-yl)amino)-2-fluoro-5-(isopropylamino) benzoate To a mixture of methyl 4-amino-2-fluoro-5-(isopropylamino)benzoate (4.5 g, 19.89 mmol), 2-(difluoromethoxy)-5-fluoro-4-iodopyridine (6.9 g, 23.87 mmol) in THF (50 mL) was added $Cs_2CO_3$ (19.4 g, 59.7 mmol), BRETTPHOS PD G3 (1.5 g, 1.655 mmol) at 20° C. The resulting mixture was heated to 80° C. under $N_2$ for 15 h, then poured into $H_2O$ and extracted with EtOAc (×3). The combined organic layers were washed with brine, dried over $Na_2SO_4$, then filtered and concentrated under reduced pressure. The residue was purified by column chromatography on silica (0-100% EtOAc/hexanes) to afford the title compound. LC/MS=388 [M+1].

Step D: methyl 1-(2-(difluoromethoxy)-5-fluoropyridin-4-yl)-6-fluoro-3-isopropyl-2-oxo-2,3-dihydro-1H-benzo[d]imidazole-5-carboxylate A mixture of methyl 4-((2-(difluoromethoxy)-5-fluoropyridin-4-yl)amino)-2-fluoro-5-(isopropylamino)benzoate (6.35 g, 16.39 mmol) and CDI (13.29 g, 82 mmol), DIEA (8.6 mL, 49.2 mmol) in THF (80 mL) was stirred at 70° C. for 40 h, then poured into $H_2O$, and extracted with EtOAc (×3). The combined organic layers were washed with brine, dried over $Na_2SO_4$, then filtered and concentrated under reduced pressure. The residue was purified by column chromatography on silica (0-100% EtOAc/hexanes) to afford the title compound. LC/MS=414 [M+1].

Step E: 1-(2-(difluoromethoxy)-5-fluoropyridin-4-yl)-6-fluoro-3-isopropyl-2-oxo-2,3-dihydro-1H-benzo[d]imidazole-5-carboxylic acid To a solution of methyl 1-(2-(difluoromethoxy)-5-fluoropyridin-4-yl)-6-fluoro-3-isopropyl-2-oxo-2,3-dihydro-1H-benzo[d]imidazole-5-carboxylate (6.4 g, 15.48 mmol) in THF (50 mL)/Water (50 mL) was added lithium hydroxide monohydrate (1.95 g, 46.5 mmol). The reaction mixture was stirred at 40° C. for 2 hrs, then concentrated under reduced pressure. The residue was dissolved in $H_2O$, and the pH was adjusted to 4 by the addition of HCl (1N in water). Then the mixture was extracted with EtOAc (×3). The combined organic layers were washed with brine, dried over $Na_2SO_4$, then filtered and concentrated under reduced pressure to afford the title compound. LC/MS=400 [M+1].)

Step F: 1-(2-(difluoromethoxy)-5-fluoropyridin-4-yl)-6-fluoro-3-isopropyl-N-(4-methyl-1,1-dioxidotetrahydro-2H-thiopyran-4-yl)-2-oxo-2,3-dihydro-1H-benzo[d]imidazole-5-carboxamide A tube was charged with 1-(2-(difluoromethoxy)-5-fluoropyridin-4-yl)-6-fluoro-3-isopropyl-2-oxo-2,3-dihydro-1H-benzo[d]imidazole-5-carboxylic acid (6.15 g, 15.4 mmol), DIEA (13.5 mL, 77 mmol), HATU (8.78 g, 23.10 mmol), 4-amino-4-methyltetrahydro-2H-thiopyran 1,1-dioxide (3.02 g, 18.48 mmol) and DMF (80 mL) at 20° C. After stirring at 20° C. for 1 h, the mixture was poured into $H_2O$, and extracted with EtOAc (×3). The combined organic layers were washed with brine, dried over $Na_2SO_4$, then filtered and concentrated under reduced pressure. The residue was purified by column chromatography on silica (0-100% EtOAc/hexanes) and mass triggered reverse phase HPLC (ACN/water) to afford the title compound. LC/MS=545 [M+1]. $^1H$ NMR (400 MHz, DMSO-d6) δ 8.57 (d, J=1.47 Hz, 1H), 8.08 (s, 1H), 7.68-7.88 (m, 1H), 7.50 (dd, J=2.32, 5.26 Hz, 2H), 7.17 (dd, J=2.08, 9.90 Hz, 1H), 4.67-4.71 (m, 1H), 3.07-3.16 (m, 2H), 2.99-3.07 (m, 2H), 2.64-2.75 (m, 2H), 1.96-2.12 (m, 2H), 1.48 (d, J=6.85 Hz, 6H), 1.41 (s, 3H). Human DGAT2 $IC_{50}$=56 nM.

By using procedures similar to those described in Example 122 with appropriate amine reagents, the following compounds was synthesized. These compounds were characterized by LC/MS.

| Example | Structure | Name | LCMS [M + 1] | DGAT2 $IC_{50}$ (nM) |
|---|---|---|---|---|
| 123 | 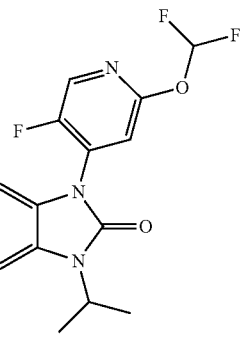 | 1-(2-(difluoromethoxy)-5-fluoropyridin-4-yl)-6-fluoro-3-isopropyl-N-(3-methyl-1,1-dioxidothietan-3-yl)-2-oxo-2,3-dihydro-1H-benzo[d]imidazole-5-carboxamide | 517 | 73 |

Example 124: (S)-1-(3-(Difluoromethoxy)phenyl)-4-fluoro-3-isopropyl-N-(3-methyl-1,1-dioxidotetrahydrothiophen-3-yl)-2-oxo-2,3-dihydro-1H-benzo[d]imidazole-5-carboxamide

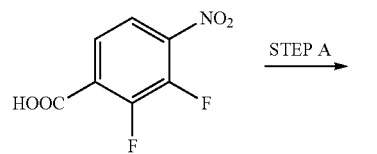
STEP A

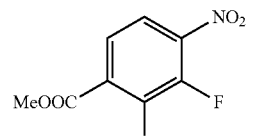
STEP B

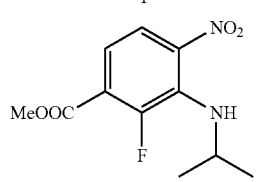
STEP C

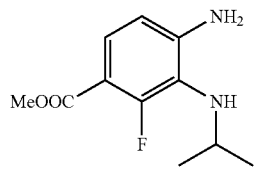
STEP D

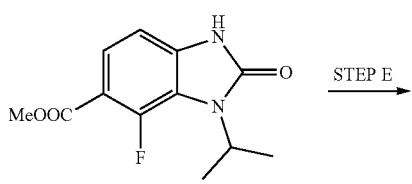
STEP E

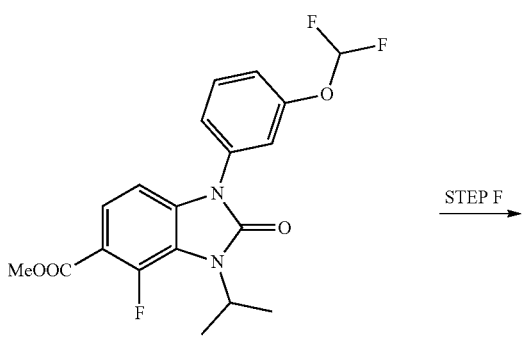
STEP F

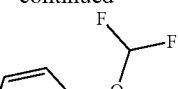
STEP G

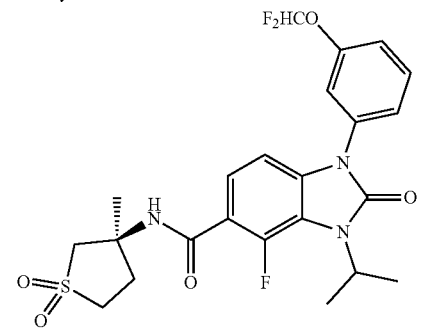

EX-124

Step A: Methyl 2,3-difluoro-4-nitrobenzoate

At 20° C., to a stirred mixture of 2,3-difluoro-4-nitrobenzoic acid (490 mg, 2.41 mmol) in MeOH (2.41 mL) was added sulfuric acid (51.4 µl, 0.965 mmol). The mixture was stirred at 80° C. for 24 h, then cooled to 20° C., concentrated, and partitioned between EtOAc and water. The organic layer was separated, washed with water and brine, dried over $Na_2SO_4$ (s), filtered, and the volatiles were evaporated to afford the title compound. LC/MS=218 [M+1].

Step B: Methyl 2-fluoro-3-(isopropylamino)-4-nitrobenzoate

At 20° C., to a stirred mixture of methyl 2,3-difluoro-4-nitrobenzoate (0.521 g, 2.40 mmol) in acetonitrile (4.80 mL) was added propan-2-amine (0.452 mL, 5.28 mmol), and the mixture was stirred at 40° C. for 12 h. The volatiles were evaporated to afford the title compound. LC/MS=257 [M+1].

Step C: Methyl 4-amino-2-fluoro-3-(isopropylamino)benzoate

At 0° C., to a stirred mixture of methyl 2-fluoro-3-(isopropylamino)-4-nitrobenzoate (0.615 g, 2.40 mmol) in THF (4.80 ml) and MeOH (2.40 ml), and saturated ammonia hydrochloride aqueous solution (4.80 ml), was added zinc (0.471 g, 7.20 mmol). The mixture was stirred at 20° C. for 1 h, then filtered over sand, and the filtrate was concentrated. The residue was partitioned between EtOAc and water. The organic layer was separated, washed with brine, dried over $Na_2SO_4$ (s), and the volatiles evaporated to afford the title compound. LC/MS=227 [M+1].

Step D: Methyl 4-fluoro-3-isopropyl-2-oxo-2,3-dihydro-1H-benzo[d]imidazole-5-carboxylate At 20° C., to a stirred mixture of methyl 4-amino-2-fluoro-3-(isopropylamino)benzoate (543 mg, 2.40 mmol) in THF (4.80 mL) was added 1,1'-carbonyldiimidazole (1.17 g, 7.20 mmol), and the mixture was stirred at 20° C. for 16 h. The volatiles were evaporated. The residue was purified by flash silica gel column chromatography (0 to 100% EtOAc in hexanes) to afford the title compound. LC/MS=253 [M+1].

Step E: Methyl 1-(3-(difluoromethoxy)phenyl)-4-fluoro-3-isopropyl-2-oxo-2,3-dihydro-1H-benzo[d]imidazole-5-carboxylate At 20° C., to a stirred mixture of methyl 4-fluoro-3-isopropyl-2-oxo-2,3-dihydro-1H-benzo[d]imidazole-5-carboxylate (100 mg, 0.396 mmol), (3-(difluoromethoxy)phenyl)boronic acid (112 mg, 0.595 mmol), was added DCE (1.32 mL) and copper (II) acetate (108 mg, 0.595 mmol). The mixture was stirred at 50° C. for 3 days, then the volatiles were evaporated, and the residue was purified by flash silica gel column chromatography (0 to 50% EtOAc in hexanes) to afford the title compound. LC/MS=395 [M+1].

Step F: 1-(3-(Difluoromethoxy)phenyl)-4-fluoro-3-isopropyl-2-oxo-2,3-dihydro-1H-benzo[d]imidazole-5-carboxylic acid At 20° C., to a stirred mixture of methyl 1-(3-(difluoromethoxy)phenyl)-4-fluoro-3-isopropyl-2-oxo-2,3-dihydro-1H-benzo[d]imidazole-5-carboxylate (74 mg, 0.188 mmol) in THF (0.80 mL) and MeOH (0.27 mL) was added lithium hydroxide hydrate (31.5 mg, 0.751 mmol) in Water (0.80 mL). The mixture was stirred at 20° C. for 1 h, then 1N HCl (1 mL, aqueous) was added, and the mixture was partitioned between EtOAc and water. The organic layer was separated, washed with brine, dried over $Na_2SO_4$ (s), filtered, and the volatiles evaporated to afford the title compound. LC/MS=381 [M+1].

Step G: (S)-1-(3-(Difluoromethoxy)phenyl)-4-fluoro-3-isopropyl-N-(3-methyl-1,1-dioxidotetrahydrothiophen-3-yl)-2-oxo-2,3-dihydro-1H-benzo[d]imidazole-5-carboxamide At 20° C., to a stirred mixture of 1-(3-(difluoromethoxy)phenyl)-4-fluoro-3-isopropyl-2-oxo-2,3-dihydro-1H-benzo[d]imidazole-5-carboxylic acid (20 mg, 0.053 mmol) and HATU (30.0 mg, 0.079 mmol) in DMF (0.53 mL) were added DIPEA (36.7 µl, 0.210 mmol), then (S)-3-amino-3-methyltetrahydrothiophene 1,1-dioxide hydrochloride (14.7 mg, 0.079 mmol). The mixture was stirred at 20° C. for 1 h, then purified by mass triggered reverse phase HPLC (C18, 40 to 80% ACN in water, 0.1% FA modifier) to afford the title compound. $^1$H NMR (500 MHz, DMSO-$d_6$) δ 8.54 (s, 1H), 7.65 (t, J=8.1 Hz, 1H), 7.42 (d, J=8.1 Hz, 1H), 7.37 (s, 1H), 7.31 (d, J=8.9 Hz, 1H), 7.31 (t, J=73.7 Hz, 1H), 7.26-7.22 (m, 1H), 6.94 (d, J=8.2 Hz, 1H), 4.85 (hept, J=6.9 Hz, 1H), 3.94 (d, J=13.6 Hz, 1H), 3.32 (dd, J=8.9, 5.3 Hz, 1H), 3.20 (d, J=13.7 Hz, 1H), 2.65 (dd, J=12.8, 6.0 Hz, 1H), 2.20 (dt, J=13.7, 9.3 Hz, 1H), 1.57 (s, 3H), 1.50 (d, J=6.8 Hz, 6H). One proton could not be located due to overlap with solvent or water peaks. LC/MS=512 [M+1]. Human DGAT2 $IC_{50}$=191 nM.

By using procedures similar to those described in Example 124 with appropriate amine reagents, the following compounds were synthesized. These compounds were characterized by LC/MS.

| Example | Structure | Name | LCMS [M + 1] | DGAT2 $IC_{50}$ (nM) |
|---|---|---|---|---|
| 125 | 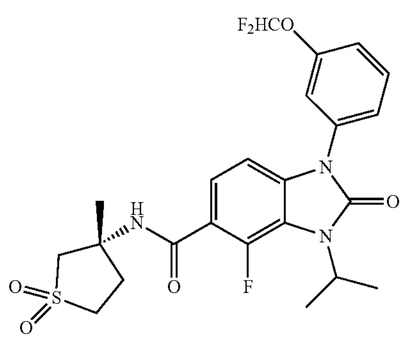 [SMILES: CC(C)n1c(=O)n(-c2cccc(OC(F)F)c2)c2ccc(C(=O)N[C@]3(C)CCS(=O)(=O)C3)c(F)c21] | (R)-1-(3-(Difluoromethoxy)phenyl)-4-fluoro-3-isopropyl-N-(3-methyl-1,1-dioxidotetrahydrothiophen-3-yl)-2-oxo-2,3-dihydro-1H-benzo[d]imidazole-5-carboxamide | 512 | 203 |
| 126 | 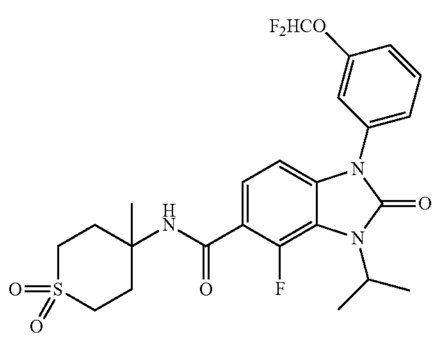 [SMILES: CC(C)n1c(=O)n(-c2cccc(OC(F)F)c2)c2ccc(C(=O)NC3(C)CCS(=O)(=O)CC3)c(F)c21] | 1-(3-(Difluoromethoxy)phenyl)-4-fluoro-3-isopropyl-N-(4-methyl-1,1-dioxidotetrahydro-2H-thiopyran-4-yl)-2-oxo-2,3-dihydro-1H-benzo[d]imidazole-5-carboxamide | 526 | 257 |

201

Example 127: (S)-6-Chloro-1-(3-(difluoromethoxy)phenyl)-3-isopropyl-N-(3-methyl-1,1-dioxidotetrahydrothiophen-3-yl)-2-oxo-2,3-dihydro-1H-benzo[d]imidazole-5-carboxamide

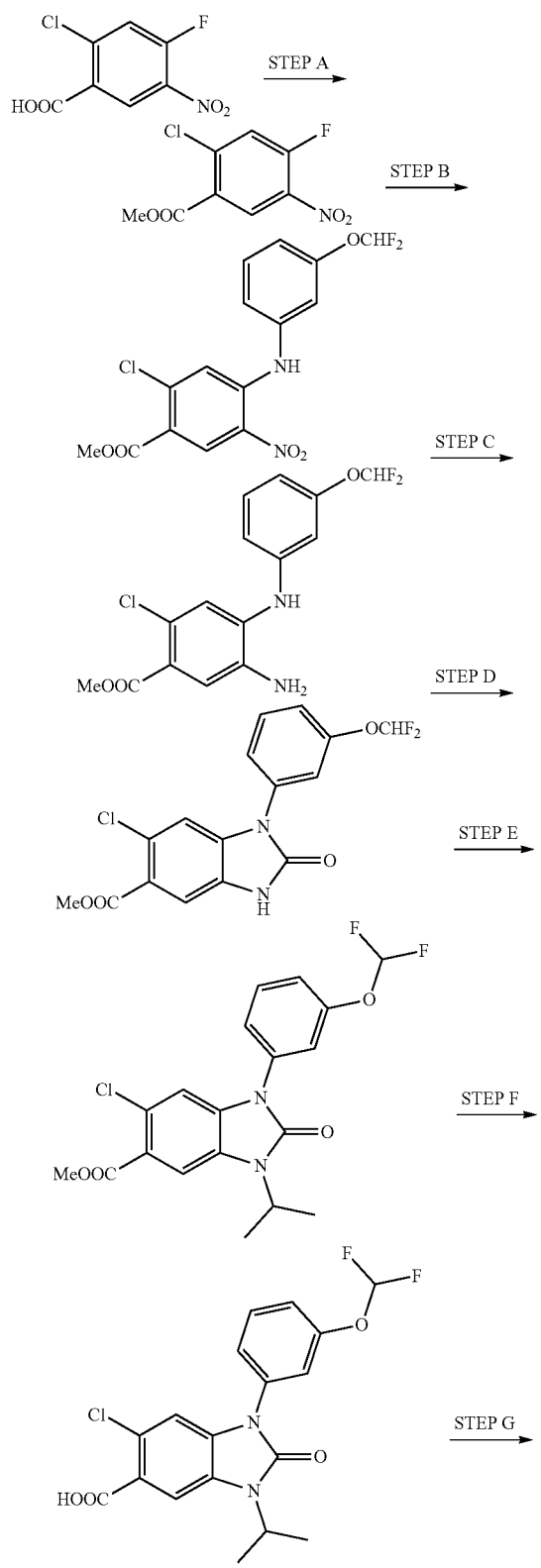

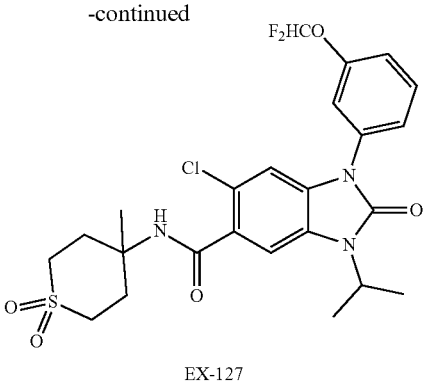

EX-127

Step A: Methyl 2-chloro-4-fluoro-5-nitrobenzoate

At 20° C., to a stirred mixture of 2-chloro-4-fluoro-5-nitrobenzoic acid (1.00 g, 4.55 mmol) in MeOH (4.55 ml) was added sulfuric acid (0.097 ml, 1.82 mmol). The mixture was stirred at 80° C. for 24 h, then concentrated, and partitioned between EtOAc and water. The organic layer was separated, washed with water and brine, dried over $Na_2SO_4$ (s), and filtered. The volatiles were evaporated to afford the title compound. LC/MS=234 [M+1].

Step B: Methyl 2-chloro-4-((3-(difluoromethoxy)phenyl)amino)-5-nitrobenzoate At 20° C., to a stirred mixture of methyl 2-chloro-4-fluoro-5-nitrobenzoate (1.06 g, 4.55 mmol) in Acetonitrile (9.10 ml) was added 3-(difluoromethoxy)aniline (0.668 ml, 5.46 mmol) and DIPEA (0.874 ml, 5.01 mmol). The mixture was stirred at 80° C. for 16 h. Then, the volatiles were evaporated to afford the title compound. LC/MS=373 [M+1].

Step C: Methyl 5-amino-2-chloro-4-((3-(difluoromethoxy)phenyl)amino)benzoate At 0° C., to a stirred mixture of methyl 2-chloro-4-((3-(difluoromethoxy)phenyl)amino)-5-nitrobenzoate (1.696 g, 4.55 mmol) in THF (9.10 ml) and MeOH (4.55 ml), and saturated ammonia hydrochloride aqueous solution (9.10 ml), was added zinc (0.892 g, 13.65 mmol). The mixture was stirred at 20° C. for 1 h, then filtered, and was partitioned between EtOAc and water. The organic layer was separated, washed with brine, dried over $Na_2SO_4$ (s), and the volatiles evaporated to afford the title compound. LC/MS=343 [M+1].

Step D: Methyl 6-chloro-1-(3-(difluoromethoxy)phenyl)-2-oxo-2,3-dihydro-1H-benzo[d]imidazole-5-carboxylate At 20° C., to a stirred mixture of methyl 5-amino-2-chloro-4-((3-(difluoromethoxy)phenyl)amino)benzoate (1.56 g, 4.55 mmol) in THF (15.0 ml) was added 1,1'-carbonyldiimidazole (2.21 g, 13.7 mmol). The mixture was stirred at 20° C. for 16 h. Then, the volatiles were evaporated, and the residue was purified by flash silica gel chromatography (0 to 100% EtOAc in hexanes) to afford the title compound. LC/MS=369 [M+1].

Step E: Methyl 6-chloro-1-(3-(difluoromethoxy) phenyl)-3-isopropyl-2-oxo-2,3-dihydro-1H-benzo[d]imidazole-5-carboxylate At 20° C., to a stirred mixture of methyl 6-chloro-1-(3-(difluoromethoxy)phenyl)-2-oxo-2,3-dihydro-1H-benzo[d]imidazole-5-carboxylate (93.0 mg, 0.252 mmol) in DMF (2.52 mL) were added 2-iodopropane (49.0 µl, 0.504 mmol) and $Cs_2CO_3$ (247 mg, 0.757 mmol). The mixture was stirred at 80° C. for 2 h, then partitioned between EtOAc and water. The organic layer was separated, washed with brine, and the solvents evaporated to afford the title compound. LC/MS=411 [M+1].

Step F: 6-Chloro-1-(3-(difluoromethoxy)phenyl)-3-isopropyl-2-oxo-2,3-dihydro-1H-benzo[d]imidazole-5-carboxylic acid At 20° C., to a stirred mixture of methyl 6-chloro-1-(3-(difluoromethoxy)phenyl)-3-isopropyl-2-oxo-2,3-dihydro-1H-benzo[d]imidazole-5-carboxylate (104 mg, 0.253 mmol) in THF (1.09 mL) and MeOH (0.36 mL) was added lithium hydroxide hydrate (42.5 mg, 1.01 mmol) in Water (1.09 mL). The mixture was stirred at 20° C. for 1 h. Then, 1N HCl (1 mL, aqueous) was added, and the mixture was partitioned between EtOAc and water. The organic layer was separated, washed with brine, dried over $Na_2SO_4$ (s), filtered, and the volatiles evaporated to afford the title compound. LC/MS=397 [M+1].

Step G: 6-Chloro-1-(3-(difluoromethoxy)phenyl)-3-isopropyl-N-(4-methyl-1,1-dioxidotetrahydro-2H-thiopyran-4-yl)-2-oxo-2,3-dihydro-1H-benzo[d]imidazole-5-carboxamide At 20° C., to a stirred mixture of 6-chloro-1-(3-(difluoromethoxy)phenyl)-3-isopropyl-2-oxo-2,3-dihydro-1H-benzo[d]imidazole-5-carboxylic acid (30 mg, 0.076 mmol) and HATU (43.1 mg, 0.113 mmol) in DMF (0.76 mL) was added DIPEA (52.8 µl, 0.302 mmol), then (4-amino-4-methyltetrahydro-2H-thiopyran 1,1-dioxide (18.5 mg, 0.113 mmol). The mixture was stirred at 20° C. for 1 h, then directly purified by mass triggered reverse phase HPLC (C18, 40 to 70% ACN in water, 0.1% FA modifier) to afford the title compound. $^1$H NMR (500 MHz, DMSO-$d_6$) δ 8.25 (s, 1H), 7.65 (t, J=8.1 Hz, 1H), 7.49 (s, 1H), 7.41 (d, J=8.1 Hz, 1H), 7.36 (s, 1H), 7.31 (t, J=73.7 Hz, 1H), 7.31 (d, J=8.5 Hz, 1H), 7.10 (s, 1H), 4.69 (hept, J=6.7 Hz, 1H), 3.24 (t, J=12.8 Hz, 2H), 3.04 (d, J=13.5 Hz, 2H), 2.68 (d, J=13.7 Hz, 2H), 1.98 (t, J=13.5 Hz, 2H), 1.51 (d, J=6.8 Hz, 6H), 1.46 (s, 3H). LC/MS=542 [M+1]. Human DGAT2 $IC_{50}$=112 nM

Example 128: 4-chloro-1-(3-(difluoromethoxy)phenyl)-3-isopropyl-N-(4-methyl-1,1-dioxidotetrahydro-2H-thiopyran-4-yl)-2-oxo-2,3-dihydro-1H-benzo[d]imidazole-5-carboxamide

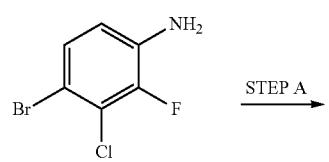

STEP A

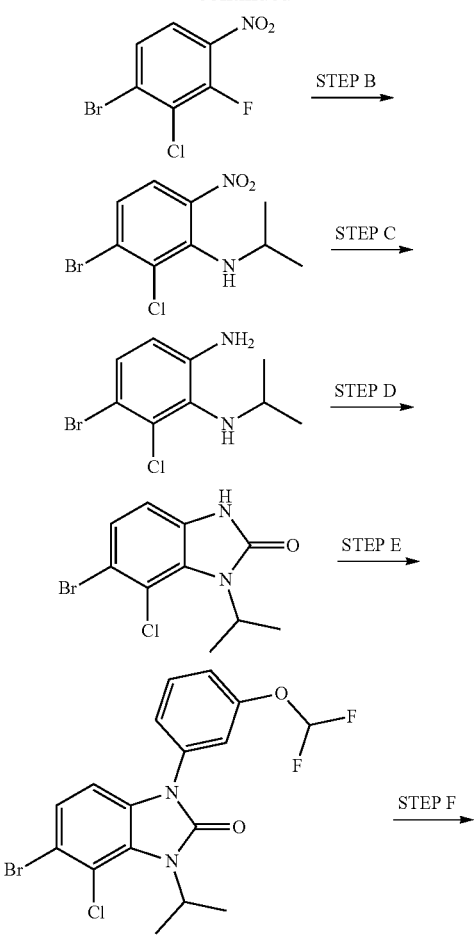

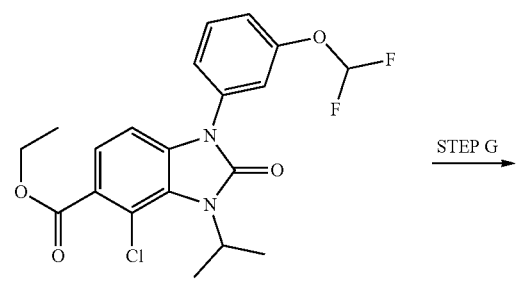

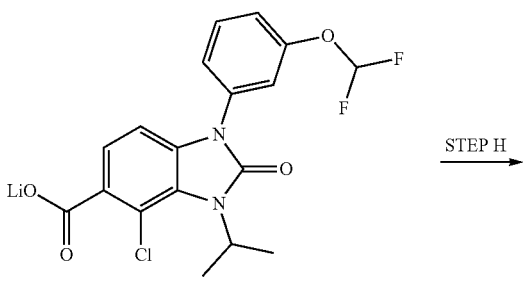

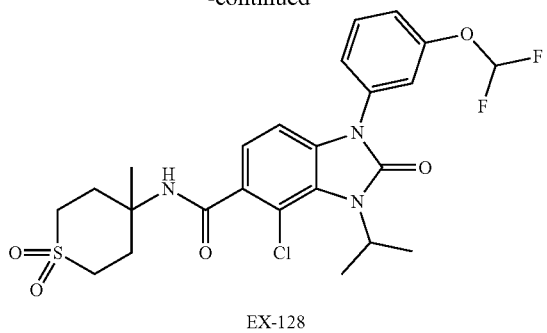

EX-128

Step A: 1-bromo-2-chloro-3-fluoro-4-nitrobenzene

To a solution of 4-bromo-3-chloro-2-fluoroaniline (5 g, 22.28 mmol) in toluene (70 mL) was added mCPBA (19.22 g, 89 mmol). The mixture was stirred for 12 h at 50° C., then poured into sat. Na$_2$SO$_3$ (80 mL) and stirred at 25° C. for 10 min. The pH value of the solution was adjusted to pH=10 by adding HCl (1N) and the mixture was extracted with DCM (50 mL). The combined organic layers were washed with brine (20 mL), dried over Na$_2$SO$_4$, filtered and concentrated in vacuo to afford the title compound. $^1$H NMR (400 MHz, CHLOROFORM-d) δ 7.23-7.29 (m, 1H), 7.09-7.20 (m, 1H).

Step B: 3-bromo-2-chloro-N-isopropyl-6-nitroaniline

Solid K$_2$CO$_3$ (6.52 g, 47.2 mmol) was added to a mixture of 1-bromo-2-chloro-3-fluoro-4-nitrobenzene (6 g, 23.58 mmol) and propan-2-amine (1.951 g, 33.0 mmol) in DMF (40 mL) at 25° C. The mixture was heated at 60° C. for 3 h, then poured into sat. NaHCO$_3$ and extracted with DCM (×3). The combined organic layers were washed with brine, dried over Na$_2$SO$_4$, filtered and concentrated in vacuo. The residue was purified by column chromatography on silica (0-100% EtOAc/hexanes) to afford the title compound. LC/MS=293 and 295 [M+1].

Step C: 5-bromo-6-chloro-N-isopropylbenzene-1,2-diamine

Iron powder (1.5 g, 26.9 mmol) was added to a mixture of ammonium chloride (1.676 g, 31.3 mmol) and 3-bromo-2-chloro-N-isopropyl-6-nitroaniline (2.3 g, 7.84 mmol) in THF (10 mL), water (10 mL) and EtOH (10 mL). The mixture was stirred at 60° C. for 2 h, then poured into sat. NaHCO$_3$ and extracted with DCM (×3). The combined organic layers were washed with brine, dried over Na$_2$SO$_4$, filtered and concentrated in vacuo. The residue was purified by column chromatography on silica (0-100% EtOAc/hexanes) to afford the title compound. LC/MS=263 and 265 [M+1].

Step D: 6-bromo-7-chloro-1-isopropyl-1H-benzo[d]imidazol-2(3H)-one

A mixture of 5-bromo-6-chloro-N1-isopropylbenzene-1,2-diamine (1.2 g, 4.55 mmol) and CDI (4.43 g, 27.3 mmol) in THF (15 mL) was stirred at 60° C. for 12 h. TLC showed that the starting material was used up and 2 new spots appeared. The mixture was poured into H$_2$O and extracted with DCM (×3). The combined organic layers were washed with brine, dried over Na$_2$SO$_4$, filtered and concentrated in vacuo. The residue was purified by column chromatography on silica (0-100% EtOAc/hexanes) to afford the title compound. LC/MS=289 and 291 [M+1].

Step E: 5-bromo-4-chloro-1-(3-(difluoromethoxy)phenyl)-3-isopropyl-1H-benzo[d]imidazol-2(3H)-one To a solution of 6-bromo-7-chloro-1-isopropyl-1H-benzo[d]imidazol-2(3H)-one (300 mg, 1.036 mmol) in DMF (4 mL) was added 2-(3-(difluoromethoxy)phenyl)-4,4,5,5-tetramethyl-1,3,2-dioxaborolane (1 g, 3.70 mmol), Pyridine (1.676 mL, 20.72 mmol), 4 A molecular sieve (200 mg) and diacetoxycopper (376 mg, 2.072 mmol). The mixture was stirred at 80° C. for 13 h, open to air with a drying tube. LCMS showed the starting material was consumed completely. The mixture was poured into H$_2$O and was extracted with DCM (×3). The combined organic layers were washed with brine, dried over Na$_2$SO$_4$, then filtered and concentrated in vacuo. The residue was purified by column chromatography on silica (0-100% EtOAc/hexanes) to afford the title compound (300 mg). LC/MS=431 and 433 [M+1].

Step F: ethyl 4-chloro-1-(3-(difluoromethoxy)phenyl)-3-isopropyl-2-oxo-2,3-dihydro-1H-benzo[d]imidazole-5-carboxylate Pd(dppf)Cl$_2$ (50.9 mg, 0.069 mmol) was added to the mixture of 5-bromo-4-chloro-1-(3-(difluoromethoxy)phenyl)-3-isopropyl-1H-benzo[d]imidazol-2(3H)-one (300 mg, 0.695 mmol) and potassium acetate (205 mg, 2.085 mmol) in dry EtOH (10 mL) at 25° C. under CO (15 psi). The mixture was stirred at 80° C. for 15 h under CO (15 psi), then concentrated, and the residue was purified by column chromatography on silica (0-100% EtOAc/hexanes) to afford the title compound. LC/MS=425 [M+1].

Step G: lithium 4-chloro-1-(3-(difluoromethoxy)phenyl)-3-isopropyl-2-oxo-2,3-dihydro-1H-benzo[d]imidazole-5-carboxylate Lithium hydroxide monohydrate (12 mg, 0.286 mmol) was added to a mixture of ethyl 4-chloro-1-(3-(difluoromethoxy)phenyl)-3-isopropyl-2-oxo-2,3-dihydro-1H-benzo[d]imidazole-5-carboxylate (40 mg, 0.094 mmol) in MeOH (3 mL) and water (0.4 mL). The mixture was stirred at 25° C. for 12 h, then lyophilized to afford the title compound. LC/MS=397 [M+1].

Step H: 4-chloro-1-(3-(difluoromethoxy)phenyl)-3-isopropyl-N-(4-methyl-1,1-dioxidotetrahydro-2H-thiopyran-4-yl)-2-oxo-2,3-dihydro-1H-benzo[d]imidazole-5-carboxamide 4-amino-4-methyltetrahydro-2H-thiopyran 1,1-dioxide (10 mg, 0.061 mmol) was added to a mixture of lithium 4-chloro-1-(3-(difluoromethoxy)phenyl)-3-isopropyl-2-oxo-2,3-dihydro-1H-benzo[d]imidazole-5-carboxylate (30 mg, 0.074 mmol), HATU (56.7 mg, 0.149 mmol) and DIEA (0.052 mL, 0.298 mmol) in DMF (1 mL). The mixture was stirred at 25° C. for 15 min, then purified by mass triggered reverse phase HPLC (ACN/water with 0.1% TFA modifier) to afford the title compound. LC/MS=542 [M+1]. Human DGAT2 IC$_{50}$=1381 nM

Example 129: 4-cyano-1-(3-(difluoromethoxy)phenyl)-3-isopropyl-N-(4-methyl-1,1-dioxidotetrahydro-2H-thiopyran-4-yl)-2-oxo-2,3-dihydro-1H-benzo[d]imidazole-5-carboxamide

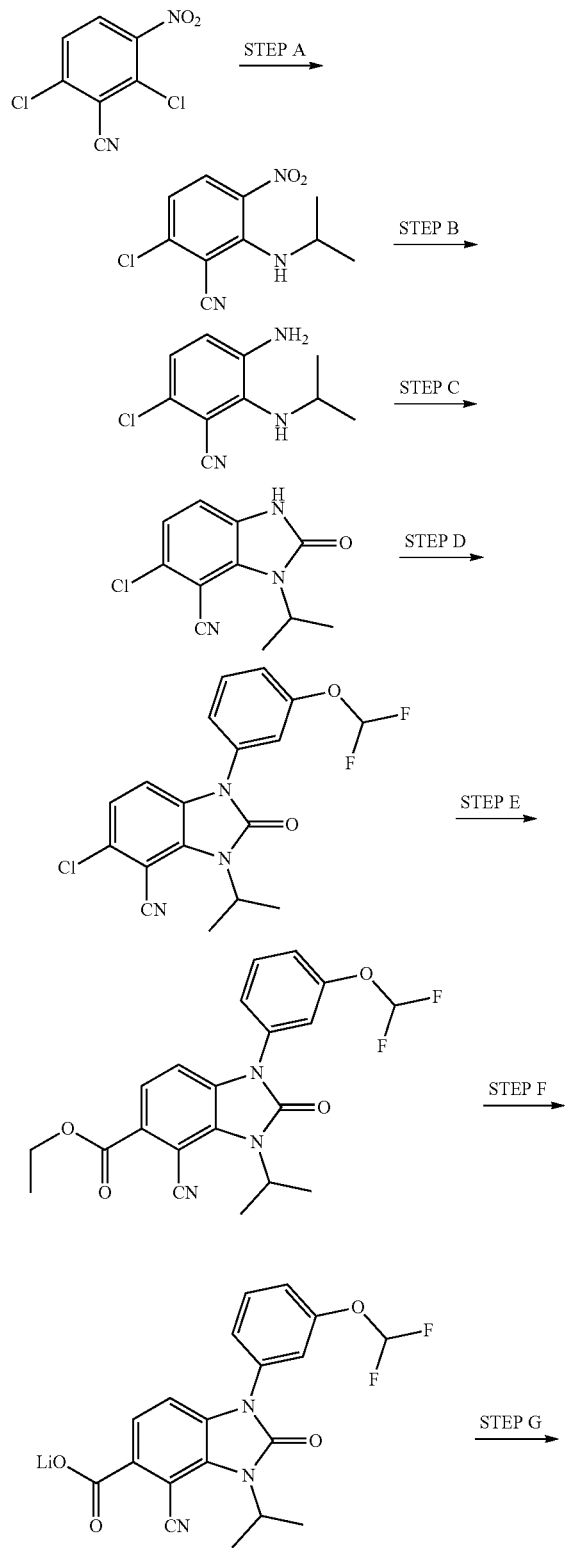

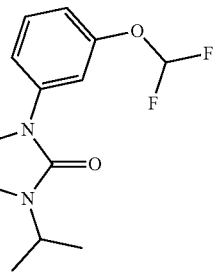

EX-129

Step A: 6-chloro-2-(isopropylamino)-3-nitrobenzonitrile

Isopropylamine (1.421 mL, 16.59 mmol) was added to a mixture of 2,6-dichloro-3-nitrobenzonitrile (3 g, 13.82 mmol) in THF (20 mL). The mixture was stirred at 0° C. for 2 h, then poured into sat. NH₄Cl and extracted with DCM (×3). The combined organic layers were washed with brine, dried over Na₂SO₄, filtered and concentrated in vacuo. The residue was purified by column chromatography on silica (0-100% EtOAc/hexanes) to afford the title compound. LC/MS=240 [M+1].

Step B: 3-amino-6-chloro-2-(isopropylamino)benzonitrile

Iron powder (0.932 g, 16.69 mmol) was added to a mixture of 6-chloro-2-(isopropylamino)-3-nitrobenzonitrile (1 g, 4.17 mmol) and ammonium chloride (0.339 mL, 6.34 mmol) in THF (5 mL). The mixture was stirred at 60° C. for 5 h, then poured into sat. NH₄Cl and extracted with DCM (×3). The combined organic layers were washed with brine, dried over Na₂SO₄, filtered and concentrated in vacuo. The residue was purified by flash silica gel column chromatography (0-100% EtOAc/hexanes) to afford the title compound. LC/MS=210 [M+1].

Step C: 5-chloro-3-isopropyl-2-oxo-2,3-dihydro-1H-benzo[d]imidazole-4-carbonitrile Triethylamine (0.598 ml, 4.29 mmol) was added to a mixture of 3-amino-6-chloro-2-(isopropylamino)benzonitrile (300 mg, 1.431 mmol) and CDI (1160 mg, 7.15 mmol) in THF (3 mL). The mixture was stirred at 25° C. for 24 h, then concentrated in vacuo. The crude product was poured into sat. NH₄Cl and extracted with EtOAc (×3). The combined organic layers were washed with brine, dried over Na₂SO₄, filtered and concentrated in vacuo. Then, the crude product was poured into H₂O and stirred at 25° C. for 3 min (white solid appeared). The mixture was filtered to afford the title compound. LC/MS=236 [M+1].

Step D: 5-chloro-1-(3-(difluoromethoxy)phenyl)-3-isopropyl-2-oxo-2,3-dihydro-1H-benzo[d]imidazole-4-carbonitrile Pyridine (0.820 mL, 10.18 mmol) was added to a mixture of 5-chloro-3-isopropyl-2-oxo-2,3-dihydro-1H-benzo[d]imidazole-4-carbonitrile (120 mg, 0.509 mmol), (3-(difluoromethoxy)phenyl)boronic acid (478 mg, 2.55 mmol) and diacetoxycopper (111 mg, 0.611 mmol) in DMF (15 mL).

The mixture was stirred at 50° C. for 12 h, then poured into sat. NH₄Cl and extracted with DCM (×3). The combined organic layers were washed with brine, dried over Na₂SO₄, filtered and concentrated in vacuo. The residue was purified by flash silica gel column chromatography (0-100% EtOAc/hexanes) to afford the title compound. LC/MS=378 [M+1].

Step E: ethyl 4-cyano-1-(3-(difluoromethoxy)phenyl)-3-isopropyl-2-oxo-2,3-dihydro-1H-benzo[d]imidazole-5-carboxylate Pd(dppf)Cl₂ (58.1 mg, 0.079 mmol) was added to a mixture of potassium acetate (0.149 mL, 2.382 mmol) and 5-chloro-1-(3-(difluoromethoxy)phenyl)-3-isopropyl-2-oxo-2,3-dihydro-1H-benzo[d]imidazole-4-carbonitrile (300 mg, 0.794 mmol) in EtOH (20 mL) and the solution was stirred at 100° C. for 18 h under CO (15 psi balloon). The mixture was poured into sat. NH₄Cl and was extracted with DCM (×3). The combined organic layers were washed with brine, dried over Na₂SO₄, then filtered and concentrated in vacuo. The residue was purified by flash silica gel column chromatography (0-100% EtOAc/hexanes) to afford the title compound. LC/MS=416 [M+1].

Step F: lithium 4-cyano-1-(3-(difluoromethoxy)phenyl)-3-isopropyl-2-oxo-2,3-dihydro-1H-benzo[d]imidazole-5-carboxylate Ethyl 4-cyano-1-(3-(difluoromethoxy)phenyl)-3-isopropyl-2-oxo-2,3-dihydro-1H-benzo[d]imidazole-5-carboxylate (70 mg, 0.169 mmol) was added to a mixture of lithium hydroxide hydrate (14.14 mg, 0.337 mmol) in MeOH (1 mL) and water (0.1 mL). The mixture was stirred at 25° C. for 1 h and was freeze-dried to afford the title compound. LC/MS=388 [M+1].

Step G: 4-cyano-1-(3-(difluoromethoxy)phenyl)-3-isopropyl-N-(4-methyl-1,1-dioxidotetrahydro-2H-thiopyran-4-yl)-2-oxo-2,3-dihydro-1H-benzo[d]imidazole-5-carboxamide 4-cyano-1-(3-(difluoromethoxy)phenyl)-3-isopropyl-2-oxo-2,3-dihydro-1H-benzo[d]imidazole-5-carboxylic acid (17.08 mg, 0.044 mmol) was added to a mixture of 4-amino-4-methyltetrahydro-2H-thiopyran 1,1-dioxide (6 mg, 0.037 mmol), HATU (28.0 mg, 0.074 mmol) and DIEA (0.026 mL, 0.147 mmol) in DMF (5 mL) and the mixture was stirred at 25° C. for 1 h. The crude mixture was purified directly by mass triggered reverse phase HPLC (ACN/water with 0.1% TFA modifier) to afford the title compound. LC/MS=533 [M+1]. ¹H NMR (400 MHz, METHANOL-d4, ppm) δ 8.41 (s, 1H), 7.55-7.71 (m, 1H), 7.34-7.40 (m, 2H), 7.31 (t, J=7.58 Hz, 3H), 6.73-7.14 (m, 1H), 5.39 (td, J=6.82, 13.51 Hz, 1H), 3.33-3.42 (m, 2H), 2.98 (br d, J=12.96 Hz, 2H), 2.83 (br d, J=14.67 Hz, 2H), 2.18 (br t, J=13.45 Hz, 2H), 1.69 (d, J=6.85 Hz, 6H), 1.54 (s, 3H). Human DGAT2 IC₅₀=248 nM Assays Insect Cell Expression and Membrane Preparation Sf-9 insect cells were maintained in Grace's insect cell culture medium with 10% heated-inactivated fetal bovine serum, 1% Pluronic F-68 and 0.14 μg/ml Kanamycine sulfate at 27° C. in a shaker incubator. After infection with untagged baculovirus expressing human DGAT (hDGAT2) at multiplicity of infection (MOI) 3 for 48 hours, cells were harvested. Cell pellets were suspended in buffer containing 10 mM Tris-HCl pH 7.5, 1 mM EDTA, 250 mM sucrose and Complete Protease Inhibitor Cocktail (Sigma Aldrich), and sonicated on ice. Cell debris were removed by centrifugation at 2000×g for 15 minutes. Membrane fractions were isolated by ultracentrifugation (100,000×g), resuspended in the same buffer, and frozen (−80° C.) for later use. The protein concentration was determined with the Pierce™ BCA Protein Assay Kit (Thermo Fisher Scientific). Expression of protein levels was analyzed by immunoblotting with rabbit anti-DGAT2 antibody (Abcam, ab102831) and donkey anti-rabbit IgG H&L Alexa Fluor® 647 (Abcam, ab150075) followed by detection using Typhoon FLA9000 (GE Healthcare).

LC/MS/MS Analysis Method

LC/MS/MS analyses were performed using Thermal Fisher's LX4-TSQ Vantage system. This system consists of an Agilent binary high-performance liquid chromatography (HPLC) pump and a TSQ Vantage triple quadrupole MS/MS instrument. For each sample, 2 μL samples from the top organic layer of in-plate liquid-liquid extraction were injected onto a Thermo Betabasic C4 column (2.1 mm×20 mm, 5 μm particle size). The samples were then eluted using the following conditions; mobile phase: Isopropanol:acetonitrile/10 mM ammonium formate=50/35/15 (v/v/v), flow rate: 0.8 mL/min, temperature: 25° C. Data was acquired in positive mode using a heated electrospray ionization (HESI) interface. The operational parameters for the TSQ Vantage MS/MS instrument were a spray voltage of 3000 V, capillary temperature of 280° C., vaporizer temperature 400° C., sheath gas 45 arbitrary unit, Aux gas 10 arbitrary units, S-lens 165 and collision gas 1.0 mTorr. Standard reference material (SRM) chromatograms of ¹³C₁₈-triolein (Q1: 920.8>Q3: 621.3) and internal standard ¹³C₂₁-triolein (Q1: 923.8>Q3: 617.3) were collected for 33 sec. The peak area was integrated by Xcalibur Quan software. The ratio between the ¹³C₁₈triolein generated in the reaction and spiked in internal standard ¹³C₂₁-triolein was used to generate percentage inhibition and IC₅₀ values. Compound percentage inhibition was calculated by the following formula: Inhibition %=1−[(compound response−low control)/(high control−low control)]×100%. Potent compounds were titrated and IC₅₀ were calculated by 4 parameter sigmoidal curve fitting formula.

DGAT2 Enzymatic Activity Assay

DGAT2 activity was determined by measuring the amount of enzymatic product ¹³C₁₈-triolein (¹³C-1,2,3-Tri(cis-9-octadecenoyl)glycerol) using the membrane prep mentioned above. The assay was carried out in ABgene 384-well assay plates in a final volume of 25 μL at rt. The assay mixture contained the following: assay buffer (100 mM Tris·Cl, pH 7.0, 20 mM MgCl₂, 5% ethanol), 25 μM of diolein, 5 μM of ¹³C oleoyl-CoA and 8 ng/μL of DGAT2 membrane.

What is claimed is:
1. A compound of Formula I:

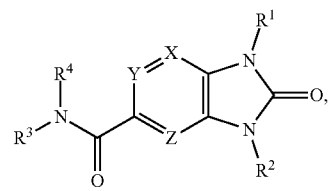

or a pharmaceutically acceptable salt thereof wherein:

X, Y, and Z are independently selected from N and C($R^5$);

$R^1$ is
- (1) phenyl unsubstituted or substituted with 1, 2, or 3 $R^6$,
- (2) 5- or 6-membered heteroaryl containing 1, 2, 3 or 4 heteroatoms independently selected from N, O, and S, wherein the heteroaryl is unsubstituted or substituted with 1, 2, or 3 $R^6$, or
- (3) 8- to 10-membered fused heteroaryl containing 1, 2, 3 heteroatoms independently selected from N, O, and S, wherein the heteroaryl is unsubstituted or substituted with 1, 2, or 3 $R^6$;

$R^2$ is
- (1) phenyl unsubstituted or substituted with 1, 2, or 3 $R^7$,
- (2) 5- or 6-membered heteroaryl containing 1, 2 or 3 heteroatoms independently selected from N, O, and S, wherein the heteroaryl is unsubstituted or substituted with 1, 2, or 3 $R^7$,
- (3) $C_{1-6}$alkyl unsubstituted or optionally mono-substituted or disubstituted with halogen, OH, CF3, or CN,
- (4) ($C_{3-6}$)cycloalkyl unsubstituted or optionally mono-substituted or disubstituted with $C_{1-3}$alkyl, halogen, OH, CF$_3$, or —CN,
- (5) —($C_{3-6}$)alkylC(O)NH$_2$,
- (6) 4- to 6-membered heterocyclyl containing 1 or 2 heteroatoms independently selected from N, O and S wherein the heterocyclyl is unsubstituted or substituted by 1, 2, or 3 $R^7$,
- (7) —CH$_2$-aryl unsubstituted or substituted by 1, 2, or 3 $R^7$,
- (8) —SO$_2$($C_{1-6}$)alkyl unsubstituted or substituted with 1, 2, or 3 $R^7$, or
- (9) —SO$_2$-aryl unsubstituted or substituted with 1, 2, or 3 $R^7$;

$R^3$ is
- (1) 4- to 7-membered heterocyclyl containing 1, 2, or 3 heteroatoms independently selected from N, O, and S,
- (2) 5- or 6-membered heteroaryl containing 1, 2, or 3 heteroatoms independently selected from N, O, and S,
- (3) -($C_{1-6}$)alkyl-heteroaryl, wherein the heteroaryl is a 5- or 6-membered heteroaryl containing 1, 2, or 3 heteroatoms independently selected from N, O and S,
- (4) -($C_{1-6}$)alkyl-aryl,
- (5) -($C_{1-6}$)alkyl-heterocyclyl, wherein the heterocyclyl is a 3- to 6-membered ring containing 1 or 2 heteroatoms independently selected from N, O and S,
- (6) —($C_{1-6}$)alkyl,
- (7) —($C_{3-6}$)cycloalkyl,
- (8) —($C_{1-6}$)hydroxyalkyl,
- (9) —($C_{1-6}$)alkyl-S(O)$_2$—NR$^{8a}$R$^{8b}$, or
- (10) —($C_{1-6}$)alkyl-S(O)$_2$-($C_{1-3}$)alkyl, wherein each aryl, fused aryl, heteroaryl, cycloalkyl, or heterocyclyl is unsubstituted or substituted with 1, 2, or 3 $R^9$, and wherein each alkyl is unsubstituted or substituted with 1, 2, or 3 $R^{10}$;

$R^4$ is
- (1) hydrogen, or
- (2) ($C_{1-3}$)alkyl, or $R^3$ and $R^4$ combine along with the nitrogen atom to which they are attached to form a mono- or bicyclic heterocyclyl ring containing 1 or 2 heteroatoms independently selected from N, O and S, wherein the heterocyclyl ring is unsubstituted or substituted by 1, 2, or 3 $R^{11}$, when present, each $R^5$ is selected from
- (1) hydrogen,
- (2) ($C_{1-6}$)alkyl,
- (3) ($C_{3-6}$)cycloalkyl,
- (4) ($C_{1-6}$)haloalkyl,
- (5) cyano, and
- (6) halogen, when present, each $R^6$ is independently selected from
- (1) cyano,
- (2) halogen,
- (3) —OC$_{1-6}$alkyl,
- (4) ($C_{3-6}$)cycloalkyl, optionally substituted with halogen, $C_{1-3}$alkyl, $C_{1-6}$haloalkyl, or OH,
- (5) —C(=O)NH$_2$,
- (6) —O($C_{3-6}$) cycloalkyl wherein the cycloalkyl is optionally substituted with halogen, $C_{1-3}$alkyl, or OH,
- (7) hydroxy,
- (8) N($R^{11}$)$_2$,
- (9) ($C_{1-6}$)haloalkyl-,
- (10) —O($C_{1-6}$)haloalkyl-,
- (11) —SO$_2$($C_{1-6}$)alkyl,
- (12) —SO$_2$NH($C_{1-6}$)alkyl,
- (13) —S$C_{1-6}$alkyl,
- (14) N($R^{11}$)C(O)$R^{11}$,
- (15) —S$C_{1-6}$haloalkyl, and
- (16) ($C_{1-6}$)alkyl;

when present, each $R^7$ is independently selected from
- (1) ($C_{1-3}$)alkyl,
- (2) halogen,
- (3) ($C_{1-6}$)alkoxy-,
- (4) ($C_{1-6}$)haloalkyl-, and
- (5) hydroxy;

when present, $R^{8a}$ and $R^{8b}$ are independently selected from
- (1) hydrogen,
- (2) ($C_{1-3}$)alkyl, and
- (3) ($C_{3-7}$)cycloalkyl;

when present, each $R^9$ is independently selected from
- (1) ($C_{1-3}$)alkyl,
- (2) ($C_{1-3}$)haloalkyl-,
- (3) oxo,
- (4) ($C_{3-6}$)cycloalkyl,
- (5) N($R^{11}$)$_2$,
- (6) hydroxy,
- (7) ($C_{1-3}$)alkoxyl-,
- (8) cyano, and
- (9) halogen;

when present, $R^{10}$ is independently selected from
- (1) ($C_{1-3}$)alkoxy-,
- (2) hydroxy,
- (3) halogen,
- (4) ($C_{1-3}$)haloalkyl-, and
- (5) N($R^{11}$)$_2$;

$R^{11}$, when present, is independently
- (1) hydrogen, or
- (2) ($C_{1-3}$)alkyl.

2. The compound of claim 1, or a pharmaceutically acceptable salt thereof, wherein $R^1$ is
- (a) phenyl optionally substituted with one to three substituents independently selected from halogen, hydroxy, CN, $C_{1-3}$alkyl, $C_{1-3}$haloalkyl, $C_{3-6}$cycloalkyl, OC$_{1-3}$alkyl, OC$_{1-3}$haloalkyl, OC$_{3-6}$cycloalkyl, NHC(O)$C_{1-3}$alkyl, N(CH$_3$)$_2$, C(O)NH$_2$, —SC$_{1-3}$alkyl, S(O)

$_2NHC_{1-3}$alkyl, —$SC_{1-3}$haloalkyl, and $S(O)_2C_{1-3}$alkyl, and wherein the cycloalkyl is optionally independently substituted with 1-3 halogen or OH;
(b) 6-membered heteroaryl containing one or two nitrogen atom optionally substituted with one to three substituents independently selected from halogen, hydroxy, $C_{1-6}$alkyl, $C_{1-6}$haloalkyl, $C_{3-6}$cycloalkyl, $OC_{1-3}$alkyl, $OC_{1-3}$haloalkyl, O—$C_{3-6}$cycloalkyl, and CN, and when the cycloalkyl is cyclopropyl, the cyclopropyl is optionally substituted with halogen, or OH; or
(c) -8- to 10-membered fused heteroaryl containing 1, 2, 3 heteroatoms independently selected from N, O, and S, wherein the heteroaryl is unsubstituted or substituted with one substituent selected from halogen, $(C_{1-3})$alkyl, $(C_{3-6})$cycloalkyl, $(C_{1-3})$haloalkyl-, OH and $OC_{1-3}$alkyl.

3. The compound of claim 2, or a pharmaceutically acceptable salt thereof, wherein $R^1$ is
(a) phenyl optionally substituted with one to three substituents independently selected from halogen, OH, $C_{1-3}$alkyl, $C_{1-3}$haloalkyl, $C_{3-6}$cycloalkyl, O-$C_{3-6}$cycloalkyl, CN, $NHC(O)C_{1-3}$alkyl, $N(CH_3)_2$, $C(O)NH_2$, $SC_{1-3}$alkyl, $S(O)_2NHC_{1-3}$alkyl, $S(O)_2C_{1-3}$alkyl, $OC_{1-3}$alkyl, and $OC_{1-3}$haloalkyl, wherein the cycloalkyl is additionally optionally substituted with 1-3 halogen;
(b) pyridyl optionally substituted with one to three substituents independently selected from halogen, $C_{1-3}$alkyl, $C_{3-6}$cycloalkyl, $OC_{1-3}$alkyl, and $OC_{1-3}$haloalkyl; or
(c) 8- to 10-membered fused heteroaryl containing 1, 2, 3 heteroatoms independently selected from N, O, and S, wherein the heteroaryl is unsubstituted or substituted with one substituent selected from halogen, $(C_{1-3})$alkyl, $(C_{3-6})$cycloalkyl, $(C_{1-3})$haloalkyl-, OH and $OC_{1-3}$alkyl.

4. The compound of claim 3, or a pharmaceutically acceptable salt thereof, wherein $R^1$ is
(a) phenyl optionally substituted with one to three substituents independently selected from F, OH, $CF_3$, CN, $N(CH_3)_2$, $C(O)NH_2$, $SCH_3$, $S(O)_2NHCH_3$, $S(O)_2CH_3$, $OCH_2CH_3$, $OCH(CH_3)_2$, $OCHF_2$, $OCH_2CHF_2$, $OCF_3$, $OCF_2CHF_2$, $NHC(O)CH_3$, cyclopropyl, and O-cyclopropyl, wherein the cyclopropyl is additionally optionally substituted with 1-3 F;
(b) pyridyl optionally substituted with one to three substituents independently selected from F, $OC(F)_2(CH_3)$, $OCH_2CH_3$, $OCH(CH_3)_2$, $OCHF_2$, $OCF_3$, $OCF_2CHF_2$, $OCH_2CHF_2$ and cyclopropyl; or
(c) 8-10 membered fused heteroaryl containing one to three heteroatoms selected from N, O, or S atom, wherein the fused heterosryl optionally substituted with $CH_3$.

5. The compound of claim 4, or a pharmaceutically acceptable salt thereof, wherein $R^1$ is

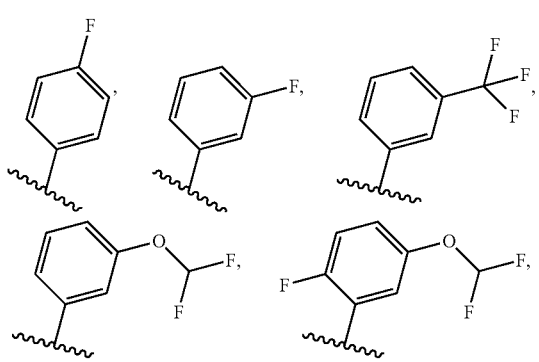

-continued

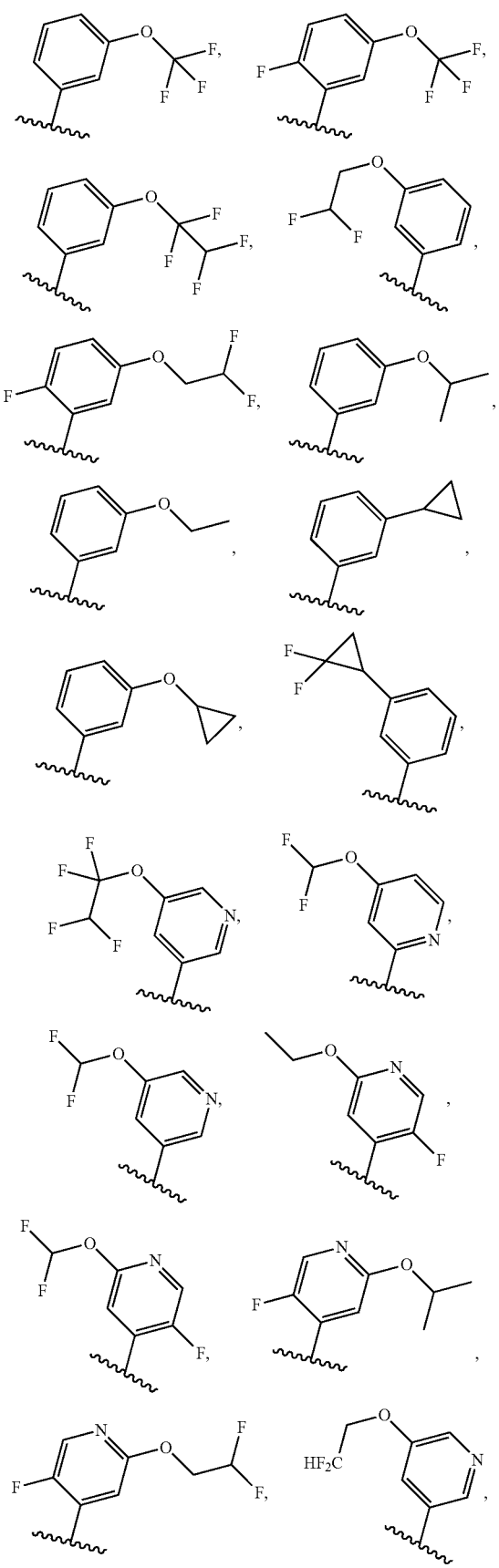

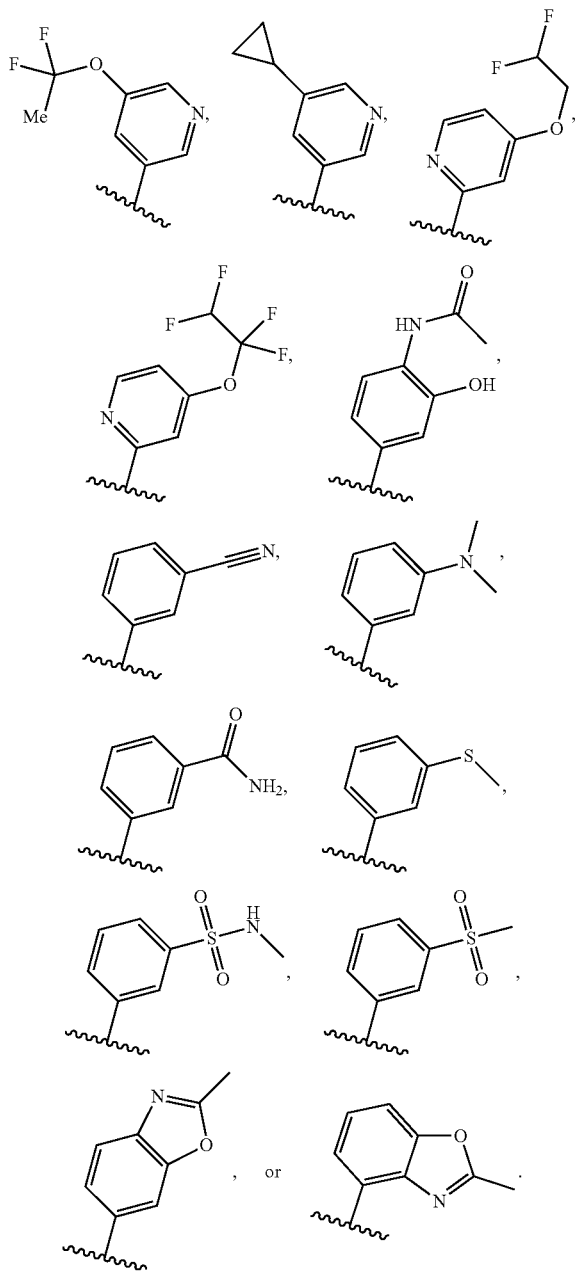

6. The compound of claim 3, or a pharmaceutically acceptable salt thereof, wherein $R^1$ is a phenyl unsubstituted or substituted with 1, 2, or 3 substituents independently selected from F, $CF_3$, CN, $N(CH_3)_2$, $C(O)NH_2$, $SCH_3$, $S(O)_2NHCH_3$, $S(O)_2CH_3$, $OCHF_2$, $OCF_3$, $OCH(CH_3)(CH_3)$, $OCF_2CHF_2$, $OCH_2CHF_2$, $OCH_2CH_3$, $NHC(O)CH_3$, cyclopropyl, and O-cyclopropyl, wherein the cyclopropyl is additionally optionally substituted with one to three halogen atoms.

7. The compound of claim 3, or a pharmaceutically acceptable salt thereof, wherein $R^1$ is pyridyl and wherein the pyridyl is unsubstituted or substituted with 1, or 2 substituents independently selected from F, $OC(F)_2(CH_3)$, $OCH_2CH_3$, $OCH(CH_3)_2$, $OCHF_2$, $OCH_2CHF_2$, $OCF_3$, $OCF_2CHF_2$, and cyclopropyl.

8. The compound of claim 3, or a pharmaceutically acceptable salt thereof, wherein $R^1$ is

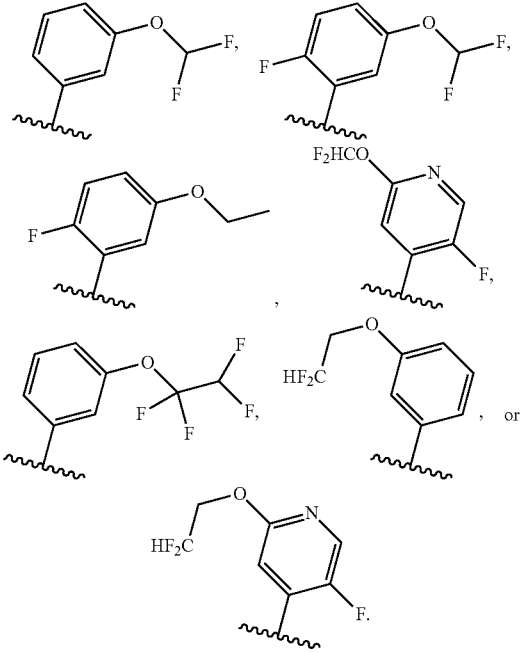

9. The compound of claim 1, or a pharmaceutically acceptable salt thereof, wherein $R^2$ is $C_{1-6}$alkyl, $C_{3-6}$cycloalkyl, $C_{1-6}$alkylOH, phenyl, $C_{3-6}$heterocycle, $C_{3-6}$alkylC(O)NH_2, $S(O)_2$-phenyl, $CH_2$-phenyl, wherein the alkyl is optionally substituted with 1-2 halogens, OH or $CF_3$, and wherein the phenyl is optionally substituted with 1-3 halogens.

10. The compound of claim 9, or a pharmaceutically acceptable salt thereof, wherein $R^2$ is $C_{1-6}$alkyl monosubstituted, or disubstituted with substituents independently selected from halogen, OH and $CF_3$.

11. The compound of claim 9, or a pharmaceutically acceptable salt thereof, wherein $R^2$ is $C_{3-6}$cycloalkyl.

12. The compound of claim 9, or a pharmaceutically acceptable salt thereof, wherein $R^2$ is

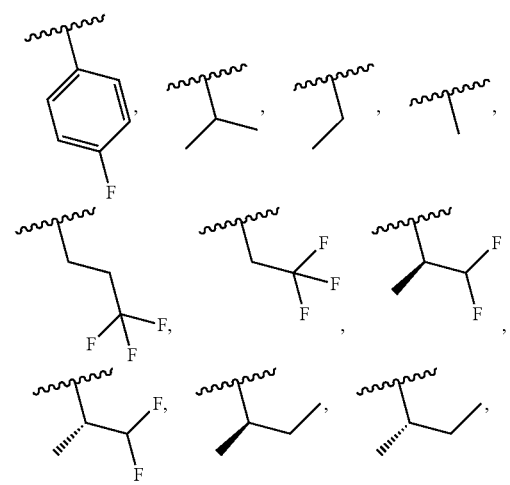

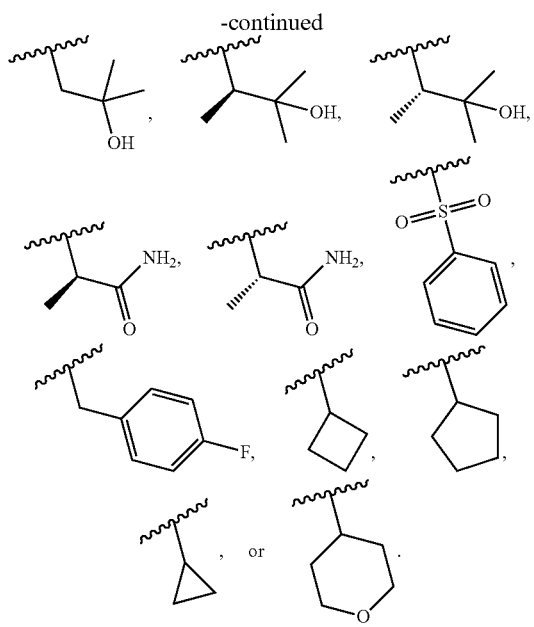

13. The compound of claim 9, or a pharmaceutically acceptable salt thereof, wherein $R^2$ is

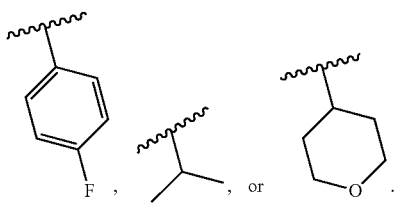

14. The compound of claim 1, or a pharmaceutically acceptable salt thereof, wherein $R^3$ is
   (a) 4- to 7 membered heterocyclyl containing 1, 2 or 3 heteroatoms independently selected from N, O and S,
   (b) 5- or 6-membered heteroaryl containing 1, 2 or 3 heteroatoms independently selected from N, O and S,
   (c) —($C_{1-6}$)alkyl-heteroaryl, wherein the heteroaryl is a 5- or 6-membered heteroaryl containing 1, 2 or 3 heteroatoms independently selected from N, O and S,
   (d) —($C_{1-6}$)alkyl-aryl,
   (e) —($C_{1-6}$)alkyl-heterocyclyl, wherein the heterocyclyl is a 3- to 6-membered ring containing 1 or 2 heteroatoms independently selected from N, O and S,
   (f) —($C_{1-6}$)alkyl,
   (g) —($C_{3-6}$)cycloalkyl, or
   (h) ($C_{1-6}$)hydroxyalkyl,
wherein each aryl, heteroaryl, cycloalkyl, or heterocyclyl is unsubstituted or substituted with 1, 2, or 3 $R^9$, and wherein each alkyl is unsubstituted or substituted with 1, 2, or 3 $R^{10}$.

15. The compound of claim 14, or a pharmaceutically acceptable salt thereof, wherein $R^3$ is a 4 to 6 membered heterocyclyl containing 1 sulfur atom, wherein the heterocycle is optionally mono-substituted, disubstituted, or trisubstituted with halogen, $C_{1-3}$alkyl, or oxo.

16. The compound of claim 14, or a pharmaceutically acceptable salt thereof, wherein $R^3$ is
   (a) 4 to 6 membered cycloalkyl optionally mono-substituted, disubstituted, or trisubstituted with F, $CH_3$, or OH,
   (b) 4 to 6 membered heterocyclyl containing 1 sulfur atom optionally, wherein the heterocycle is mono-substituted, disubstituted, or trisubstituted with oxo, $CHF_2$, or $CH_3$,
   (c) 5 or 6 membered heterocyclyl containing 1 oxygen atom optionally, wherein the heterocycle is mono-substituted, disubstituted, or trisubstituted with $CH_3$, or OH,
   (d) $C_{1-6}$alkyl-heterocyclyl, wherein the heterocyclyl is a 5 membered-heterocyclyl containing 1 oxygen atom optionally, wherein the heterocycle is mono-substituted, disubstituted, or trisubstituted with OH,
   (e) $C_{1-6}$alkyl-heteroaryl, wherein the heteroaryl contains 2 nitrogen atoms, wherein the heteroaryl is optionally mono-substituted, disubstituted, or trisubstituted with $CH_3$, or $CH_2CH_3$,
   (f) 5 membered heteroaryl containing 2 nitrogen atoms and 1 sulfur atoms, wherein the heteroaryl is optionally mono-substituted, disubstituted, or trisubstituted with $CH_3$, or
   (g) $C_{1-6}$alkyl, wherein the alkyl is optionally mono-substituted, disubstituted, or trisubstituted with OH.

17. The compound of claim 14, or a pharmaceutically acceptable salt thereof, wherein $R^3$ is

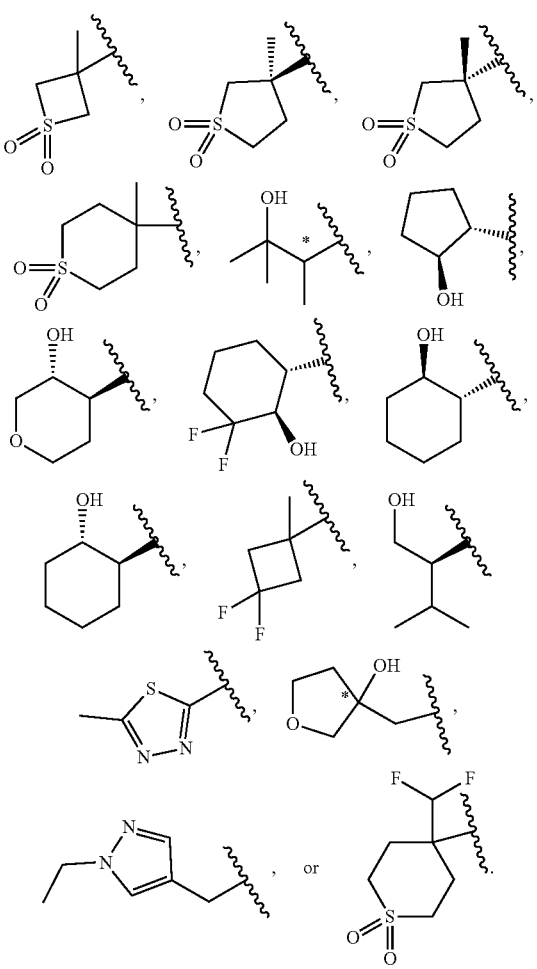

18. The compound of claim 14, or a pharmaceutically acceptable salt thereof, wherein $R^3$ is

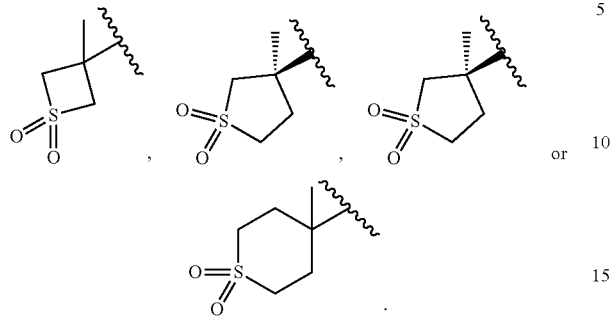

19. The compound of claim 1, or a pharmaceutically acceptable salt thereof, wherein $R^4$ is H.

20. The compound of claim 1, or a pharmaceutically acceptable salt thereof, wherein $R^5$ is H, halogen, or CN.

21. The compound of claim 20, or a pharmaceutically acceptable salt thereof, wherein $R^5$ is H, F, Cl, or CN.

22. The compound of claim 1, or a pharmaceutically acceptable salt thereof, wherein $R^6$ is halogen, hydroxy, CN, $C_{1-3}$alkyl, $C_{1-3}$haloalkyl, $C_{3-6}$cycloalkyl, $OC_{1-3}$alkyl, $OC_{1-3}$haloalkyl, $OC_{3-6}$cycloalkyl, $S(O)_2C_{1-3}$alkyl, NHC(O)$C_{1-3}$alkyl, $N(CH_3)_2$, $C(O)NH_2$, $SC_{1-6}$alkyl, or $S(O)_2NHC_{1-6}$alkyl, and wherein the cycloalkyl is optionally substituted with halogen.

23. The compound of claim 1, or a pharmaceutically acceptable salt thereof, wherein $R^6$ is F, $CF_3$, $OCHF_2$, $OCF_3$, $OCH_2CH_3$, $OCH(CH_3)_2$, $OCH_2CHF_2$, cyclopropyl, O-cyclopropyl, CN, $N(CH_3)_2$, $C(O)NH_2$, $SCH_3$, $S(O)_2NHCH_3$, $NHC(O)CH_3$, OH, $OCF_2CHF_2$, or $S(O)_2CH_3$, wherein the cyclopropyl is additionally optionally substituted with one to three halogen atoms.

24. The compound of claim 1, or a pharmaceutically acceptable salt thereof, wherein $R^7$ is F, $CF_3$, or OH.

25. The compound of claim 1, or a pharmaceutically acceptable salt thereof, wherein $R^9$ is =O, OH, $C_{1-3}$alkyl, $C_{1-3}$haloalkyl, or halogen.

26. The compound of claim 25, or a pharmaceutically acceptable salt thereof, wherein $R^9$ is =O, OH, $CH_3$, $CH_2CH_3$, F, $CF_3$, or $CHF_2$.

27. The compound of claim 1, or a pharmaceutically acceptable salt thereof, wherein $R^{10}$ is OH.

28. The compound of claim 1, or a pharmaceutically acceptable salt thereof, wherein $R^{10}$ is OH, F, or $CF_3$.

29. The compound of claim 1, or a pharmaceutically acceptable salt thereof, wherein X is N, Y is $C(R^5)$, and Z is $C(R^5)$.

30. The compound of claim 1, or a pharmaceutically acceptable salt thereof, wherein X is $C(R^5)$, Y is N, and Z is $C(R^5)$.

31. The compound of claim 1, or a pharmaceutically acceptable salt thereof, wherein X is $C(R^5)$, Y is $C(R^5)$ and Z is N.

32. The compound of claim 1, or a pharmaceutically acceptable salt thereof, wherein X, Y, and Z are $C(R^5)$.

33. The compound of claim 1, or a pharmaceutically acceptable salt thereof, which is

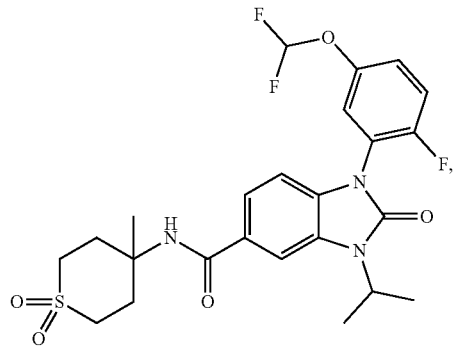

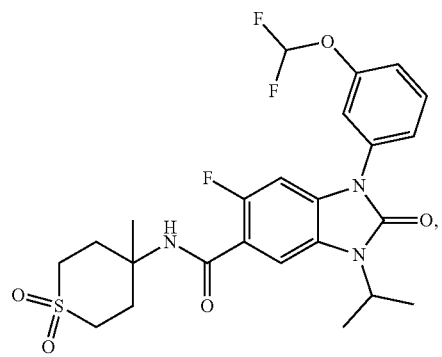

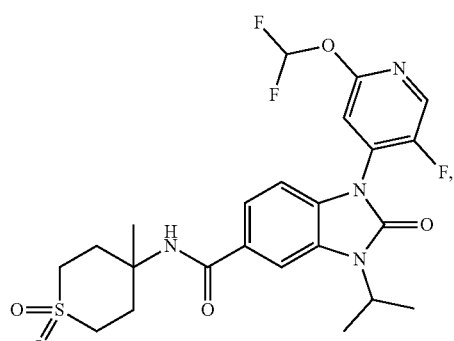

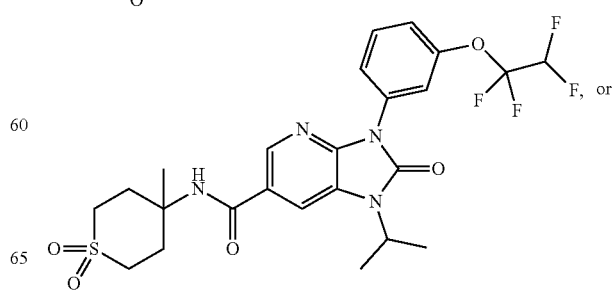

-continued
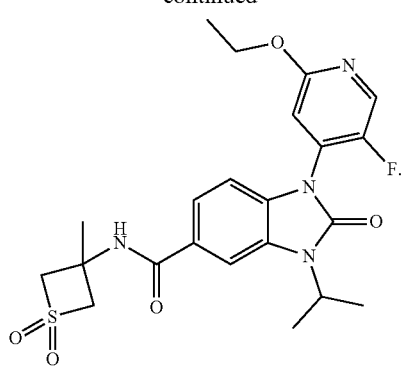
34. The compound of claim 1, or a pharmaceutically acceptable salt thereof, which is
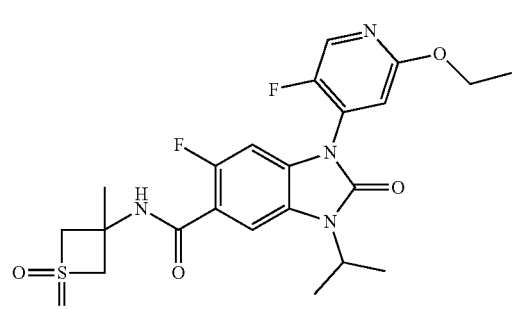
,
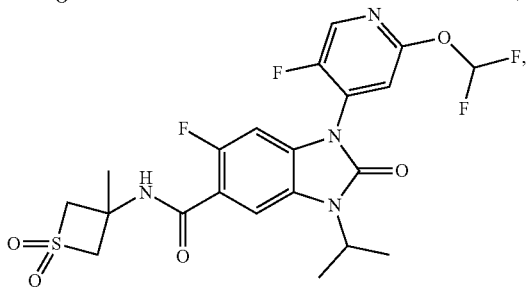
,
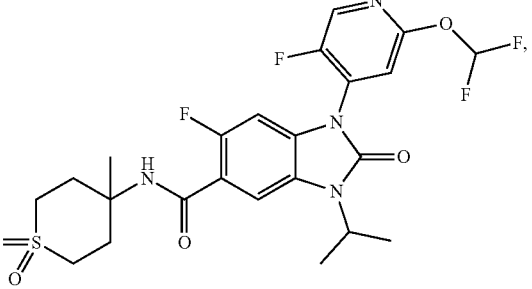
, or
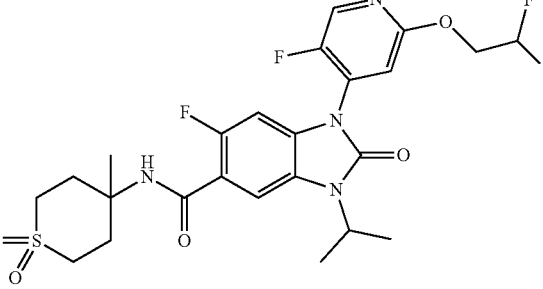
.
35. The compound of claim 1, selected from:
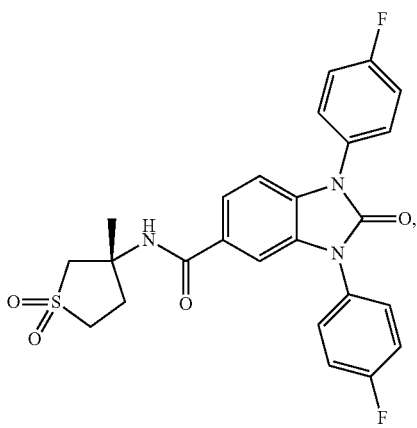
,
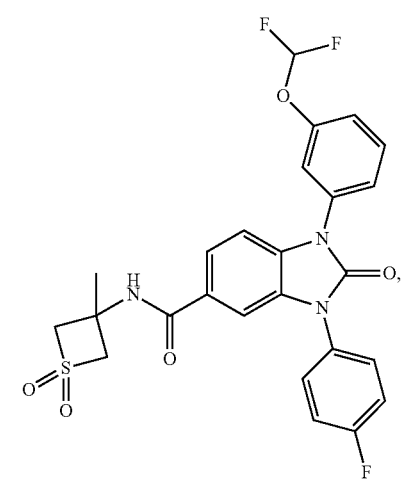
,
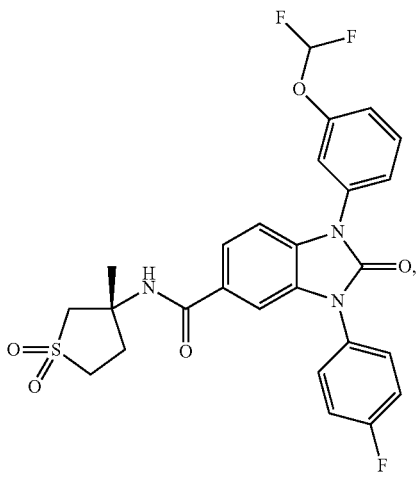
, 223
-continued
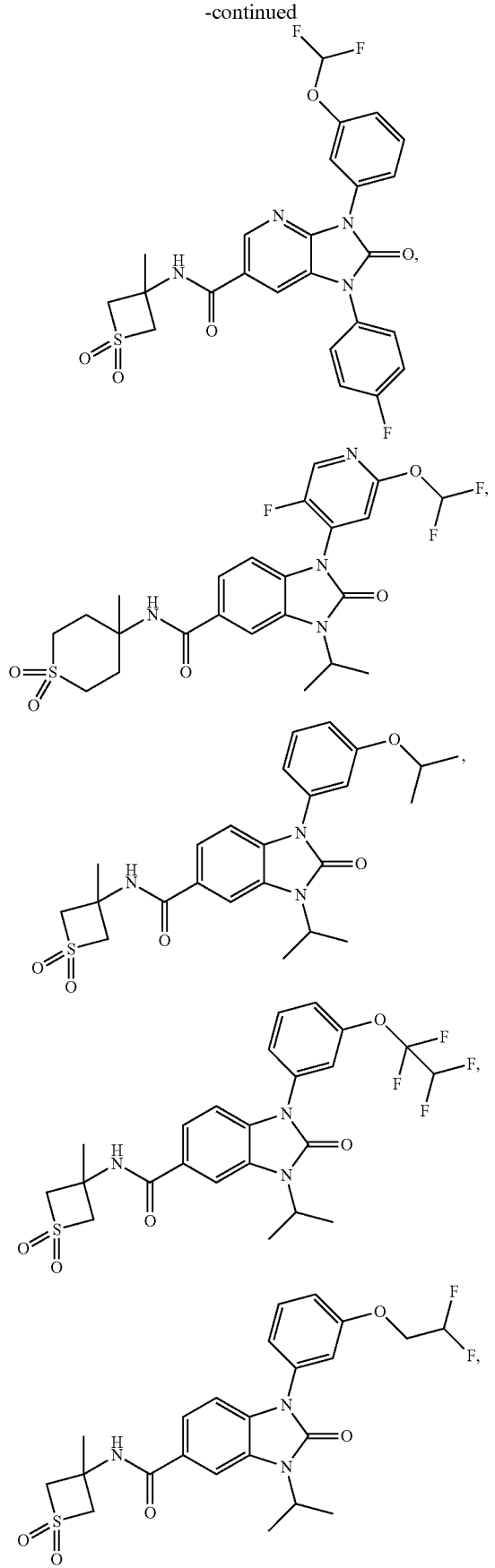
224
-continued
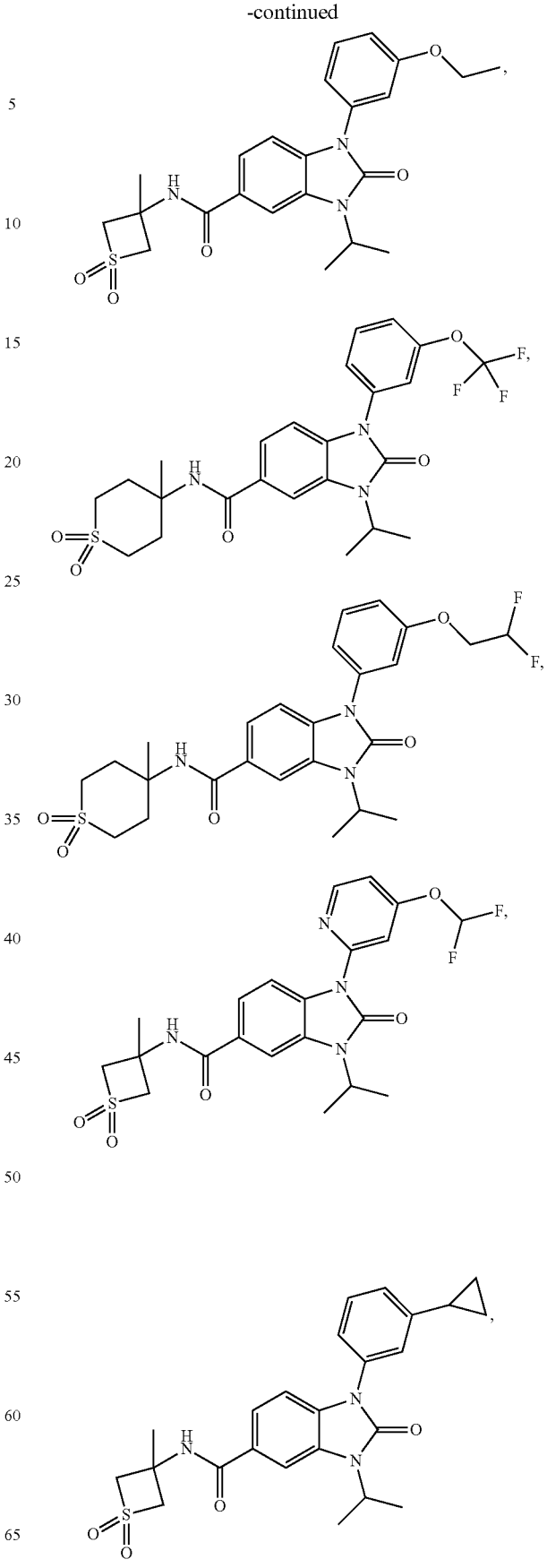

225
-continued
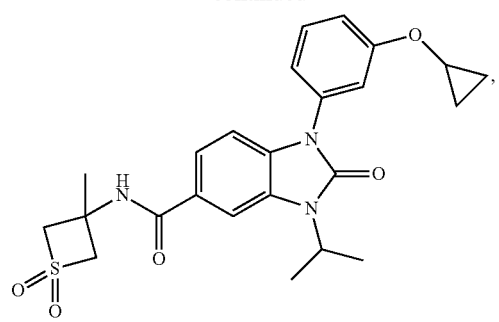
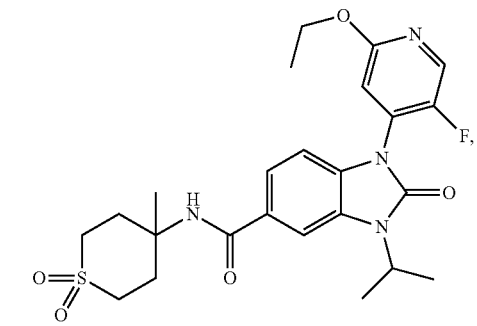
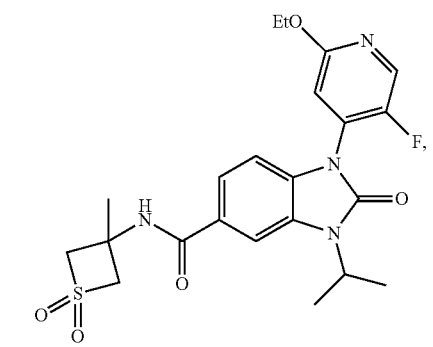
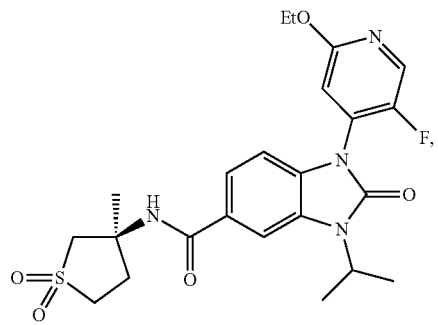
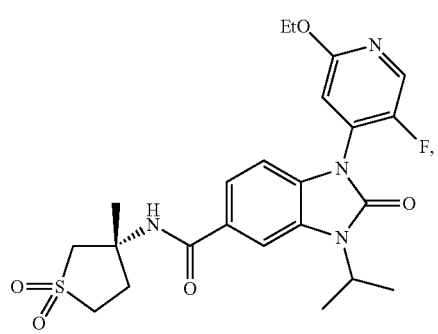
226
-continued
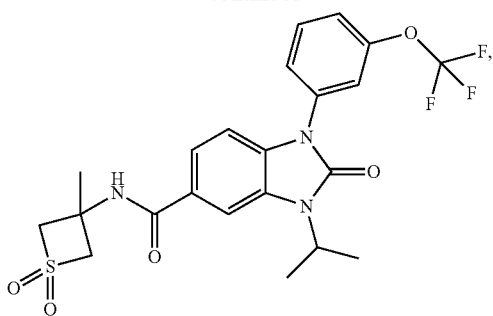
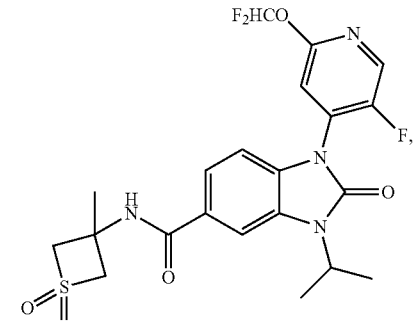
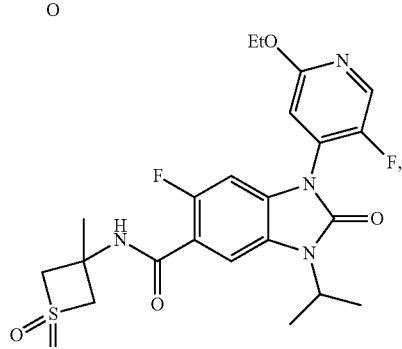
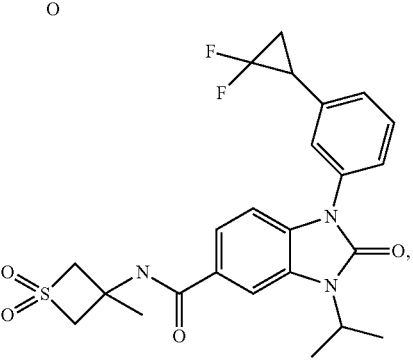
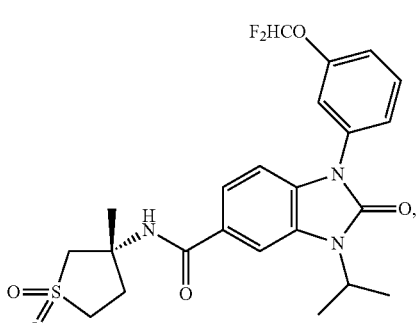

227
-continued
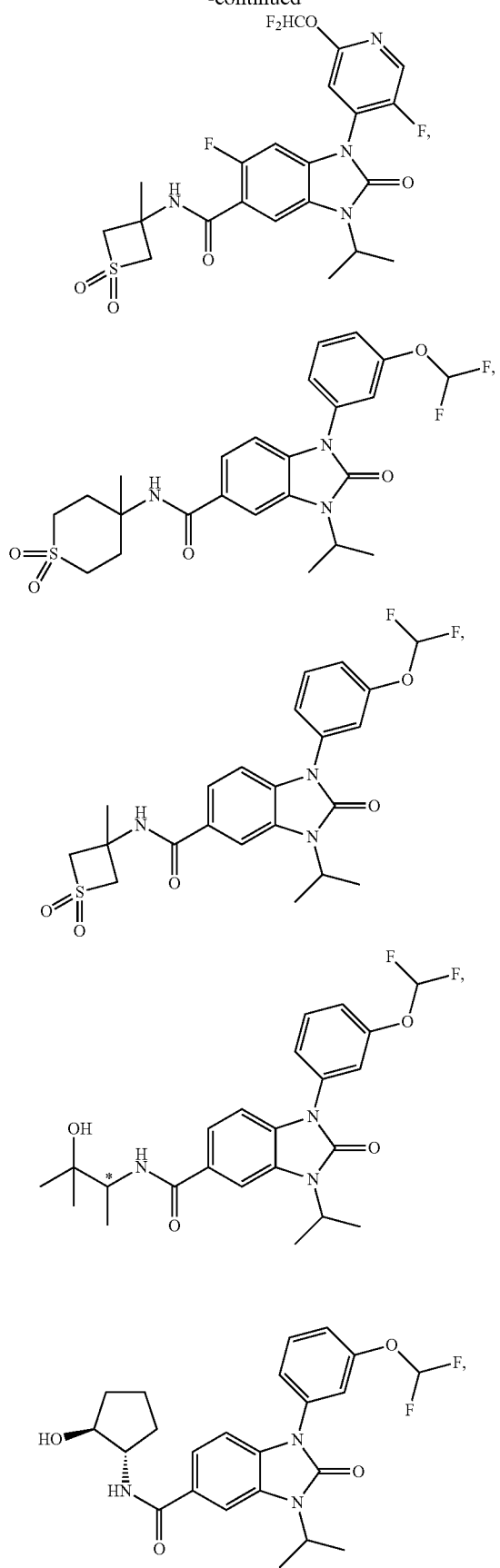
228
-continued
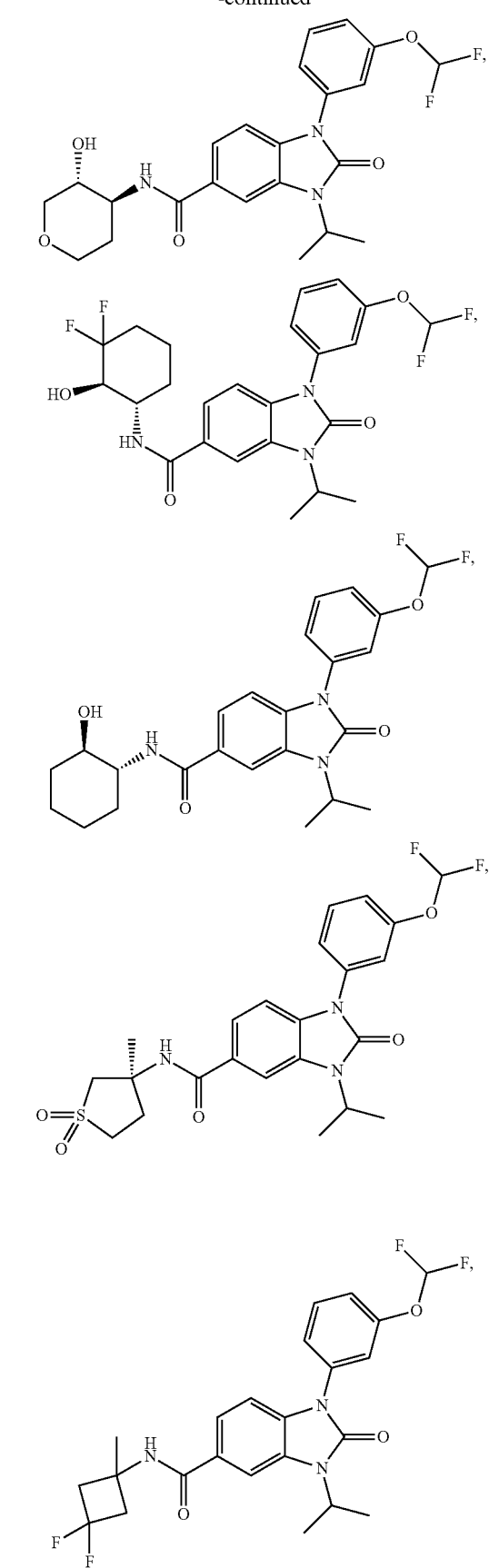

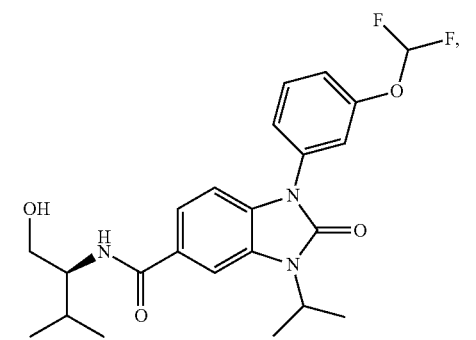
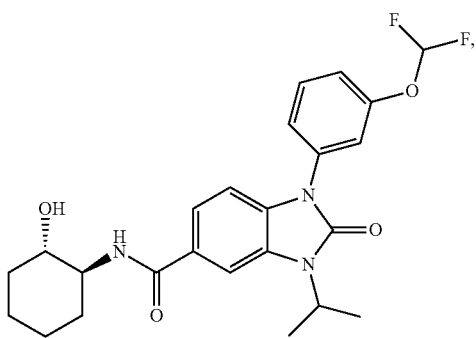
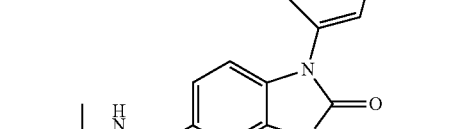
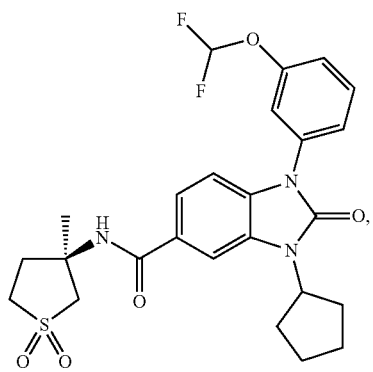
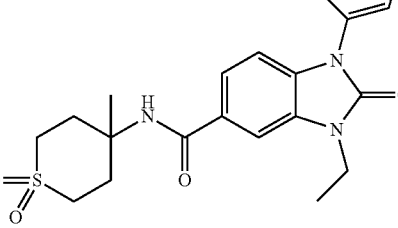
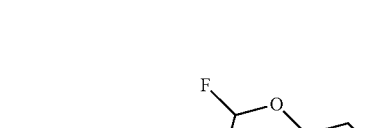
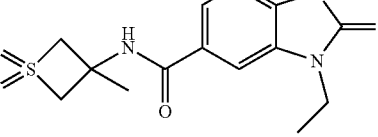
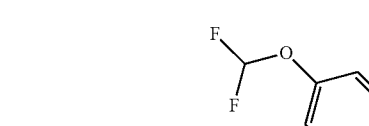

231
-continued
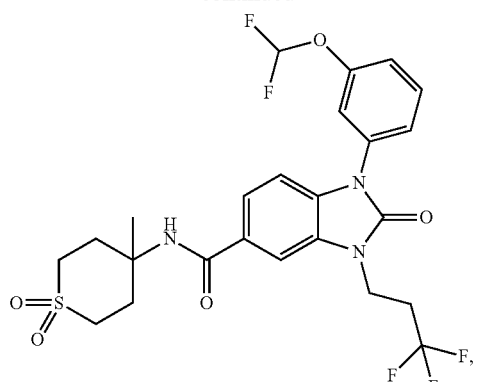
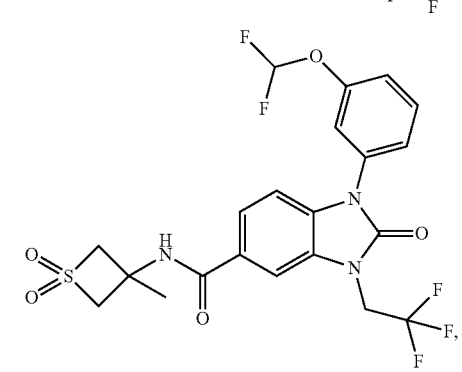
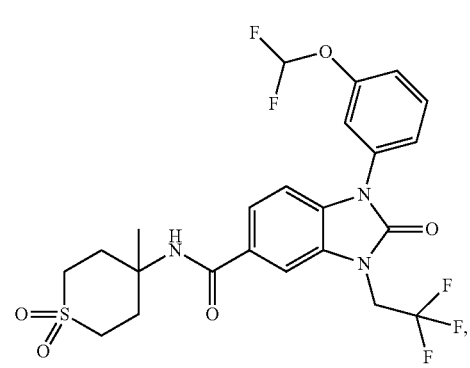
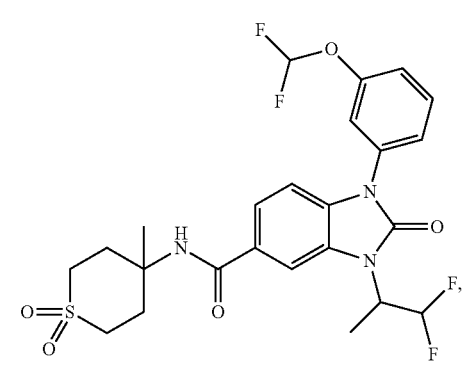
232
-continued
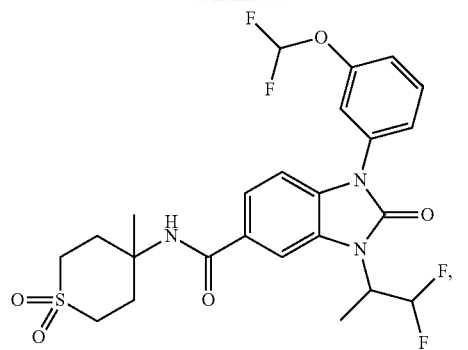
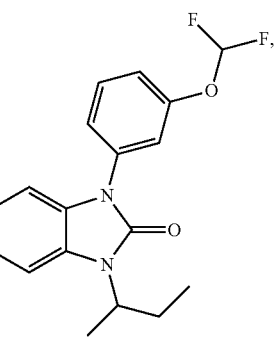
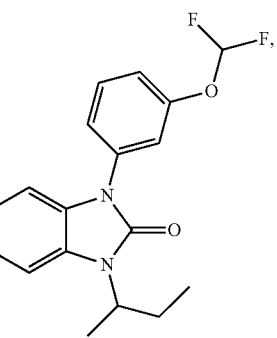
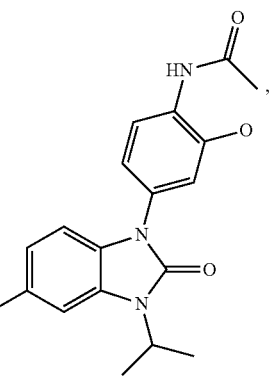

233
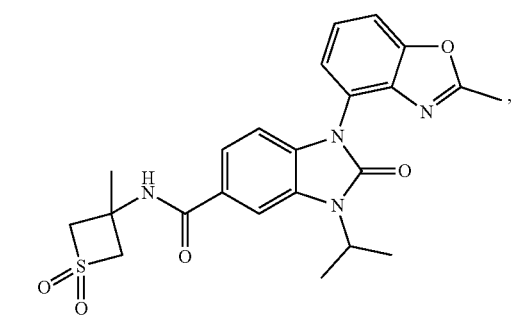
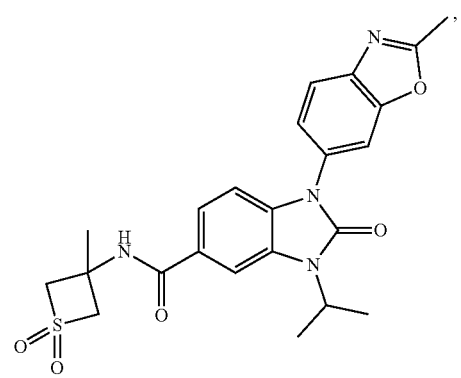
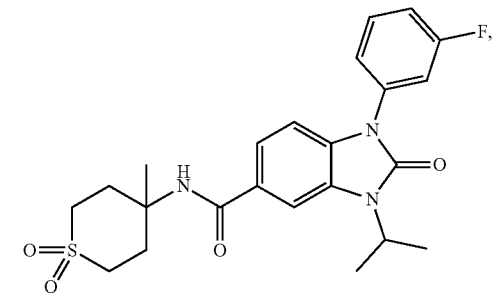
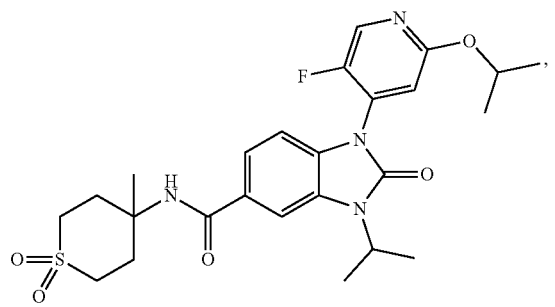
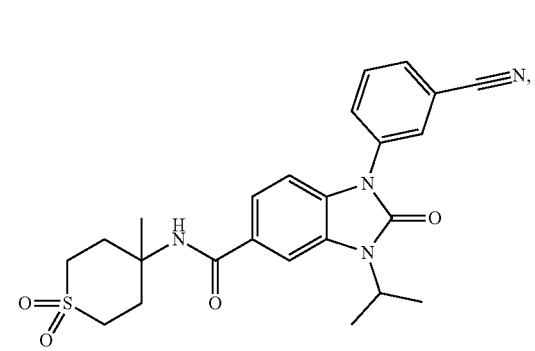
234
-continued
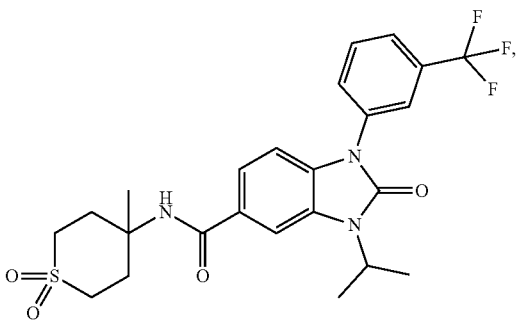
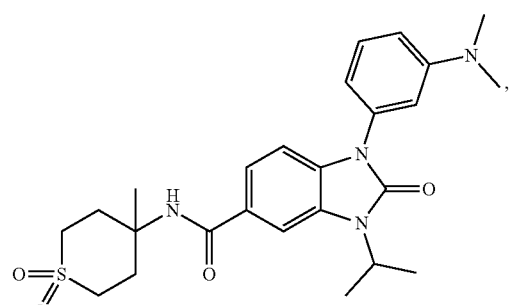
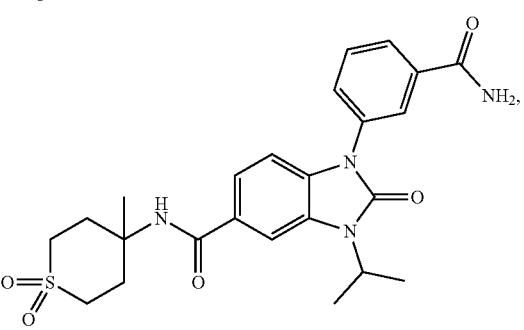
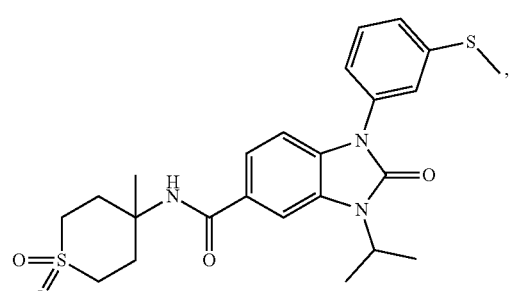
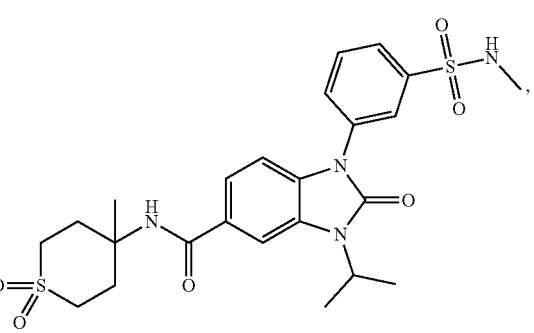

235
-continued
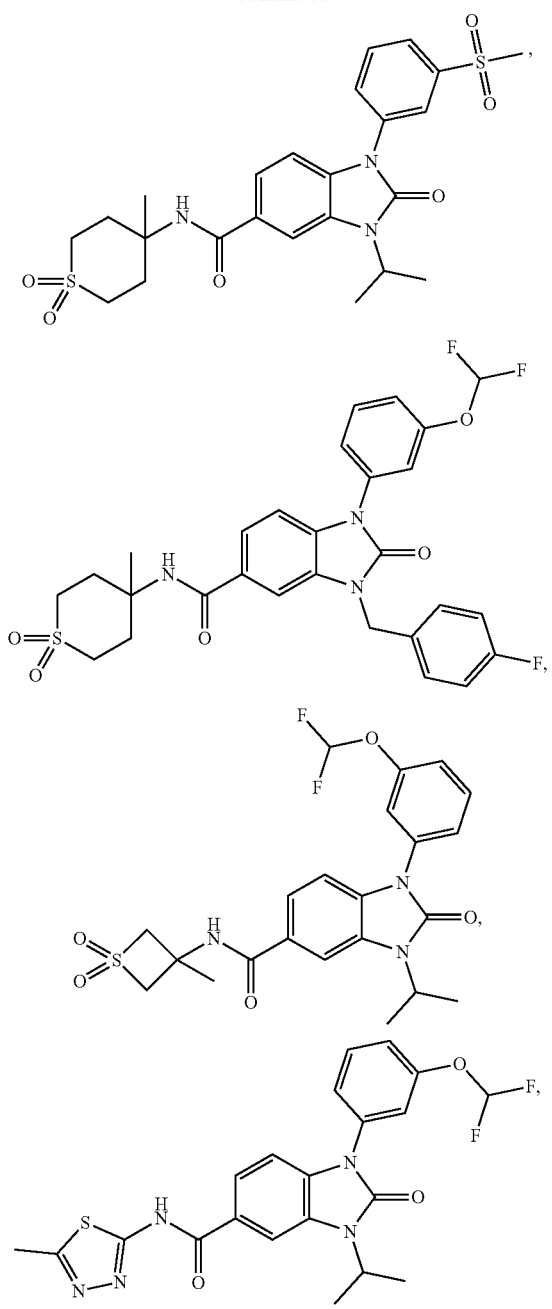
236
-continued
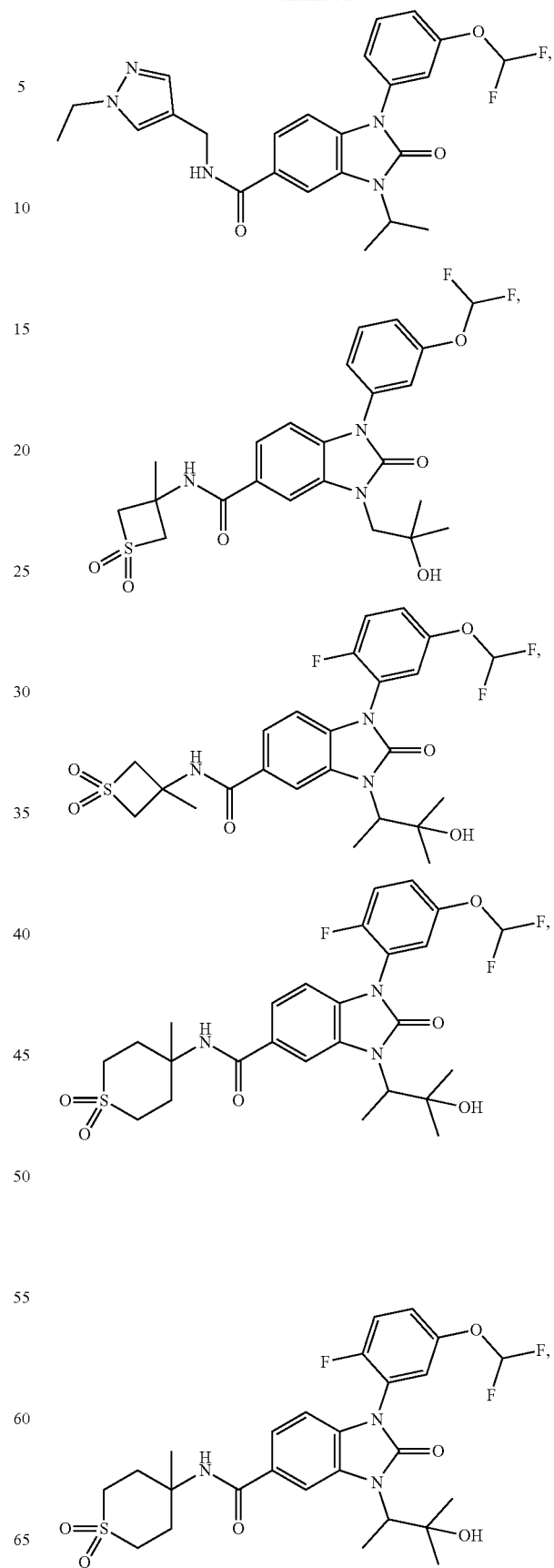

237
-continued
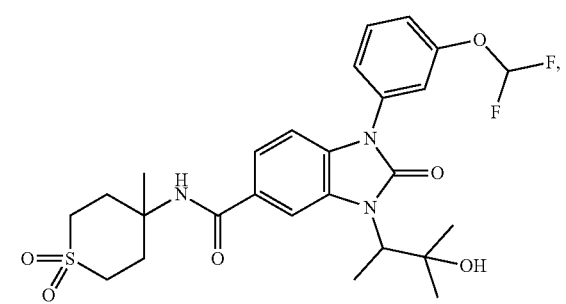
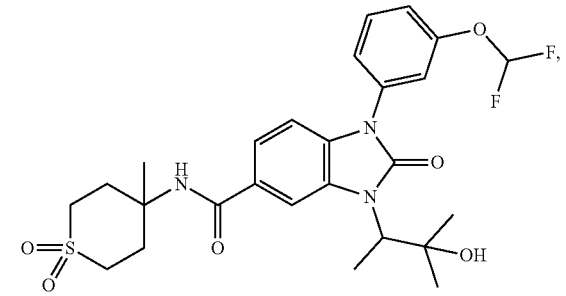
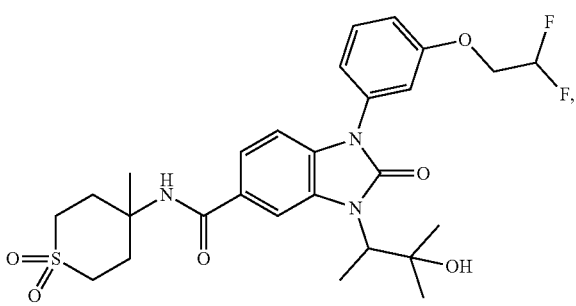
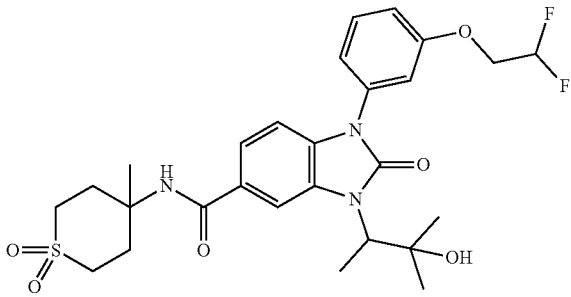
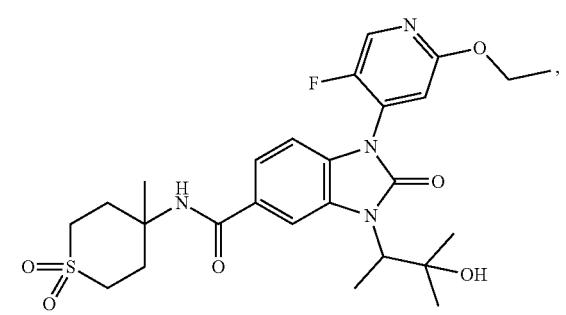
238
-continued
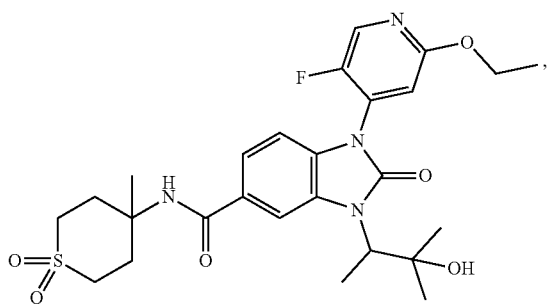
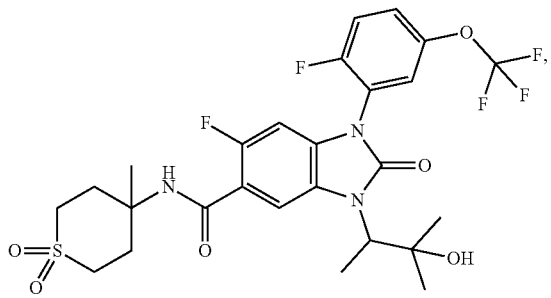
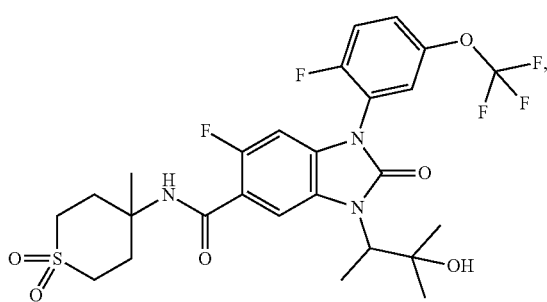
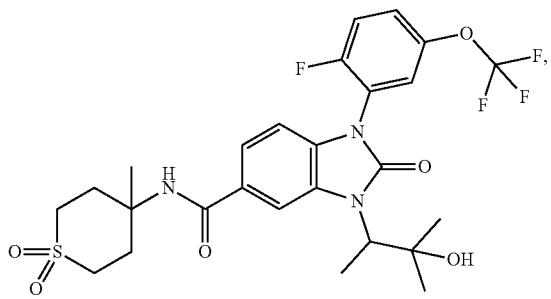
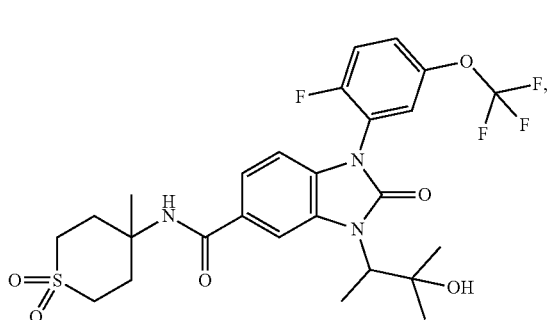

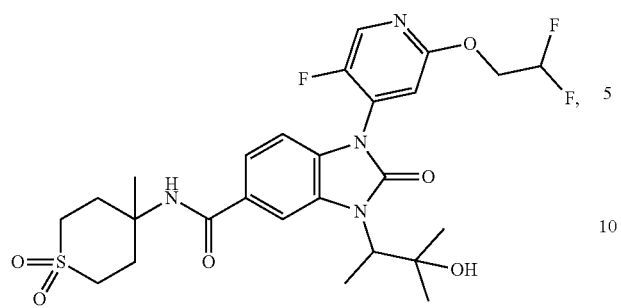
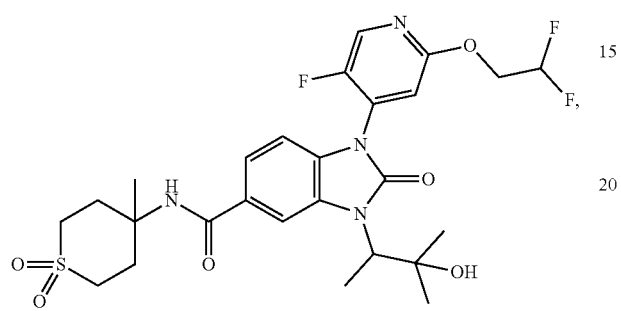
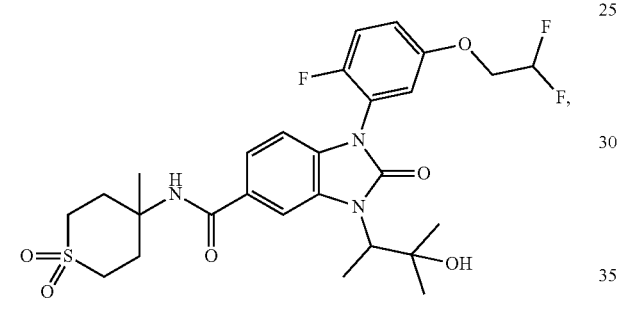
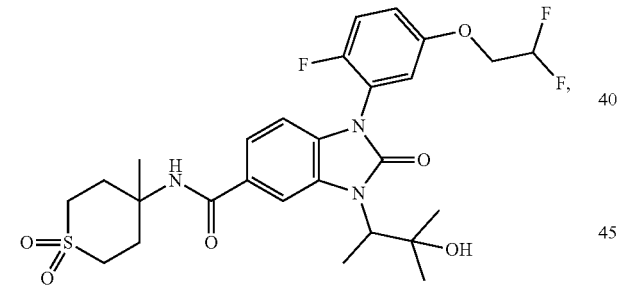
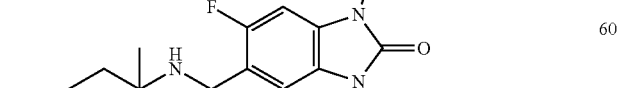
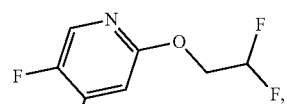
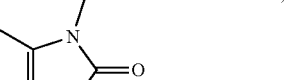
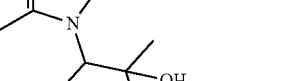
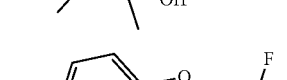
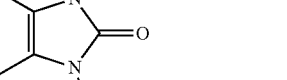

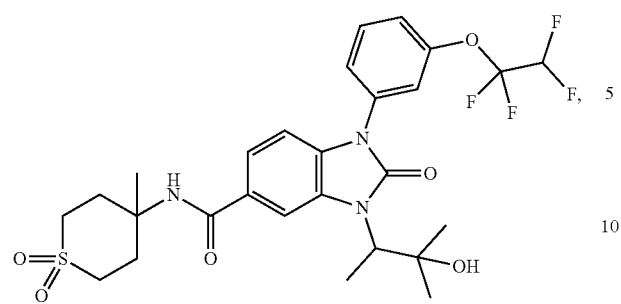
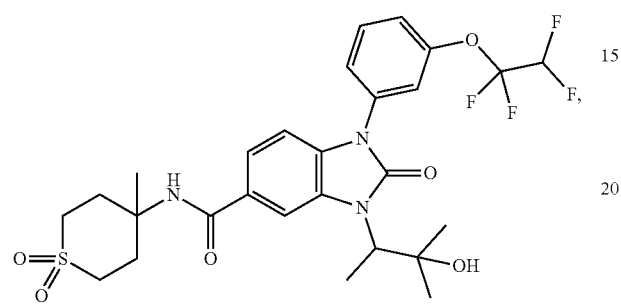
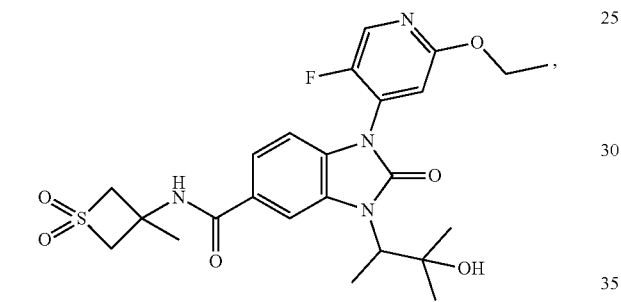
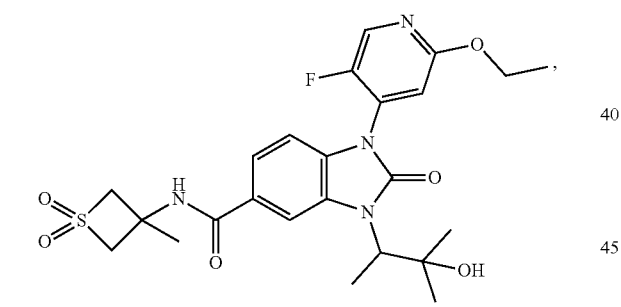
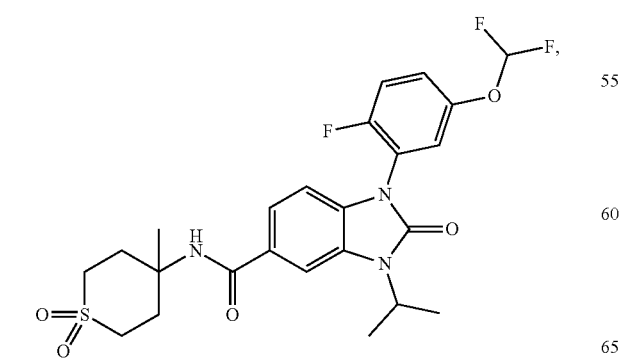
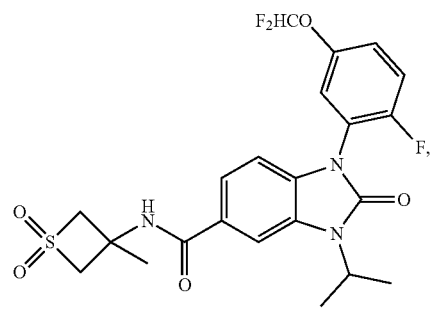
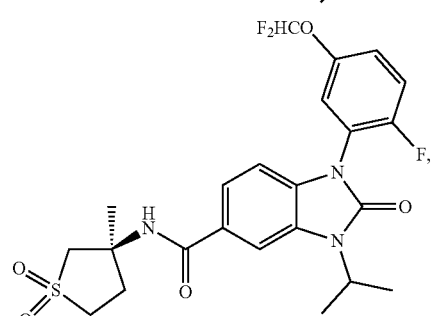
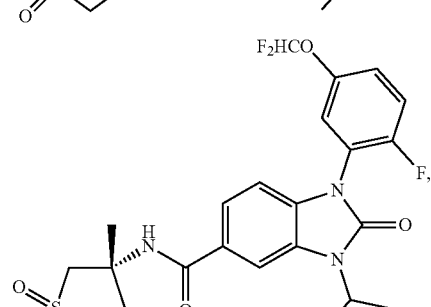
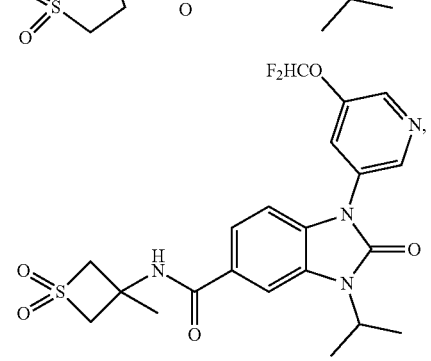
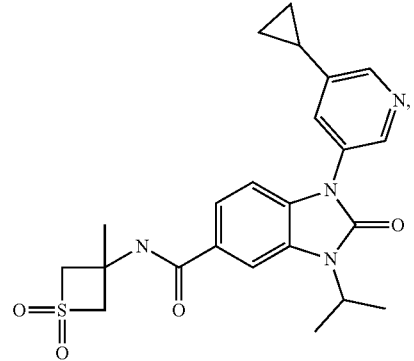

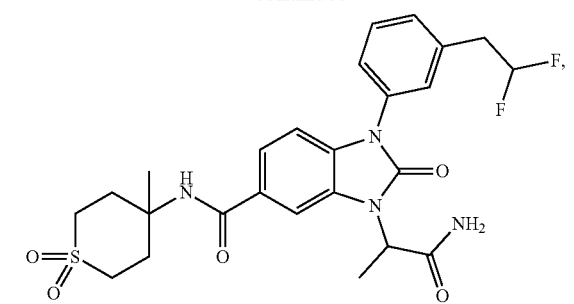
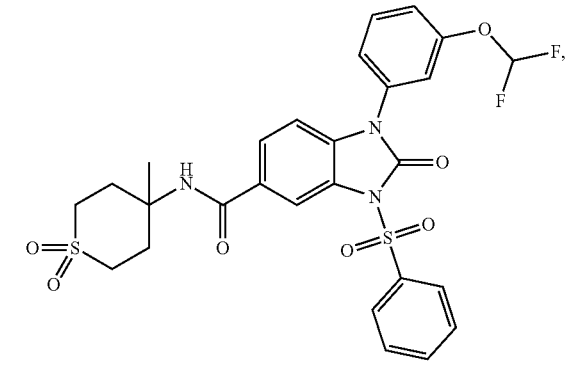
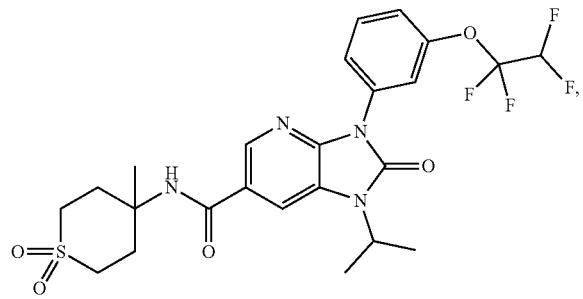
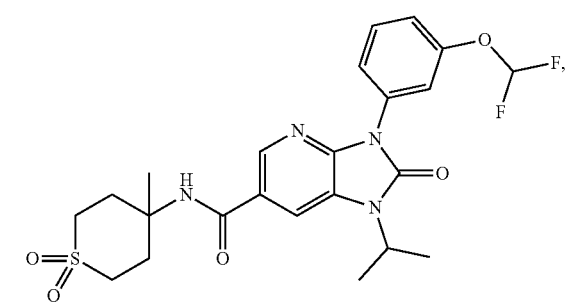
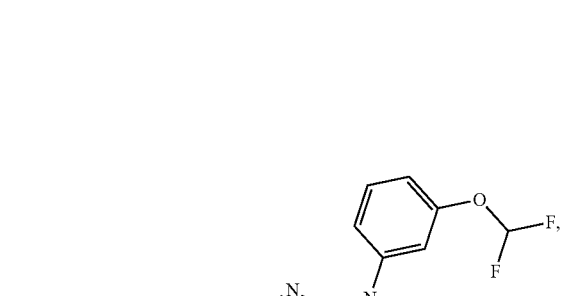
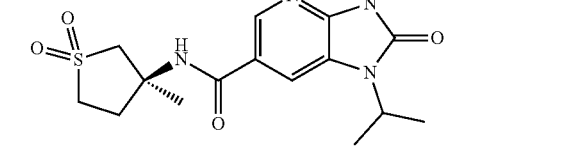
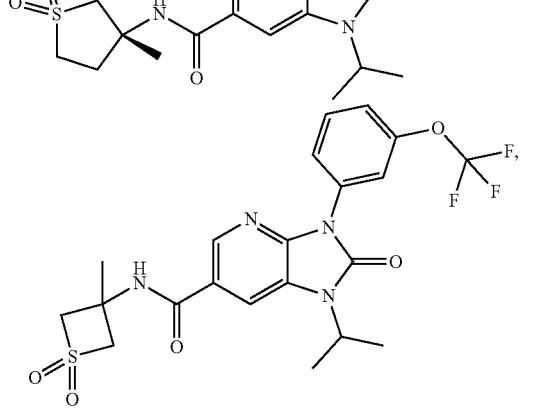
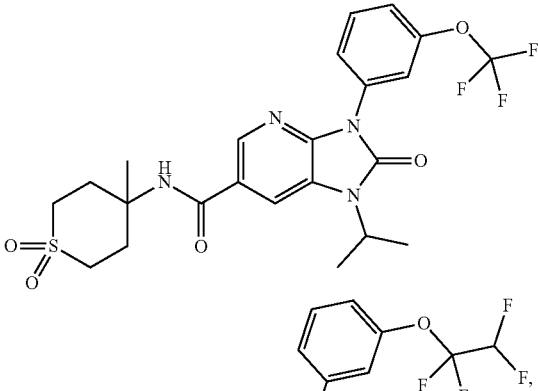
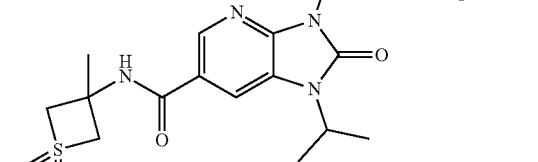
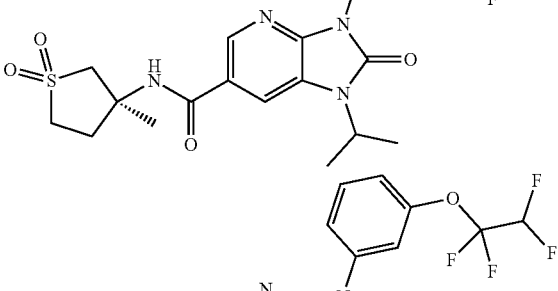
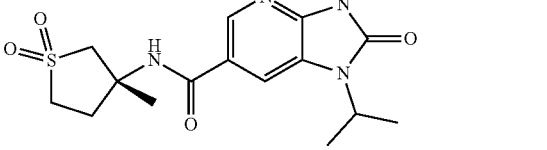

245
-continued
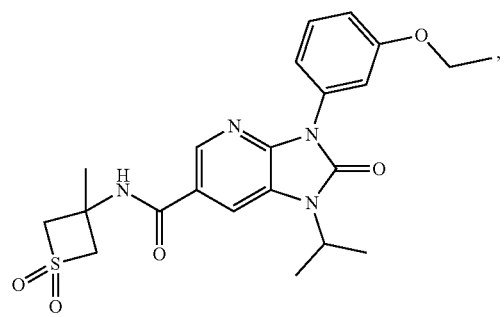
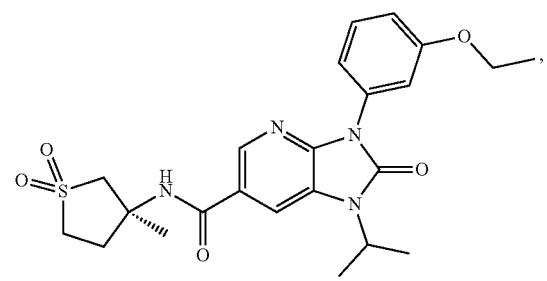
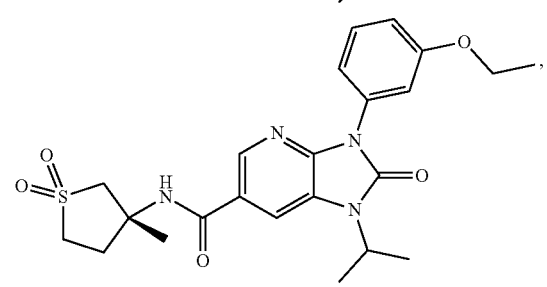
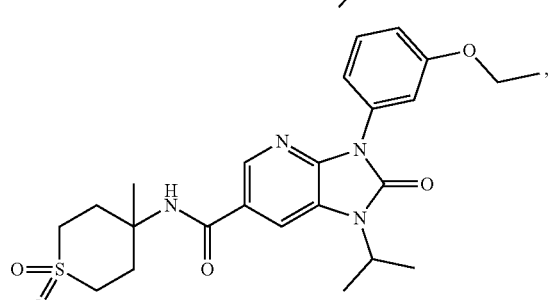
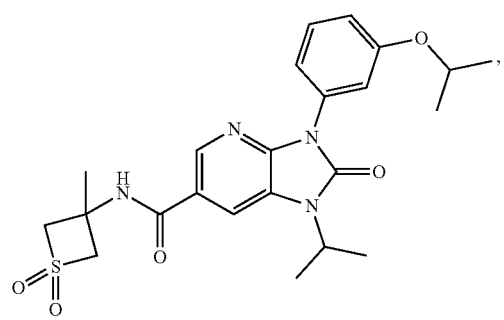
246
-continued
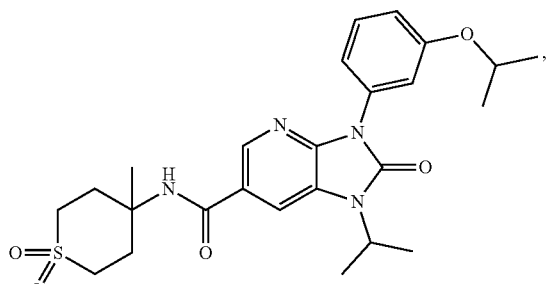
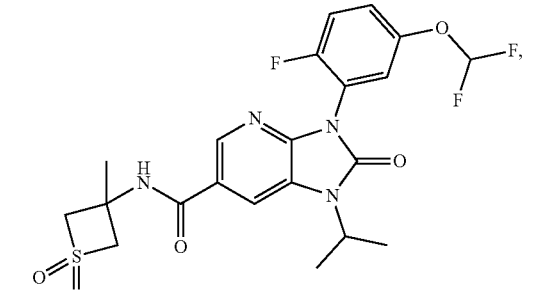
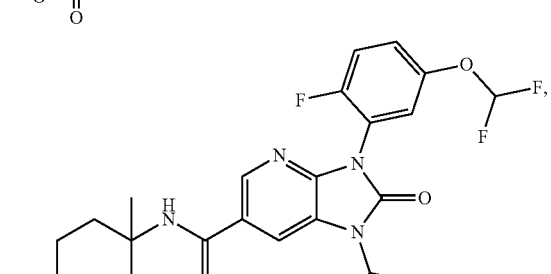
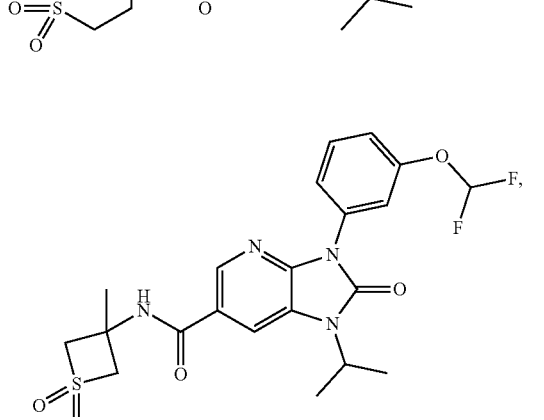
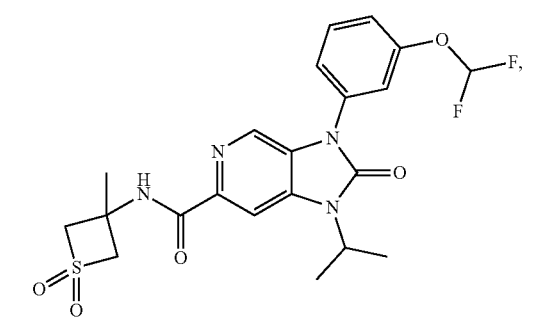

247
-continued
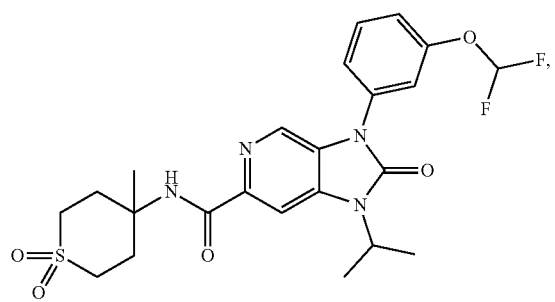
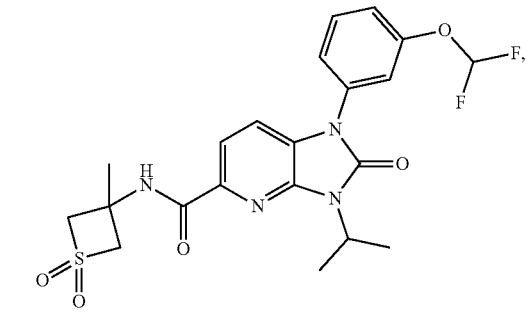
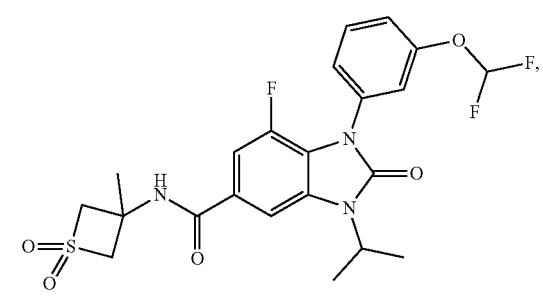
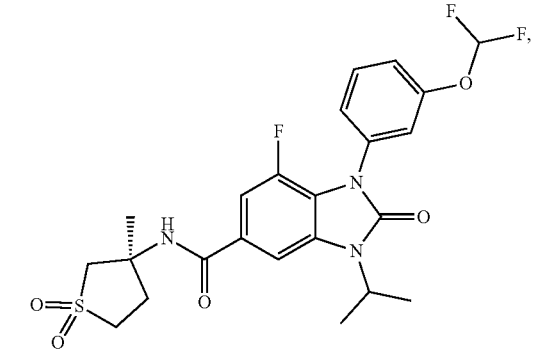
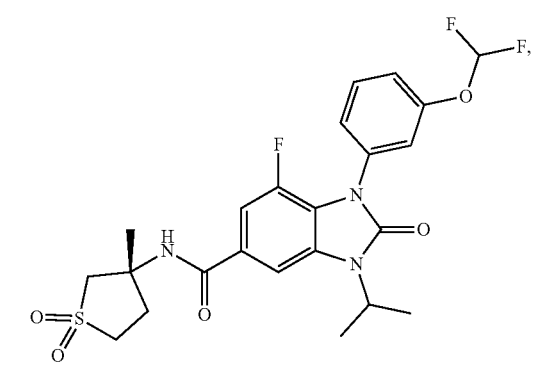
248
-continued
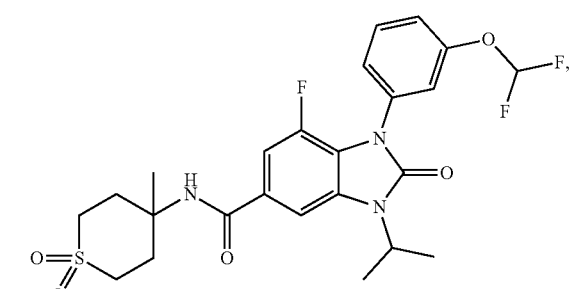
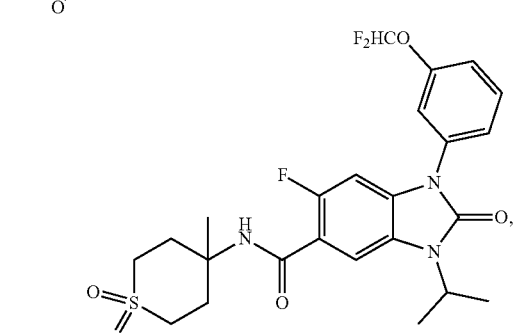
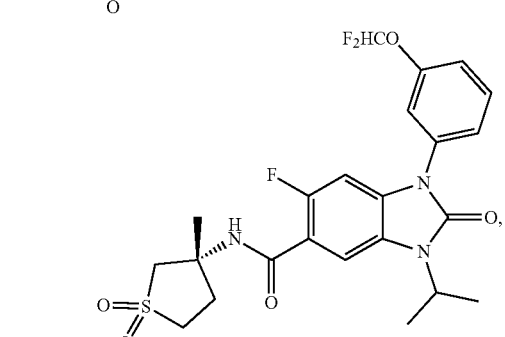
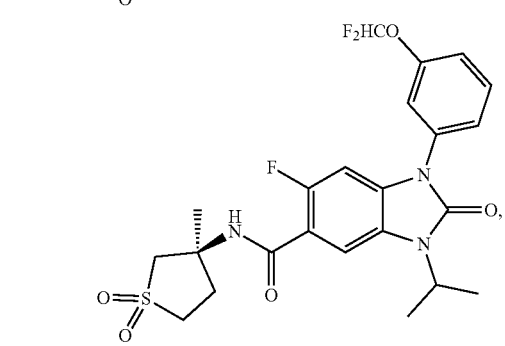
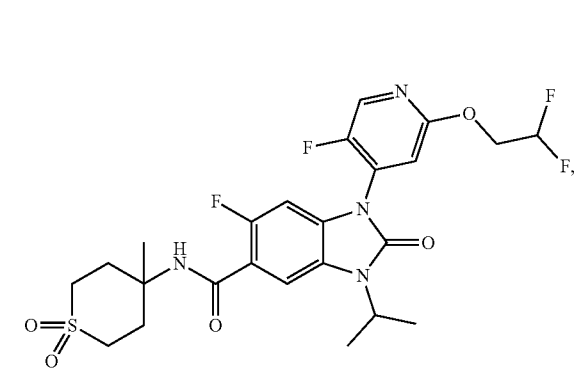

249
-continued
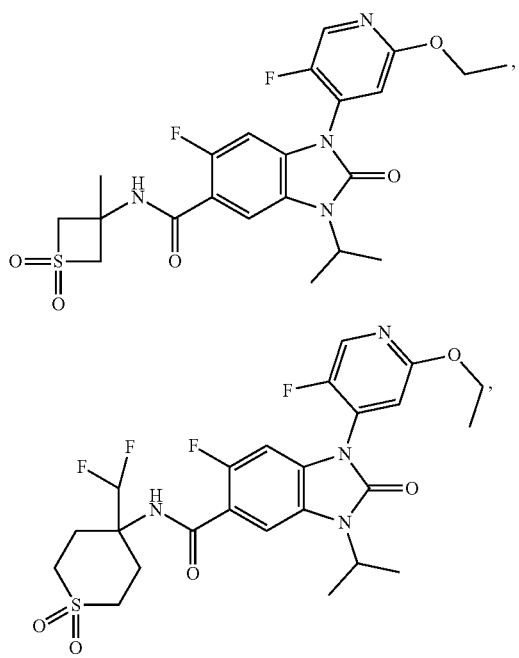
250
-continued
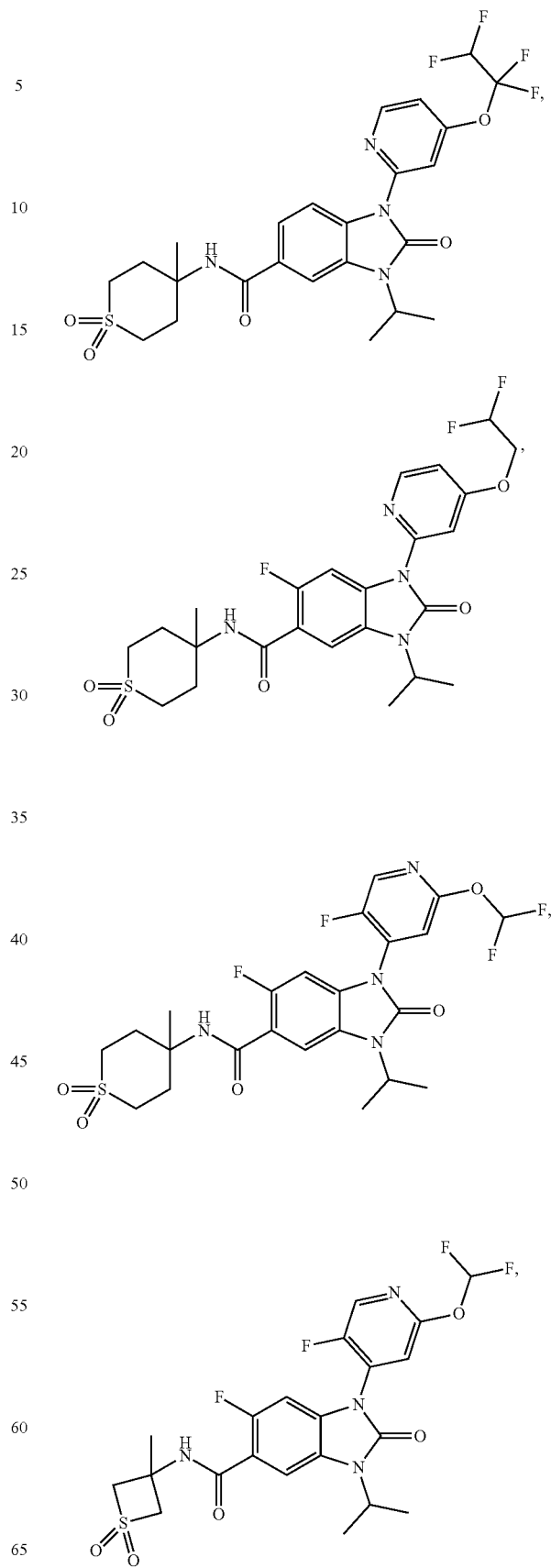

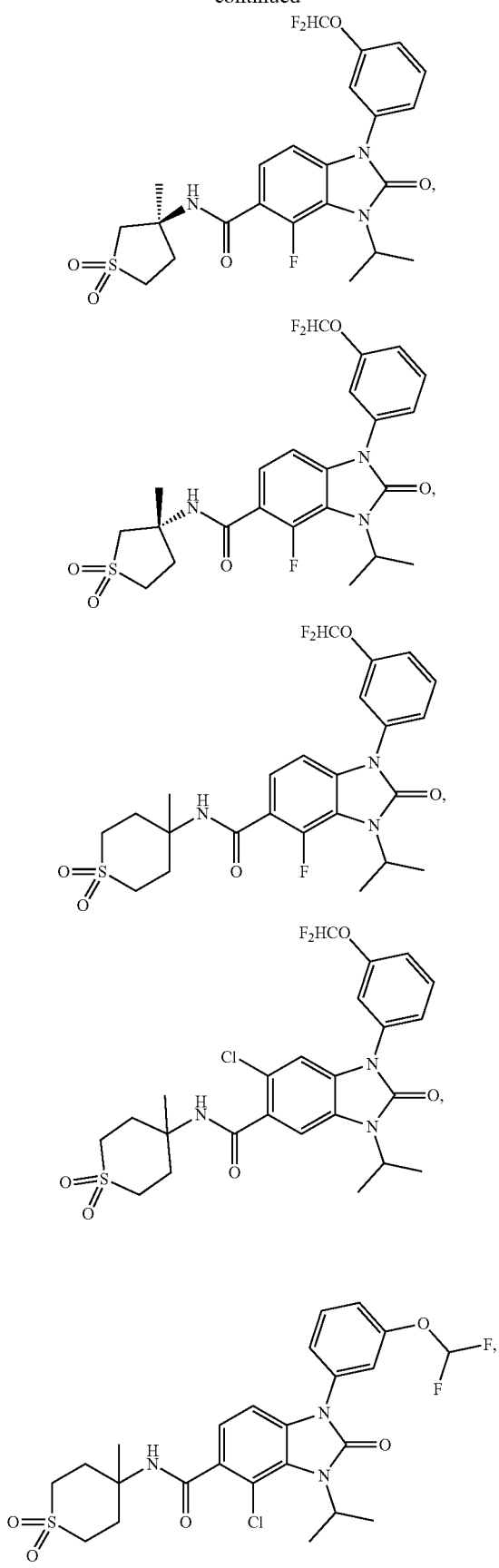

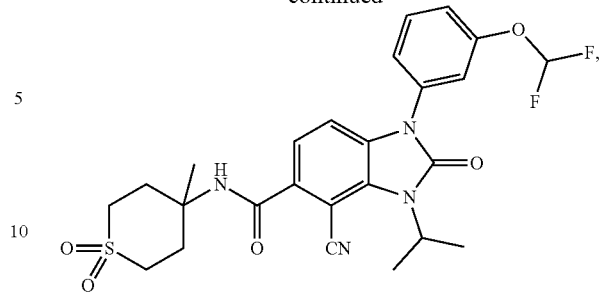

or a pharmaceutically acceptable salt thereof.

36. The compound of claim 1, or a pharmaceutically acceptable salt thereof, which is (R)-1,3-bis(4-fluorophenyl)-N-(3-methyl-1,1-dioxidotetrahydrothiophen-3-yl)-2-oxo-2,3-dihydro-1H-benzo[d]imidazole-5-carboxamide, 1-(3-(difluoromethoxy)phenyl)-3-(4-fluorophenyl)-N-(3-methyl-1,1-dioxidothietan-3-yl)-2-oxo-2,3-dihydro-1H-benzo[d]imidazole-5-carboxamide, (R)-1-(3-(difluoromethoxy)phenyl)-3-(4-fluorophenyl)-N-(3-methyl-1,1-dioxidotetrahydrothiophen-3-yl)-2-oxo-2,3-dihydro-1H-benzo[d]imidazole-5-carboxamide, 3-(3-(difluoromethoxy)phenyl)-1-(4-fluorophenyl)-N-(3-methyl-1,1-dioxidothietan-3-yl)-2-oxo-2,3-dihydro-1H-imidazo[4,5-b]pyridine-6-carboxamide, 1-(2-(Difluoromethoxy)-5-fluoropyridin-4-yl)-3-isopropyl-N-(4-methyl-1,1-dioxidotetrahydro-2H-thiopyran-4-yl)-2-oxo-2,3-dihydro-1H-benzo[d]imidazole-5-carboxamide, 1-(3-isopropoxyphenyl)-3-isopropyl-N-(3-methyl-1,1-dioxo-thietan-3-yl)-2-oxo-benzimidazole-5-carboxamide, 3-isopropyl-N-(3-methyl-1,1-dioxo-thietan-3-yl)-2-oxo-1-[3-(1,1,2,2-tetrafluoroethoxy)phenyl]benzimidazole-5-carboxamide, 1-[3-(2,2-difluoroethoxy)phenyl]-3-isopropyl-N-(3-methyl-1,1-dioxo-thietan-3-yl)-2-oxo-benzimidazole-5-carboxamide, 1-(3-ethoxyphenyl)-3-isopropyl-N-(3-methyl-1,1-dioxo-thietan-3-yl)-2-oxo-benzimidazole-5-carboxamide, 3-isopropyl-N-(4-methyl-1,1-dioxo-thian-4-yl)-2-oxo-1-[3-(trifluoromethoxy)phenyl]benzimidazole-5-carboxamide, 1-[3-(2,2-difluoroethoxy)phenyl]-3-isopropyl-N-(4-methyl-1,1-dioxo-thian-4-yl)-2-oxo-benzimidazole-5-carboxamide, 1-[4-(difluoromethoxy)-2-pyridyl]-3-isopropyl-N-(3-methyl-1,1-dioxo-thietan-3-yl)-2-oxo-benzimidazole-5-carboxamide, 1-(3-cyclopropylphenyl)-3-isopropyl-N-(3-methyl-1,1-dioxo-thietan-3-yl)-2-oxo-benzimidazole-5-carboxamide, 1-[3-(cyclopropoxy)phenyl]-3-isopropyl-N-(3-methyl-1,1-dioxo-thietan-3-yl)-2-oxo-benzimidazole-5-carboxamide, 1-(2-Ethoxy-5-fluoropyridin-4-yl)-3-isopropyl-N-(4-methyl-1,1-dioxidotetrahydro-2H-thiopyran-4-yl)-2-oxo-2,3-dihydro-1H-benzo[d]imidazole-5-carboxamide, 1-(2-ethoxy-5-fluoropyridin-4-yl)-3-isopropyl-N-(3-methyl-1,1-dioxidothietan-3-yl)-2-oxo-2,3-dihydro-1H-benzo[d]imidazole-5-carboxamide, (S)-1-(2-Ethoxy-5-fluoropyridin-4-yl)-3-isopropyl-N-(3-methyl-1,1-dioxidotetrahydrothiophen-3-yl)-2-oxo-2,3-dihydro-1H-benzo[d]imidazole-5-carboxamide, (R)-1-(2-Ethoxy-5-fluoropyridin-4-yl)-3-isopropyl-N-(3-methyl-1,1-dioxidotetrahydrothiophen-3-yl)-2-oxo-2,3-dihydro-1H-benzo[d]imidazole-5-carboxamide, 3-isopropyl-N-(3-methyl-1,1-dioxo-thietan-3-yl)-2-oxo-1-[3-(trifluoromethoxy)phenyl]benzimidazole-5-carboxamide, 1-(2-(difluoromethoxy)-5-fluoropyridin-4-yl)-3-isopropyl-N-(3-methyl-1,1-dioxidothietan-3-yl)-2-oxo-2,3-dihydro-1H-benzo[d]imidazole-5-carboxamide, 1-(2-Ethoxy-5-fluoropyridin-4-yl)-6-fluoro-3-isopropyl-N-(3-methyl-1,1-dioxidothietan-3-yl)-2-oxo-2,3-dihydro-1H-benzo[d]imidazole-5-carboxamide, 1-(3-(2,2-Difluorocyclopropyl)phenyl)-3-isopropyl-N-(3-methyl-1,1-dioxidothietan-3-yl)-2-oxo-2,3-dihydro-1H-benzo[d]imidazole-5-carboxamide, (R)-1-(3-(Difluoromethoxy)phenyl)-3-isopropyl-N-(3-methyl-1,1-dioxidotetrahydrothiophen-3-yl)-2-oxo-2,3-dihydro-1H-benzo[d]imidazole-5-carboxamide, 1-(2-(Difluoromethoxy)-5-fluoropyridin-4-yl)-6-fluoro-3-isopropyl-N-(3-methyl-1,1-dioxidothietan-3-yl)-2-oxo-2,3-dihydro-1H-benzo[d]imidazole-5-carboxamide, 1-(3-(difluoromethoxy)phenyl)-3-isopropyl-N-(4-methyl-1,1-dioxidotetrahydro-2H-thiopyran-4-yl)-2-oxo-2,3-dihydro-1H-benzo[d]imidazole-5-carboxamide, 1-[3-(difluoromethoxy)phenyl]-3-isopropyl-N-(3-methyl-1,1-dioxo-thietan-3-yl)-2-oxo-benzimidazole-5-carboxamide, 1-[3-(difluoromethoxy)phenyl]-N-(2-hydroxy-1,2-dimethyl-propyl)-3-isopropyl-2-oxo-benzimidazole-5-carboxamide, 1-[3-(difluoromethoxy)phenyl]-N-[(1S,2S)-2-hydroxycyclopentyl]-3-isopropyl-2-oxo-benzimidazole-5-carboxamide, 1-[3-(difluoromethoxy)phenyl]-N-[(3R,4S)-3-hydroxytetrahydropyran-4-yl]-3-isopropyl-2-oxo-benzimidazole-5-carboxamide, N-[(1S,2R)-3,3-difluoro-2-hydroxy-cyclohexyl]-1-[3-(difluoromethoxy)phenyl]-3-isopropyl-2-oxo-benzimidazole-5-carboxamide, 1-[3-(difluoromethoxy)phenyl]-N-[(1R,2R)-2-hydroxycyclohexyl]-3-isopropyl-2-oxo-benzimidazole-5-carboxamide, 1-[3-(difluoromethoxy)phenyl]-3-isopropyl-N-[(3S)-3-methyl-1,1-dioxo-thiolan-3-yl]-2-oxo-benzimidazole-5-carboxamide, 1-[3-(difluoromethoxy)phenyl]-N-(3,3-difluoro-1-methyl-cyclobutyl)-3-isopropyl-2-oxo-benzimidazole-5-carboxamide, 1-[3-(difluoromethoxy)phenyl]-N-[(1S)-1-(hydroxymethyl)-2-methyl-propyl]-3-isopropyl-2-oxo-benzimidazole-5-carboxamide, 1-[3-(difluoromethoxy)phenyl]-N-[(1S,2S)-2-hydroxycyclohexyl]-3-isopropyl-2-oxo-benzimidazole-5-carboxamide, 1-(3-(difluoromethoxy)phenyl)-N-(3-methyl-1,1-dioxidothietan-3-yl)-2-oxo-3-(tetrahydro-2H-pyran-4-yl)-2,3-dihydro-1H-benzo[d]imidazole-5-carboxamide, (R)-3-Cyclobutyl-1-(3-(difluoromethoxy)phenyl)-N-(3-methyl-1,1-dioxidotetrahydrothiophen-3-yl)-2-oxo-2,3-dihydro-1H-benzo[d]imidazole-5-carboxamide, (R)-3-Cyclopentyl-1-(3-(difluoromethoxy)phenyl)-N-(3-methyl-1,1-dioxidotetrahydrothiophen-3-yl)-2-oxo-2,3-dihydro-1H-benzo[d]imidazole-5-carboxamide, 1-(3-(Difluoromethoxy)phenyl)-3-ethyl-N-(4-methyl-1,1-dioxidotetrahydro-2H-thiopyran-4-yl)-2-oxo-2,3-dihydro-1H-benzo[d]imidazole-5-carboxamide, 1-(3-(Difluoromethoxy)phenyl)-3-ethyl-N-(3-methyl-1,1-dioxidothietan-3-yl)-2-oxo-2,3-dihydro-1H-benzo[d]imidazole-5-carboxamide, 3-Cyclopropyl-1-(3-(difluoromethoxy)phenyl)-N-(4-methyl-1,1-dioxidotetrahydro-2H-thiopyran-4-yl)-2-oxo-2,3-dihydro-1H-benzo[d]imidazole-5-carboxamide, 1-(3-(Difluoromethoxy)phenyl)-N-(4-methyl-1,1-dioxidotetrahydro-2H-thiopyran-4-yl)-2-oxo-3-(3,3,3-trifluoropropyl)-2,3-dihydro-1H-benzo[d]imidazole-5-carboxamide, 1-(3-(Difluoromethoxy)phenyl)-N-(3-methyl-1,1-dioxidothietan-3-yl)-2-oxo-3-(2,2,2-trifluoroethyl)-2,3-dihydro-1H-benzo[d]imidazole-5-carboxamide, 1-(3-(difluoromethoxy)phenyl)-N-(4-methyl-1,1-dioxidotetrahydro-2H-thiopyran-4-yl)-2-oxo-3-(2,2,2-trifluoroethyl)-2,3-dihydro-1H-benzo[d]imidazole-5-carboxamide, 1-(3-(Difluoromethoxy)phenyl)-3-(1,1-difluoropropan-2-yl)-N-(4-methyl-1,1-dioxidotetrahydro-2H-thiopyran-4-yl)-2-oxo-2,3-dihydro-1H-benzo[d]imidazole-5-carboxamide, 1-(3-(Difluoromethoxy)phenyl)-3-(1,1-difluoropropan-2-yl)-N-(4-methyl-1,1-dioxidotetrahydro-2H-thiopyran-4-yl)-2-oxo-2,3-dihydro-1H-benzo[d]imidazole-5-carboxamide, 3-(sec-butyl)-1-(3-(difluoromethoxy)phenyl)-N-(3-methyl-1,1-dioxidothietan-3-yl)-2-oxo-2,3-dihydro-1H-benzo[d]imidazole-5-carboxamide, 3-(sec-butyl)-1-(3-(difluoromethoxy)phenyl)-N-(3-methyl-1,1-dioxidothietan-3-yl)-2-oxo-2,3-dihydro-1H-benzo[d]imidazole-5-carboxamide, 1-(4-acetamido-3-hydroxyphenyl)-3-isopropyl-N-(3-methyl-1,1-dioxidothietan-3-yl)-2-oxo-2,3-dihydro-1H-benzo[d]imidazole-5-carboxamide, 3-isopropyl-N-(3-methyl-1,1-dioxidothietan-3-yl)-1-(2-methylbenzo[d]oxazol-4-yl)-2-oxo-2,3-dihydro-1H-benzo[d]imidazole-5-carboxamide, 3-isopropyl-N-(3-methyl-1,1-dioxidothietan-3-yl)-1-(2-methylbenzo[d]oxazol-6-yl)-2-oxo-2,3-dihydro-1H-benzo[d]imidazole-5-carboxamide, 1-(3-fluorophenyl)-3-isopropyl-N-(4-methyl-1,1-dioxidotetrahydro-2H-thiopyran-4-yl)-2-oxo-2,3-dihydro-1H-benzo[d]imidazole-5-carboxamide, 1-(5-fluoro-2-isopropoxypyridin-4-yl)-3-isopropyl-N-(4-methyl-1,1-dioxidotetrahydro-2H-thiopyran-4-yl)-2-oxo-2,3-dihydro-1H-benzo[d]imidazole-5-carboxamide, 1-(3-cyanophenyl)-3-isopropyl-N-(4-methyl-1,1-dioxidotetrahydro-2H-thiopyran-4-yl)-2-oxo-2,3-dihydro-1H-benzo[d]imidazole-5-carboxamide, 3-isopropyl-N-(4-methyl-1,1-dioxidotetrahydro-2H-thiopyran-4-yl)-2-oxo-1-(3-(trifluoromethyl)phenyl)-2,3-dihydro-1H-benzo[d]imidazole-5-carboxamide, 1-(3-(dimethylamino)phenyl)-3-isopropyl-N-(4-methyl-1,1-dioxidotetrahydro-2H-thiopyran-4-yl)-2-oxo-2,3-dihydro-1H-benzo[d]imidazole-5-carboxamide, 1-(3-carbamoylphenyl)-3-isopropyl-N-(4-methyl-1,1-dioxidotetrahydro-2H-thiopyran-4-yl)-2-oxo-2,3-dihydro-1H-benzo[d]imidazole-5-carboxamide, 3-isopropyl-N-(4-methyl-1,1-dioxidotetrahydro-2H-thiopyran-4-yl)-1-(3-(methylthio)phenyl)-2-oxo-2,3-dihydro-1H-benzo[d]imidazole-5-carboxamide, 3-isopropyl-N-(4-methyl-1,1-dioxidotetrahydro-2H-thiopyran-4-yl)-1-(3-(N-methylsulfamoyl)phenyl)-2-oxo-2,3-dihydro-1H-benzo[d]imidazole-5-carboxamide, 3-isopropyl-N-(4-methyl-1,1-dioxidotetrahydro-2H-thiopyran-4-yl)-1-(3-(methylsulfonyl)phenyl)-2-oxo-2,3-dihydro-1H-benzo[d]imidazole-5-carboxamide, 1-(3-(difluoromethoxy)phenyl)-3-(4-fluorobenzyl)-N-(4-methyl-1,1-dioxidotetrahydro-2H-thiopyran-4-yl)-2-oxo-2,3-dihydro-1H-benzo[d]imidazole-5-carboxamide, 1-(3-(difluoromethoxy)phenyl)-3-methyl-N-(3-methyl-1,1-dioxidothietan-3-yl)-2-oxo-2,3-dihydro-1H-benzo[d]imidazole-5-carboxamide, 1-(3-(difluoromethoxy)phenyl)-3-isopropyl-N-(5-methyl-1,3,4-thiadiazol-2-yl)-2-oxo-2,3-dihydro-1H-benzo[d]imidazole-5-carboxamide, 1-(3-(difluoromethoxy)phenyl)-N-((3-hydroxytetrahydrofuran-3-yl)methyl)-3-isopropyl-2-oxo-2,3-dihydro-1H-benzo[d]imidazole-5-carboxamide, 1-(3-(difluoromethoxy)phenyl)-N-((1-ethyl-1H-pyrazol-4-yl)methyl)-3-isopropyl-2-oxo-2,3-dihydro-1H-benzo[d]imidazole-5-carboxamide, 1-(3-(difluoromethoxy)phenyl)-3-(2-hydroxy-2-methylpropyl)-N-(3-methyl-1,1-dioxidothietan-3-yl)-2-oxo-2,3-dihydro-1H-benzo[d]imidazole-5-carboxamide, 1-(5-(difluoromethoxy)-2-fluorophenyl)-3-(3-hydroxy-3-methylbutan-2-yl)-N-(3-methyl-1,1-dioxidothietan-3-yl)-2-oxo-2,3-dihydro-1H-benzo[d]imidazole-5-carboxamide, 1-(5-(difluoromethoxy)-2-fluorophenyl)-3-(3-hydroxy-3-methylbutan-2-yl)-N-(4-methyl-1,1-dioxidotetrahydro-2H-thiopyran-4-yl)-2-oxo-2,3-dihydro-1H-benzo[d]imidazole-5-carboxamide, 1-(5-(difluoromethoxy)-2-fluorophenyl)-3-(3-hydroxy-3-methylbutan-2-yl)-N-(4-methyl-1,1-dioxidotetrahydro-2H-thiopyran-4-yl)-2-oxo-2,3-dihydro-1H-benzo[d]imidazole-5-carboxamide, 1-(3-(difluoromethoxy)phenyl)-3-(3-hydroxy-3-methylbutan-2-yl)-N-(4-methyl-1,1-dioxidotetrahydro-2H-thiopyran-4-yl)-2-oxo-2,3-dihydro-1H-benzo[d]imidazole-5-carboxamide, 1-(3-(difluoromethoxy)phenyl)-3-(3-hydroxy-3-methylbutan-2-yl)-N-(4-methyl-1,1-dioxidotetrahydro-2H-thiopyran-4-yl)-2-oxo-2,3-dihydro-1H-benzo[d]imidazole-5-carboxamide, 1-(3-(2,2-difluoroethoxy)phenyl)-3-(3-hydroxy-3-methylbutan-2-yl)-N-(4-methyl-1,1-dioxidotetrahydro-2H-thiopyran-4-yl)-2-oxo-2,3-dihydro-1H-benzo[d]imidazole-5-carboxamide, 1-(3-(2,2-difluoroethoxy)phenyl)-3-(3-hydroxy-3-methylbutan-2-yl)-N-(4-methyl-1,1-dioxidotetrahydro-2H-thiopyran-4-yl)-2-oxo-2,3-dihydro-1H-benzo[d]imidazole-5-carboxamide, 1-(2-ethoxy-5-fluoropyridin-4-yl)-3-(3-hydroxy-3-methylbutan-2-yl)-N-(4-methyl-1,1-dioxidotetrahydro-2H-thiopyran-4-yl)-2-oxo-2,3-dihydro-1H-benzo[d]imidazole-5-carboxamide, 1-(2-ethoxy-5-fluoropyridin-4-yl)-3-(3-hydroxy-3-methylbutan-2-yl)-N-(4-methyl-1,1-dioxidotetrahydro-2H-thiopyran-4-yl)-2-oxo-2,3-dihydro-1H-benzo[d]imidazole-5-carboxamide, 6-fluoro-1-(2-fluoro-5-(trifluoromethoxy)phenyl)-3-(3-hydroxy-3-methylbutan-2-yl)-N-(4-methyl-1,1-dioxidotetrahydro-2H-thiopyran-4-yl)-2-oxo-2,3-dihydro-1H-benzo[d]imidazole-5-carboxamide, 6-fluoro-1-(2-fluoro-5-(trifluoromethoxy)phenyl)-3-(3-hydroxy-3-methylbutan-2-yl)-N-(4-methyl-1,1-dioxidotetrahydro-2H-thiopyran-4-yl)-2-oxo-2,3-dihydro-1H-benzo[d]imidazole-5-carboxamide, 1-(2-fluoro-5-(trifluoromethoxy)phenyl)-3-(3-hydroxy-3-methylbutan-2-yl)-N-(4-methyl-1,1-dioxidotetrahydro-2H-thiopyran-4-yl)-2-oxo-2,3-dihydro-1H-benzo[d]imidazole-5-carboxamide, 1-(2-fluoro-5-(trifluoromethoxy)phenyl)-3-(3-hydroxy-3-methylbutan-2-yl)-N-(4-methyl-1,1-dioxidotetrahydro-2H-thiopyran-4-yl)-2-oxo-2,3-dihydro-1H-benzo[d]imidazole-5-carboxamide, 1-(2-(2,2-difluoroethoxy)-5-fluoropyridin-4-yl)-3-(3-hydroxy-3-methylbutan-2-yl)-N-(4-methyl-1,1-dioxidotetrahydro-2H-thiopyran-4-yl)-2-oxo-2,3-dihydro-1H-benzo[d]imidazole-5-carboxamide, 1-(2-(2,2-difluoroethoxy)-5-fluoropyridin-4-yl)-3-(3-hydroxy-3-methylbutan-2-yl)-N-(4-methyl-1,1-dioxidotetrahydro-2H-thiopyran-4-yl)-2-oxo-2,3-dihydro-1H-benzo[d]imidazole-5-carboxamide, 1-(5-(2,2-difluoroethoxy)-2-fluorophenyl)-3-(3-hydroxy-3-methylbutan-2-yl)-N-(4-methyl-1,1-dioxidotetrahydro-2H-thiopyran-4-yl)-2-oxo-2,3-dihydro-1H-benzo[d]imidazole-5-carboxamide, 1-(5-(2,2-difluoroethoxy)-2-fluorophenyl)-6-fluoro-3-(3-hydroxy-3-methylbutan-2-yl)-N-(4-methyl-1,1-dioxidotetrahydro-2H-thiopyran-4-yl)-2-oxo-2,3-dihydro-1H-benzo[d]imidazole-5-carboxamide, 1-(2-(2,2-difluoroethoxy)-5-fluoropyridin-4-yl)-6-fluoro-3-(3-hydroxy-3-methylbutan-2-yl)-N-(4-methyl-1,1-dioxidotetrahydro-2H-thiopyran-4-yl)-2-oxo-2,3-dihydro-1H-benzo[d]imidazole-5-carboxamide, 1-(2-(2,2-difluoroethoxy)-5-fluoropyridin-4-yl)-6-fluoro-3-(3-hydroxy-3-methylbutan-2-yl)-N-(4-methyl-1,1-dioxidotetrahydro-2H-thiopyran-4-yl)-2-oxo-2,3-dihydro-1H-benzo[d]imidazole-5-carboxamide, 1-(5-(2,2-difluoroethoxy)-2-fluorophenyl)-6-fluoro-3-(3-hydroxy-3-methylbutan-2-yl)-N-(4-methyl-1,1-dioxidotetrahydro-2H-thiopyran-4-yl)-2-oxo-2,3-dihydro-1H-benzo[d]imidazole-5-carboxamide, 1-(5-(2,2-difluoroethoxy)-2-fluorophenyl)-6-fluoro-3-(3-hydroxy-3-methylbutan-2-yl)-N-(4-methyl-1,1-dioxidotetrahydro-2H-thiopyran-4-yl)-2-oxo-2,3-dihydro-1H-benzo[d]imidazole-5-carboxamide, 3-(3-hydroxy-3-methylbutan-2-yl)-N-(3-methyl-1,I-dioxidothietan-3-yl)-2-oxo-1-(3-(1,1,2,2-tetrafluoroethoxy)phenyl)-2,3-dihydro-1H-benzo[d]imidazole-5-carboxamide, 3-(3-hydroxy-3-methylbutan-2-yl)-N-(3-methyl-1,I-dioxidothietan-3-yl)-2-oxo-1-(3-(1,1,2,2-tetrafluoroethoxy)phenyl)-2,3-dihydro-1H-benzo[d]imidazole-5-carboxamide, 3-(3-hydroxy-3-methylbutan-2-yl)-N-(4-methyl-1,I-dioxidotetrahydro-2H-thiopyran-4-yl)-2-oxo-1-(3-(1,1,2,2-tetrafluoroethoxy)phenyl)-2,3-dihydro-H-benzo[d]imidazole-5-carboxamide, 3-(3-hydroxy-3-methylbutan-2-yl)-N-(4-methyl-1,I-dioxidotetrahydro-2H-thiopyran-4-yl)-2-oxo-1-(3-(1,1,2,2-tetrafluoroethoxy)phenyl)-2,3-dihydro-H-benzo[d]imidazole-5-carboxamide, 1-(2-ethoxy-5-fluoropyridin-4-yl)-3-(3-hydroxy-3-methylbutan-2-yl)-N-(3-methyl-1,1-dioxidothietan-3-yl)-2-oxo-2,3-dihydro-1H-benzo[d]imidazole-5-carboxamide, 1-(2-ethoxy-5-fluoropyridin-4-yl)-3-(3-hydroxy-3-methylbutan-2-yl)-N-(3-methyl-1,1-dioxidothietan-3-yl)-2-oxo-2,3-dihydro-1H-benzo[d]imidazole-5-carboxamide, 1-(5-(Difluoromethoxy)-2-fluorophenyl)-3-isopropyl-N-(4-methyl-1,1-dioxidotetrahydro-2H-thiopyran-4-yl)-2-oxo-2,3-dihydro-1H-benzo[d]imidazole-5-carboxamide, 1-(5-(Difluoromethoxy)-2-fluorophenyl)-3-isopropyl-N-(3-methyl-1,1-dioxidothietan-3-yl)-2-oxo-2,3-dihydro-1H-benzo[d]imidazole-5-carboxamide, (S)-1-(5-(Difluoromethoxy)-2-fluorophenyl)-3-isopropyl-N-(3-methyl-1,1-dioxidotetrahydrothiophen-3-yl)-2-oxo-2,3-dihydro-1H-benzo[d]imidazole-5-carboxamide, (R)-1-(5-(Difluoromethoxy)-2-fluorophenyl)-3-isopropyl-N-(3-methyl-1,1-dioxidotetrahydrothiophen-3-yl)-2-oxo-2,3-dihydro-1H-benzo[d]imidazole-5-carboxamide, 1-(5-(Difluoromethoxy)pyridin-3-yl)-3-isopropyl-N-(3-methyl-1,1-dioxidothietan-3-yl)-2-oxo-2,3-dihydro-1H-benzo[d]imidazole-5-carboxamide, 1-(5-Cyclopropylpyridin-3-yl)-3-isopropyl-N-(3-methyl-1,1-dioxidothietan-3-yl)-2-oxo-2,3-dihydro-1H-benzo[d]imidazole-5-carboxamide, 3-(1-amino-1-oxopropan-2-yl)-1-(3-(difluoromethoxy)phenyl)-N-(4-methyl-1,1-dioxidotetrahydro-2H-thiopyran-4-yl)-2-oxo-2,3-dihydro-1H-benzo[d]imidazole-5-carboxamide, 1-(3-(difluoromethoxy)phenyl)-N-(4-methyl-1,1-dioxidotetrahydro-2H-thiopyran-4-yl)-2-oxo-3-(phenylsulfonyl)-2,3-dihydro-1H-benzo[d]imidazole-5-carboxamide, 1-isopropyl-N-(4-methyl-1,1-dioxo-thian-4-yl)-2-oxo-3-[3-(1,1,2,2-tetrafluoroethoxy)phenyl]imidazo[4,5-b]pyridine-6-carboxamide, 3-[3-(difluoromethoxy)phenyl]-1-isopropyl-N-(4-methyl-1,1-dioxo-thian-4-yl)-2-oxo-imidazo[4,5-b]pyridine-6-carboxamide, 3-[3-(difluoromethoxy)phenyl]-1-isopropyl-N-[(3S)-3-methyl-1,1-dioxo-thiolan-3-yl]-2-oxo-imidazo[4,5-b]pyridine-6-carboxamide, 3-[3-(difluoromethoxy)phenyl]-1-isopropyl-N-[(3R)-3-methyl-1,1-dioxo-thiolan-3-yl]-2-oxo-imidazo[4,5-b]pyridine-6-carboxamide, 1-isopropyl-N-(3-methyl-1,1-dioxo-thietan-3-yl)-2-oxo-3-[3-(trifluoromethoxy)phenyl]imidazo[4,5-b]pyridine-6-carboxamide, 1-isopropyl-N-(4-methyl-1,1-dioxo-thian-4-yl)-2-oxo-3-[3-(trifluoromethoxy)phenyl]imidazo[4,5-b]pyridine-6-carboxamide, 1-isopropyl-N-(3-methyl-1,1-dioxo-thietan-3-yl)-2-oxo-3-[3-(1,1,2,2-tetrafluoroethoxy)phenyl]imidazo[4,5-b]pyridine-6-carboxamide, 1-isopropyl-N-[(3S)-3-methyl-1,1-dioxo-thiolan-3-yl]-2-oxo-3-[3-(1,1,2,2-tetrafluoroethoxy)phenyl]imidazo[4,5-b]pyridine-6-carboxamide, 1-isopropyl-N-[(3R)-3-methyl-1,1-dioxo-thiolan-3-yl]-2-oxo-3-[3-(1,1,2,2-tetrafluoroethoxy)phenyl]imidazo[4,5-b]pyridine-6-carboxamide, 3-(3-ethoxyphenyl)-1-isopropyl-N-(3-methyl-1,1-dioxo-thietan-3-yl)-2-oxo-imidazo[4,5-b]pyridine-6-carboxamide, 3-(3-ethoxyphenyl)-1-isopropyl-N-[(3S)-3-methyl-1,1-dioxo-thiolan-3-yl]-2-oxo-imidazo[4,5-b]pyridine-6-carboxamide, 3-(3-ethoxyphenyl)-1-isopropyl-N-[(3R)-3-methyl-1,1-dioxo-thiolan-3-yl]-2-oxo-imidazo[4,5-b]pyridine-6-carboxamide, 3-(3-ethoxyphenyl)-1-isopropyl-N-(4-methyl-1,1-dioxo-thian-4-yl)-2-oxo-imidazo[4,5-b]pyridine-6-carboxamide, 3-(3-isopropoxyphenyl)-1-isopropyl-N-(3-methyl-1,1-dioxo-thietan-3-yl)-2-oxo-imidazo[4,5-b]pyridine-6-carboxamide, 3-(3-isopropoxyphenyl)-1-isopropyl-N-(4-methyl-1,1-dioxo-thian-4-yl)-2-oxo-imidazo[4,5-b]pyridine-6-carboxamide, 3-[5-(difluoromethoxy)-2-fluoro-phenyl]-1-isopropyl-N-(3-methyl-1,1-dioxo-thietan-3-yl)-2-oxo-imidazo[4,5-b]pyridine-6-carboxamide, 3-[5-(difluoromethoxy)-2-fluoro-phenyl]-1-isopropyl-N-(4-methyl-1,1-dioxo-thian-4-yl)-2-oxo-imidazo[4,5-b]pyridine-6-carboxamide, 3-[3-(difluoromethoxy)phenyl]-1-isopropyl-N-(3-methyl-1,1-dioxo-thietan-3-yl)-2-oxo-imidazo[4,5-b]pyridine-6-carboxamide, 3-(3-(difluoromethoxy)phenyl)-1-isopropyl-N-(3-methyl-1,1-dioxidothietan-3-yl)-2-oxo-2,3-dihydro-1H-imidazo[4,5-c]pyridine-6-carboxamide, 3-(3-(difluoromethoxy)phenyl)-1-isopropyl-N-(4-methyl-1,1-dioxidotetrahydro-2H-thiopyran-4-yl)-2-oxo-2,3-dihydro-1H-imidazo[4,5-c]pyridine-6-carboxamide, 1-(3-(difluoromethoxy)phenyl)-3-isopropyl-N-(3-methyl-1,1-dioxidothietan-3-yl)-2-oxo-2,3-dihydro-1H-imidazo[4,5-b]pyridine-5-carboxamide, 1-[3-(difluoromethoxy)phenyl]-7-fluoro-3-isopropyl-N-(3-methyl-1,1-dioxo-thietan-3-yl)-2-oxo-benzimidazole-5-carboxamide, 1-[3-(difluoromethoxy)phenyl]-7-fluoro-3-isopropyl-N-[(3S)-3-methyl-1,1-dioxo-thiolan-3-yl]-2-oxo-benzimidazole-5-carboxamide, 1-[3-(difluoromethoxy)phenyl]-7-fluoro-3-isopropyl-N-[(3R)-3-methyl-1,1-dioxo-thiolan-3-yl]-2-oxo-benzimidazole-5-carboxamide, 1-[3-(difluoromethoxy)phenyl]-7-fluoro-3-isopropyl-N-(4-methyl-1,1-dioxo-thian-4-yl)-2-oxo-benzimidazole-5-carboxamide, 1-(3-(Difluoromethoxy)phenyl)-6-fluoro-3-isopropyl-N-(4-methyl-1,1-dioxidotetrahydro-2H-thiopyran-4-yl)-2-oxo-2,3-dihydro-1H-benzo[d]imidazole-5-carboxamide, (R)-1-(3-(Difluoromethoxy)phenyl)-6-fluoro-3-isopropyl-N-(3-methyl-1,1-dioxidotetrahydrothiophen-3-1)-2-oxo-2,3-dihydro-1H-benzo[d]imidazole-5-carboxamide, (S)-1-(3-(Difluoromethoxy)phenyl)-6-fluoro-3-isopropyl-N-(3-methyl-1,1-dioxidotetrahydrothiophen-3-yl)-2-oxo-2,3-dihydro-1H-benzo[d]imidazole-5-carboxamide, 1-(2-(2,2-difluoroethoxy)-5-fluoropyridin-4-yl)-6-fluoro-3-isopropyl-N-(4-methyl-1,1-dioxidotetrahydro-2H-thiopyran-4-yl)-2-oxo-2,3-dihydro-1H-benzo[d]imidazole-5-carboxamide, 1-(2-ethoxy-5-fluoropyridin-4-yl)-6-fluoro-3-isopropyl-N-(3-methyl-1,1-dioxidothietan-3-yl)-2-oxo-2,3-dihydro-1H-benzo[d]imidazole-5-carboxamide, N-(4-(difluoromethyl)-1,1-dioxidotetrahydro-2H-thiopyran-4-yl)-1-(2-ethoxy-5-fluoropyridin-4-yl)-6-fluoro-3-isopropyl-2-oxo-2,3-dihydro-1H-benzo[d]imidazole-5-carboxamide, 6-fluoro-3-isopropyl-N-(4-methyl-1,1-dioxidotetrahydro-2H-thiopyran-4-yl)-2-oxo-1-(4-(1,1,2,2-tetrafluoroethoxy)pyridin-2-yl)-2,3-dihydro-1H-benzo[d]imidazole-5-carboxamide 1-(4-(2,2-difluoroethoxy)pyridin-2-yl)-3-isopropyl-N-(4-methyl-1,1-dioxidotetrahydro-2H-thiopyran-4-yl)-2-oxo-2,3-dihydro-1H-benzo[d]imidazole-5-carboxamide, 3-isopropyl-N-(4-methyl-1,1-dioxidotetrahydro-2H-thiopyran-4-yl)-2-oxo-1-(4-(1,1,2,2-tetrafluoroethoxy)pyridin-2-yl)-2,3-dihydro-1H-benzo[d]imidazole-5-carboxamide, 1-(4-(2,2-difluoroethoxy)pyridin-2-yl)-6-fluoro-3-isopropyl-N-(4-methyl-1,1-dioxidotetrahydro-2H-thiopyran-4-yl)-2-oxo-2,3-dihydro-1H-benzo[d]imidazole-5-carboxamide, 1-(2-(difluoromethoxy)-5-fluoropyridin-4-yl)-6-fluoro-3-isopropyl-N-(4-methyl-1,1-dioxidotetrahydro-2H-thiopyran-4-yl)-2-oxo-2,3-dihydro-1H-benzo[d]imidazole-5-carboxamide, 1-(2-(difluoromethoxy)-5-fluoropyridin-4-yl)-6-fluoro-3-isopropyl-N-(3-methyl-1,1-dioxidothietan-3-yl)-2-oxo-2,3-dihydro-1H-benzo[d]imidazole-5-carboxamide, (S)-1-(3-(Difluoromethoxy)phenyl)-4-fluoro-3-isopropyl-N-(3-methyl-1,1-dioxidotetrahydrothiophen-3-yl)-2-oxo-2,3-dihydro-1H-benzo[d]imidazole-5-carboxamide, (R)-1-(3-(Difluoromethoxy)phenyl)-4-fluoro-3-isopropyl-N-(3-methyl-1,1-dioxidotetrahydrothiophen-3-yl)-2-oxo-2,3-dihydro-1H-benzo[d]imidazole-5-carboxamide, 1-(3-(Difluoromethoxy)phenyl)-4-fluoro-3-isopropyl-N-(4-methyl-1,1-dioxidotetrahydro-2H-thiopyran-4-yl)-2-oxo-2,3-dihydro-1H-benzo[d]imidazole-5-carboxamide, (S)-6-Chloro-1-(3-(difluoromethoxy)phenyl)-3-isopropyl-N-(3-methyl-1,1-dioxidotetrahydrothiophen-3-yl)-2-oxo-2,3-dihydro-1H-benzo[d]imidazole-5-carboxamide, 4-chloro-1-(3-(difluoromethoxy)phenyl)-3-isopropyl-N-(4-methyl-1,1-dioxidotetrahydro-2H-thiopyran-4-yl)-2-oxo-2,3-dihydro-1H-benzo[d]imidazole-5-carboxamide, or 4-cyano-1-(3-(difluoromethoxy)phenyl)-3-isopropyl-N-(4-methyl-1,1-dioxidotetrahydro-2H-thiopyran-4-yl)-2-oxo-2,3-dihydro-1H-benzo[d]imidazole-5-carboxamide.

37. A composition for treating a condition selected from hepatic steatosis, nonalcoholic steatohepatitis (NASH), fibrosis, type-2 diabetes mellitus, obesity, hyperlipidemia, hypercholesterolemia, atherosclerosis, cognitive decline, dementia, cardiorenal diseases and heart failure comprising a compound of claim 1, or a pharmaceutically acceptable salt thereof, and a pharmaceutically carrier.

38. A composition comprising a pharmaceutically acceptable carrier and a compound according to claim 1, or a pharmaceutically acceptable salt thereof.

39. A method for treating a condition selected from hepatic steatosis, nonalcoholic steatohepatitis (NASH), fibrosis, type-2 diabetes mellitus, obesity, hyperlipidemia, hypercholesterolemia, atherosclerosis, cognitive decline, dementia, cardiorenal diseases and heart failure comprising administering to a patient in need thereof therapeutically effective amount of a compound of claim 1, or a pharmaceutically acceptable salt thereof.

\* \* \* \* \*